(12) United States Patent
Xia et al.

(10) Patent No.: US 11,578,074 B2
(45) Date of Patent: *Feb. 14, 2023

(54) NITROGENOUS HETEROCYCLIC COMPOUND, PREPARATION METHOD, INTERMEDIATE, COMPOSITION, AND APPLICATION

(71) Applicant: SHANGHAI PHARMACEUTICALS HOLDING CO., LTD., Shanghai (CN)

(72) Inventors: Guangxin Xia, Shanghai (CN); Di Li, Shanghai (CN); Jing Zhang, Shanghai (CN); Lingjun Duan, Shanghai (CN); Hongjian Zuo, Shanghai (CN); Wenbo Xiao, Shanghai (CN); Jia Xu, Shanghai (CN); Yanjun Liu, Shanghai (CN)

(73) Assignee: Shanghai Pharmaceuticals Holding Cd., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/643,196

(22) PCT Filed: Aug. 31, 2018

(86) PCT No.: PCT/CN2018/103523
§ 371 (c)(1),
(2) Date: Feb. 28, 2020

(87) PCT Pub. No.: WO2019/042409
PCT Pub. Date: Mar. 7, 2019

(65) Prior Publication Data
US 2020/0190091 A1    Jun. 18, 2020

(30) Foreign Application Priority Data
Sep. 1, 2017 (CN) .......................... 201710780779.7

(51) Int. Cl.
| | | |
|---|---|---|
| C07D 403/12 | (2006.01) | |
| C07D 471/04 | (2006.01) | |
| C07D 487/04 | (2006.01) | |
| A61P 35/00 | (2006.01) | |

(52) U.S. Cl.
CPC ............ C07D 487/04 (2013.01); A61P 35/00 (2018.01); C07D 403/12 (2013.01); C07D 471/04 (2013.01)

(58) Field of Classification Search
CPC ... C07D 403/12; C07D 471/04; C07D 487/04
See application file for complete search history.

(56) References Cited

U.S. PATENT DOCUMENTS

| | | |
|---|---|---|
| 6,828,320 B2 | 12/2004 | Cockerill et al. |
| 2005/0101630 A1 | 5/2005 | Boyle et al. |
| 2012/0165352 A1 | 6/2012 | Tang et al. |
| 2017/0252317 A1 | 9/2017 | Lyssikatos et al. |
| 2019/0091226 A1 | 3/2019 | Xia et al. |

FOREIGN PATENT DOCUMENTS

| | | |
|---|---|---|
| AU | 772846 B2 | 5/2004 |
| AU | 2010202330 A1 | 7/2010 |
| CN | 1365355 A | 8/2002 |
| CN | 101356171 A | 1/2009 |
| CN | 103965120 A | 8/2014 |
| CN | 103965120 B | 8/2016 |
| CN | 107141293 A | 9/2017 |
| EP | 1178967 B1 | 3/2006 |
| EP | 3424928 A1 | 1/2019 |
| JP | 2002544196 A | 12/2002 |

(Continued)

OTHER PUBLICATIONS

Partial supplementary European Search Report issued in European Patent Application No. 18850013.6, dated Mar. 19, 2021.
International Search Report and Written Opinion of PCT/CN2018/103523 dated Nov. 29, 2018.
English translation of Chinese priority application No. 201710780779.7, filed Sep. 1, 2017.

(Continued)

Primary Examiner — Brian E McDowell
(74) Attorney, Agent, or Firm — Pilloff Passino & Cosenza LLP; Sean A. Passino; Rachel K. Pilloff

(57) ABSTRACT

A nitrogenous heterocyclic compound, a preparation method, an intermediate, a composition, and an application. The present invention provides a nitrogenous heterocyclic compound as represented by formula I, pharmaceutically acceptable salts thereof, enantiomers thereof, diastereoisomers thereof, tautomers thereof, solvates thereof, metabolites thereof, or prodrugs thereof. The compound has high inhibitory activity against ErbB2 tyrosine kinase, has good inhibitory activity against human breast cancer cells BT-474, human gastric cancer cells NCI-N87 and the like with high expression of ErbB2, and in addition has relatively weak inhibitory activity against EGFR kinase, that is, the compound is an EGFR/ErbB2 double target inhibitor that attenuates EGFR kinase inhibitory activity or a small-molecule inhibitor having selectivity for an ErbB2 target.

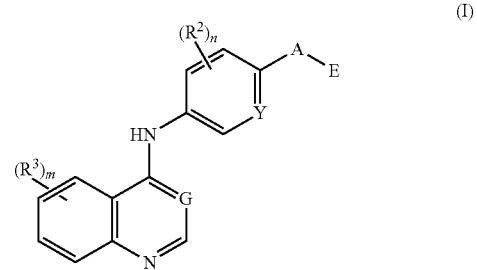

(I)

24 Claims, No Drawings

(56) References Cited

FOREIGN PATENT DOCUMENTS

| JP | 2004517059 A  | 6/2004 |
| JP | 2009515988 A  | 4/2009 |
| JP | 2019507170 A  | 3/2019 |
| WO |  0236570 A1   | 5/2002 |
| WO | 2005034955 A1 | 4/2005 |
| WO | 2007059257 A2 | 5/2007 |
| WO | 2017148391 A1 | 9/2017 |

OTHER PUBLICATIONS

Office Action for related Japan Application No. 2020-512350, dated Jun. 7, 2022.
Office Action for related China Application No. 201811015240.3, dated Aug. 12, 2022.
Registry (STN) [online], [search date: Jan. 14, 2006], CAS Registration No. 937362 to 43-1 Apr. 18, 2022], 2007.

NITROGENOUS HETEROCYCLIC COMPOUND, PREPARATION METHOD, INTERMEDIATE, COMPOSITION, AND APPLICATION

The present application claims the priority of Chinese Patent Application No. CN201710780779.7 filed on Sep. 1, 2017, the contents of which are incorporated herein by reference in their entirety.

FIELD OF INVENTION

The present disclosure relates to a nitrogenous heterocyclic compound, a preparation method, an intermediate, a composition and a use thereof.

DESCRIPTION OF RELATED ART

The epidermal growth factor receptor (EGFR, also known as ErbB or HER) family includes four receptor tyrosine kinases, namely EGFR (ErbB1 or HER1), ErbB2 (HER2), ErbB3 (HER3) and ErbB4 (HER4). Some researchers have proved the role of EGFR and ErbB2 in cancer progression, and EGFR is also expressed at high levels in squamous cell carcinoma of head, neck and lung. Overexpression of ErbB2 occurs in 30% of all breast cancers, which is also associated with other human cancers such as the cancers of colon, ovary, bladder, stomach, esophagus, lung, uterus and prostate. Overexpression of ErbB2 is also associated with the poor prognosis of other cancers, including metastasis and early recurrence.

Epidermal growth factor receptor family has become an active field in anti-cancer research, for example, U.S. Pat. No. 6,828,320 has disclosed certain substituted quinoline and quinazoline compounds as protein tyrosine kinase inhibitors. In 1998, Herceptin (a humanized anti-ErbB2 monoclonal antibody) was approved to be used for breast cancer in the United States. The small molecule EGFR inhibitors, such as Iressa, Tarceva, Tykerb, etc., have also been approved for listing. At present, ErbB2 has become a therapeutic target for breast cancer and gastric/esophageal cancer, and other studies have shown that ErbB2 is a potential therapeutic target for ovarian cancer. At the same time, there are ongoing trials of single or combined therapy of novel ErbB2-targeted drugs, which are expected to bring out new changes to ErbB2-targeted therapy in the near future.

The treatment of ErbB2-positive breast cancer is currently mainly based on the antibody therapy, and there are few effective small molecule inhibitors (although Lapatinib was launched on the market rather early, its efficacy was far from satisfactory). The ErbB2 inhibitors already launched on the market and under development usually have inhibitory effect on EGFR at the same time, thereby causing some toxic and side effects related to the targets, including the toxic and side effects to gastrointestinal tract such as diarrhea, and skin-related toxic and side effects such as rash. These toxic and side effects have been found in clinical trials of Cetuximab, Gefitinib, Erlotinib, Lapatinib and Linatinib, which are generally believed to be caused by strong inhibition of the activity of EGFR. Reducing the inhibitory activity of the compound on EGFR and appropriately improving the selectivity of the compound to ErbB2 can effectively alleviate the above toxic and side effects.

Therefore, there is an urgent need in the art for a selective small molecule inhibitor of ErbB2.

BRIEF SUMMARY OF THE INVENTION

The problem to be solved by the present disclosure is to overcome the defects of the existing compounds such as poor effect, etc., thus providing a nitrogenous heterocyclic compound, a preparation method, an intermediate, a composition and a use thereof. The compound has a high inhibitory activity on ErbB2 tyrosine kinase, a relatively good inhibitory activity on human breast cancer cell BT-474 and human gastric cancer cell NCI-N87 with high ErbB2 expression, and a relatively weak inhibitory activity on EGFR kinase, namely the compound is an EGFR/ErbB2 dual-target inhibitor with reduced EGFR kinase inhibitory activity or a selective small molecule inhibitor targeting ErbB2.

The present disclosure provides a nitrogenous heterocyclic compound represented by formula I, a pharmaceutically acceptable salt thereof, an enantiomer thereof, a diastereomer thereof, a tautomer thereof, a solvate thereof, a metabolite thereof or a prodrug thereof,

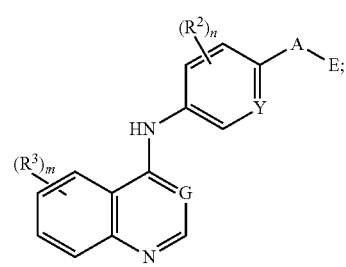

I wherein, E is "9-10 membered fused heteroaryl containing 1-4 heteroatoms selected from the group consisting of N, O and S" (e.g., "9-10 membered fused heteroaryl containing 1-4 N atoms (the rest are C atoms)",

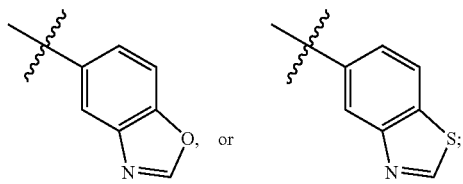

the "9-10 membered fused heteroaryl containing 1-4 N atoms" is, for example

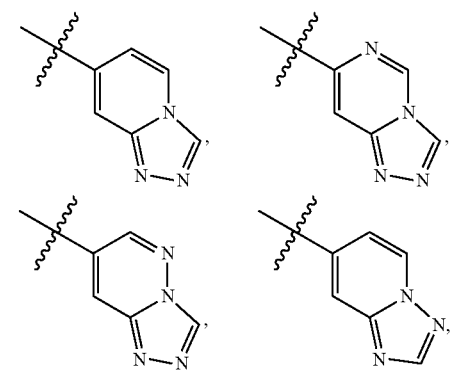

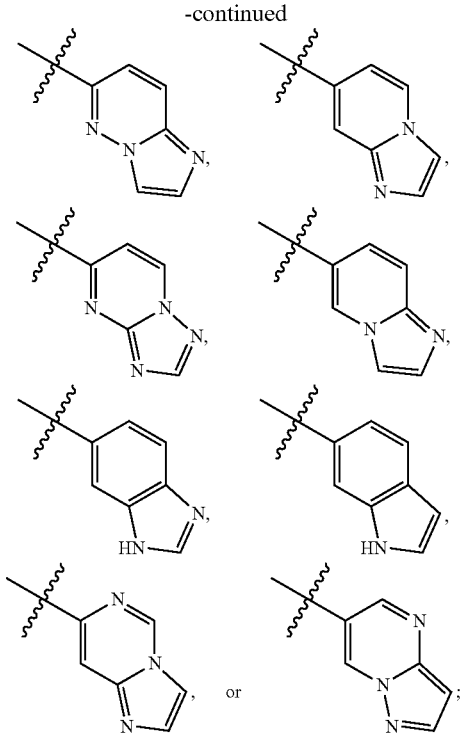

the number of the N atom in the ring connected to A in the "9-10 membered fused heteroaryl containing 1-4 heteroatoms selected from the group consisting of N, O and S" can be 0, 1 or 2, and can also be 1 or 2; the number of the N atom in the ring not connected to A in the "9-10 membered fused heteroaryl containing 1-4 heteroatoms selected from the group consisting of N, O and S" can be 1, 2 or 3, or can also be 2 or 3; when the "9-10 membered fused heteroaryl containing 1-4 heteroatoms selected from the group consisting of N, O and S" is "9-10 membered fused heteroaryl group containing 1-4 N atoms", the number of the N atom in the ring connected to A in the "9-10 membered fused heteroaryl group containing 1-4 N atoms" can be 0, 1 or 2, and can also be 1 or 2; when the "9-10 membered fused heteroaryl containing 1-4 heteroatoms selected from the group consisting of N, O and S" is "9-10 membered fused heteroaryl group containing 1-4 N atoms", the number of N atom in the ring not connected to A in the "9-10 membered fused heteroaryl group containing 1-4 N atoms" can be 1, 2 or 3, and can also be 2 or 3);

A is —O—, —S—, —C(=O)—, —SO— or —SO$_2$—;
n is 0, 1, 2, 3 or 4;
each R$^2$ is independently halogen (e.g. fluorine, chlorine, bromine or iodine, also e.g., chlorine), or, C$_1$-C$_6$ alkyl (e.g., C$_1$-C$_4$ alkyl, also e.g., methyl, ethyl, n-propyl, isopropyl, n-butyl, isobutyl, sec-butyl or tert-butyl, further e.g., methyl);
Y is N or CH;
G is N or C—CN;
m is 1, 2, 3, 4 or 5 (R$^3$ can be connected to any position on the fused ring);
each R$^3$ is independently halogen (e.g., fluorine, chlorine, bromine or iodine, also e.g., fluorine), R$^{3-0}$ substituted or unsubstituted C$_1$-C$_6$ alkoxy (the number of the R$^{3-0}$ can be one or more than one <e.g., 2, 3, 4 or 5>, and when a plurality of R$^{3-0}$ exist, any of two R$^{3-0}$ are the same or different; the "C$_1$-C$_6$ alkoxy" is, for example, C$_1$-C$_4$ alkoxy, and is, for example, methoxy, ethoxy, n-propoxy, isopropoxy, n-butoxy, isobutoxy, sec-butoxy or tert-butoxy, and is for example, ethoxy; the "R$^{3-0}$ substituted C$_1$-C$_6$ alkoxy" is, for example,

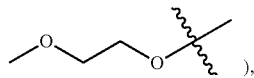 [SMILES: *OCCOC]

R$^{3-1}$ substituted or unsubstituted "3-7 membered heterocycloalkyl containing 1-4 heteroatoms selected from the group consisting of N, O and S" (the number of the R$^{3-1}$ can be one or more than one <e.g., 2, 3, 4 or 5>, and when a plurality of R$^{3-1}$ exist, any of two R$^{3-1}$ are the same or different; the "3-7 membered heterocycloalkyl containing 1-4 heteroatoms selected from the group consisting of N, O and S" can be a "5-6 membered heterocycloalkyl containing 1-2 heteroatoms selected from the group consisting of N, O and S", and can be piperidinyl, and can also be piperidin-1-yl or piperidin-4-yl <relative to

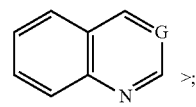

the "3-7 membered heterocycloalkyl containing 1-4 heteroatoms selected from the group consisting of N, O and S" can be connected to

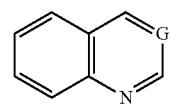

through C atom or N atom; each R$^{3-1}$ can be independently located at the ortho, meta or para position relative to the "connection site of heterocycloalkyl and

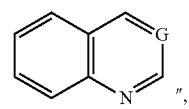

and can also be located at the meta or para position), R$^{3-2}$ substituted or unsubstituted 5-7 membered cycloalkenyl (the number of the R$^{3-2}$ can be one or more than one <e.g., 2, 3, 4 or 5>, and when a plurality of R$^{3-2}$ exist, any of two R$^{3-2}$ are the same or different; the "5-7 membered cycloalkenyl" can be cyclohexenyl, and can also be cyclohexene-1-yl <relative to

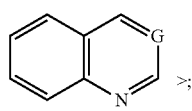

each R$^{32}$ can be independently located at the ortho, meta or para position relative to the "connection site of cycloalkenyl and

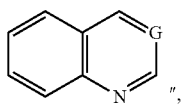

and can also be located at the meta position), $R^{3-3}$ substituted or unsubstituted "5-7 membered heterocycloalkenyl containing 1-4 heteroatoms selected from the group consisting of N, O and S" (the number of the $R^{3-3}$ can be one or more than one <e.g., 2, 3, 4 or 5>, and when a plurality of $R^{3-3}$ exist, any of two $R^{3-3}$ are the same or different; the "5-7 membered heterocycloalkenyl containing 1-4 heteroatoms selected from the group consisting of N, O and S" can be a "5-6 membered heterocycloalkenyl containing 1-2 heteroatoms selected from the group consisting of N, O, and S", and can be 1,2,5,6-tetrahydropyridyl, and can also be 1,2,5,6-tetrahydropyridin-4-yl <relative to

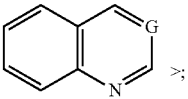

the "5-7 membered heterocycloalkenyl containing 1-4 heteroatoms selected from the group consisting of N, O and S" can be connected to

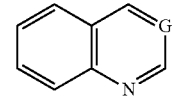

through C atom or N atom; each $R^{3-3}$ can be independently located at the ortho, meta or para position relative to the "connection site of heterocycloalkenyl and

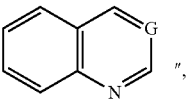

and can also be located at the para position), $R^{3-5}$ substituted or unsubstituted "5-6 membered heteroaryl containing 1-3 heteroatoms selected from the group consisting of N, O, and S" (the number of the $R^{3-5}$ can be one or more than one <e.g., 2, 3, 4 or 5>, when a plurality of $R^{3-5}$ exist, any of two $R^{3-5}$ are the same or different; the "5-6 membered heteroaryl containing 1-3 heteroatoms selected from the group consisting of N, O, and S" can be a "5-6 membered heteroaryl containing 1-2 heteroatoms selected from the group consisting of N, O, and S", and can also be pyrazolyl or furanyl; the pyrazolyl can be pyrazole-5-yl or pyrazole-1-yl <relative to

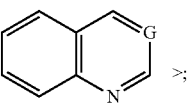

the furanyl can be furan-2-yl <relative to

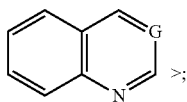

the "5-6 membered heteroaryl containing 1-3 heteroatoms selected from the group consisting of N, O, and S" can be connected to

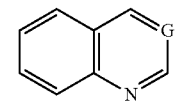

through C atom or N atom; each $R^{3-5}$ can be independently located at the ortho, meta or para position relative to the "connection site of heteroaryl and

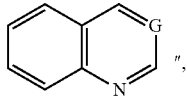

and can also be located at the meta position), $N(R^{3-6})(R^{3-7})$— (one of the $R^{3-6}$ and $R^{3-7}$ can be hydrogen), $(R^{3-8})(R^{3-9})N$—(Z)—HC=CH— (wherein the double bond can be Z-configured, E-configured or a mixture thereof, also e.g., E-configured), $(R^{3-10})(R^{3-11})C=C(R^{3-12})$—C(=O)—NH— (wherein the double bond can be Z-configured, E-configured or a mixture thereof, e.g., E-configured or Z-configured), or, $R^{3-13}$—O— (e.g.,

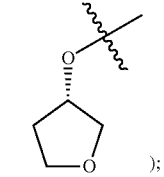 [SMILES: *O[C@H]1CCOC1]

);

each $R^{3-0}$ is independently $C_1$-$C_6$ alkoxy (e.g., $C_1$-$C_4$ alkoxy, further e.g., methoxy, ethoxy, n-propoxy, isopropoxy, n-butoxy, isobutoxy, sec-butoxy or tert-butoxy, further e.g., methoxy);

each $R^{3-1}$ is independently $H_2C$=CH—C(=O)—NH— or $H_2C$=C—C(=O)— (the $H_2C$=C—C(=O)—NH— can be connected to the C atom in the "3-7 membered heterocycloalkyl containing 1-4 heteroatoms selected from the group consisting of N, O and S"; the $H_2C$=C—C(=O)— can be connected to the N atom in the "3-7 membered heterocycloalkyl containing 1-4 heteroatoms selected from the group consisting of N, O and S");

each $R^{3-2}$ is independently $H_2C$=CH—C(=O)—NH—;
each $R^{3-3}$ is independently $H_2C$=$CR^{3-3-1}$—C(=O)—NH— or $H_2C$=$CR^{3-3-1}$—C(=O)—; each $R^{3-3-1}$ is independently H or halogen (e.g., fluorine, chlorine, bromine or iodine, further e.g., fluorine);

each $R^{3-5}$ is independently amino or hydroxymethyl;
each $R^{3-6}$ and $R^{3-7}$ is independently H, $R^{3-6-1}$ substituted or unsubstituted "3-7 membered heterocycloalkyl containing 1-4 heteroatoms selected from the group consisting of N, O and S" (the number of the $R^{3-6-1}$ can be one or more than one <e.g., 2, 3, 4 or 5>, and when a plurality of $R^{3-6-1}$ exist, any of two $R^{3-6-1}$ are the same or different; the "3-7 membered heterocycloalkyl containing 1-4 heteroatoms selected from the group consisting of N, O and S" can be "5-6 membered heterocycloalkyl containing 1-2 heteroatoms selected from the group consisting of N, O and S", and can be piperidyl, and can also be piperidin-3-yl <relative to the N atom>; the "3-7 membered heterocycloalkyl containing 1-4 heteroatoms selected from the group consisting of N, O and S" can be connected to the N atom through the C atom; each $R^{3-6-1}$ can be independently located at the ortho, meta or para position relative to the "connection site of heterocycloalkyl and the N atom", and can also be located at the meta position), or, $R^{3-6-2}$ substituted or unsubstituted "5-7 membered heterocycloalkenyl containing 1-4 heteroatoms selected from the group consisting of N, O and S" (the number of the $R^{3-6-2}$ can be one or more than one <e.g., 2, 3, 4 or 5>, and when a plurality of $R^{3-6-2}$ exist, any of two $R^{3-6-2}$ are the same or different; the "5-7 membered heterocycloalkenyl containing 1-4 heteroatoms selected from the group consisting of N, O and S" can be a "5-6 membered heterocycloalkenyl containing 1-2 heteroatoms selected from the group consisting of N, O and S", and can be 4,5-dihydrooxazolyl, and can also be 4,5-dihydrooxazol-2-yl <relative to the N atom>; the "5-7 membered heterocycloalkenyl containing 1-4 heteroatoms selected from the group consisting of N, O and S" can be connected to the N atom through the C atom; each $R^{3-6-2}$ can be independently located at the ortho, meta or para position relative to the "connection site of heterocycloalkenyl and the N atom", and can also be located at the meta position); each $R^{3-6-1}$ is independently $H_2C=CH-C(=O)-NH-$; each $R^{3-6-2}$ is independently $C_1-C_6$ alkyl (e.g., $C_1-C_4$ alkyl, further e.g., methyl, ethyl, n-propyl, isopropyl, n-butyl, isobutyl, sec-butyl or tert-butyl, further e.g., methyl);

each Z is independently $-C(=O)-$ or $-CH_2-$; each $R^{3-8}$ and $R^{3-9}$ is independently H, hydroxyl substituted or unsubstituted $C_1-C_6$ alkyl (the number of the hydroxyl can be one or more than one <e.g., 2, 3, 4, or 5>; the "$C_1-C_6$ alkyl" is, for example, $C_1-C_4$ alkyl, further e.g., methyl, ethyl, n-propyl, isopropyl, n-butyl, isobutyl, sec-butyl or tert-butyl, further e.g., methyl or ethyl; the "hydroxyl substituted $C_1-C_6$ alkyl" is, for example, 2-hydroxylethyl), $C_3-C_6$ cycloalkyl (e.g., cyclopropyl or cyclobutyl, further e.g., cyclopropyl), or, $R^{3-8-1}-C(=O)-$; each $R^{3-8-1}$ is independently oxa-$C_1-C_6$ alkyl (the number of the oxa can be one or more than one <e.g., 2, 3, 4 or 5>; the "$C_1-C_6$ alkyl" is for example, $C_1-C_4$ alkyl, further e.g., methyl, ethyl, n-propyl, isopropyl, n-butyl, isobutyl, sec-butyl or tert-butyl, further e.g., methyl or ethyl; the "oxa-$C_1-C_6$ alkyl" is, for example, methoxylmethyl);

each $R^{3-10}$ and $R^{3-11}$ is independently H, $R^{3-10-1}$ substituted or unsubstituted "3-7 membered heterocycloalkyl containing 1-4 heteroatoms selected from the group consisting of N, O and S" (the number of the $R^{3-10-1}$ can be one or more than one <e.g., 2, 3, 4, or 5>, when a plurality of $R^{3-10-1}$ exist, any of two $R^{3-10-1}$ are the same or different; the "3-7 membered heterocycloalkyl containing 1-4 heteroatoms selected from the group consisting of N, O and S" can be "5-6 membered heterocycloalkyl containing 1-2 heteroatoms selected from the group consisting of N, O and S", and can also be pyrrolidinyl or morpholinyl; the pyrrolidinyl can be pyrrolidin-2-yl <relative to the double bond>; the pyrrolidin-2-yl can be 2S-pyrrolidin-2-yl, 2R-pyrrolidin-2-yl or a mixture thereof <relative to the double bond>; the morpholinyl can be morpholinyl-3-yl <relative to the double bond>; the "3-7 membered heterocycloalkyl containing 1-4 heteroatoms selected from the group consisting of N, O and S" can be connected to the double bond through the C atom or N atom; each $R^{3-10-1}$ can be independently located at the ortho, meta or para position relative to the "connection site of heterocycloalkyl and the double bond", and can also be located at the ortho position), or, $NR^{3-10-2}R^{3-10-3}$ substituted or unsubstituted $C_1-C_6$ alkyl (the number of the $NR^{3-10-2}R^{3-10-3}-$ can be one or more than one <e.g., 2, 3, 4 or 5>, and when a plurality of $NR^{3-10-2}R^{3-10-3}-$ exist, any of two $NR^{3-10-2}R^{3-10-3}-$ are the same or different; the "$C_1-C_6$ alkyl" is, for example, $C_1-C_4$ alkyl, further e.g., methyl, ethyl, n-propyl, isopropyl, n-butyl, isobutyl, sec-butyl or tert-butyl, further e.g., methyl or ethyl; the "$NR^{3-10-2}R^{3-10-3}-$ substituted $C_1-C_6$ alkyl" is, for example, dimethylaminomethyl); each $R^{3-10-1}$, $R^{3-10-2}$ and $R^{3-10-3}$ is independently $C_1-C_6$ alkyl (e.g., $C_1-C_4$ alkyl, further e.g., methyl, ethyl, n-propyl, isopropyl, n-butyl, isobutyl, sec-butyl or tert-butyl, further e.g., methyl);

each $R^{3-12}$ is independently H or halogen (e.g., fluorine, chlorine, bromine or iodine, further e.g., fluorine);

each $R^{3-13}$ is independently "3-7 membered heterocycloalkyl containing 1-4 heteroatoms selected from the group consisting of N, O and S" (e.g., "5-6 membered heterocycloalkyl containing 1-2 heteroatoms selected from the group consisting of N, O and S", and can also be furanyl, further e.g., furan-3-yl <relative to the O atom>, further e.g.,

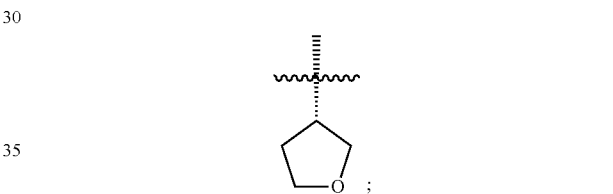

the "3-7 membered heterocycloalkyl containing 1-4 heteroatoms selected from the group consisting of N, O and S" can be connected to the O atom through the C atom);

the compound I excludes any one of the compounds as follows:

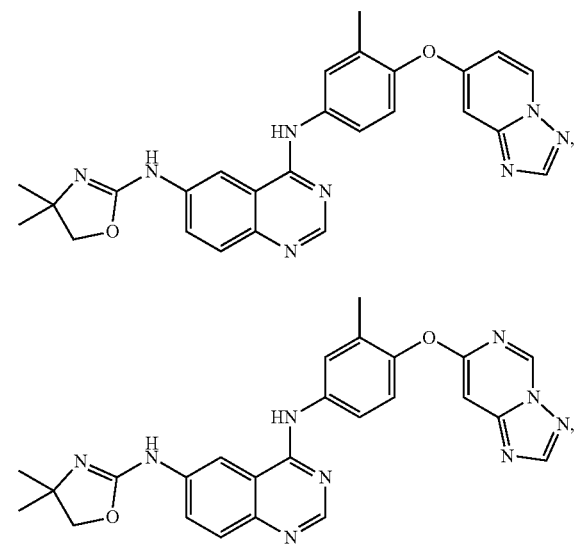

-continued
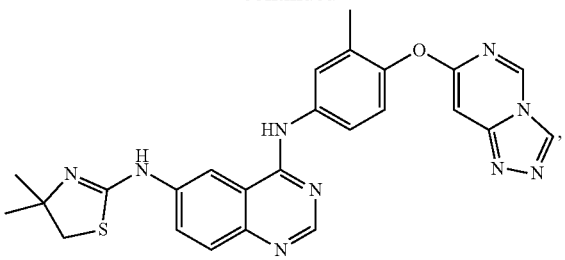
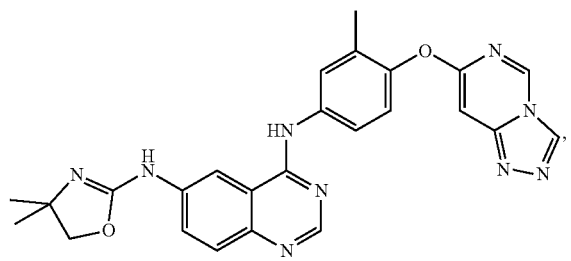
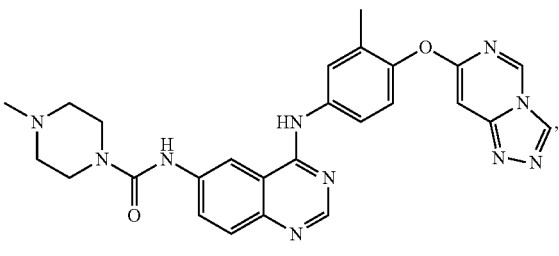
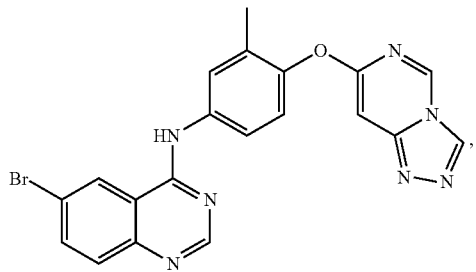
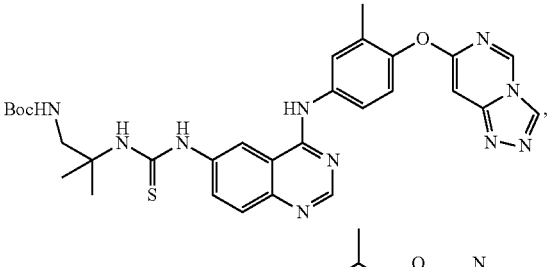
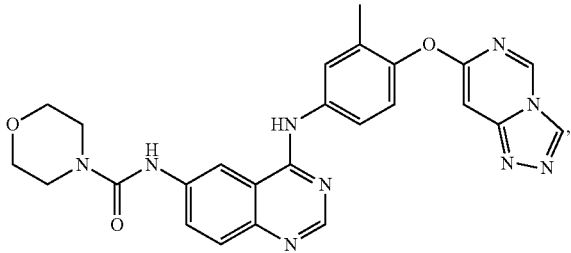
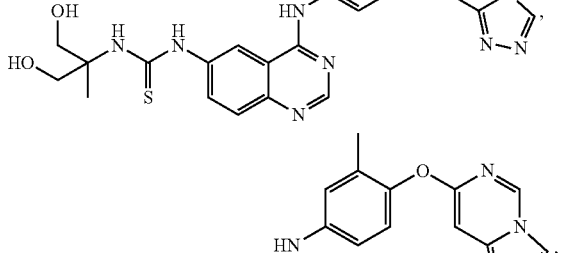
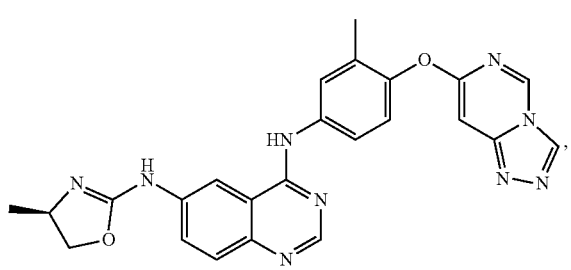
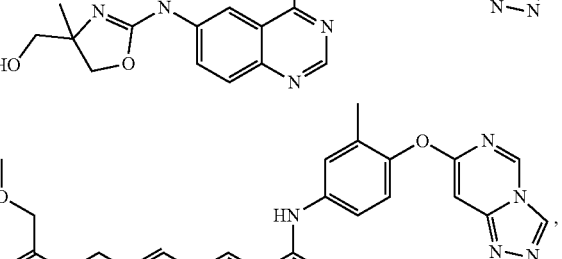
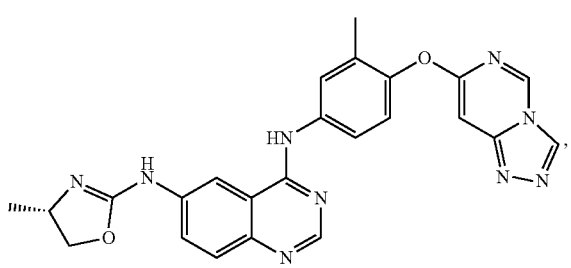
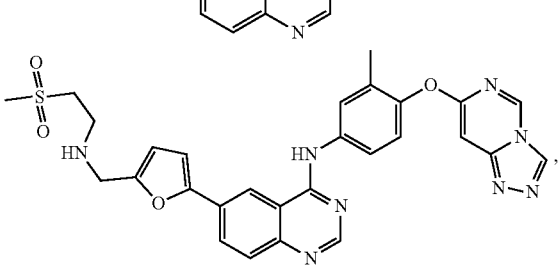

-continued
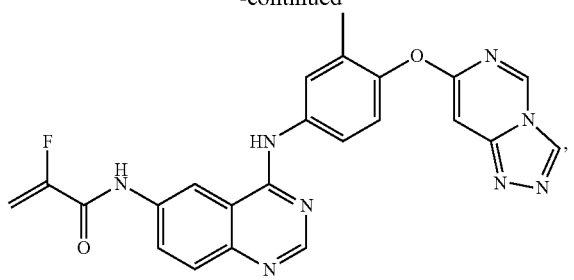
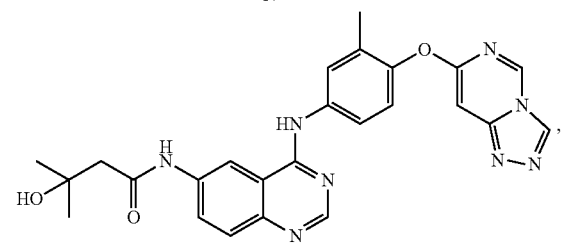
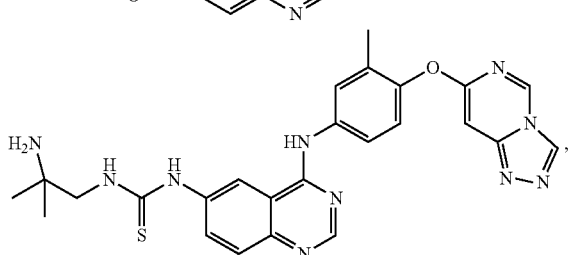
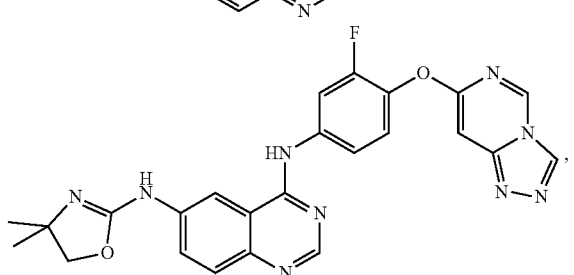
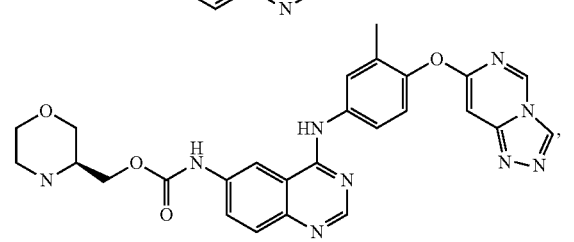
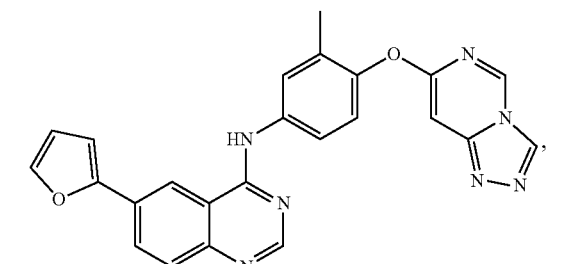
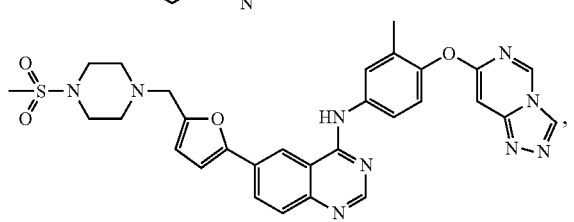
-continued
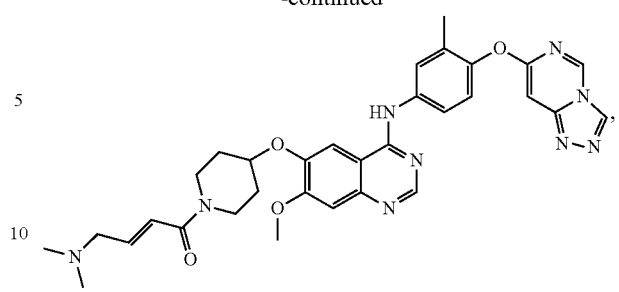
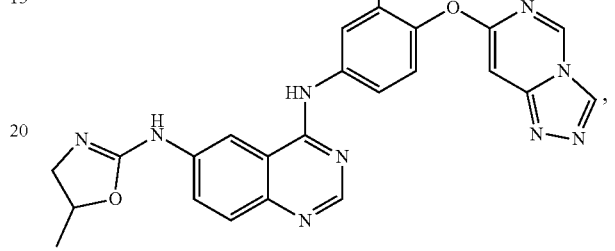
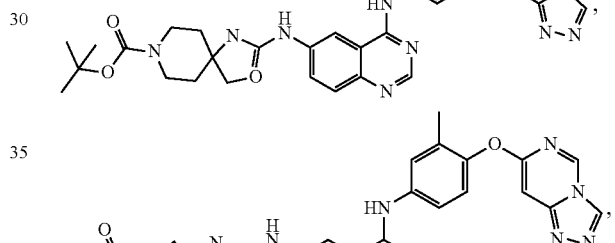
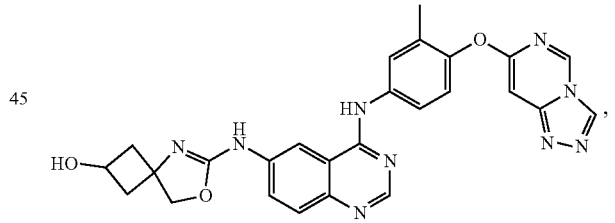
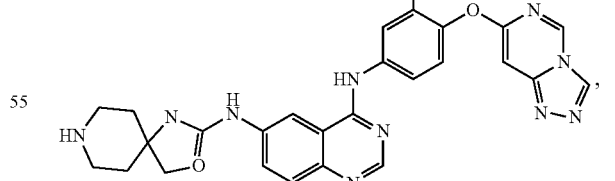
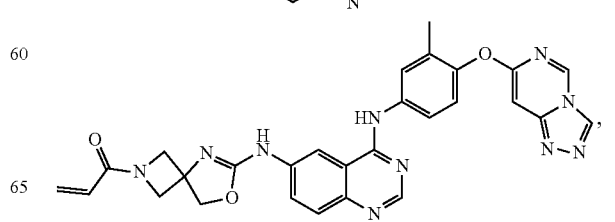

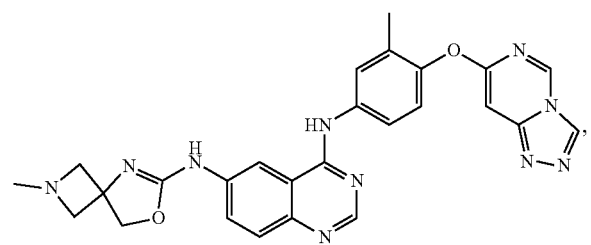
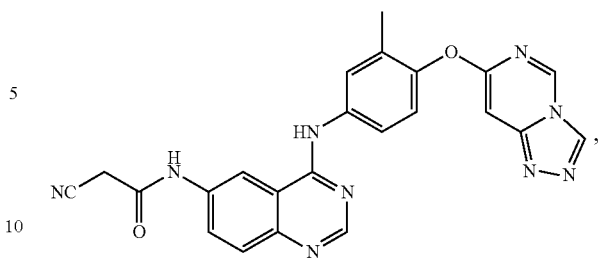
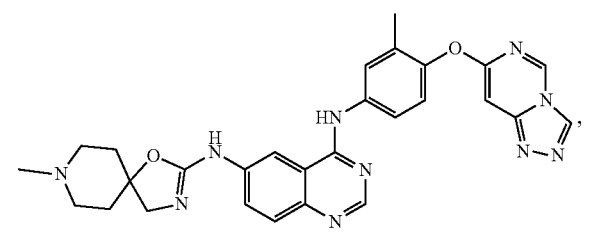
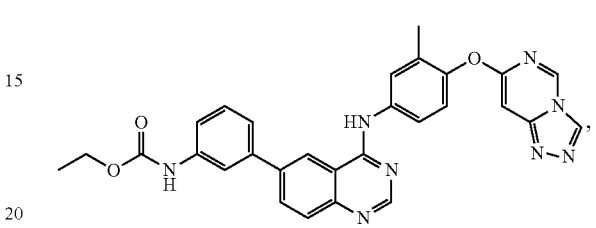
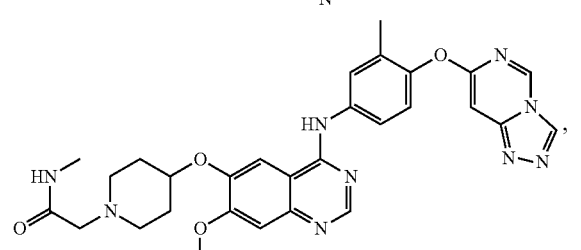
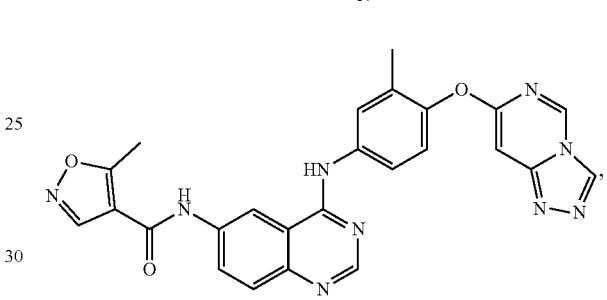
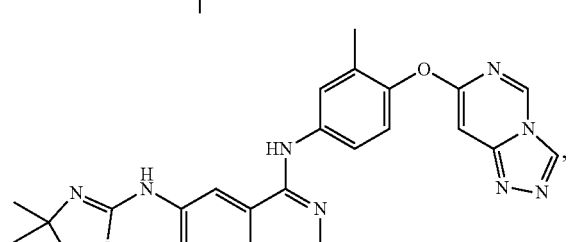
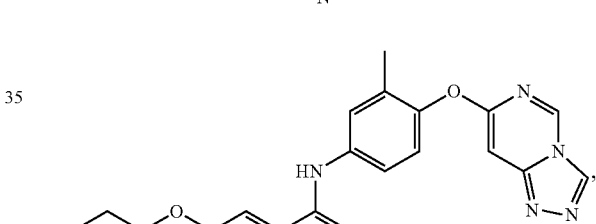
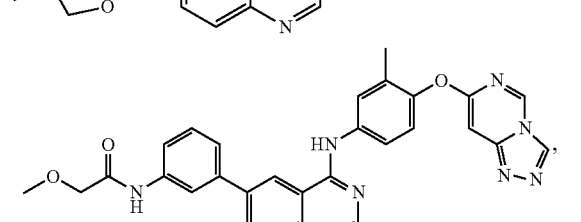
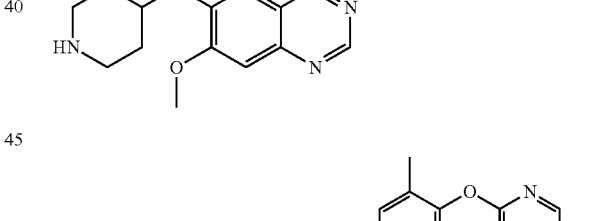
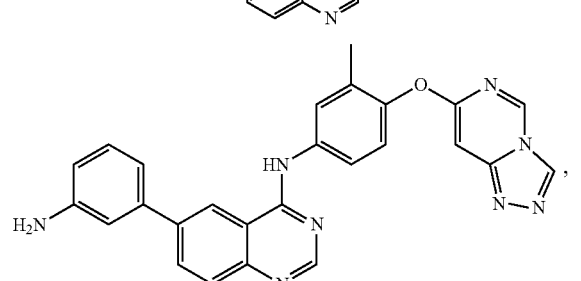
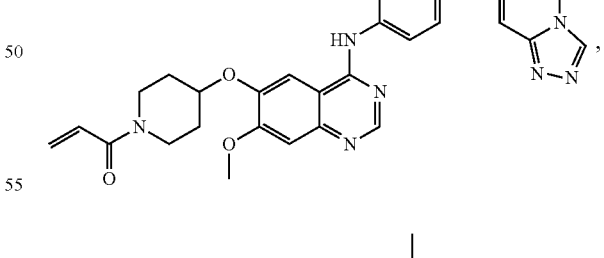
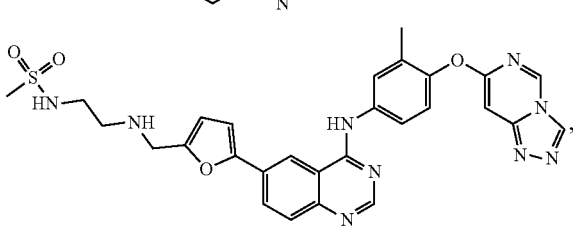
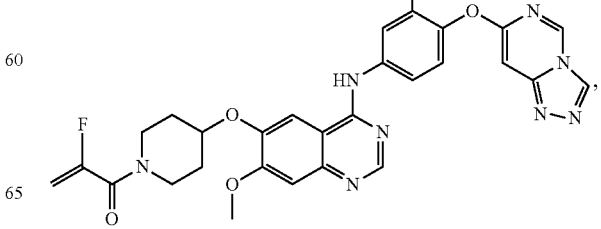

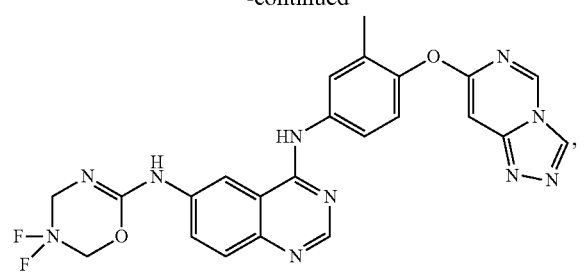
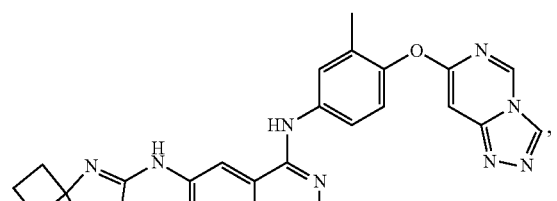
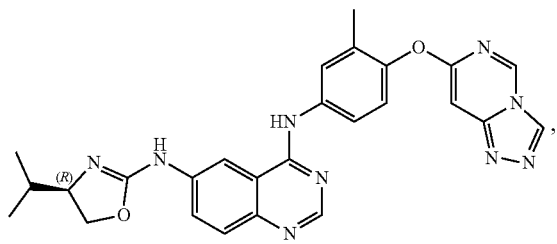
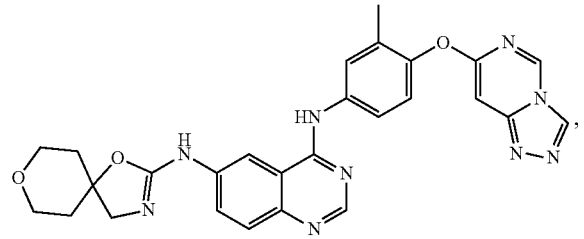
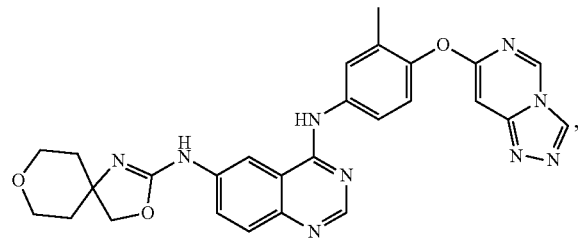
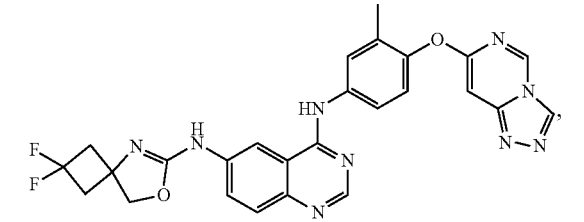
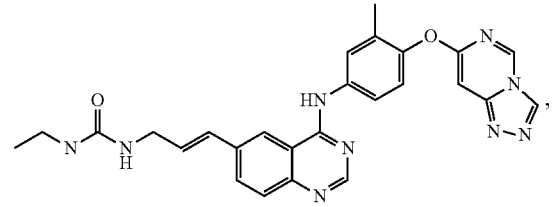
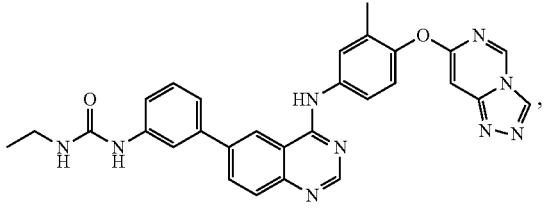
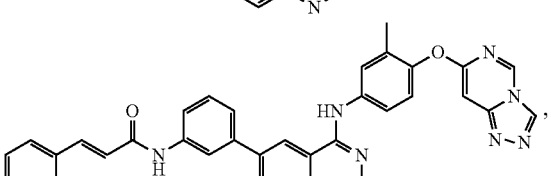
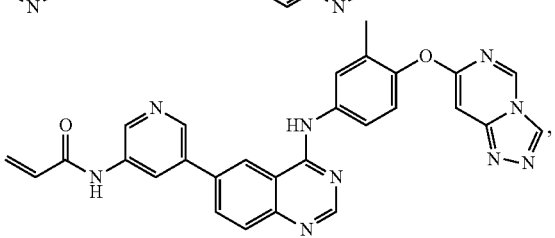
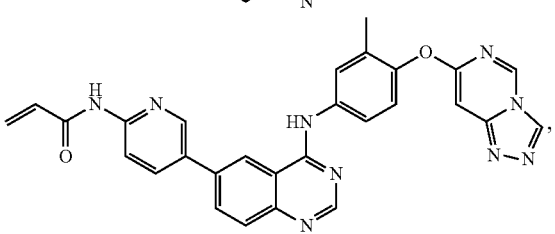
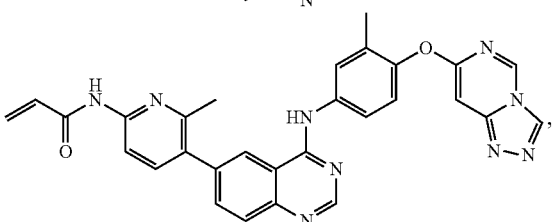
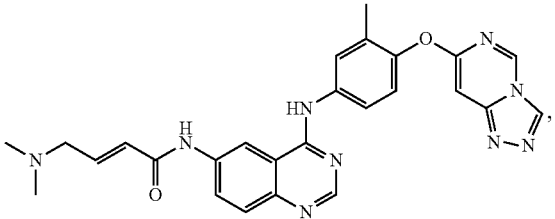

17
-continued
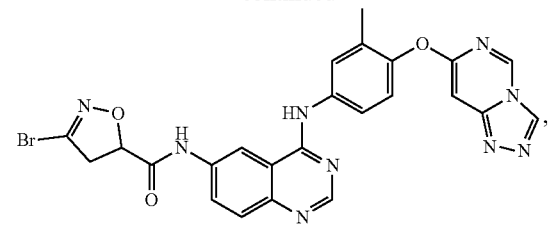
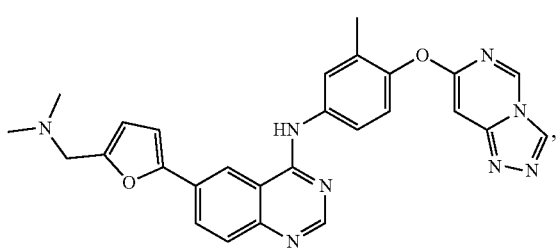
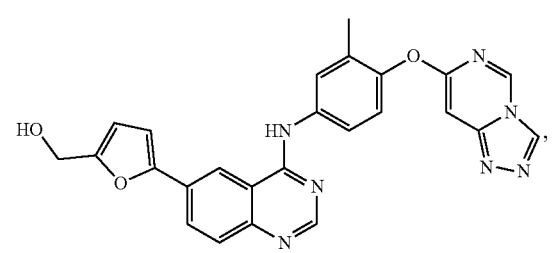
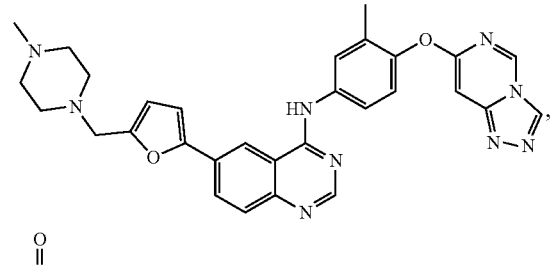
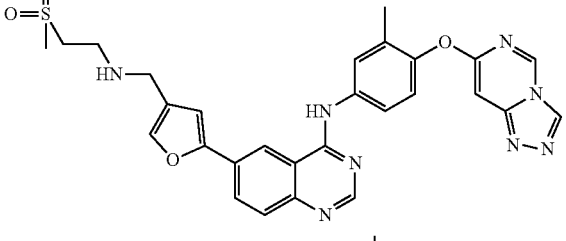
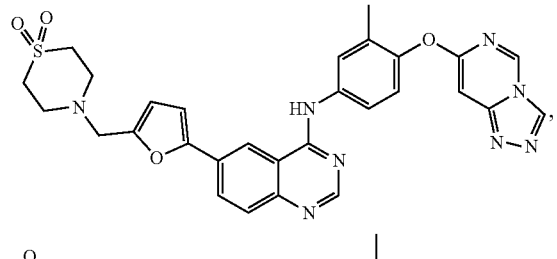
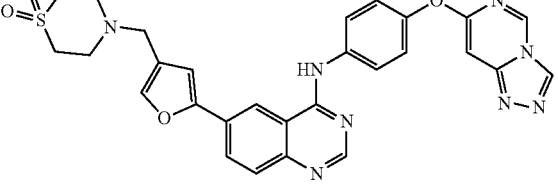
18
-continued
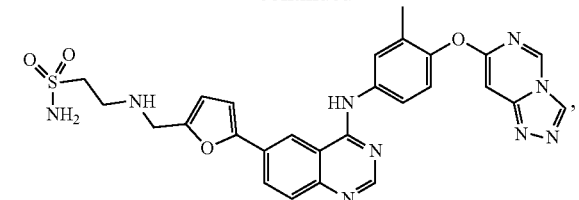
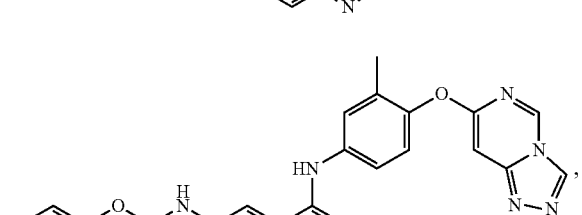
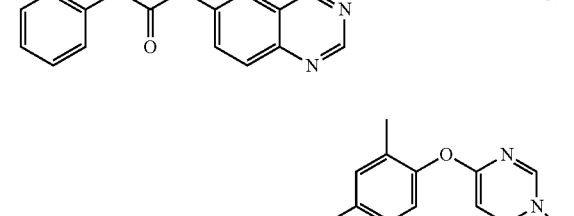
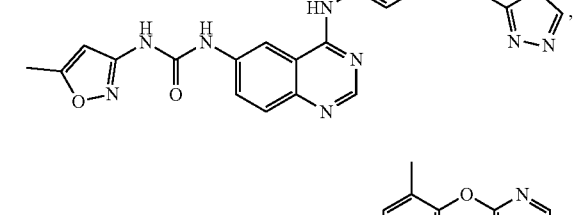
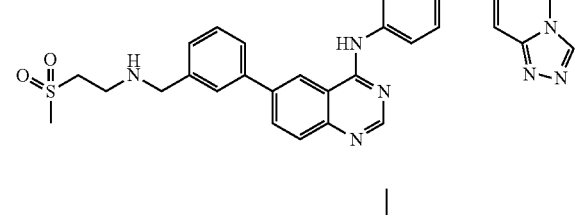
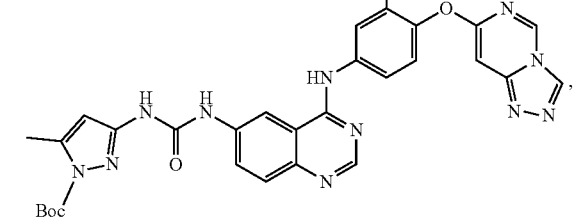
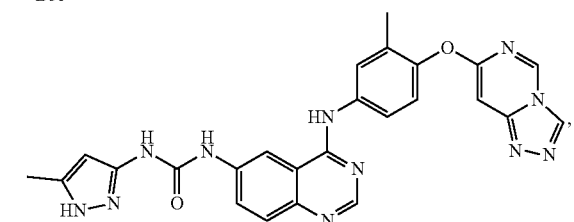
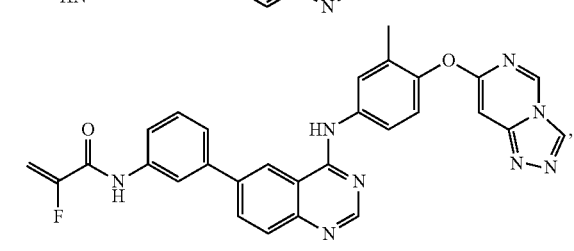

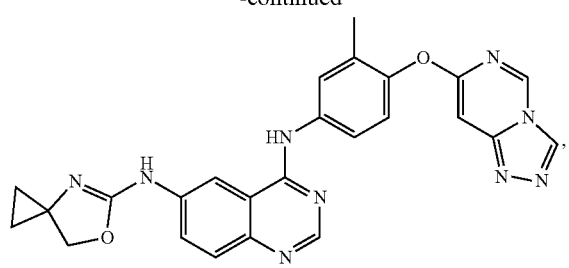
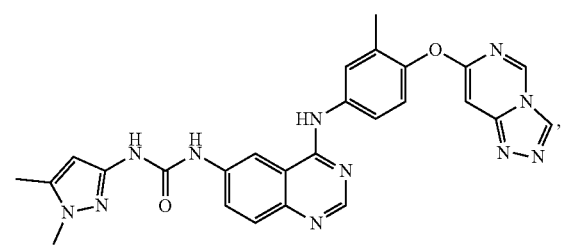
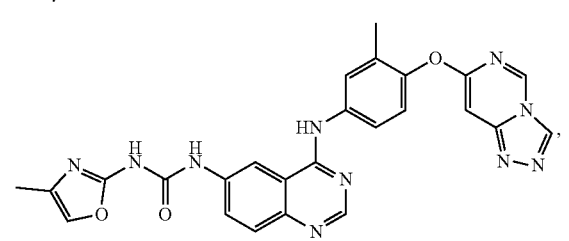
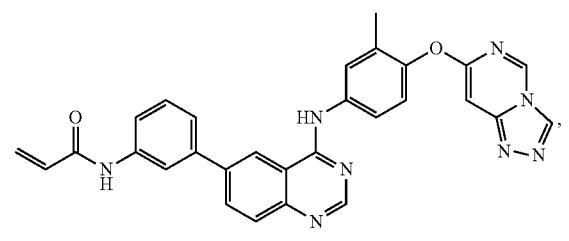
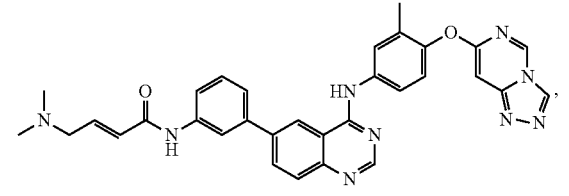
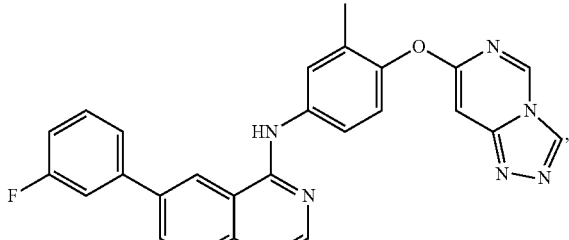
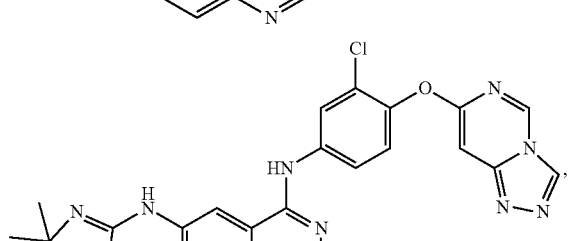
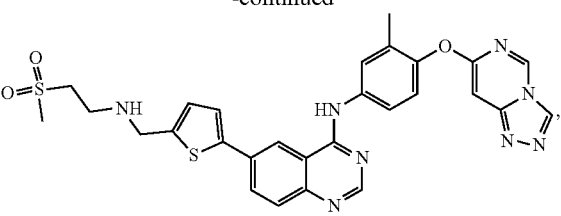
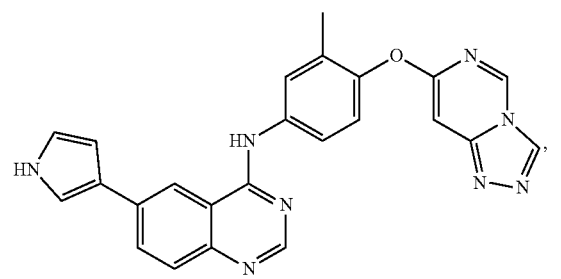
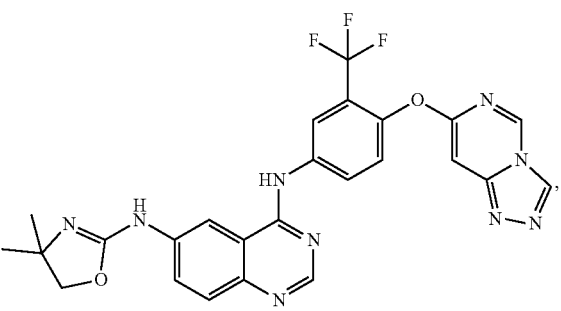
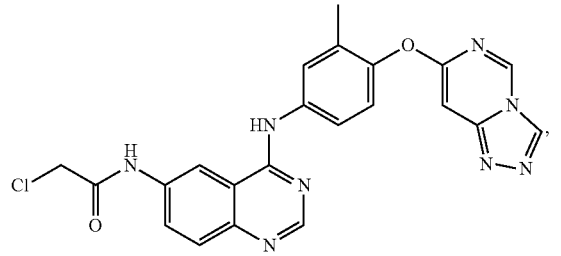
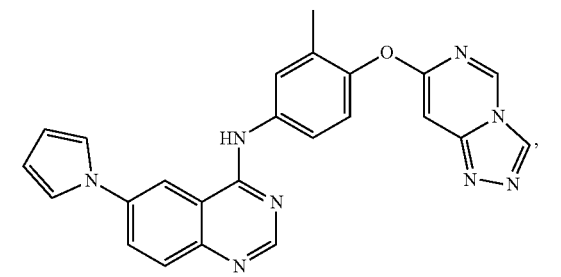
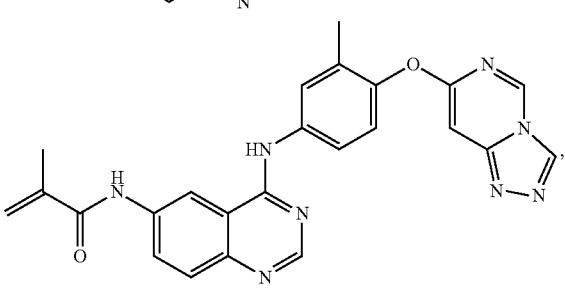

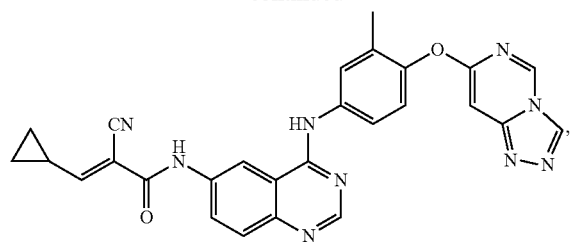
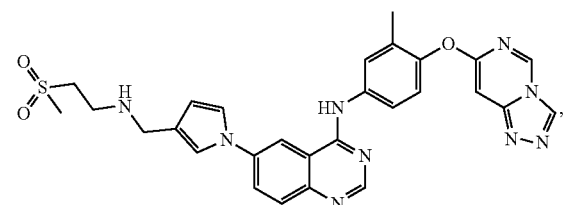
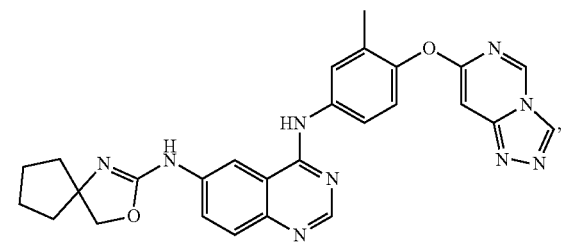
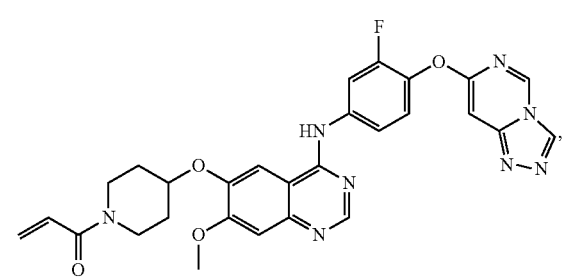
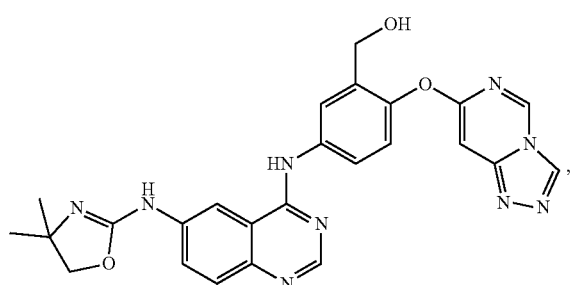
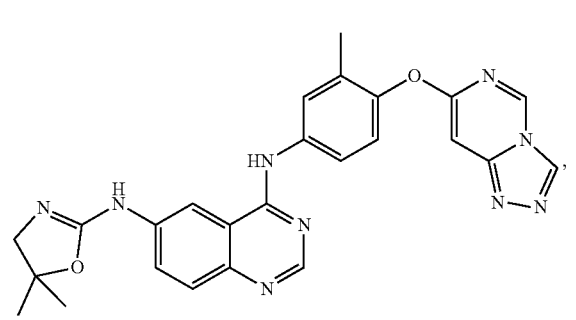
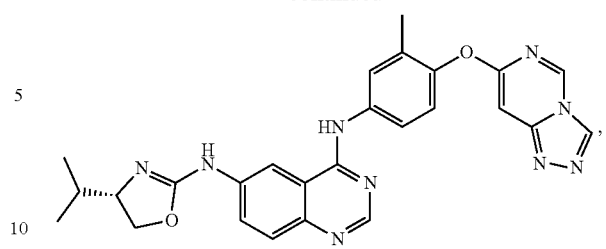
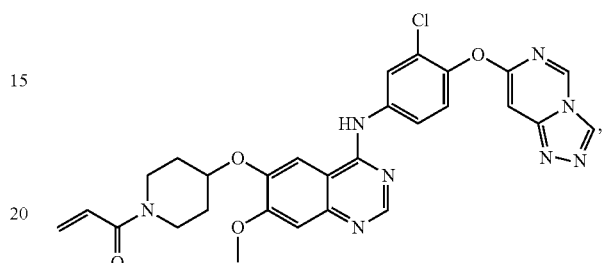
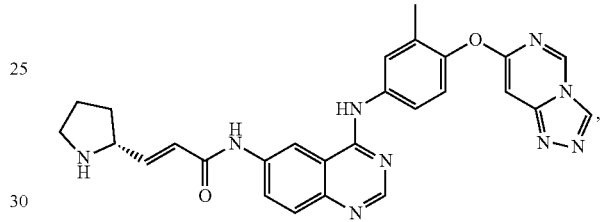
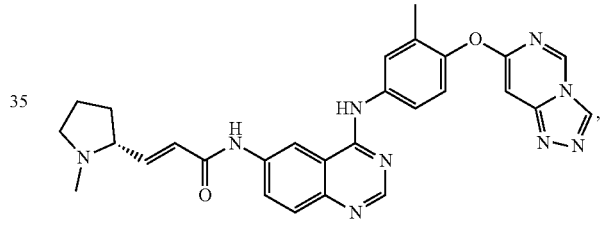
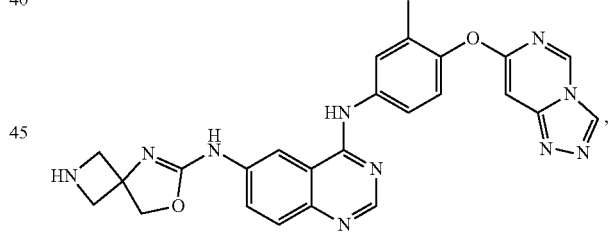
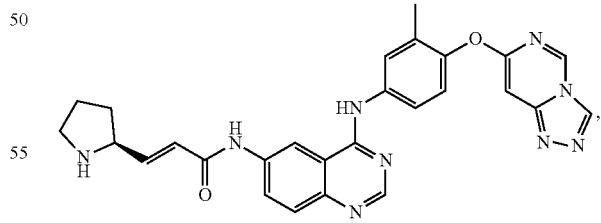
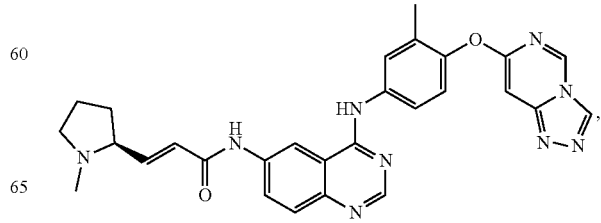

23
-continued
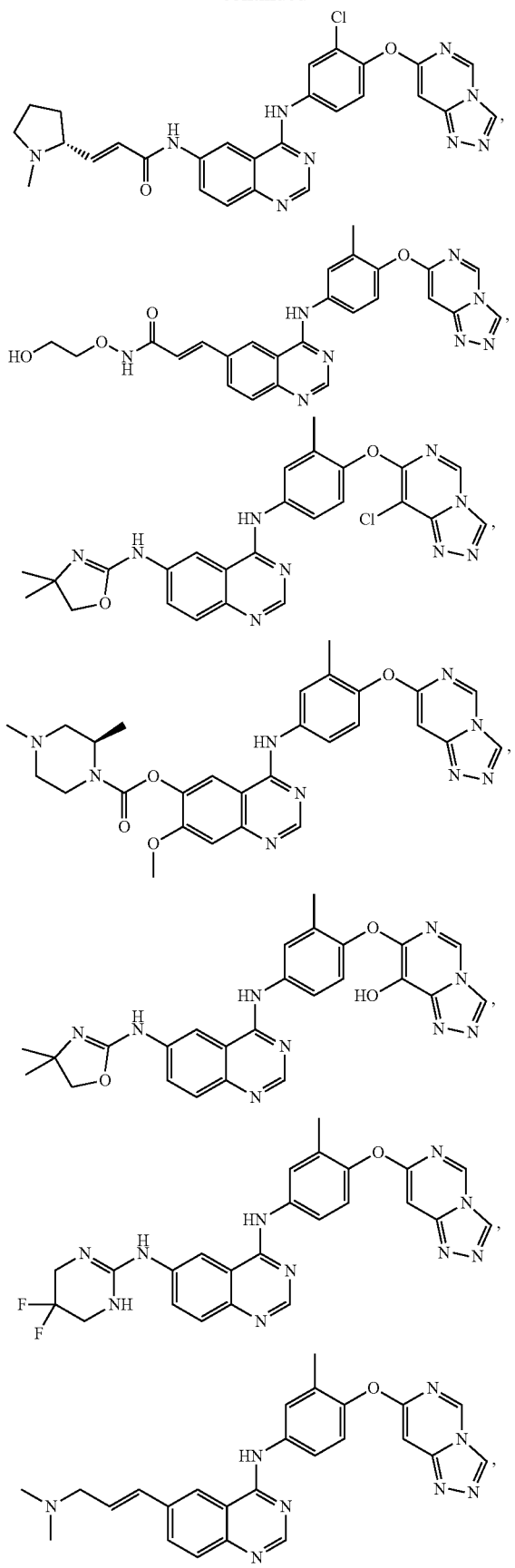
24
-continued
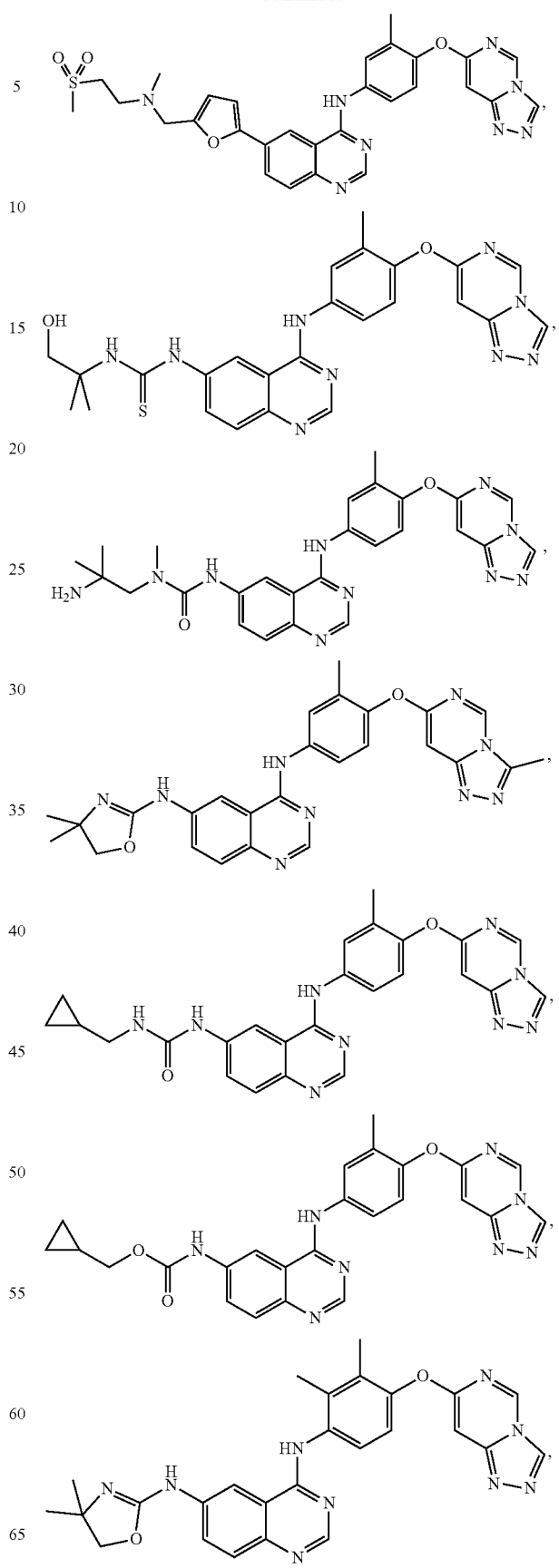

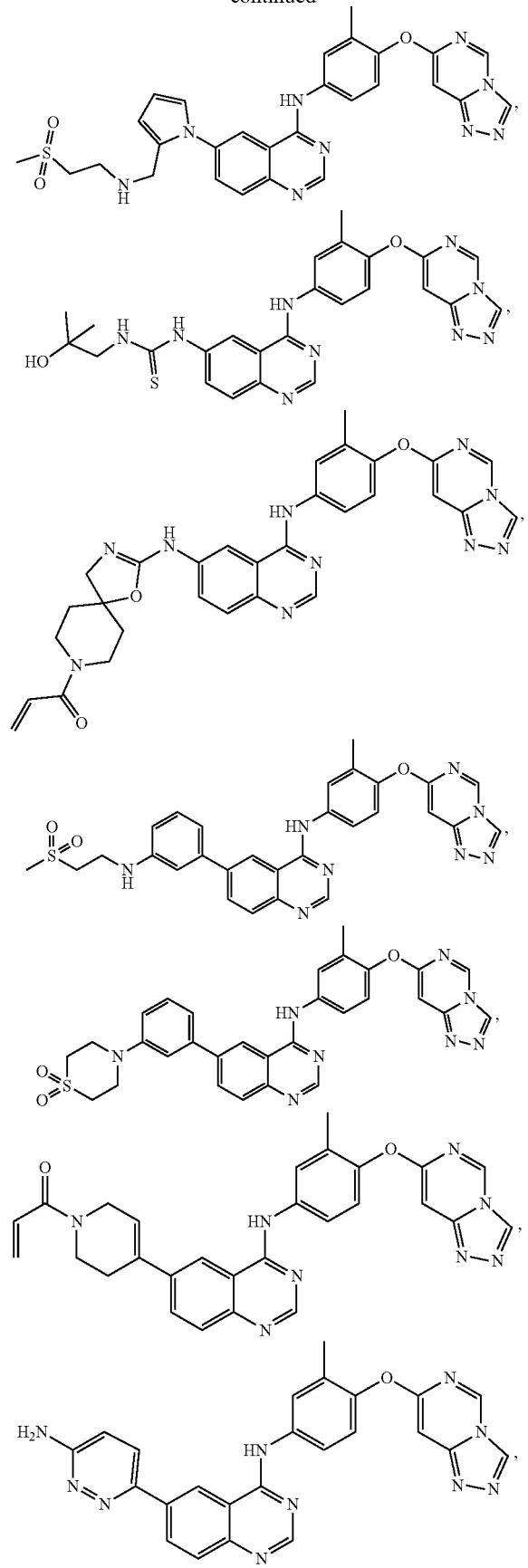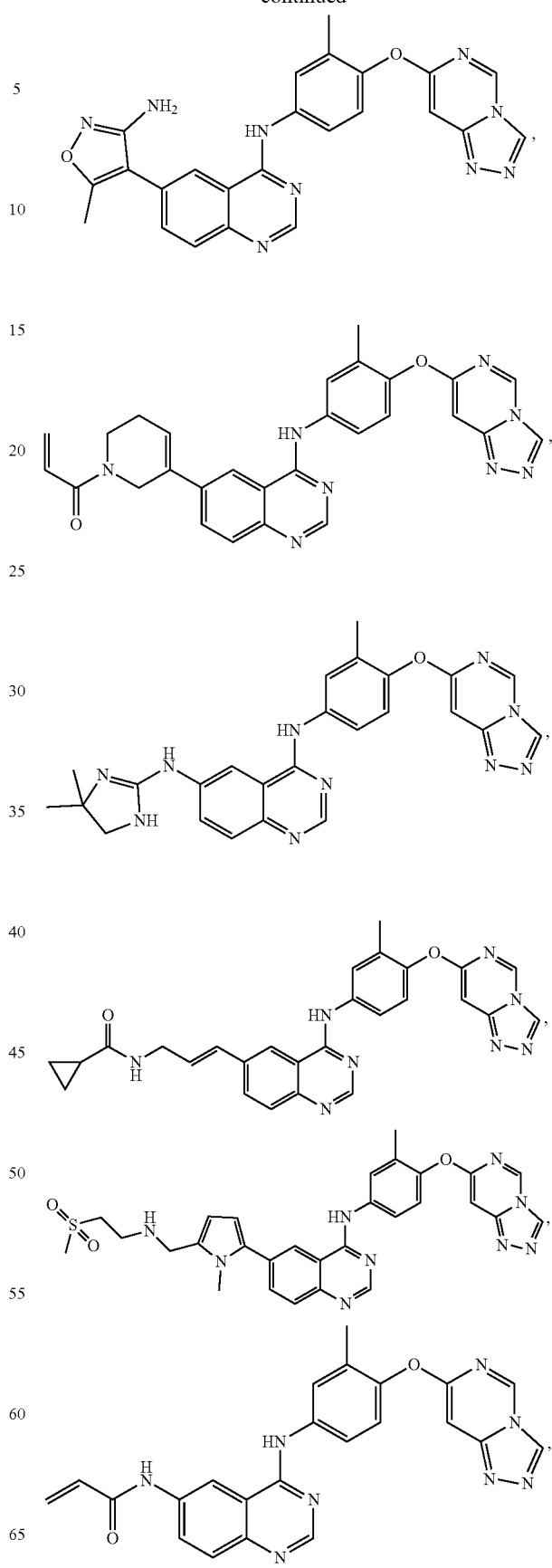

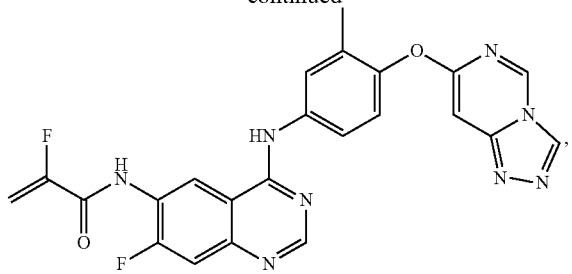

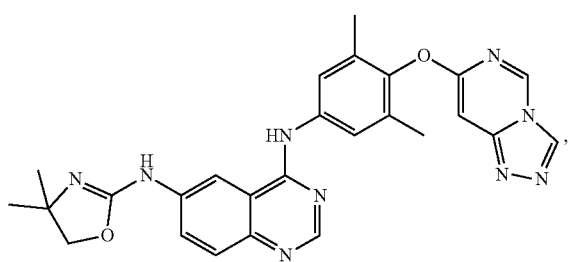

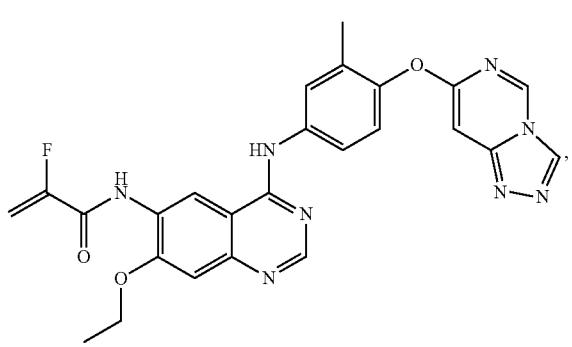

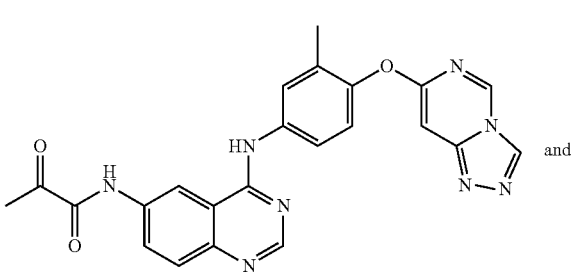 and

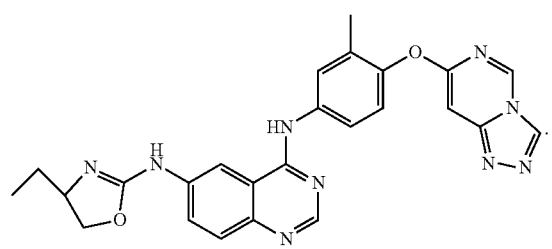

In an embodiment, the definitions of some substituents in the compound I can be as follows, and the definitions of the non-mentioned substituents are all as defined in any one of the embodiments above:

E is not

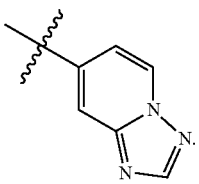 [SMILES: *c1ccn2ncnc2c1]

In an embodiment, the definitions of some substituents in the compound I can be as follows, and the definitions of the non-mentioned substituents are all as defined in any one of the embodiments above:

E is

[structures shown]

In an embodiment, the definitions of some substituents in the compound I can be as follows, and the definitions of the non-mentioned substituents are all as defined in any one of the embodiments above:

E is

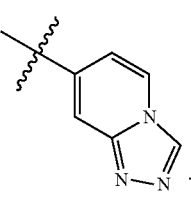 [SMILES: *c1ccn2cnnc2c1]

In an embodiment, the definitions of some substituents in the compound I can be as follows, and the definitions of the non-mentioned substituents are all as defined in any one of the embodiments above:

E is

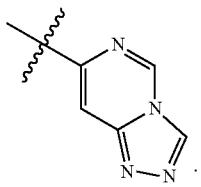 [SMILES: *c1cc2nncn2cn1]

In an embodiment, the definitions of some substituents in the compound I can be as follows, and the definitions of the non-mentioned substituents are all as defined in any one of the embodiments above:

E is

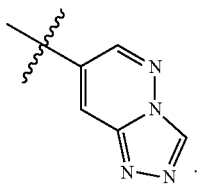 [SMILES: *c1cnn2cnnc2c1]

In an embodiment, the definitions of some substituents in the compound I can be as follows, and the definitions of the non-mentioned substituents are all as defined in any one of the embodiments above:

E is

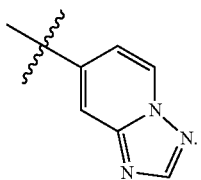 [SMILES: *c1ccn2ncnc2c1]

In an embodiment, the definitions of some substituents in the compound I can be as follows, and the definitions of the non-mentioned substituents are all as defined in any one of the embodiments above:

E is

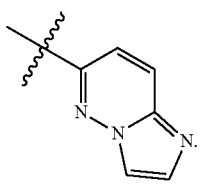 [SMILES: *c1ccc2nccn2n1]

In an embodiment, the definitions of some substituents in the compound I can be as follows, and the definitions of the non-mentioned substituents are all as defined in any one of the embodiments above:

E is

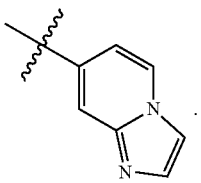 [SMILES: *c1ccn2ccnc2c1]

In an embodiment, the definitions of some substituents in the compound I can be as follows, and the definitions of the non-mentioned substituents are all as defined in any one of the embodiments above:

E is

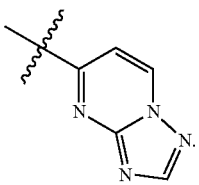

In an embodiment, the definitions of some substituents in the compound I can be as follows, and the definitions of the non-mentioned substituents are all as defined in any one of the embodiments above:

E is

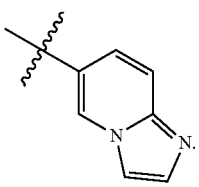 [SMILES: *c1ccc2nccn2c1]

In an embodiment, the definitions of some substituents in the compound I can be as follows, and the definitions of the non-mentioned substituents are all as defined in any one of the embodiments above:

E is

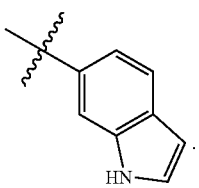 [SMILES: *c1ccc2cc[nH]c2c1]

In an embodiment, the definitions of some substituents in the compound I can be as follows, and the definitions of the non-mentioned substituents are all as defined in any one of the embodiments above:

E is

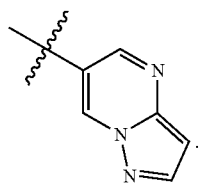 [SMILES: *c1cnc2ccnn2c1]

In an embodiment, the definitions of some substituents in the compound I can be as follows, and the definitions of the non-mentioned substituents are all as defined in any one of the embodiments above:

E is

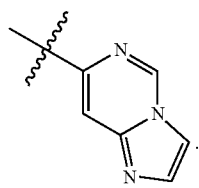 [SMILES: *c1cc2nccn2cn1]

In an embodiment, the definitions of some substituents in the compound I can be as follows, and the definitions of the non-mentioned substituents are all as defined in any one of the embodiments above:

E is

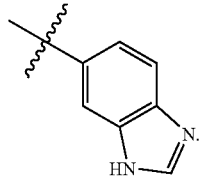 [SMILES: *c1ccc2nc[nH]c2c1]

In an embodiment, the definitions of some substituents in the compound I can be as follows, and the definitions of the non-mentioned substituents are all as defined in any one of the embodiments above:

when the E is

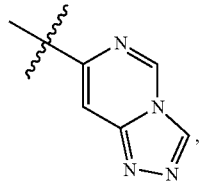

then each $R^3$ can be independently any one of the substituents as defined therein.

In an embodiment, the definitions of some substituents in the compound I can be as follows, and the definitions of the non-mentioned substituents are all as defined in any one of the embodiments above:

when the E is not

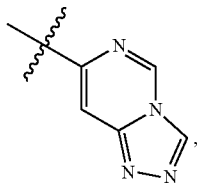 [SMILES: *c1cc2nncn2cn1]

then each $R^3$ can be independently $(R^{3-10})(R^{3-11})C=C(R^{3-12})-C(=O)-NH-$ or $C_1$-$C_6$ alkoxyl.

In an embodiment, the definitions of some substituents in the compound I can be as follows, and the definitions of the non-mentioned substituents are all as defined in any one of the embodiments above:

A is —O— or —S—.

In an embodiment, the definitions of some substituents in the compound I can be as follows, and the definitions of the non-mentioned substituents are all as defined in any one of the embodiments above:

A is —O—.

In an embodiment, the definitions of some substituents in the compound I can be as follows, and the definitions of the non-mentioned substituents are all as defined in any one of the embodiments above:

n is 1.

In an embodiment, the definitions of some substituents in the compound I can be as follows, and the definitions of the non-mentioned substituents are all as defined in any one of the embodiments above:

when n is 1, then the compound I can be

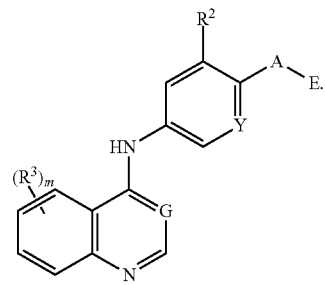

I-1

In an embodiment, the definitions of some substituents in the compound I can be as follows, and the definitions of the non-mentioned substituents are all as defined in any one of the embodiments above:

Y is CH.

In an embodiment, the definitions of some substituents in the compound I can be as follows, and the definitions of the non-mentioned substituents are all as defined in any one of the embodiments above:

G is N.

In an embodiment, the definitions of some substituents in the compound I can be as follows, and the definitions of the non-mentioned substituents are all as defined in any one of the embodiments above:

G is C—CN.

In an embodiment, the definitions of some substituents in the compound I can be as follows, and the definitions of the non-mentioned substituents are all as defined in any one of the embodiments above:

m is 1 or 2.

In an embodiment, the definitions of some substituents in the compound I can be as follows, and the definitions of the non-mentioned substituents are all as defined in any one of the embodiments above:

when m is 1, then the compound I can be

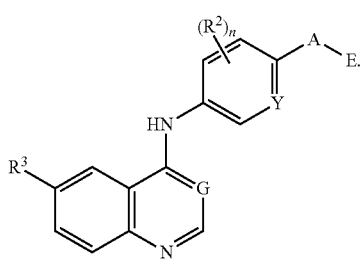

I-2

In an embodiment, the definitions of some substituents in the compound I can be as follows, and the definitions of the non-mentioned substituents are all as defined in any one of the embodiments above:

when m is 2, then the compound I can be

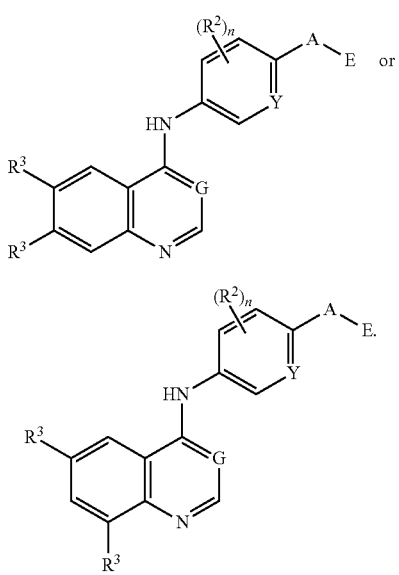

I-3 or I-4

In an embodiment, the definitions of some substituents in the compound I can be as follows, and the definitions of the non-mentioned substituents are all as defined in any one of the embodiments above:

m is 1, $R^3$ is $R^{3-1}$ substituted or unsubstituted "3-7 membered heterocycloalkyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

m is 1, $R^3$ is $R^{3-2}$ substituted or unsubstituted 5-7 membered cycloalkenyl.

In an embodiment, the definitions of some substituents in the compound I can be as follows, and the definitions of the non-mentioned substituents are all as defined in any one of the embodiments above:

m is 1, $R^3$ is $R^{3-3}$ substituted or unsubstituted "5-7 membered heterocycloalkenyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

m is 1, $R^3$ is $R^{3-3}$ substituted or unsubstituted "5-7 membered heterocycloalkenyl containing 1-4 heteroatoms selected from the group consisting of N, O and S", $R^{3-3}$ is $H_2C=CR^{3-3-1}-C(=O)-$.

In an embodiment, the definitions of some substituents in the compound I can be as follows, and the definitions of the non-mentioned substituents are all as defined in any one of the embodiments above:

m is 2, $R^3$ is $R^{3-3}$ substituted or unsubstituted "5-7 membered heterocycloalkenyl containing 1-4 heteroatoms selected from the group consisting of N, O and S" and halogen, respectively (i.e., one $R^3$ is a $R^{3-3}$ substituted or unsubstituted "5-7 membered heterocycloalkenyl containing 1-4 heteroatoms selected from the group consisting of N, O and S", and the other $R^3$ is halogen, hereinafter the disclosure has the same definition).

In an embodiment, the definitions of some substituents in the compound I can be as follows, and the definitions of the non-mentioned substituents are all as defined in any one of the embodiments above:

m is 1, each $R^3$ is independently $R^{3-5}$ substituted or unsubstituted "5-6 membered heteroaryl containing 1-3 heteroatoms selected from the group consisting of N, O and S".

In an embodiment, the definitions of some substituents in the compound I can be as follows, and the definitions of the non-mentioned substituents are all as defined in any one of the embodiments above:

m is 2, $R^3$ is $R^{3-5}$ substituted or unsubstituted "5-6 membered heteroaryl containing 1-3 heteroatoms selected from the group consisting of N, O and S" and halogen, respectively.

In an embodiment, the definitions of some substituents in the compound I can be as follows, and the definitions of the non-mentioned substituents are all as defined in any one of the embodiments above:

m is 1, $R^3$ is $N(R^{3-6})(R^{3-7})-$.

In an embodiment, the definitions of some substituents in the compound I can be as follows, and the definitions of the non-mentioned substituents are all as defined in any one of the embodiments above:

m is 1, $R^3$ is $(R^{3-8})(R^{3-9})N-(Z)-HC=CH-$.

In an embodiment, the definitions of some substituents in the compound I can be as follows, and the definitions of the non-mentioned substituents are all as defined in any one of the embodiments above:

m is 2, $R^3$ is $(R^{3-8})(R^{3-9})N-(Z)-HC=CH-$ and halogen, respectively.

In an embodiment, the definitions of some substituents in the compound I can be as follows, and the definitions of the non-mentioned substituents are all as defined in any one of the embodiments above:

m is 1, $R^3$ is $(R^{3-10})(R^{3-11})C=C(R^{3-12})-C(=O)-NH-$.

In an embodiment, the definitions of some substituents in the compound I can be as follows, and the definitions of the non-mentioned substituents are all as defined in any one of the embodiments above:

m is 2, $R^3$ is $(R^{3-10})(R^{3-11})C=C(R^{3-12})-C(=O)-NH-$ and $R^{3-0}$ substituted or unsubstituted $C_1$-$C_6$ alkoxyl, respectively.

In an embodiment, the definitions of some substituents in the compound I can be as follows, and the definitions of the non-mentioned substituents are all as defined in any one of the embodiments above:

m is 2, $R^3$ is $(R^{3-10})(R^{3-11})C=C(R^{3-12})-C(=O)-NH-$ and $R^{3-0}$ substituted $C_1$-$C_6$ alkoxyl, respectively.

In an embodiment, the definitions of some substituents in the compound I can be as follows, and the definitions of the non-mentioned substituents are all as defined in any one of the embodiments above:

compound I is

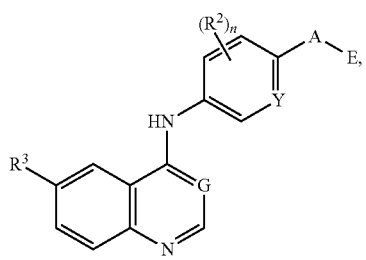

I-2

$R^3$ is $R^{3-1}$ substituted or unsubstituted "3-7 membered heterocycloalkyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

compound I is

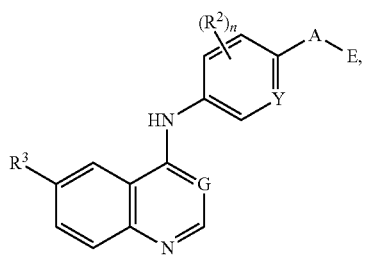

I-2 the $R^3$ is $R^{3-2}$ substituted or unsubstituted 5-7 membered cycloalkenyl.

In an embodiment, the definitions of some substituents in the compound I can be as follows, and the definitions of the non-mentioned substituents are all as defined in any one of the embodiments above:

compound I is

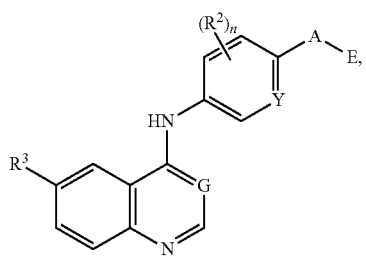

I-2

$R^3$ is $R^{3-3}$ substituted or unsubstituted "5-7 membered heterocycloalkenyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

compound I is

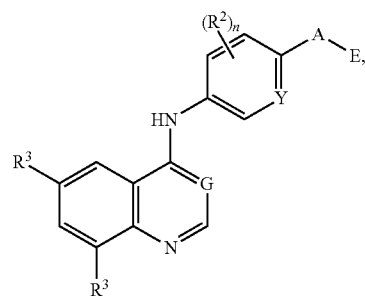

I-4

$R^3$ is $R^{3-3}$ substituted or unsubstituted "5-7 membered heterocycloalkenyl containing 1-4 heteroatoms selected from the group consisting of N, O and S" and halogen, respectively.

In an embodiment, the definitions of some substituents in the compound I can be as follows, and the definitions of the non-mentioned substituents are all as defined in any one of the embodiments above:

compound I is

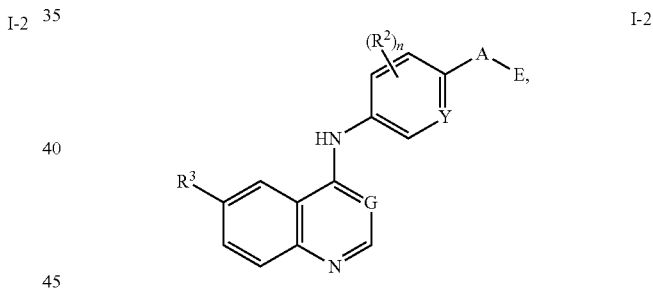

I-2

$R^3$ is $R^{3-5}$ substituted or unsubstituted "5-6 membered heteroaryl containing 1-3 heteroatoms selected from the group consisting of N, O and S".

In an embodiment, the definitions of some substituents in the compound I can be as follows, and the definitions of the non-mentioned substituents are all as defined in any one of the embodiments above:

compound I is

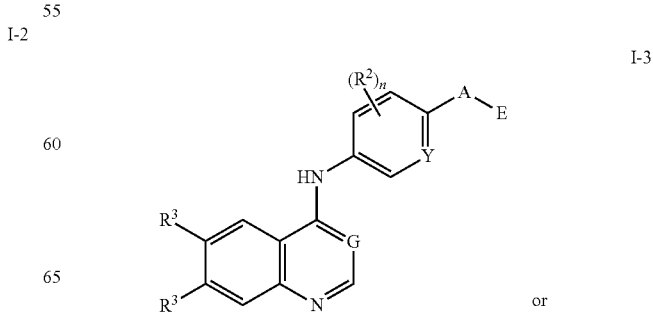

I-3 or

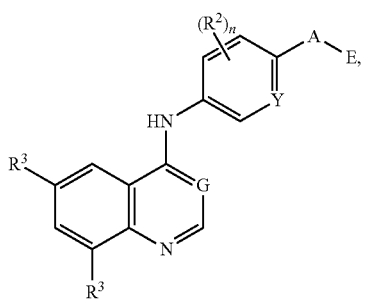

I-4

$R^3$, $R^3$ is $R^{3-5}$ substituted or unsubstituted "5-6 membered heteroaryl containing 1-3 heteroatoms selected from the group consisting of N, O and S" and halogen, respectively.

In an embodiment, the definitions of some substituents in the compound I can be as follows, and the definitions of the non-mentioned substituents are all as defined in any one of the embodiments above:

compound I is

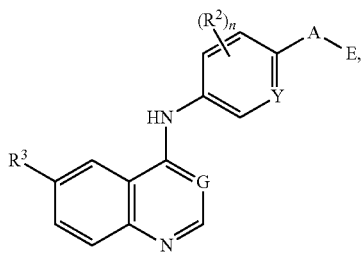

I-2

$R^3$ is $N(R^{3-6})(R^{3-7})$—.

In an embodiment, the definitions of some substituents in the compound I can be as follows, and the definitions of the non-mentioned substituents are all as defined in any one of the embodiments above:

compound I is

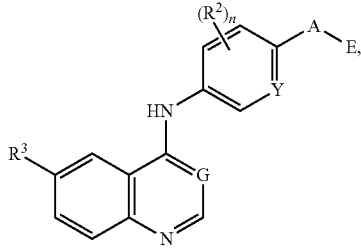

I-2

$R^3$ is $(R^{3-8})(R^{3-9})N$—(Z)—HC=CH—.

In an embodiment, the definitions of some substituents in the compound I can be as follows, and the definitions of the non-mentioned substituents are all as defined in any one of the embodiments above:

compound I is

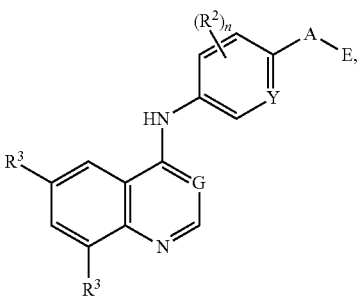

I-4

$R^3$ is $(R^{3-8})(R^{3-9})N$—(Z)—HC=CH— and halogen, respectively.

In an embodiment, the definitions of some substituents in the compound I can be as follows, and the definitions of the non-mentioned substituents are all as defined in any one of the embodiments above:

compound I is

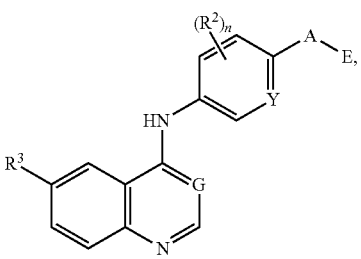

I-2

$R^3$ is $(R^{3-10})(R^{3-11})C=C(R^{3-12})$—C(=O)—NH—.

In an embodiment, the definitions of some substituents in the compound I can be as follows, and the definitions of the non-mentioned substituents are all as defined in any one of the embodiments above:

compound I is

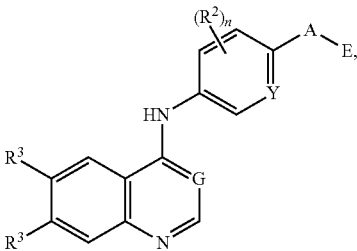

I-3

$R^3$ is $(R^{3-10})(R^{3-11})C=C(R^{3-12})$—C(=O)—NH— and $R^{3-0}$ substituted or unsubstituted $C_1$-$C_6$ alkoxyl, respectively.

In an embodiment, the definitions of some substituents in the compound I can be as follows, and the definitions of the non-mentioned substituents are all as defined in any one of the embodiments above:

compound I is

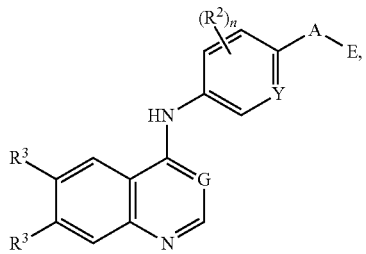

$R^3$ is $(R^{3-10})(R^{3-11})C=C(R^{3-12})$—$C(=O)$—NH— and $R^{3-0}$ substituted $C_1$-$C_6$ alkoxyl, respectively.

In an embodiment, the definitions of some substituents in the compound I can be as follows, and the definitions of the non-mentioned substituents are all as defined in any one of the embodiments above:

in $R^3$, $R^{3-3}$ substituted or unsubstituted "5-7 membered heterocycloalkenyl containing 1-4 heteroatoms selected from the group consisting of N, O and S", "5-6 membered heteroaryl containing 1-3 heteroatoms selected from the group consisting of N, O and S", $(R^{3-8})(R^{3-9})N$—(Z)—HC=CH—, or, $(R^{3-10})(R^{3-11})C=C(R^{3-12})$—$C(=O)$—NH—, is located at the para position relative to the N atom (not G) in

of the compound I.

In an embodiment, the definitions of some substituents in the compound I can be as follows, and the definitions of the non-mentioned substituents are all as defined in any one of the embodiments above:

when none of $R^3$ is $(R^{3-10})(R^{3-11})C=C(R^{3-12})$—$C(=O)$—NH—, then the E can be

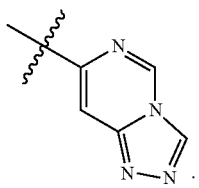 [SMILES: *c1cc2nncn2cn1]

In an embodiment, the definitions of some substituents in the compound I can be as follows, and the definitions of the non-mentioned substituents are all as defined in any one of the embodiments above:

the "$R^{3-1}$ substituted or unsubstituted 3-7 membered heterocycloalkyl containing 1-4 heteroatoms selected from the group consisting of N, O and S" can be

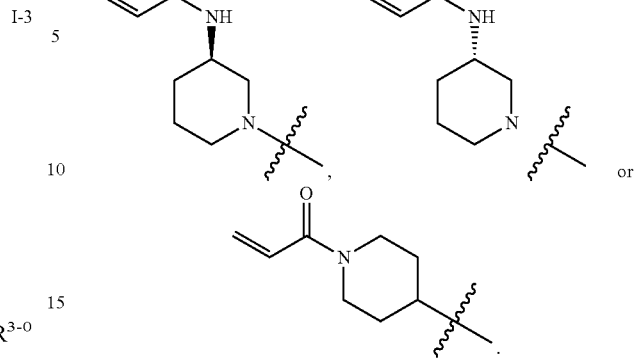

In an embodiment, the definitions of some substituents in the compound I can be as follows, and the definitions of the non-mentioned substituents are all as defined in any one of the embodiments above:

the $R^{3-2}$ substituted or unsubstituted 5-7 membered cycloalkenyl can be

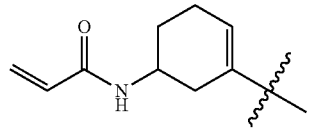

In an embodiment, the definitions of some substituents in the compound I can be as follows, and the definitions of the non-mentioned substituents are all as defined in any one of the embodiments above:

the "$R^{3-3}$ substituted or unsubstituted 5-7 membered heterocycloalkenyl containing 1-4 heteroatoms selected from the group consisting of N, O and S" can be

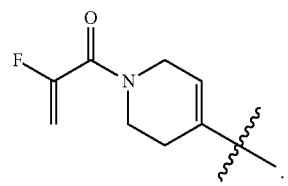 [SMILES: *C1=CCN(C(=O)C(=C)F)CC1]

In an embodiment, the definitions of some substituents in the compound I can be as follows, and the definitions of the non-mentioned substituents are all as defined in any one of the embodiments above:

the "$R^{3-5}$ substituted or unsubstituted 5-6 membered heteroaryl containing 1-3 heteroatoms selected from the group consisting of N, O and S" can be

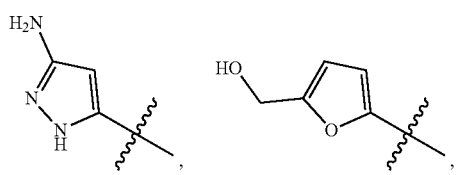

-continued

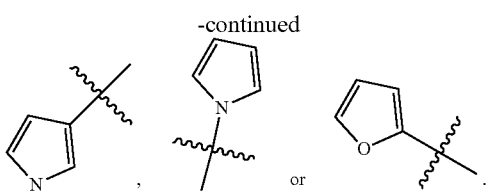

In an embodiment, the definitions of some substituents in the compound I can be as follows, and the definitions of the non-mentioned substituents are all as defined in any one of the embodiments above:

the $NR^{3-6}R^{3-7}$ can be

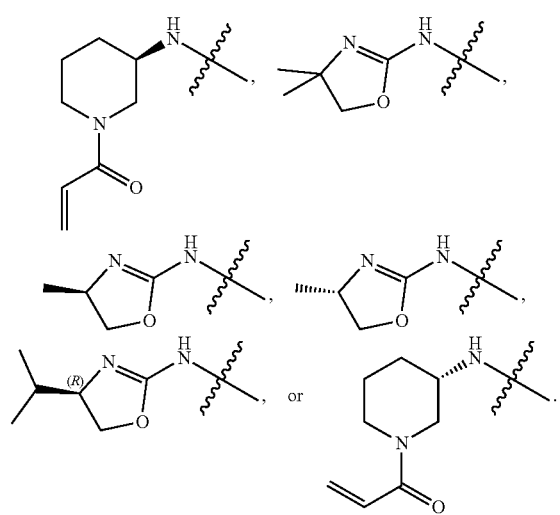

In an embodiment, the definitions of some substituents in the compound I can be as follows, and the definitions of the non-mentioned substituents are all as defined in any one of the embodiments above:

the $(R^{3-8})(R^{3-9})N$—(Z)—HC=CH— can be

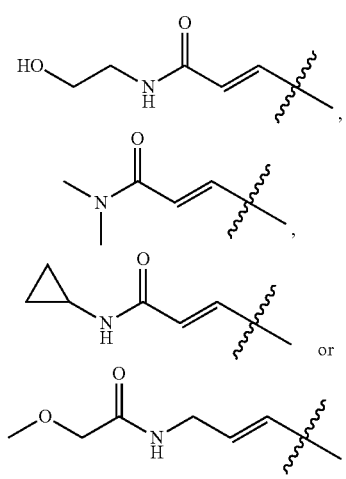

In an embodiment, the definitions of some substituents in the compound I can be as follows, and the definitions of the non-mentioned substituents are all as defined in any one of the embodiments above:

in the $(R^{3-10})(R^{3-11})C=C(R^{3-12})$—C(=O)—NH—, when $R^{3-12}$ is H, then the double bond is preferably E-configured.

In an embodiment, the definitions of some substituents in the compound I can be as follows, and the definitions of the non-mentioned substituents are all as defined in any one of the embodiments above:

in the $(R^{3-10})(R^{3-11})C=C(R^{3-12})$—C(=O)—NH—, when $R^{3-12}$ is halogen, then the double bond is preferably Z-configured.

In an embodiment, the definitions of some substituents in the compound I can be as follows, and the definitions of the non-mentioned substituents are all as defined in any one of the embodiments above:

the $(R^{3-10})(R^{3-11})C=C(R^{3-12})$—C(=O)—NH— can be

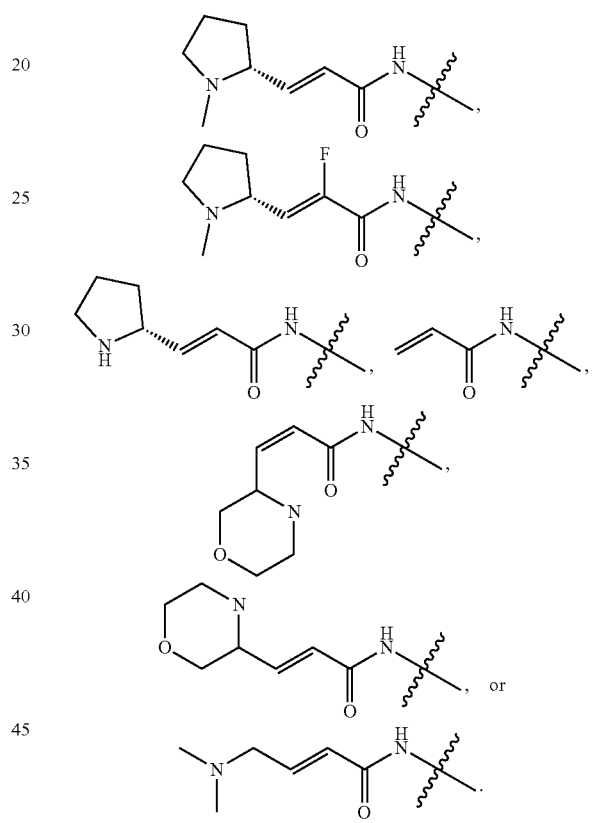

In an embodiment, the definitions of some substituents in the compound I can be as follows, and the definitions of the non-mentioned substituents are all as defined in any one of the embodiments above:

the $(R^{3-10})(R^{3-11})C=C(R^{3-12})$—C(=O)—NH— can be

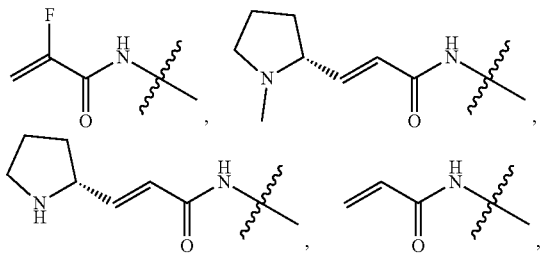

-continued

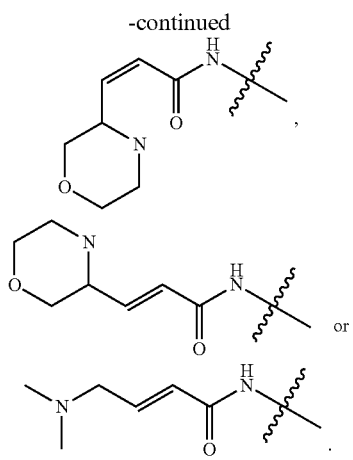

In an embodiment, the definitions of some substituents in the compound I can be as follows, and the definitions of the non-mentioned substituents are all as defined in any one of the embodiments above:

the $(R^{3-10})(R^{3-11})C=C(R^{3-12})-C(=O)-NH-$ can be

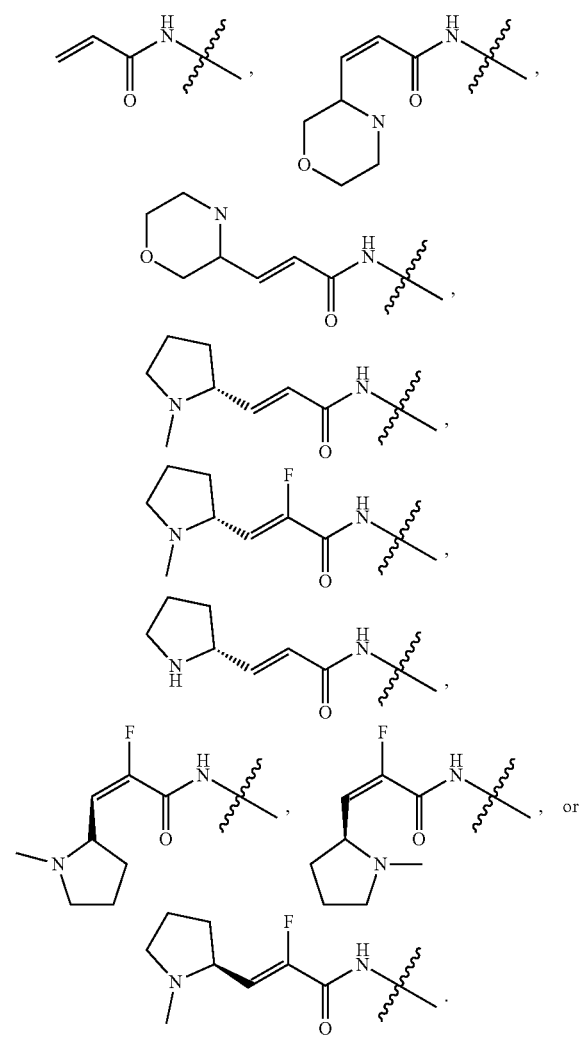

In an embodiment, the definitions of some substituents in the compound I can be as follows, and the definitions of the non-mentioned substituents are all as defined in any one of the embodiments above:

the $(R^{3-10})(R^{3-11})C=C(R^{3-12})-C(=O)-NH-$ can be

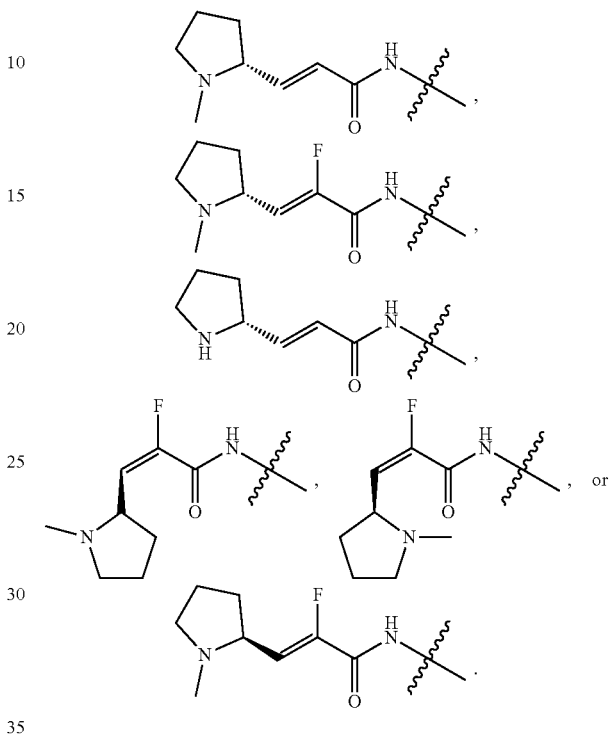

In an embodiment, the definitions of some substituents in the compound I can be as follows, and the definitions of the non-mentioned substituents are all as defined in any one of the embodiments above:

E is "9-10 membered fused heteroaryl containing 1-4 heteroatoms selected from the group consisting of N, O and S", preferably is

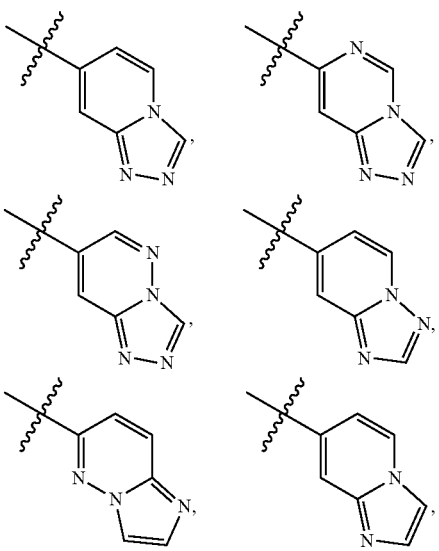

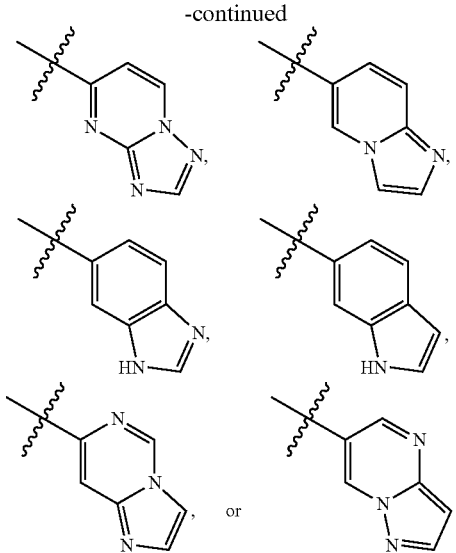

A is —O—;

n is 1;

Y is CH;

G is N or C—CN;

m is 1 or 2;

each $R^2$ is independently halogen, or, $C_1$-$C_6$ alkyl;

each $R^3$ is independently $R^{3-0}$ substituted or unsubstituted $C_1$-$C_6$ alkoxyl, $R^{3-1}$ substituted or unsubstituted "3-7 membered heterocycloalkyl containing 1-4 heteroatoms selected from the group consisting of N, O and S", $R^{3-2}$ substituted or unsubstituted 5-7 membered cycloalkenyl, $R^{3-3}$ substituted or unsubstituted "5-7 membered heterocycloalkenyl containing 1-4 heteroatoms selected from the group consisting of N, O and S", $R^{3-5}$ substituted or unsubstituted "5-6 membered heteroaryl containing 1-3 heteroatoms selected from the group consisting of N, O and S", N($R^{3-6}$)($R^{3-7}$)—, ($R^{3-8}$)($R^{3-9}$)N—(Z)—HC═CH—, or, ($R^{3-10}$)($R^{3-11}$)C═C($R^{3-12}$)—C(═O)—NH—;

each $R^{3-3}$ is independently $H_2$C═C$R^{3-3-1}$—C(═O)—;

each $R^{3-5}$ is independently amino;

each $R^{3-6}$ and $R^{3-7}$ is independently H, or, $R^{3-6-1}$ substituted or unsubstituted "3-7 membered heterocycloalkyl containing 1-4 heteroatoms selected from the group consisting of N, O and S";

each Z is independently —C(═O)—;

each $R^{3-8}$ and $R^{3-9}$ is independently H, hydroxyl substituted or unsubstituted $C_1$-$C_6$ alkyl, or, $C_3$-$C_6$ cycloalkyl;

each $R^{3-10}$ and $R^{3-11}$ is independently H, or, $R^{3-10-1}$ substituted or unsubstituted "3-7 membered heterocycloalkyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

E is "9-10 membered fused heteroaryl containing 1-4 heteroatoms selected from the group consisting of N, O and S", preferably is A is —O—;

n is 1;

Y is CH;

G is N or C—CN;

m is 1 or 2;

each $R^2$ is independently $C_1$-$C_6$ alkyl;

each $R^3$ is independently $R^{3-0}$ substituted or unsubstituted $C_1$-$C_6$ alkoxyl, or, ($R^{3-10}$)($R^{3-11}$)C═C($R^{3-12}$)—C(═O)—NH—;

each $R^{3-10}$ and $R^{3-11}$ is independently H, or, $R^{3-10-1}$ substituted or unsubstituted "3-7 membered heterocycloalkyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

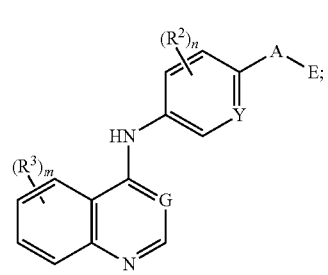

I wherein E is "9-10 membered fused heteroaryl containing 1-4 heteroatoms selected from the group consisting of N, O and S" (e.g., "9-10 membered fused heteroaryl containing 1-4 N atoms (the rest are C atoms)",

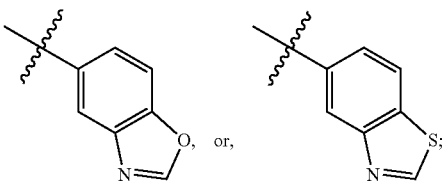 [SMILES: *c1ccc2ocnc2c1 ; *c1ccc2scnc2c1]

the "9-10 membered fused heteroaryl containing 1-4 N atoms" is, for example,

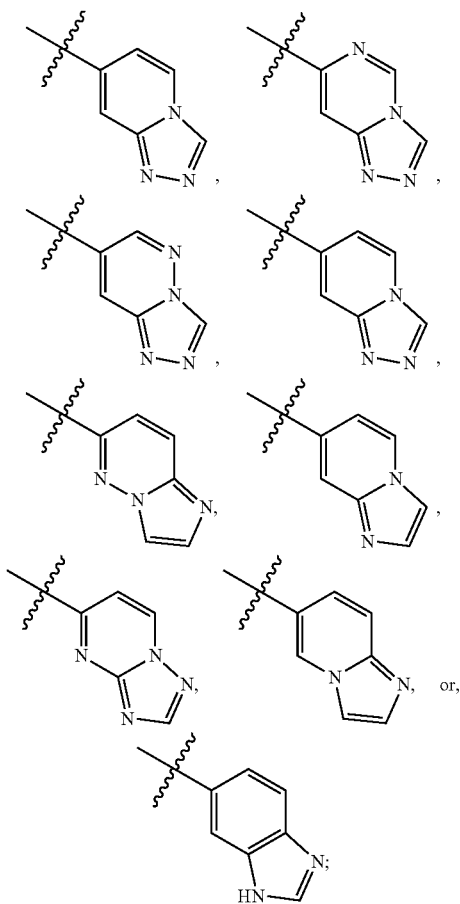

the number of the N atom in the ring connected to A in the "9-10 membered fused heteroaryl containing 1-4 heteroatoms selected from the group consisting of N, O and S" can be 0, 1 or 2, and can also be 1 or 2; the number of the N atom in the ring not connected to A in the "9-10 membered fused heteroaryl containing 1-4 heteroatoms selected from the group consisting of N, O and S" can be 1, 2, or 3, and can also be 2 or 3; when the "9-10 membered fused heteroaryl containing 1-4 heteroatoms selected from the group consisting of N, O and S" is "9-10 membered fused heteroaryl containing 1-4 N atoms", the number of the N atom in the ring connected to A in the "9-10 membered fused heteroaryl containing 1-4 N atoms" A can be 0, 1 or 2, and can also be 1 or 2; when the "9-10 membered fused heteroaryl containing 1-4 heteroatoms selected from the group consisting of N, O and S" is "9-10 membered fused heteroaryl containing 1-4 N atoms", the number of the N atoms in the ring not connected to A in the "9-10 membered fused heteroaryl containing 1-4 N atoms" can be 1, 2, or 3, and can also be 2 or 3);

A is —O—, —S—, —C(=O)—, —SO— or —SO$_2$—;

n is 0, 1, 2, 3 or 4;

each $R^2$ is independently halogen (e.g., fluorine, chlorine, bromine or iodine, also e.g., chlorine), or, $C_1$-$C_6$ alkyl (e.g., $C_1$-$C_4$ alkyl, also e.g., methyl, ethyl, n-propyl, isopropyl, n-butyl, isobutyl, sec-butyl or tert-butyl, further e.g., methyl);

Y is N or CH;

G is N or C—CN;

m is 1, 2, 3, 4 or 5 ($R^3$ can be connected to any position on the fused ring);

each $R^3$ is independently halogen (e.g., fluorine, chlorine, bromine or iodine, also e.g., fluorine), $R^{3-0}$ substituted or unsubstituted $C_1$-$C_6$ alkoxy (the number of the $R^{3-0}$ can be one or more than one <e.g., 2, 3, 4 or 5>, and when a plurality of $R^{3-0}$ exist, any of two $R^{3-0}$ are the same or different; the "$C_1$-$C_6$ alkoxy" is, for example, $C_1$-$C_4$ alkoxy, and is, for example, methoxy, ethoxy, n-propoxy, isopropoxy, n-butoxy, isobutoxy, sec-butoxy or tert-butoxy, and is, for example, ethoxy; the "$R^{3-0}$ substituted $C_1$-$C_6$ alkoxy" is, for example,

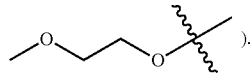 [SMILES: *OCCOC]).

$R^{3-1}$ substituted or unsubstituted "3-7 membered heterocycloalkyl containing 1-4 heteroatoms selected from the group consisting of N, O and S" (the number of the $R^{3-1}$ can be one or more than one <e.g., 2, 3, 4 or 5>, and when a plurality of $R^{3-1}$ exist, any of two $R^{3-1}$ are the same or different; the "3-7 membered heterocycloalkyl containing 1-4 heteroatoms selected from the group consisting of N, O and S" can be a "5-6 membered heterocycloalkyl containing 1-2 heteroatoms selected from the group consisting of N, O and S", and can be piperidinyl, and can also be piperidin-1-yl or piperidin-4-yl <relative to

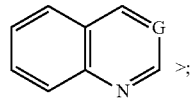

the "3-7 membered heterocycloalkyl containing 1-4 heteroatoms selected from the group consisting of N, O and S" can be connected to

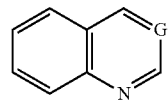

through C atom or N atom; each $R^{3-1}$ can be independently located at the ortho, meta or para position relative to the "connection site of heterocycloalkyl and

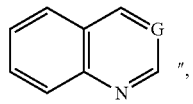, and can also be located at the meta or para position), $R^{3-2}$ substituted or unsubstituted 5-7 membered cycloalkenyl (the number of the $R^{3-2}$ can be one or more than one <e.g., 2, 3, 4 or 5>, and when a plurality of $R^{3-2}$ exist, any of two $R^{3-2}$ are the same or different; the "5-7 membered cycloalkenyl" can be cyclohexenyl, and can also be cyclohexene-1-yl <relative to

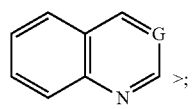>;

each $R^{3-2}$ can be independently located at the ortho, meta or para position relative to the "connection site of cycloalkenyl and

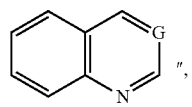", and can also be located at the meta position), $R^{3-3}$ substituted or unsubstituted "5-7 membered heterocycloalkenyl containing 1-4 heteroatoms selected from the group consisting of N, O and S" (the number of the $R^{3-3}$ can be one or more than one <e.g., 2, 3, 4 or 5>, and when a plurality of $R^{3-3}$ exist, any of two $R^{3-3}$ are the same or different; the "5-7 membered heterocycloalkenyl containing 1-4 heteroatoms selected from the group consisting of N, O and S" can be a "5-6 membered heterocycloalkenyl containing 1-2 heteroatoms selected from the group consisting of N, O, and S", and can be 1,2,5,6-tetrahydropyridyl, and can also be 1,2,5,6-tetrahydropyridin-4-yl <relative to

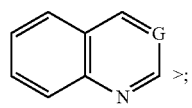>;

the "5-7 membered heterocycloalkenyl containing 1-4 heteroatoms selected from the group consisting of N, O and S" can be connected to

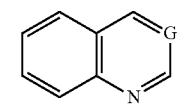

through C atom or N atom; each $R^{3-3}$ can be independently located at the ortho, meta or para position relative to the "connection site of heterocycloalkenyl and

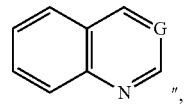", and can also be located at the para position), $R^{3-5}$ substituted or unsubstituted "5-6 membered heteroaryl containing 1-3 heteroatoms selected from the group consisting of N, O, and S" (the number of the $R^{3-5}$ can be one or more than one <e.g., 2, 3, 4 or 5>, when a plurality of $R^{3-5}$ exist, any of two $R^{3-5}$ are the same or different; the "5-6 membered heteroaryl containing 1-3 heteroatoms selected from the group consisting of N, O, and S" can be a "5-6 membered heteroaryl containing 1-2 heteroatoms selected from the group consisting of N, O, and S", and can also be pyrazolyl or furanyl; the pyrazolyl can be pyrazole-5-yl or pyrazole-1-yl <relative to

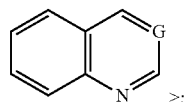>;

the furanyl can be furan-2-yl <relative to

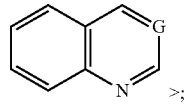>;

the "5-6 membered heteroaryl containing 1-3 heteroatoms selected from the group consisting of N, O, and S" can be connected to

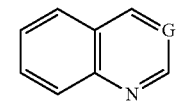

through C atom or N atom; each $R^{3-5}$ can be independently located at the ortho, meta or para position relative to the "connection site of heteroaryl and

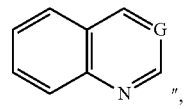", and can also be located at the meta position), $N(R^{3-6})(R^{3-7})$— (one of the $R^{3-6}$ and $R^{3-7}$ can be hydrogen), $(R^{3-8})(R^{3-9})N$—(Z)—HC=CH— (wherein the double bond can be Z-configured, E-configured or a mixture thereof, also e.g., E-configured), $(R^{3-10})(R^{3-11})C=C(R^{3-12})$—C(=O)—NH— (wherein the double bond can be Z-configured, E-configured or a mixture thereof, e.g., E-configured), or, $R^{3-13}$—O—

(e.g., 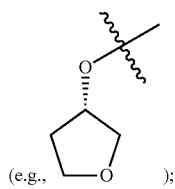 [SMILES: *O[C@H]1CCOC1]);

each $R^{3-0}$ is independently $C_1$-$C_6$ alkoxy (e.g., $C_1$-$C_4$ alkoxy, further e.g., methoxy, ethoxy, n-propoxy, isopropoxy, n-butoxy, isobutoxy, sec-butoxy or tert-butoxy, further e.g., methoxy);

each $R^{3-1}$ is independently $H_2C$=CH—C(=O)—NH— or $H_2C$=C—C(=O)— (the $H_2C$=C—C(=O)—NH— can be connected to the C atom in the "3-7 membered heterocycloalkyl containing 1-4 heteroatoms selected from the group consisting of N, O and S"; the $H_2C$=C—C(=O)— can be connected to the N atom in the "3-7 membered heterocycloalkyl containing 1-4 heteroatoms selected from the group consisting of N, O and S");

each $R^{3-2}$ is independently $H_2C$=CH—C(=O)—NH—;
each $R^{3-3}$ is independently $H_2C$=C$R^{3-3-1}$—C(=O)—NH—; each $R^{3-3-1}$ is independently H or halogen (e.g., fluorine, chlorine, bromine or iodine, further e.g., fluorine);

each $R^{3-5}$ is independently amino or hydroxymethyl;

each $R^{3-6}$ and $R^{3-7}$ is independently H, $R^{3-6-1}$ substituted or unsubstituted "3-7 membered heterocycloalkyl containing 1-4 heteroatoms selected from the group consisting of N, O and S" (the number of the $R^{3-6-1}$ can be one or more than one <e.g., 2, 3, 4 or 5>, and when a plurality of $R^{3-6-1}$ exist, any of two $R^{3-6-1}$ are the same or different; the "3-7 membered heterocycloalkyl containing 1-4 heteroatoms selected from the group consisting of N, O and S" can be a "5-6 membered heterocycloalkyl containing 1-2 heteroatoms selected from the group consisting of N, O and S", and can be piperidyl, and can also be piperidin-3-yl <relative to the N atom>; the "3-7 membered heterocycloalkyl containing 1-4 heteroatoms selected from the group consisting of N, O and S" can be connected to the N atom through the C atom; each $R^{3-6-1}$ can be independently located at the ortho, meta or para position relative to the "connection site of heterocycloalkyl and the N atom", and can also be located at the meta position), or, $R^{3-6-2}$ substituted or unsubstituted "5-7 membered heterocycloalkenyl containing 1-4 heteroatoms selected from the group consisting of N, O and S" (the number of the $R^{3-6-2}$ can be one or more than one <e.g., 2, 3, 4 or 5>, and when a plurality of $R^{3-6-2}$ exist, any of two $R^{3-6-2}$ are the same or different; the "5-7 membered heterocycloalkenyl containing 1-4 heteroatoms selected from the group consisting of N, O and S" can be a "5-6 membered heterocycloalkenyl containing 1-2 heteroatoms selected from the group consisting of N, O and S", and can be 4,5-dihydrooxazolyl, and can also be 4,5-dihydrooxazol-2-yl <relative to the N atom>; the "5-7 membered heterocycloalkenyl containing 1-4 heteroatoms selected from the group consisting of N, O and S" can be connected to the N atom through the C atom; each $R^{3-6-2}$ can be independently located at the ortho, meta or para position relative to the "connection site of heterocycloalkenyl and the N atom", and can also be located at the meta position); each $R^{3-6-1}$ is independently $H_2C$=CH—C(=O)—NH—; each $R^{3-6-2}$ is independently $C_1$-$C_6$ alkyl (e.g., $C_1$-$C_4$ alkyl, further e.g., methyl, ethyl, n-propyl, isopropyl, n-butyl, isobutyl, sec-butyl or tert-butyl, further e.g., methyl);

each Z is independently —C(=O)— or —CH$_2$—; each $R^{3-8}$ and $R^{3-9}$ is independently H, hydroxyl substituted or unsubstituted $C_1$-$C_6$ alkyl (the number of the hydroxyl can be one or more than one <e.g., 2, 3, 4, or 5>; the "$C_1$-$C_6$ alkyl" is, for example, $C_1$-$C_4$ alkyl, further e.g., methyl, ethyl, n-propyl, isopropyl, n-butyl, isobutyl, sec-butyl or tert-butyl, further e.g., methyl or ethyl; the "hydroxyl substituted $C_1$-$C_6$ alkyl" is, for example, 2-hydroxylethyl), $C_3$-$C_6$ cycloalkyl (e.g., cyclopropyl or cyclobutyl, further e.g., cyclopropyl), or, $R^{3-8-1}$—C(=O)—; each $R^{3-8-1}$ is independently oxa-$C_1$-$C_6$ alkyl (the number of the oxa can be one or more than one <e.g., 2, 3, 4 or 5>; the "$C_1$-$C_6$ alkyl" is, for example, $C_1$-$C_4$ alkyl, further e.g., methyl, ethyl, n-propyl, isopropyl, n-butyl, isobutyl, sec-butyl or tert-butyl, further e.g., methyl or ethyl; the "oxa-$C_1$-$C_6$ alkyl" is, for example, methoxylmethyl);

each $R^{3-10}$ and $R^{3-11}$ is independently H, $R^{3-10-1}$ substituted or unsubstituted "3-7 membered heterocycloalkyl containing 1-4 heteroatoms selected from the group consisting of N, O and S" (the number of the $R^{3-10-1}$ can be one or more than one <e.g., 2, 3, 4, or 5>, when a plurality of $R^{3-10-1}$ exist, any of two $R^{3-10-1}$ are the same or different; the "3-7 membered heterocycloalkyl containing 1-4 heteroatoms selected from the group consisting of N, O and S" can be a "5-6 membered heterocycloalkyl containing 1-2 heteroatoms selected from the group consisting of N, O and S", and can also be pyrrolidinyl or morpholinyl; the pyrrolidinyl can be pyrrolidin-2-yl <relative to the double bond>; the pyrrolidin-2-yl can be 2S-pyrrolidin-2-yl, 2R-pyrrolidin-2-yl or a mixture thereof <relative to the double bond>; the morpholinyl can be morpholinyl-3-yl <relative to the double bond>; the "3-7 membered heterocycloalkyl containing 1-4 heteroatoms selected from the group consisting of N, O and S" can be connected to the double bond through the C atom or N atom; each $R^{3-10-1}$ can be independently located at the ortho, meta or para position relative to the "connection site of heterocycloalkyl and the double bond", and can also be located at the ortho position), or, $NR^{3-1-2}R^{3-10-3}$-substituted or unsubstituted $C_1$-$C_6$ alkyl (the number of the $NR^{3-10-2}R^{3-10-3}$— can be one or more than one <e.g., 2, 3, 4 or 5>, and when a plurality of $NR^{3-10-2}R^{3-10-3}$-exist, any of two $NR^{3-10-2}R^{3-10-3}$— are the same or different; the "$C_1$-$C_6$ alkyl" is, for example, $C_1$-$C_4$ alkyl, further e.g., methyl, ethyl, n-propyl, isopropyl, n-butyl, isobutyl, sec-butyl or tert-butyl, further e.g., methyl or ethyl; the "$NR^{3-10-2}R^{3-10-3}$— substituted $C_1$-$C_6$ alkyl" is, for example, dimethylaminomethyl); each $R^{3-10-1}$, $R^{3-10-2}$ and $R^{3-10-3}$ is independently $C_1$-$C_6$ alkyl (e.g., $C_1$-$C_4$ alkyl, further e.g., methyl, ethyl, n-propyl, isopropyl, n-butyl, isobutyl, sec-butyl or tert-butyl, further e.g., methyl);

each $R^{3-12}$ is independently H or halogen (e.g., fluorine, chlorine, bromine or iodine, further e.g., fluorine);

each $R^{3-13}$ is independently "3-7 membered heterocycloalkyl containing 1-4 heteroatoms selected from the group consisting of N, O and S" (e.g., "5-6 membered heterocycloalkyl containing 1-2 heteroatoms selected from the group consisting of N, O and S", and can also be furanyl, further e.g., furan-3-yl <relative to the O atom>, further e.g.,

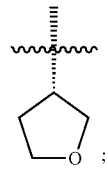

the "3-7 membered heterocycloalkyl containing 1-4 heteroatoms selected from the group consisting of N, O and S" can be connected to the O atom through the C atom);
the compound I excludes any one of the compounds as follows:
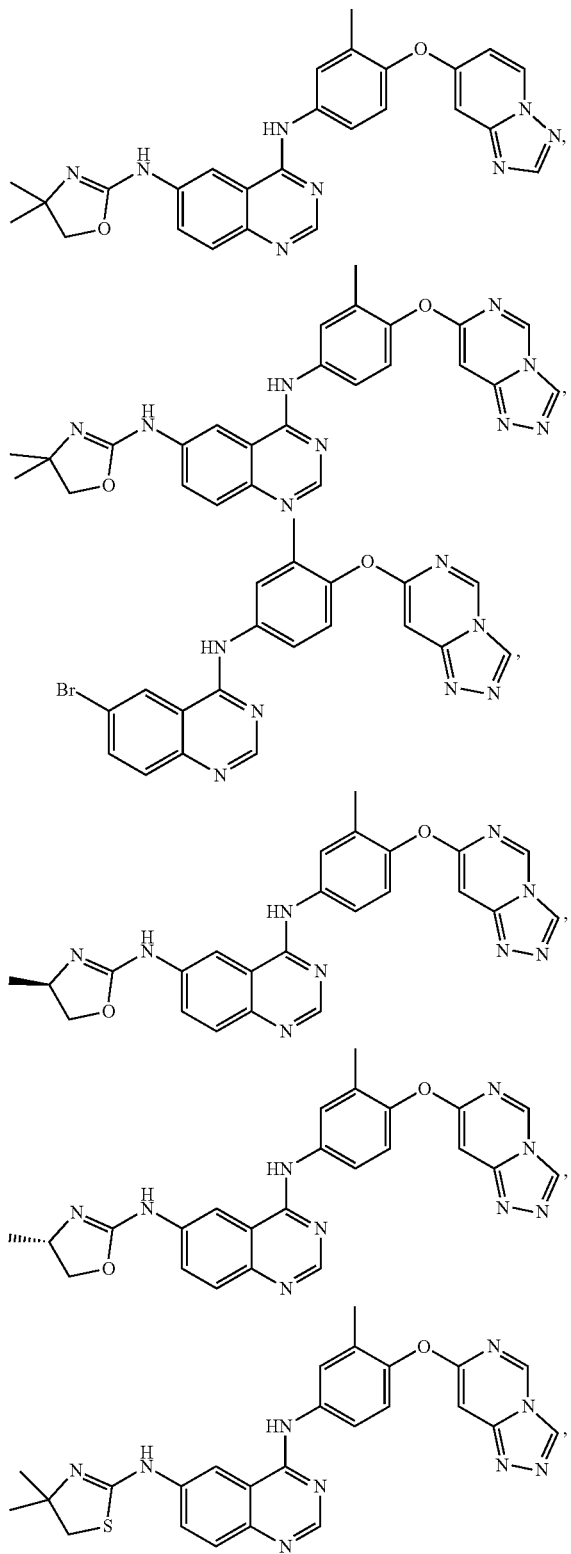
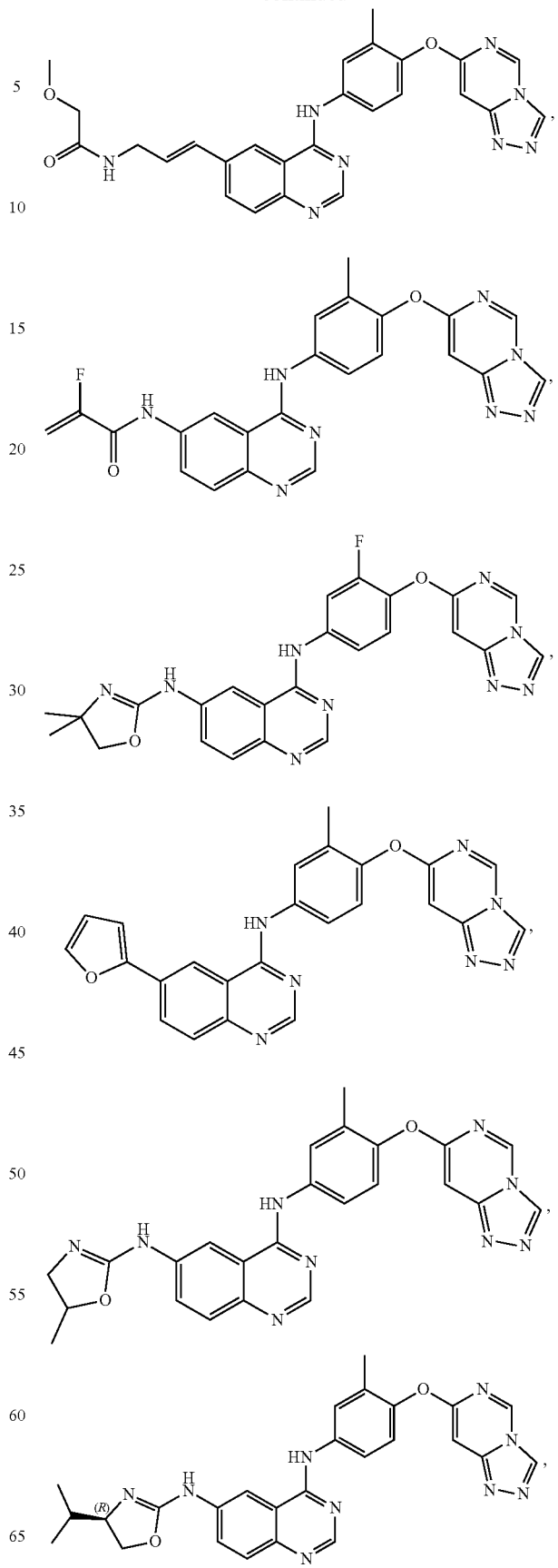

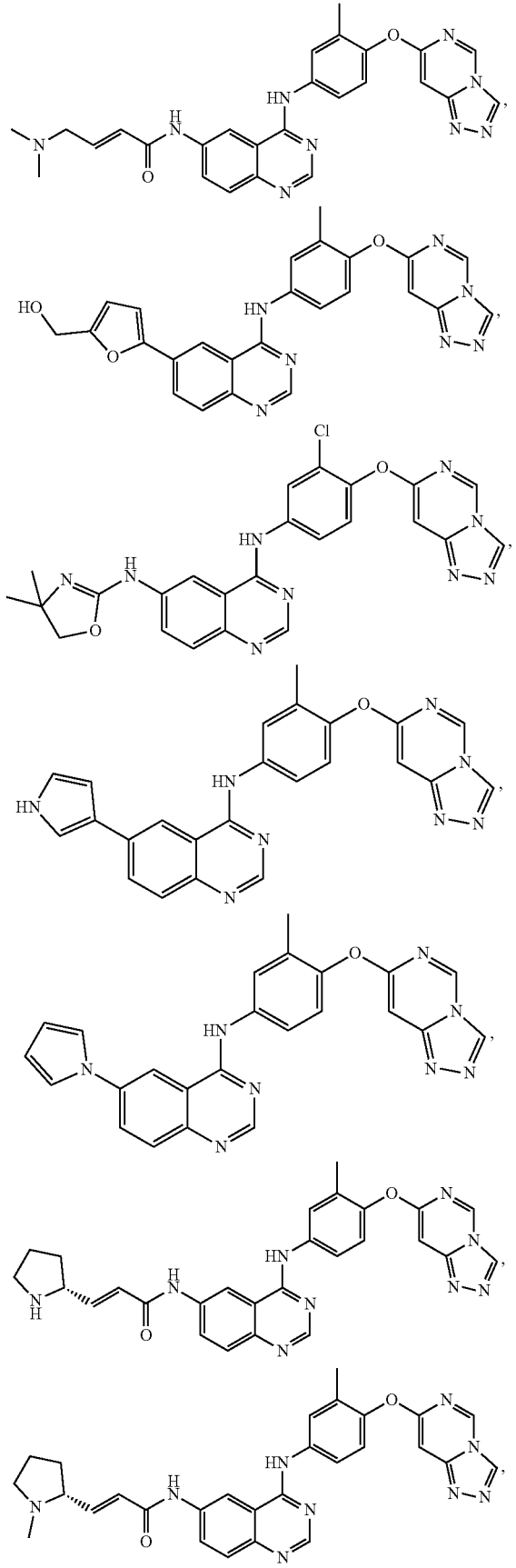
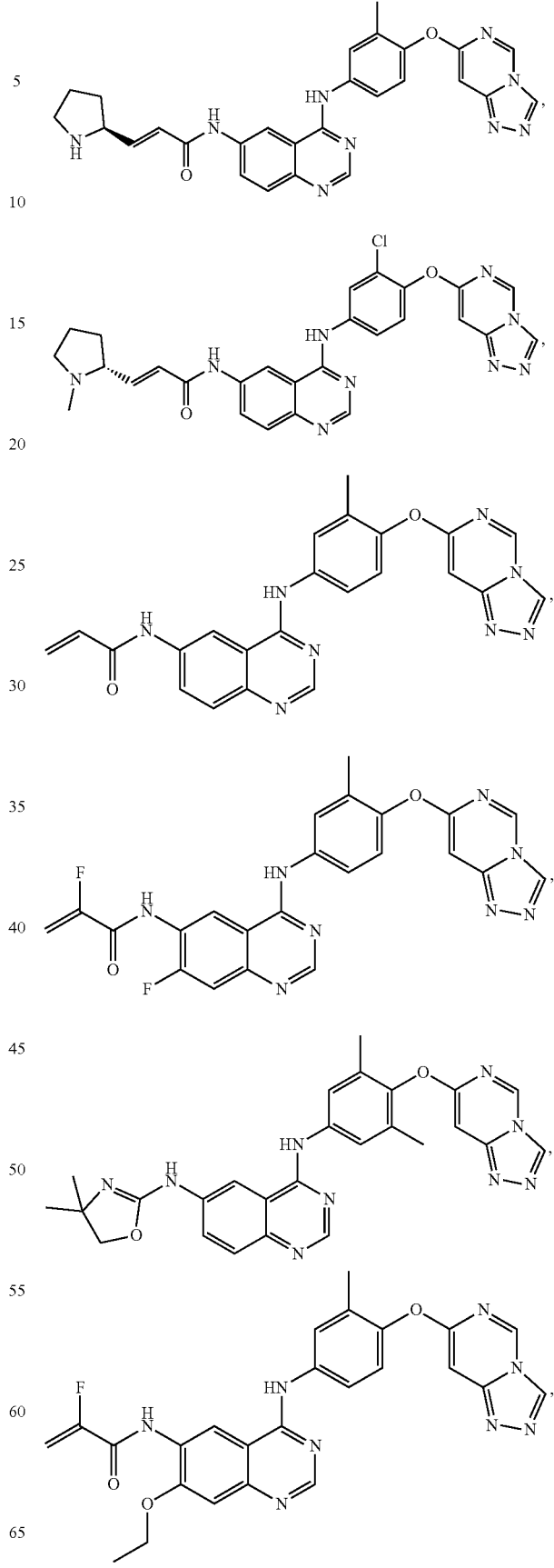

-continued

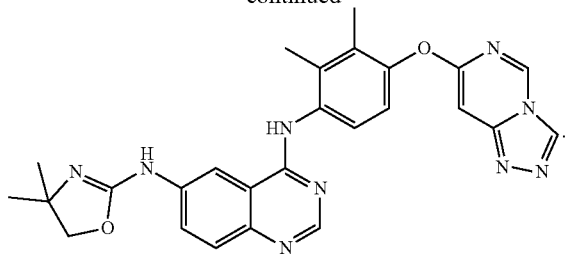

In an embodiment, the definitions of some substituents in the compound I can be as follows, and the definitions of the non-mentioned substituents are all as defined in any one of the embodiments above:

E is not

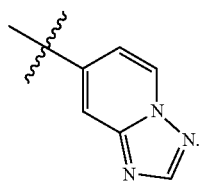 [SMILES: *c1ccn2ncnc2c1]

In an embodiment, the definitions of some substituents in the compound I can be as follows, and the definitions of the non-mentioned substituents are all as defined in any one of the embodiments above:

E is

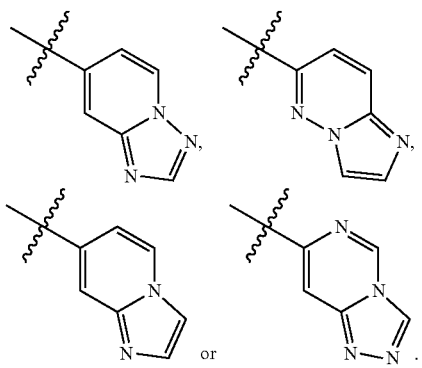

In an embodiment, the definitions of some substituents in the compound I can be as follows, and the definitions of the non-mentioned substituents are all as defined in any one of the embodiments above:

E is

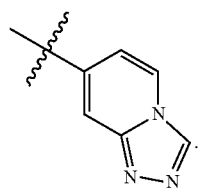 [SMILES: *c1ccn2cnnc2c1]

In an embodiment, the definitions of some substituents in the compound I can be as follows, and the definitions of the non-mentioned substituents are all as defined in any one of the embodiments above:

E is

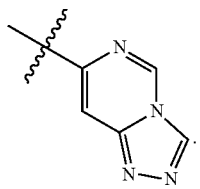 [SMILES: *c1cc2nncn2cn1]

In an embodiment, the definitions of some substituents in the compound I can be as follows, and the definitions of the non-mentioned substituents are all as defined in any one of the embodiments above:

E is

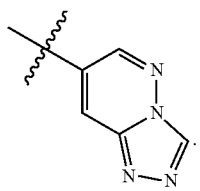 [SMILES: *c1cnn2cnnc2c1]

In an embodiment, the definitions of some substituents in the compound I can be as follows, and the definitions of the non-mentioned substituents are all as defined in any one of the embodiments above:

E is

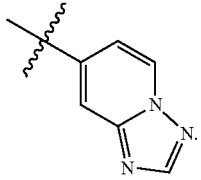 [SMILES: *c1ccn2ncnc2c1]

In an embodiment, the definitions of some substituents in the compound I can be as follows, and the definitions of the non-mentioned substituents are all as defined in any one of the embodiments above:

E is

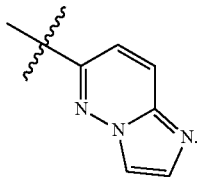 [SMILES: *c1ccc2nccn2n1]

In an embodiment, the definitions of some substituents in the compound I can be as follows, and the definitions of the non-mentioned substituents are all as defined in any one of the embodiments above:

E is N

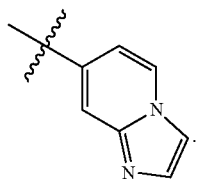 [SMILES: *c1ccn2ccnc2c1]

In an embodiment, the definitions of some substituents in the compound I can be as follows, and the definitions of the non-mentioned substituents are all as defined in any one of the embodiments above:

E is

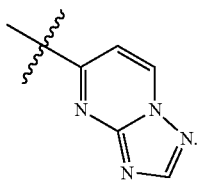 [SMILES: *c1ccn2ncnc2n1]

In an embodiment, the definitions of some substituents in the compound I can be as follows, and the definitions of the non-mentioned substituents are all as defined in any one of the embodiments above:

E is

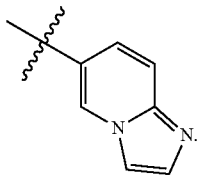 [SMILES: *c1ccc2nccn2c1]

In an embodiment, the definitions of some substituents in the compound I can be as follows, and the definitions of the non-mentioned substituents are all as defined in any one of the embodiments above:

E is

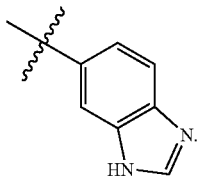 [SMILES: *c1ccc2nc[nH]c2c1]

In an embodiment, the definitions of some substituents in the compound I can be as follows, and the definitions of the non-mentioned substituents are all as defined in any one of the embodiments above:

when the E is

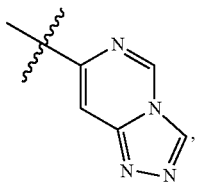 [SMILES: *c1cc2nncn2cn1]

then each $R^3$ can be independently any one of the substituents as defined therein.

In an embodiment, the definitions of some substituents in the compound I can be as follows, and the definitions of the non-mentioned substituents are all as defined in any one of the embodiments above:

when the E is not

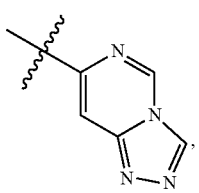 [SMILES: *c1cc2nncn2cn1]

then each $R^3$ can be independently $(R^{3-10})(R^{3-11})C=C(R^{3-12})-C(=O)-NH-$ or $C_1$-$C_6$ alkoxyl.

In an embodiment, the definitions of some substituents in the compound I can be as follows, and the definitions of the non-mentioned substituents are all as defined in any one of the embodiments above:

A is —O— or —S—.

In an embodiment, the definitions of some substituents in the compound I can be as follows, and the definitions of the non-mentioned substituents are all as defined in any one of the embodiments above:

A is —O—.

In an embodiment, the definitions of some substituents in the compound I can be as follows, and the definitions of the non-mentioned substituents are all as defined in any one of the embodiments above:

n is 1.

In an embodiment, the definitions of some substituents in the compound I can be as follows, and the definitions of the non-mentioned substituents are all as defined in any one of the embodiments above:

when n is 1, the compound I can be

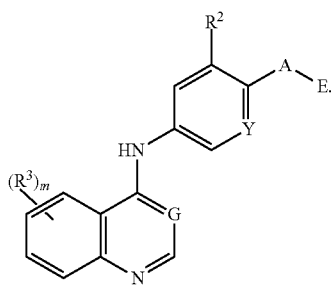

I-1

In an embodiment, the definitions of some substituents in the compound I can be as follows, and the definitions of the non-mentioned substituents are all as defined in any one of the embodiments above:

Y is CH.

In an embodiment, the definitions of some substituents in the compound I can be as follows, and the definitions of the non-mentioned substituents are all as defined in any one of the embodiments above:

G is N.

In an embodiment, the definitions of some substituents in the compound I can be as follows, and the definitions of the non-mentioned substituents are all as defined in any one of the embodiments above:

G is C—CN.

In an embodiment, the definitions of some substituents in the compound I can be as follows, and the definitions of the non-mentioned substituents are all as defined in any one of the embodiments above:

m is 1 or 2.

In an embodiment, the definitions of some substituents in the compound I can be as follows, and the definitions of the non-mentioned substituents are all as defined in any one of the embodiments above:

when m is 1, then the compound I can be

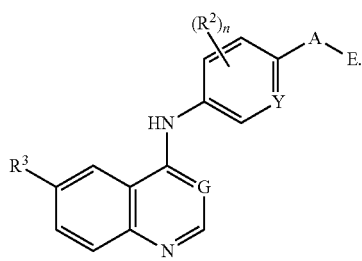

I-2

In an embodiment, the definitions of some substituents in the compound I can be as follows, and the definitions of the non-mentioned substituents are all as defined in any one of the embodiments above:

when m is 2, then the compound I can be

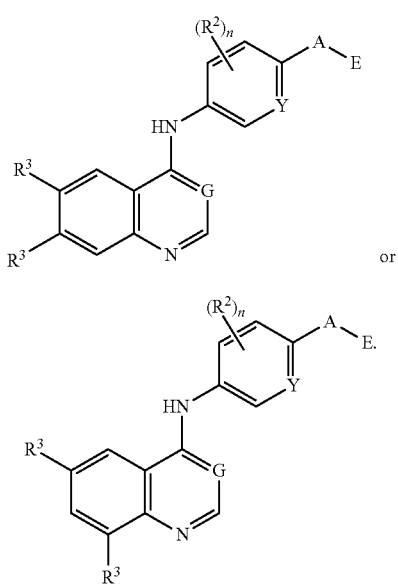

I-3 or

I-4

In an embodiment, the definitions of some substituents in the compound I can be as follows, and the definitions of the non-mentioned substituents are all as defined in any one of the embodiments above:

m is 1, $R^3$ is $R^{3-1}$ substituted or unsubstituted "3-7 membered heterocycloalkyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

m is 1, $R^3$ is $R^{3-2}$ substituted or unsubstituted 5-7 membered cycloalkenyl.

In an embodiment, the definitions of some substituents in the compound I can be as follows, and the definitions of the non-mentioned substituents are all as defined in any one of the embodiments above:

m is 1, $R^3$ is $R^{3-3}$ substituted or unsubstituted "5-7 membered heterocycloalkenyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

m is 2, $R^3$ is $R^{3-3}$ substituted or unsubstituted "5-7 membered heterocycloalkenyl containing 1-4 heteroatoms selected from the group consisting of N, O and S" and halogen, respectively (i.e., one $R^3$ is a $R^{3-3}$ substituted or unsubstituted "5-7 membered heterocycloalkenyl containing 1-4 heteroatoms selected from the group consisting of N, O and S", and the other $R^3$ is halogen, hereinafter the disclosure has the same definition).

In an embodiment, the definitions of some substituents in the compound I can be as follows, and the definitions of the non-mentioned substituents are all as defined in any one of the embodiments above:

m is 1, each $R^3$ is independently $R^{3-5}$ substituted or unsubstituted "5-6 membered heteroaryl containing 1-3 heteroatoms selected from the group consisting of N, O and S".

In an embodiment, the definitions of some substituents in the compound I can be as follows, and the definitions of the non-mentioned substituents are all as defined in any one of the embodiments above:

m is 2, $R^3$ is $R^{3-5}$ substituted or unsubstituted "5-6 membered heteroaryl containing 1-3 heteroatomes selected from the group consisting of N, O and S" and halogen, respectively.

In an embodiment, the definitions of some substituents in the compound I can be as follows, and the definitions of the non-mentioned substituents are all as defined in any one of the embodiments above:

m is 1, $R^3$ is $N(R^{3-6})(R^{3-7})$—.

In an embodiment, the definitions of some substituents in the compound I can be as follows, and the definitions of the non-mentioned substituents are all as defined in any one of the embodiments above:

m is 1, $R^3$ is $(R^{3-8})(R^{3-9})N$—(Z)—HC═CH—.

In an embodiment, the definitions of some substituents in the compound I can be as follows, and the definitions of the non-mentioned substituents are all as defined in any one of the embodiments above:

m is 2, $R^3$ is $(R^{3-8})(R^{3-9})N$—(Z)—HC═CH— and halogen, respectively.

In an embodiment, the definitions of some substituents in the compound I can be as follows, and the definitions of the non-mentioned substituents are all as defined in any one of the embodiments above:

m is 1, $R^3$ is $(R^{3-10})(R^{3-11})C=C(R^{3-12})-C(=O)-NH-$.

In an embodiment, the definitions of some substituents in the compound I can be as follows, and the definitions of the non-mentioned substituents are all as defined in any one of the embodiments above:

m is 2, $R^3$ is $(R^{3-10})(R^{3-11})C=C(R^{3-12})-C(=O)-NH-$ and $C_1$-$C_6$ alkoxyl, respectively.

In an embodiment, the definitions of some substituents in the compound I can be as follows, and the definitions of the non-mentioned substituents are all as defined in any one of the embodiments above:

compound I is

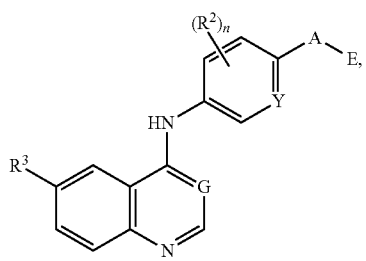

I-2

$R^3$ is $R^{3-1}$ substituted or unsubstituted "3-7 membered heterocycloalkyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

compound I is

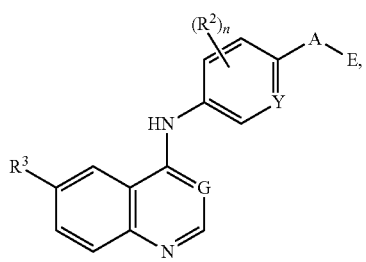

I-2 the $R^3$ is $R^{3-2}$ substituted or unsubstituted 5-7 membered cycloalkenyl.

In an embodiment, the definitions of some substituents in the compound I can be as follows, and the definitions of the non-mentioned substituents are all as defined in any one of the embodiments above:

compound I is

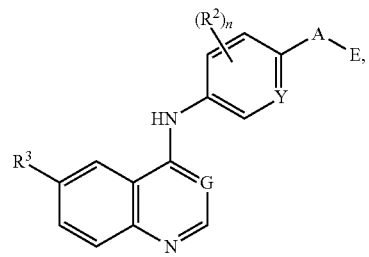

I-2

$R^3$ is $R^{3-3}$ substituted or unsubstituted "5-7 membered heterocycloalkenyl containing 1-4 heteroatoms selected from the group consisting of N, O and S".

In an embodiment, the definitions of some substituents in the compound I can be as follows, and the definitions of the non-mentioned substituents are all as defined in any one of the embodiments above:

compound I is

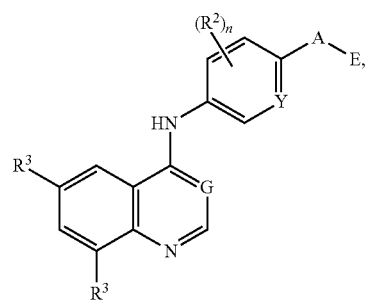

I-4

$R^3$ is $R^{3-3}$ substituted or unsubstituted "5-7 membered heterocycloalkenyl containing 1-4 heteroatoms selected from the group consisting of N, O and S" and halogen, respectively.

In an embodiment, the definitions of some substituents in the compound I can be as follows, and the definitions of the non-mentioned substituents are all as defined in any one of the embodiments above:

compound I is

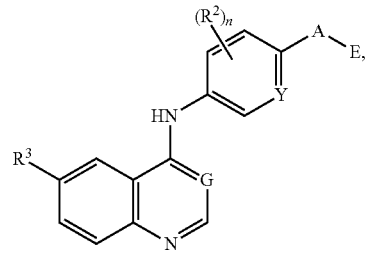

I-2

$R^3$ is $R^{3-5}$ substituted or unsubstituted "5-6 membered heteroaryl containing 1-3 heteroatoms selected from the group consisting of N, O and S".

In an embodiment, the definitions of some substituents in the compound I can be as follows, and the definitions of the non-mentioned substituents are all as defined in any one of the embodiments above:

compound I is

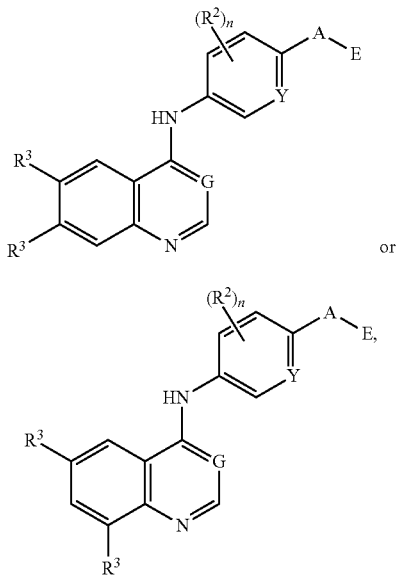

I-3 or

I-4

$R^3$ is $R^{3-5}$ substituted or unsubstituted "5-6 membered heteroaryl containing 1-3 heteroatoms selected from the group consisting of N, O and S" and halogen, respectively.

In an embodiment, the definitions of some substituents in the compound I can be as follows, and the definitions of the non-mentioned substituents are all as defined in any one of the embodiments above:
compound I is

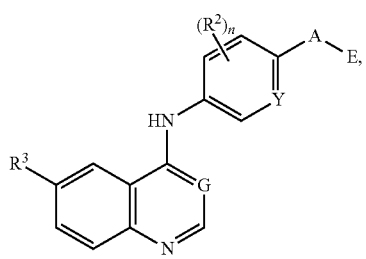

I-2

$R^3$ is $N(R^{3-6})(R^{3-7})$—.

In an embodiment, the definitions of some substituents in the compound I can be as follows, and the definitions of the non-mentioned substituents are all as defined in any one of the embodiments above:
compound I is

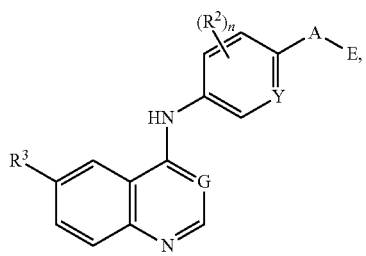

I-2

$R^3$ is $(R^{3-8})(R^{3-9})N$—(Z)—HC=CH—.

In an embodiment, the definitions of some substituents in the compound I can be as follows, and the definitions of the non-mentioned substituents are all as defined in any one of the embodiments above:
compound I is

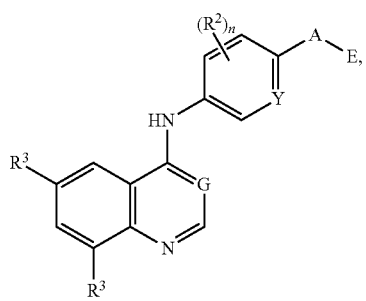

I-4

$R^3$, $R^3$ is $(R^{3-8})(R^{3-9})N$—(Z)—HC=CH— and halogen, respectively.

In an embodiment, the definitions of some substituents in the compound I can be as follows, and the definitions of the non-mentioned substituents are all as defined in any one of the embodiment above:
compound I is

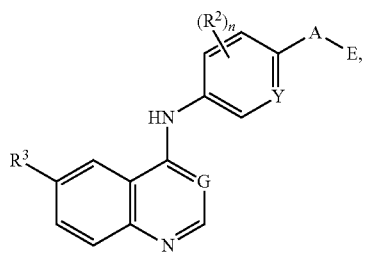

I-2

$R^3$ is $(R^{3-10})(R^{3-11})C=C(R^{3-12})$—C(=O)—NH—.

In an embodiment, the definitions of some substituents in the compound I can be as follows, and the definitions of the non-mentioned substituents are all as defined in any one of the embodiments above:
compound I is

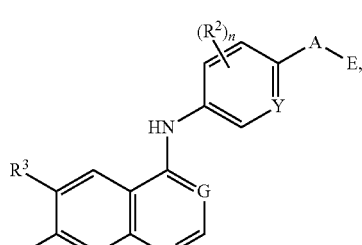

I-3

$R^3$ is $(R^{3-10})(R^{3-11})C=C(R^{3-12})$—C(=O)—NH— and $C_1$-$C_6$ alkoxyl, respectively.

In an embodiment, the definitions of some substituents in the compound I can be as follows, and the definitions of the non-mentioned substituents are all as defined in any one of the embodiments above:

in R$^3$, R$^{3-3}$ substituted or unsubstituted "5-7 membered heterocycloalkenyl containing 1-4 heteroatoms selected from the group consisting of N, O and S", "5-6 membered heteroaryl containing 1-3 heteroatoms selected from the group consisting of N, O and S", (R$^{3-8}$)(R$^{3-9}$)N—(Z)—HC=CH—, or, (R$^{3-10}$)(R$^{3-11}$)C=C(R$^{3-12}$)—C(=O)—NH—, is located in the para position relative to the N atom (not G) in

of the compound I.

In an embodiment, the definitions of some substituents in the compound I can be as follows, and the definitions of the non-mentioned substituents are all as defined in any one of the embodiments above:

when none of R$^3$ is (R$^{3-10}$)(R$^{3-11}$)C=C(R$^{3-12}$)—C(=O)—NH—, then the E can be

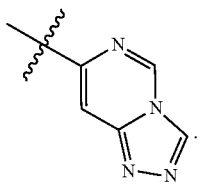 [SMILES: *c1cc2nncn2cn1]

In an embodiment, the definitions of some substituents in the compound I can be as follows, and the definitions of the non-mentioned substituents are all as defined in any one of the embodiment above:

the "R$^{3-1}$ substituted or unsubstituted 3-7 membered heterocycloalkyl containing 1-4 heteroatoms selected from the group consisting of N, O and S" can be

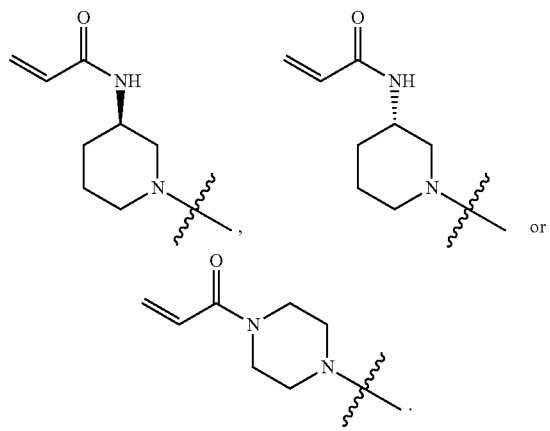

In an embodiment, the definitions of some substituents in the compound I can be as follows, and the definitions of the non-mentioned substituents are all as defined in any one of the embodiments above:

the R$^{3-2}$ substituted or unsubstituted 5-7 membered cycloalkenyl can be

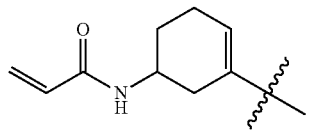

In an embodiment, the definitions of some substituents in the compound I can be as follows, and the definitions of the non-mentioned substituents are all as defined in any one of the embodiments above:

the "R$^{3-3}$ substituted or unsubstituted 5-7 membered heterocycloalkenyl containing 1-4 heteroatoms selected from the group consisting of N, O and S" can be

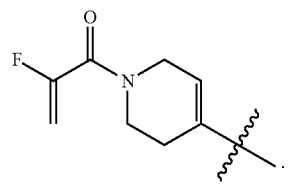

In an embodiment, the definitions of some substituents in the compound I can be as follows, and the definitions of the non-mentioned substituents are all as defined in any one of the embodiments above:

the "R$^{3-5}$ substituted or unsubstituted 5-6 membered heteroaryl containing 1-3 heteroatoms selected from the group consisting of N, O and S" can be

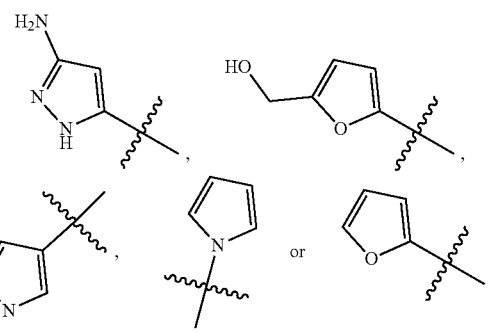

In an embodiment, the definitions of some substituents in the compound I can be as follows, and the definitions of the non-mentioned substituents are all as defined in any one of the embodiments above:

the NR$^{3-6}$R$^{3-7}$— can be

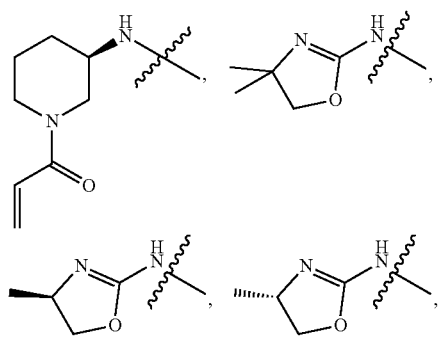

-continued

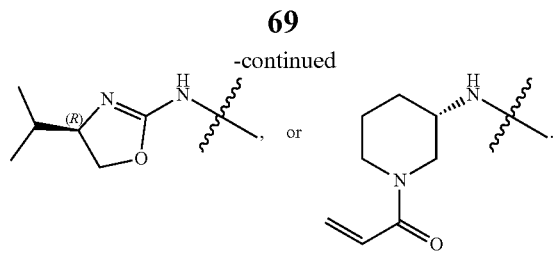

In an embodiment, the definitions of some substituents in the compound I can be as follows, and the definitions of the non-mentioned substituents are all as defined in any one of the embodiments above:

the $(R^{3-8})(R^{3-9})N\text{—}(Z)\text{—}HC\text{=}CH\text{—}$ can be

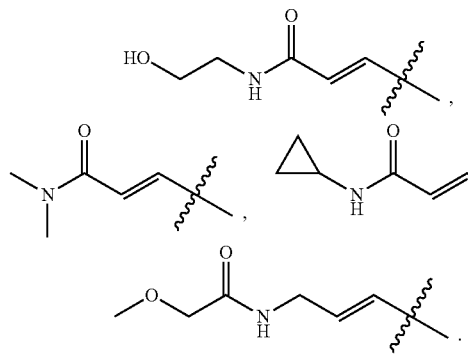

In an embodiment, the definitions of some substituents in the compound I can be as follows, and the definitions of the non-mentioned substituents are all as defined in any one of the embodiments above:

the $(R^{3-10})(R^{3-11})C\text{=}C(R^{3-12})\text{—}C(\text{=}O)\text{—}NH\text{—}$ can be

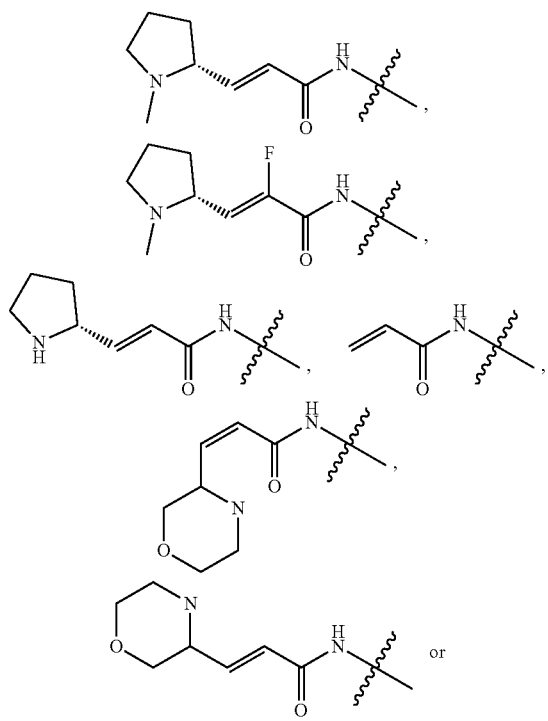

-continued

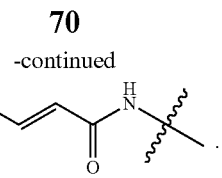

In an embodiment, the definitions of some substituents in the compound I can be as follows, and the definitions of the non-mentioned substituents are all as defined in any one of the embodiments above:

the $(R^{3-10})(R^{3-11})C\text{=}C(R^{3-12})\text{—}C(\text{=}O)\text{—}NH\text{—}$ can be

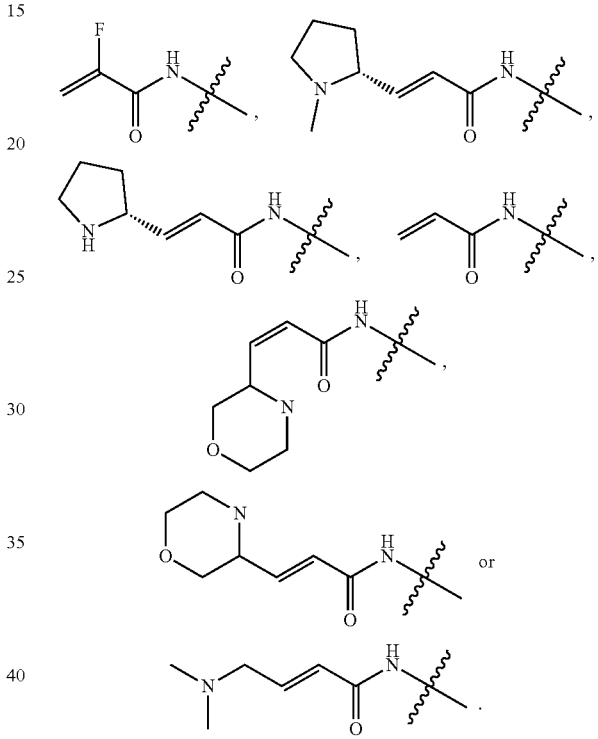

The compound I can be one of the compounds as follows:

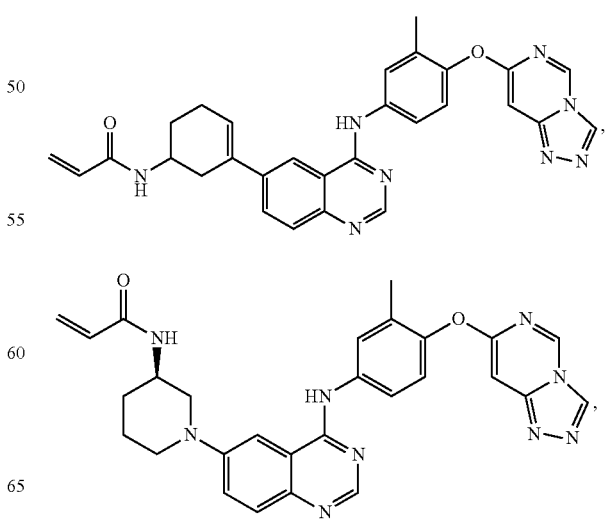

71
-continued
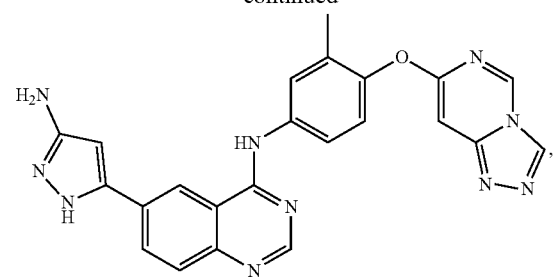
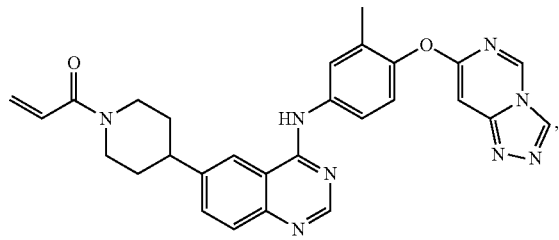
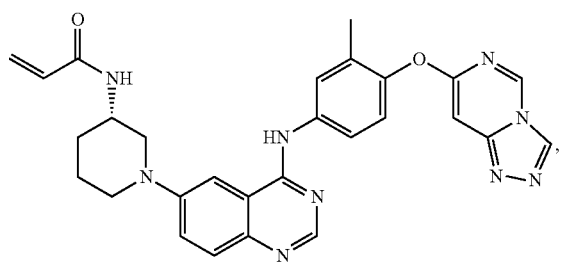
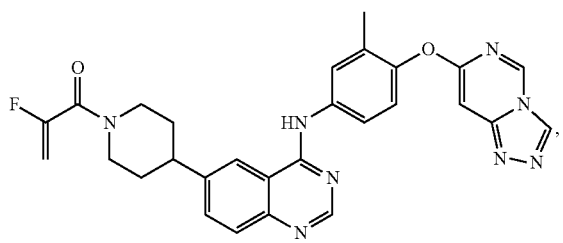
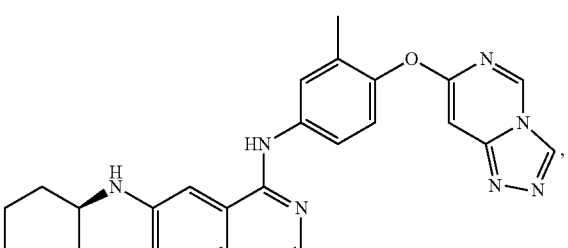
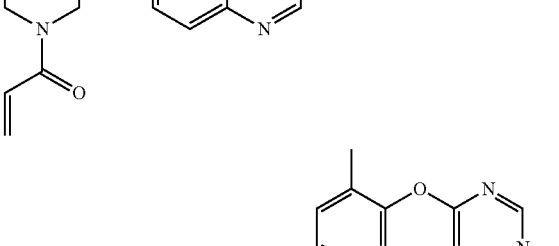
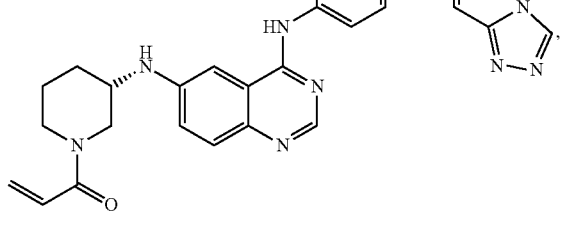
72
-continued
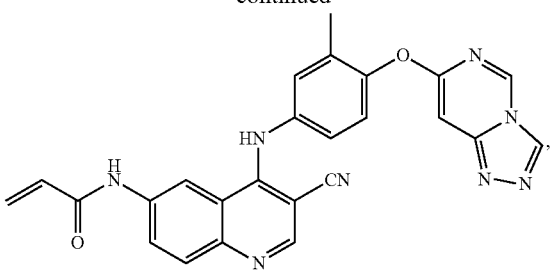
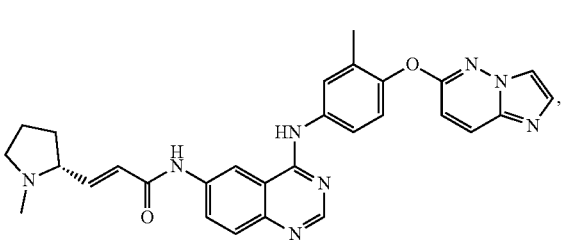
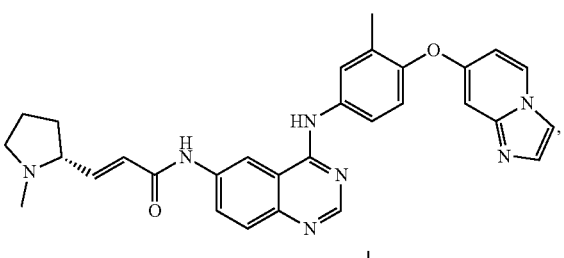
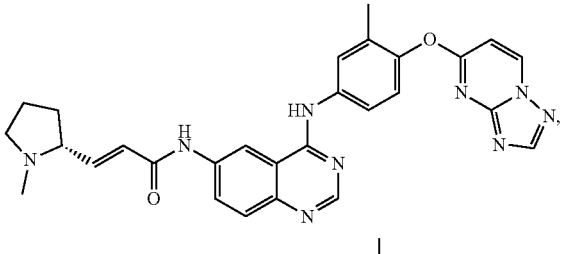
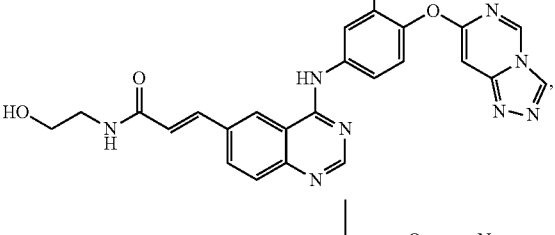
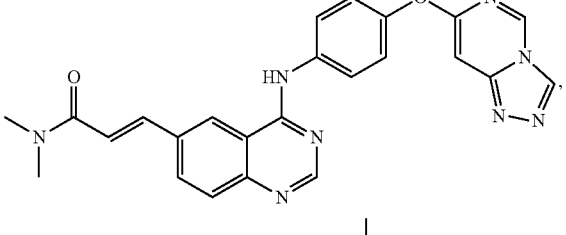
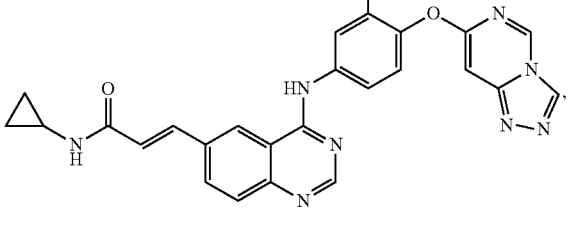

73
-continued
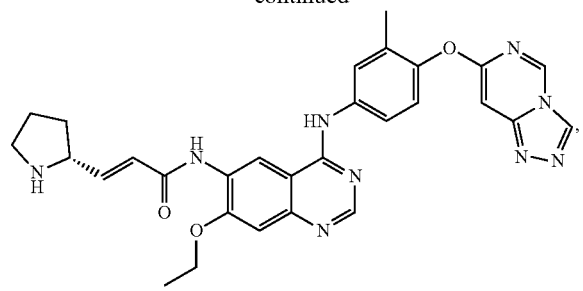
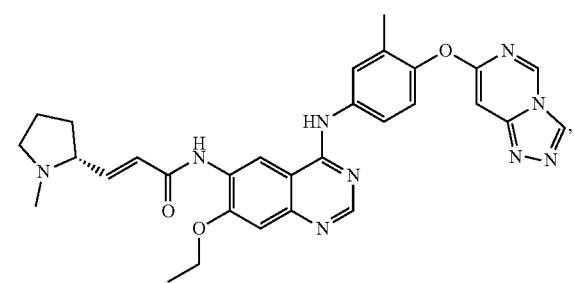
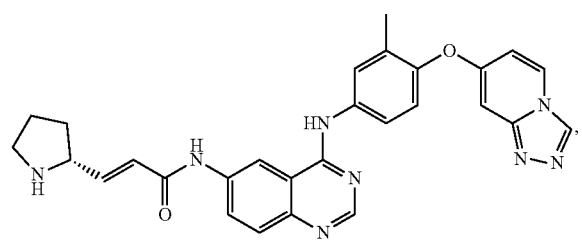
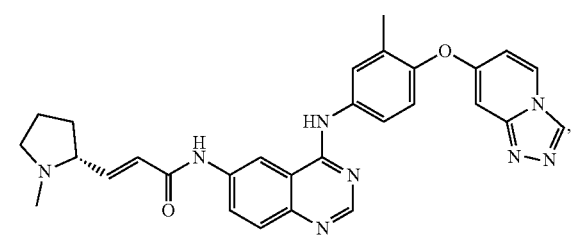
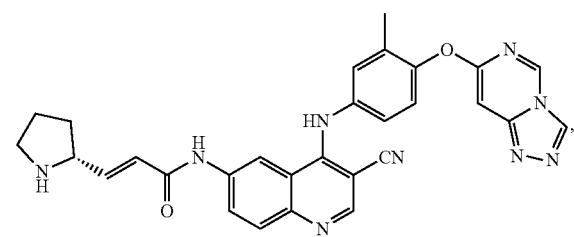
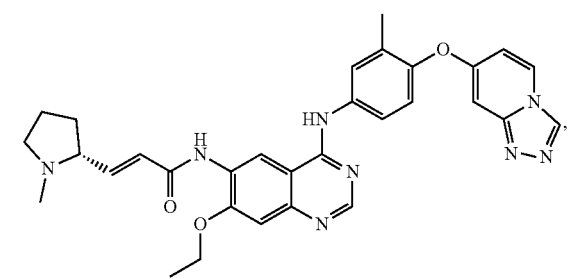
74
-continued
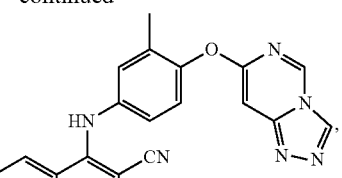
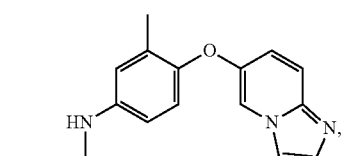
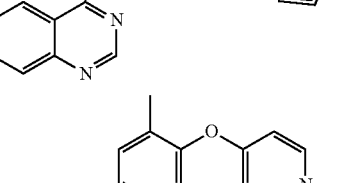
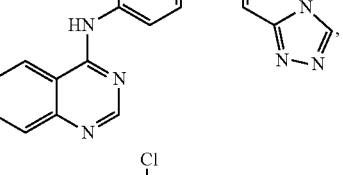
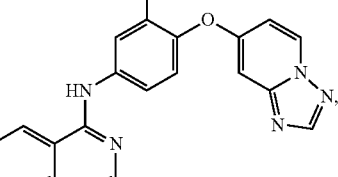
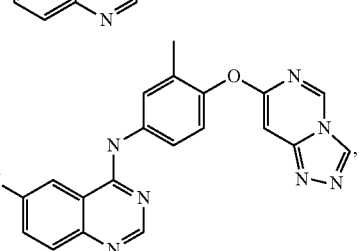
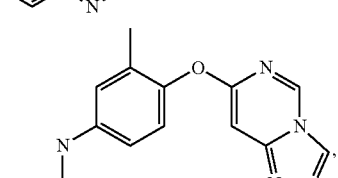
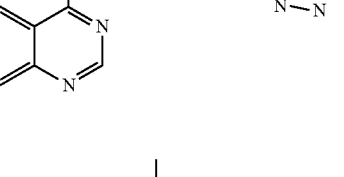
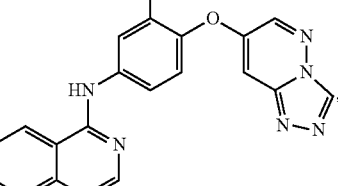

75
-continued
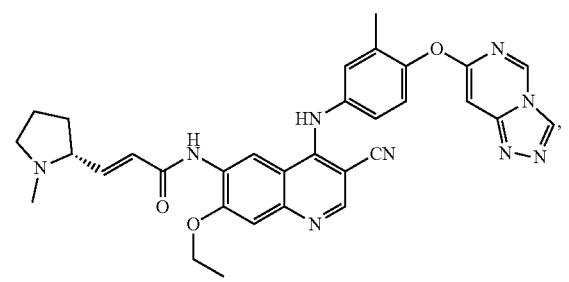
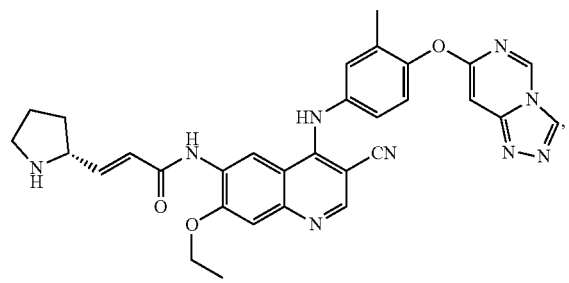
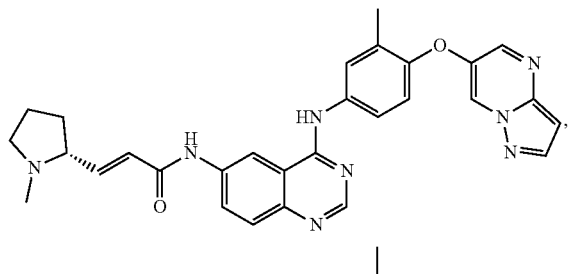
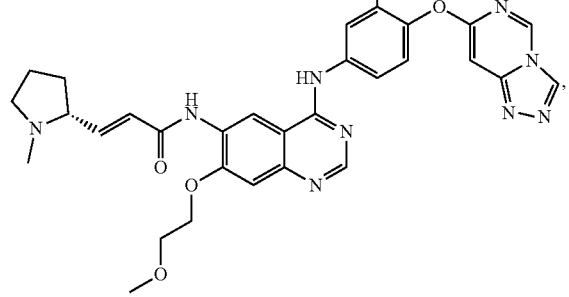
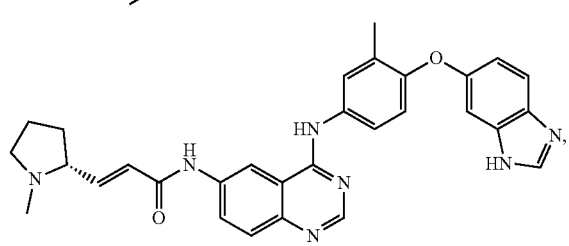
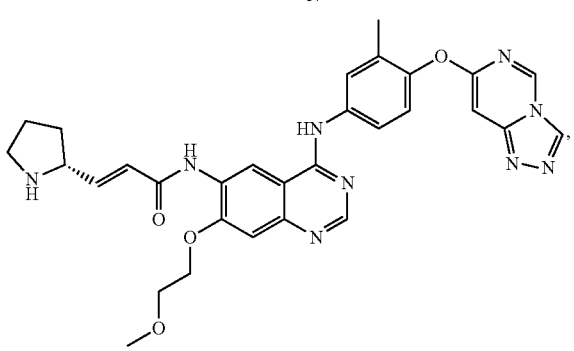
76
-continued
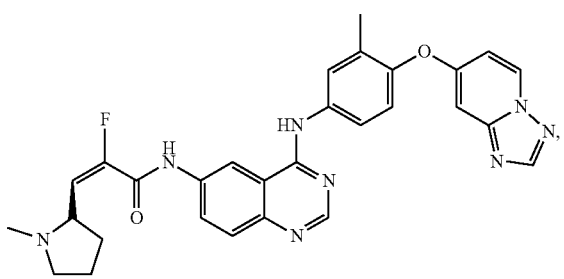
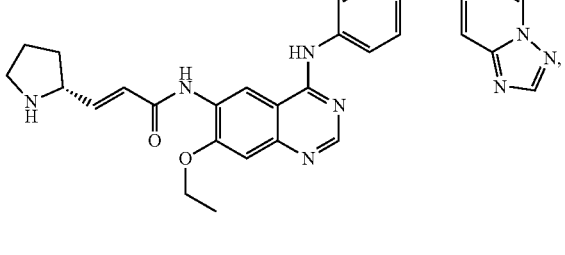
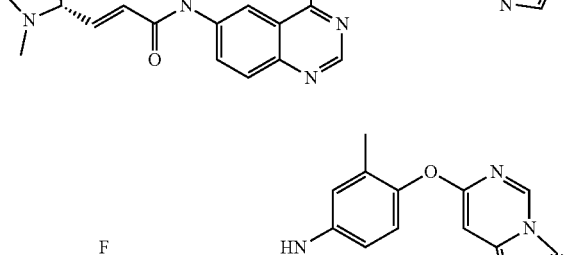
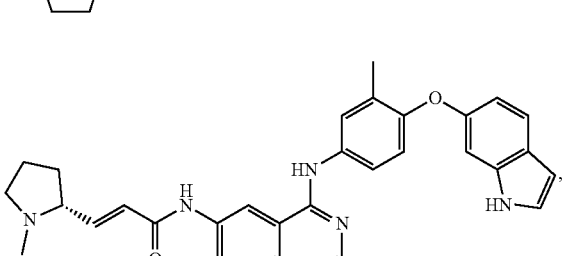
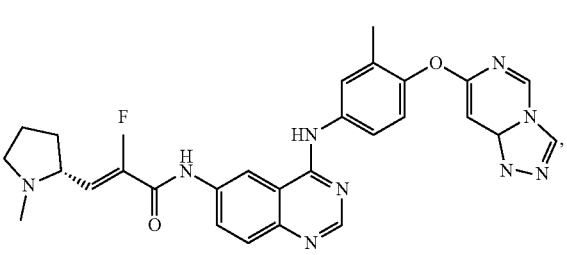

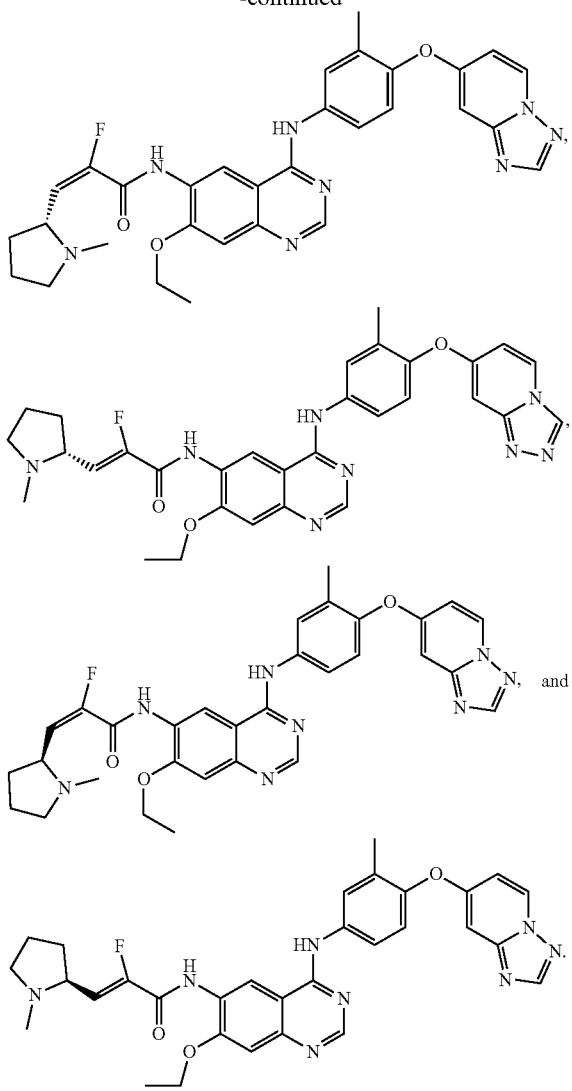

and

The nitrogenous heterocyclic compounds involved in the present disclosure can exhibit tautomerism, structural isomerism and stereoisomerism. The present application includes any tautomeric or structural isomeric or stereoisomeric forms thereof and mixtures thereof.

Compound I can be synthesized by methods similar to those known in the field of chemistry, especially according to the description herein. The starting materials are usually from commercial sources such as Aldrich or can be easily prepared using methods known to those skilled in the art (obtained from SciFinder, Reaxys online databases).

For illustrative purposes, schemes 1-5 have shown general methods for preparing the compounds of the present application and key intermediates. For more detailed descriptions of each reaction step, the following embodiments section can be referred. Those skilled in the art understand that there are other synthetic routes that can be used to synthesize the compounds of the present application. Although specific starting materials and reagents are described in the schemes and the following discussion, they can be easily replaced with other starting materials and reagents in order to provide various derivatives and/or reaction conditions. In addition, various compounds prepared by the methods described below can be further modified according to the present disclosure using conventional chemical methods known to those skilled in the art.

The present disclosure also provides a method for preparing the compound I, which is any one of the following schemes:

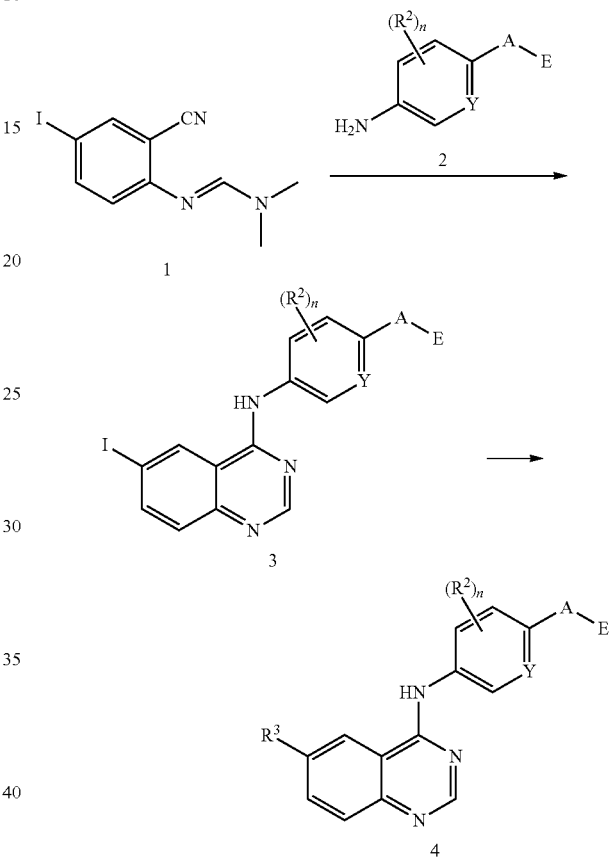

In the compound (4), $R^3$ is preferably a group which can be connected through standard Suzuki, Heck or Stille reaction.

Scheme 1 illustrates an optional synthetic route of the quinazoline compound (4) of the present application, wherein A and E are as defined herein. 4-Anilino-6-iodo-quinazoline (3) can be prepared by reacting (E)-N'-(2-cyano-4-iodophenyl)-N,N-dimethylformamidine (1) with compound (2) according to Scheme 1. The obtained iodo-quinazoline (3) is subjected to palladium-mediated cross-coupling reaction with a suitable olefin compound to give compound (4), which can be completed by treating in a suitable organic solvent such as THF, DME, DMF or toluene using a palladium catalyst such as $Pd(OAc)_2$, $Pd(PPh_3)_4$, $Pd(dppf)_2Cl_2$, $Pd_2(dba)_3$, a phosphine ligand and a base.

That is, the method for preparing compound (4) includes the following steps: conducting a coupling reaction between compound (3) and a substituted olefin in an organic solvent (such as THF, DME, DMF or toluene) in the presence of a palladium catalyst (such as $Pd(OAc)_2$, $Pd(PPh_3)_4$, $Pd(dppf)_2Cl_2$, $Pd_2(dba)_3$), a phosphine ligand and a base to give compound (4).

Scheme 2

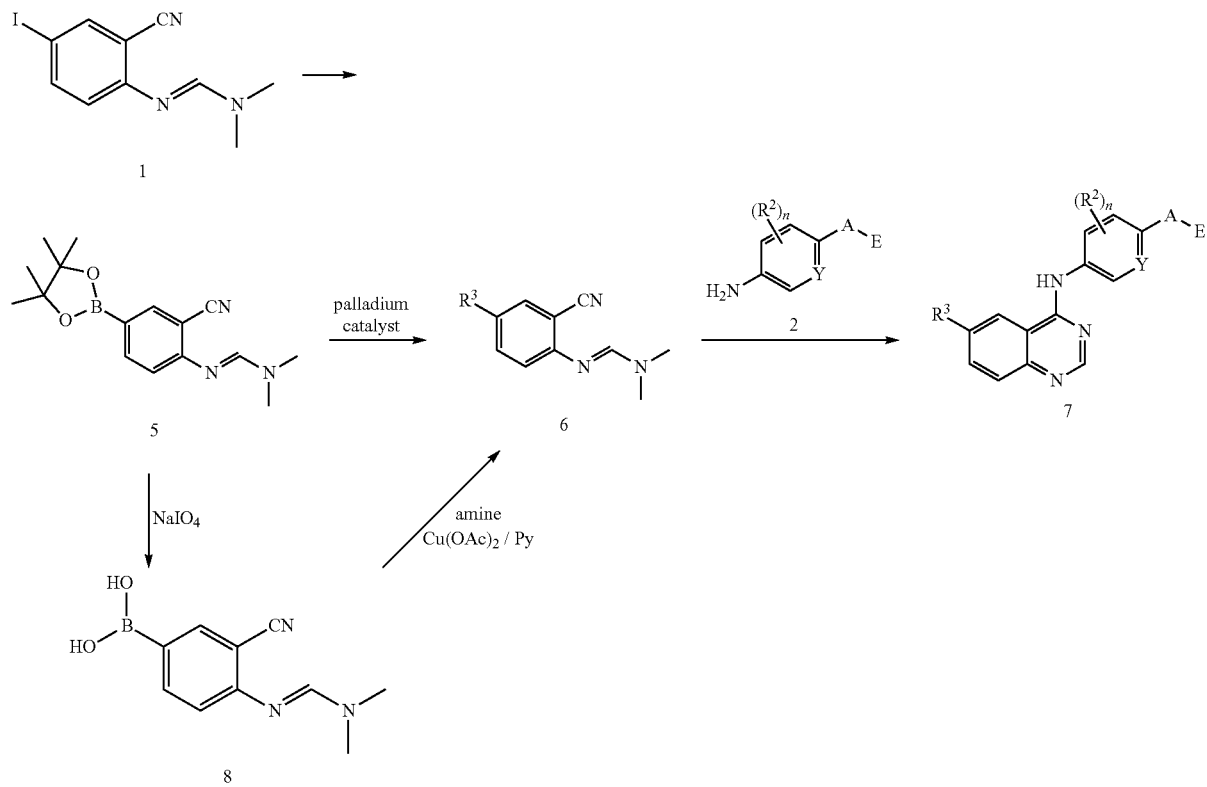

In the compound (7), R³ is preferably a group which can be connected through standard Suzuki, Heck or Stille reaction.

Scheme 2 illustrates an optional synthetic route of the quinazoline compound (7) of the present application, wherein A and E are as defined herein. According to Scheme 2, compound (5) can be prepared by reacting (E)-N'-(2-cyano-4-iodophenyl)-N,N-dimethylformamidine (1) with borate. The obtained borate compound (5) is subjected to palladium-mediated cross-coupling reaction with a suitable halogenated aryl (or halogenated heteroaryl) compound or an olefin compound to give compound (6), which can be completed by treating in a suitable organic solvent such as THF, DME, DMF or toluene using a palladium catalyst such as $Pd(OAc)_2$, $Pd(PPh_3)_4$, $Pd(dppf)_2Cl_2$, $Pd_2(dba)_3$, a phosphine ligand and a base. Compound (6) is condensed with a suitable aniline (2) in the presence of an acid such as HOAc in a suitable organic solvent such as isopropyl acetate (IPAc) to give quinazoline compound (7). Scheme 2 also illustrates the preparation of N-linked compound (7). These analogs can be prepared from compound (8) by copper-mediated cross-coupling reaction with boric acid compounds under standard Chan-Lam reaction conditions known in the art.

That is, the method for preparing compound 7 includes the following steps: conducting a couple reaction between compound (5) and a halogenated aromatic ring or a heteroaromatic ring or a olefin compound to give compound (6) in an organic solvent (such as THF, DME, DMF or toluene), in the presence of a palladium catalyst (such as $Pd(OAc)_2$, $Pd(PPh_3)_4$, $Pd(dppf)_2Cl_2$, $Pd_2(dba)_3$), a phosphine ligand and a base, then the compound (2) is condensed in the presence of an acid such as HOAc in a suitable organic solvent such as isopropyl acetate to give compound 7.

The method for preparing compound (7) comprises the following steps: conducting a coupling reaction between compound (8) and a boric acid compound in the presence of a copper catalyst, and then conducting a condensation reaction with compound (2) to give compound (7).

Scheme 3

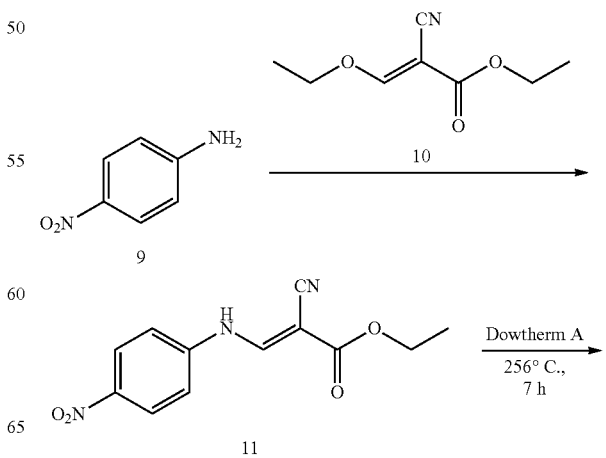

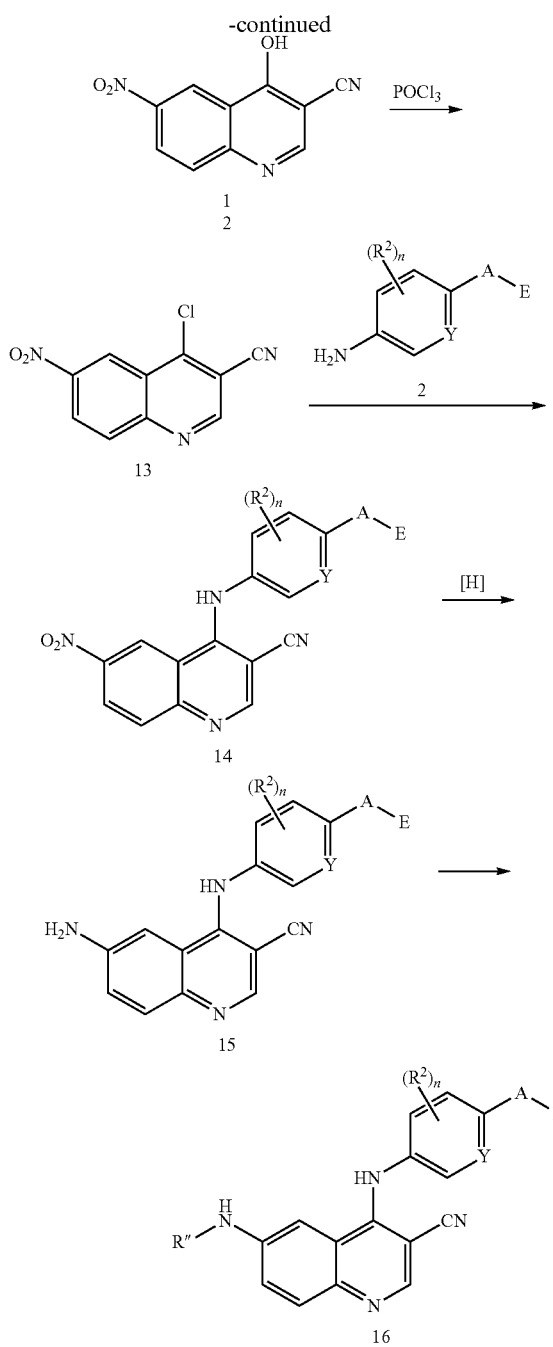

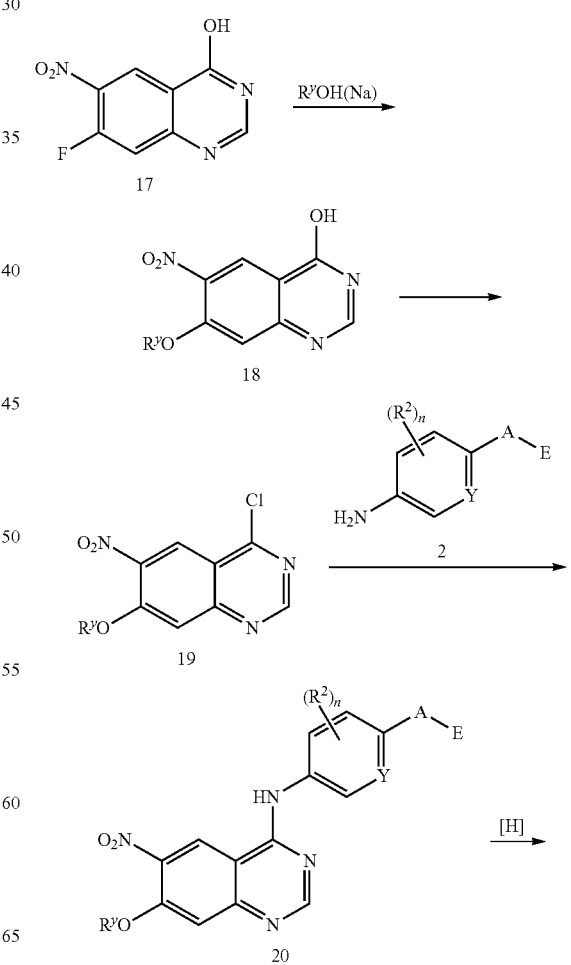

agent such as thionyl chloride, phosphorus oxychloride and the like to give compound (13). Compound (13) is then condensed with a suitable aniline (2) in the presence of an acid such as HOAc in a suitable organic solvent such as isopropyl acetate (IPAc) to give quinazoline compound (14). The reduction of the nitro group of compound (14) can be conducted by standard reduction methods such as Pd/C with $H_2$, Pd/C with hydrazine, Ni with $H_2$, Ni with hydrazine, Pt/C with NaOH, and $H_2$ with Zn/AcOH, Zn/NH$_4$Cl, Fe/NH$_4$Cl or Fe/HOAc. When $R^2$ is halogen, reduction can be achieved using Pt/C with NaOH and $H_2$ or Zn/NH$_4$Cl. The obtained aniline (15) can be subjected to condensation reaction with carboxylic acid or acyl chloride to give compound (16).

That is, the method for preparing compound 7 includes the following steps: conducting a reaction between compound (13) and compound (2) in an organic solvent (such as DCM, IPAc or toluene) in the presence of an acid (such as HOAc) to give compound (14), then reducing the nitro to amino compound (15), and then conducting a condensation reaction with acyl chloride or carboxylic acid to give compound (16).

wherein, R″ is CH=CH(C=O)— or $(R^{3-10})(R^{3-11})C=C(R^{3-12})—C(=O)—$;

In the compound (16), R″ is preferably a group that can be connected through a standard acid-base condensation reaction.

Scheme 3 illustrates an optional synthetic route of the quinazoline compound (16) of the present application, wherein A and E are as defined herein. According to Scheme 2, compound (11) can be prepared by the reaction of p-nitroaniline (9) with compound (10). The obtained compound (11) is subjected to an intramolecular cyclization reaction at a high temperature to give compound (12), and the compound (12) is reacted with a suitable chlorinating

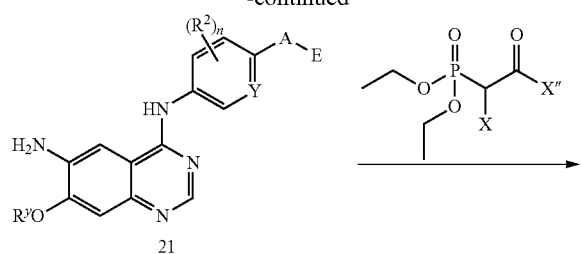

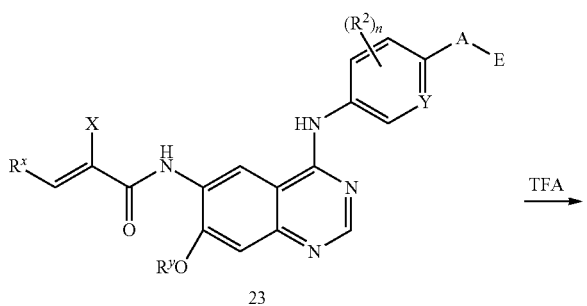

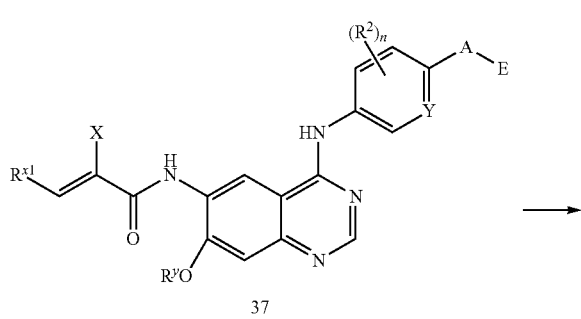

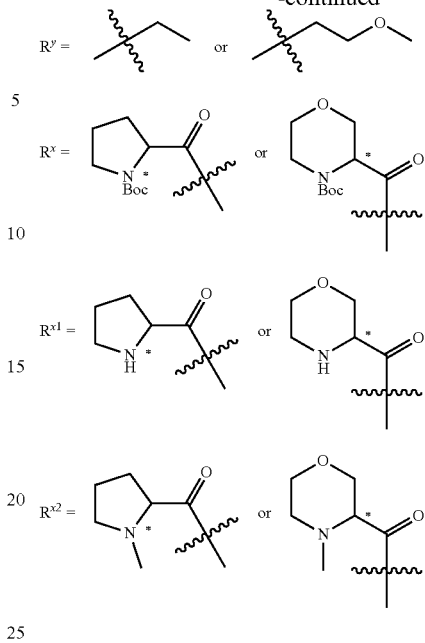

wherein X is H or F. X" represents that when X=F, X"=C$_1$; when X=H, X"=OH. * represents that the configuration of the chiral carbon atom attached to the olefin is an R configuration or an S configuration or a mixture thereof.

Scheme 4 illustrates the synthesis of quinazoline (24) linked with acrylamide side chain of the present application, wherein A and E are as defined herein. 7-fluoro-6-nitroquinazolin-4-ol (17) can be reacted with a suitable alcohol under alkaline conditions or directly with sodium alkoxide to give compound (18) according to Scheme 4. Compound (18) is reacted with a chlorinated reagent such as thionyl chloride, phosphorus oxychloride and the like to give chloride (19). The chloride (19) is condensed with the compound (2) according to the method described in the above scheme to give the quinazoline compound (20). This quinazoline compound (20) is subjected to hydrogenation, acid-amine condensation reaction to give compound (22). Compound (22) is reacted with an appropriate aldehyde (a single configuration or a racemate) in the presence of an organic base such as NaH, LiHMDS, etc. to give compound (23). Finally, the protecting group such as Boc in the compound (23) is removed under acidic condition such as trifluoroacetic acid to give the compound (37) which is then reacted with a methylating agent such as methyl iodide, dimethyl sulfate or aqueous formaldehyde solution. In order to prevent the compound from being substituted by multiple methyl groups, the reductive amination is preferred to be conducted, that is, conducting a reaction of compound (37) with aqueous formaldehyde solution/sodium boroacetate or sodium cyanoborohydride to give compound (24).

Scheme 5

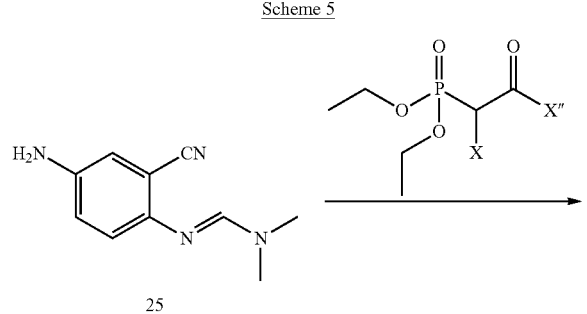

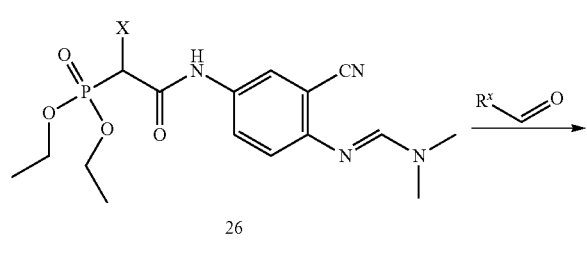

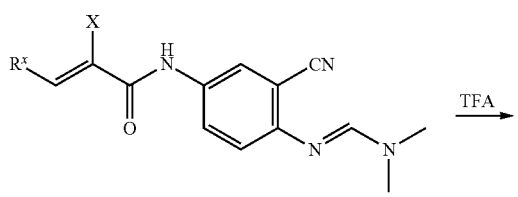

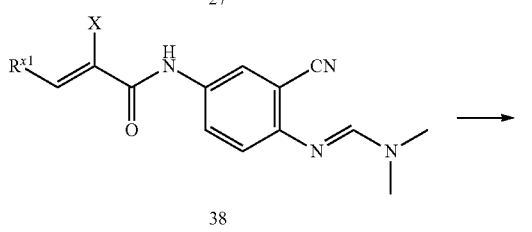

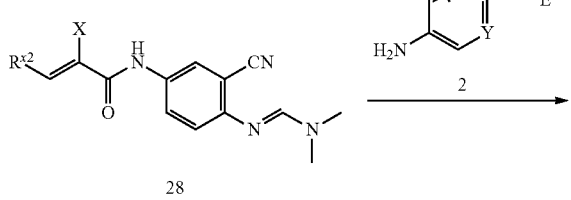

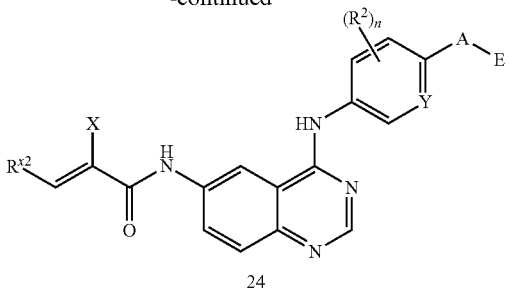

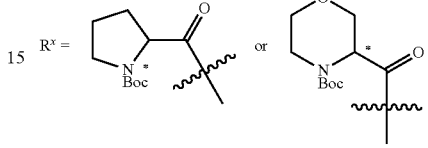

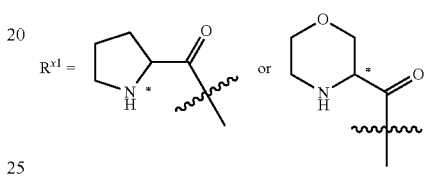

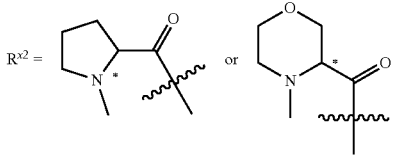

wherein X is H or F. X" represents that when X=F, X"=Cl; when X=H, X"=OH. * represents that the configuration of the chiral carbon atom attached to the olefin is an R configuration or an S configuration or a racemate.

Scheme 5 illustrates another synthesis method of the quinazoline (24) linked with acrylamide side chain of the present application, wherein A and E are as defined herein. According to Scheme 5 and the synthesis method described in Scheme 4, compound (28) linked with acrylamide side chain is first synthesized and then condensed with an appropriate compound (2) to give compound (24). The advantage of this synthesis method is that it can react with a plurality of suitable compounds (2) in parallel, reducing the dosage of compound (2) that is difficult to synthesize, and avoiding damage to compound (2) and the intermediates already obtained by the reaction of compound (2) in the presence of alkaline conditions such as NaH that occur in Scheme 4.

The method for preparing the compound I can further comprise scheme a:

Scheme a

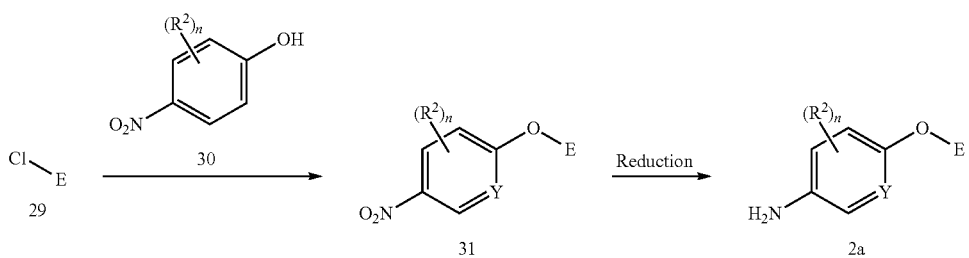

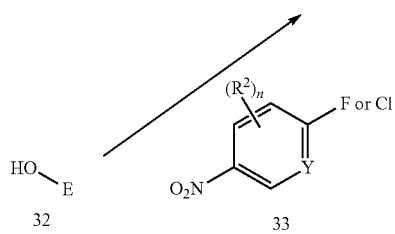

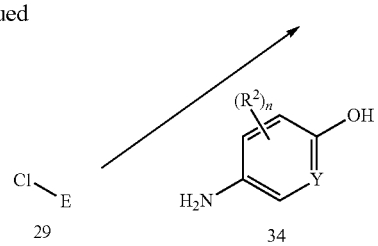

Scheme a illustrates a method for preparing aniline intermediate (2a) suitable for schemes 1-5 from chloride (29) and 4-hydroxynitrobenzene (30) or compound phenol (32) and 4-fluoronitrobenzene (33), respectively. Chloride (29) and nitrophenol (30) or compound phenol (32) and 4-fluoro (or chloro) nitrobenzene (33) are commercially available or known in the literature, or can be prepared by standard methods by those skilled in the art. A coupling product (31) can be prepared by the reaction of chloride (29) with substitutable 4-hydroxynitrobenzene (30) or the reaction of compound phenol (32) with 4-fluoro (or chloro) nitrobenzene (33) and a suitable base such as sodium carbonate, potassium carbonate or cesium carbonate in a polar organic solvent such as DMF, DMSO at a high temperature. The reduction of the nitro group of compound (31) can be conducted using standard reduction methods such as Pd/C with $H_2$, Pd/C with hydrazine, Ni with $H_2$, Ni with hydrazine, Pt/C with NaOH, and $H_2$ with Zn/AcOH, Zn/$NH_4$Cl or Fe/HOAc. When $R^2$ is halogen, reduction can be achieved using Pt/C with NaOH and $H_2$ or Zn/$NH_4$Cl.

Scheme a also illustrates that chloride (29) is directly reacted with amino compound (34) in a suitable base such as potassium carbonate or cesium carbonate in a polar organic solvent such as DMF and DMSO at high temperature to give an aniline intermediate (2a) suitable for schemes 1-5.

The scheme a may further include schemes (i) and (ii):

Scheme (i)

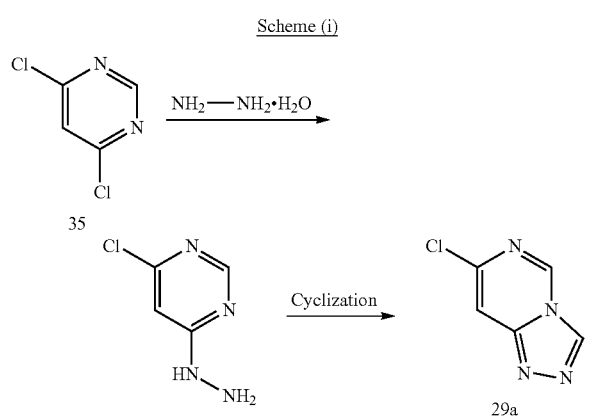

Scheme (i) illustrates a method for preparing a chloro intermediate (29a) suitable for use in Scheme a. The reaction of the substituted dichloropyrimidine (35) with hydrazine can be conducted in a solvent, for example, alcohol. The compound obtained is then subjected to a reaction with a carboxylic acid equivalent such as triethyl orthoformate or trimethyl orthoformate and an acid such as HCl, HOAc or p-toluenesulfonic acid. In one embodiment, the cyclization reaction is conducted using trimethyl orthoformate and p-toluenesulfonic acid to give a triazole.

Scheme (ii)

Scheme (i) illustrates a method for preparing a compound phenol intermediate (32a) suitable for use in Scheme a. The reaction of the substituted dichloropyridazine (36) can be conducted under alkaline conditions to give hydroxypyridazine (37), followed by the reaction with hydrazine in a solvent, for example, 1,4-dioxane. The compound obtained is then subjected to a reaction with a carboxylic acid equivalent such as triethyl orthoformate or trimethyl orthoformate and an acid such as HCl, HOAc or p-toluenesulfonic acid. In one embodiment, the cyclization reaction is conducted using trimethyl orthoformate and p-toluenesulfonic acid to give a triazole.

In any synthesis method for preparing compound I, it may be advantageous to separate the reaction products from each other or from the starting materials. The desired products of each step or series of steps are separated and/or purified to a desired degree of homogeneity by techniques conventional in the art. This separation involves, for example, multiphase extraction, crystallization from solvents or a mixture of solvents, or chromatographic separation. The chromatographic separation can involve many methods, including: normal phase and reverse phase, high pressure, medium pressure and low pressure liquid chromatography methods and devices; preparative thin or thick layer chromatography.

The selection of suitable separation methods depends on the properties of the compounds involved, for example, the chromatographic separation methods depends on the presence or absence of a polar functional group, the multiphase extraction in an acidic and alkaline media depends on the stability of the substances, etc. Those skilled in the art can employ the technology by which the desired separation is most likely to be achieved. The separation of enantiomers can be carried out by using chiral HPLC columns.

The present disclosure also provides a compound 20, 21, 22, 23, 37, 26, 27, 38 or 28 as shown below:

20

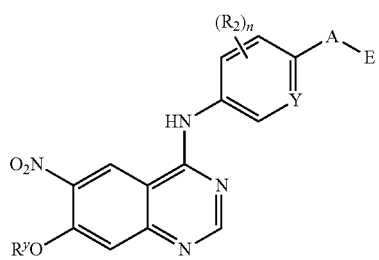

21

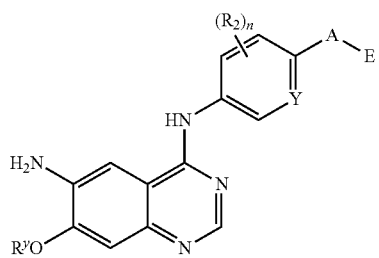

22

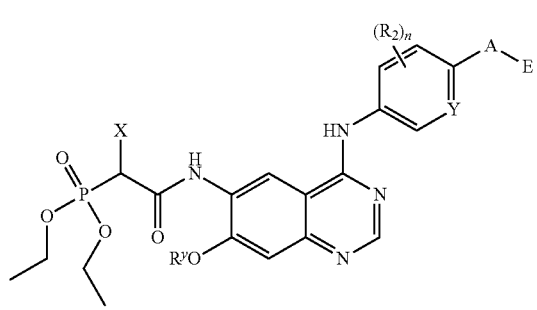

23

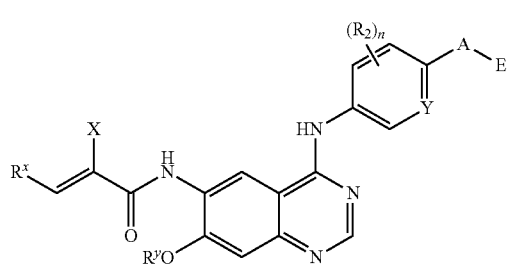

37

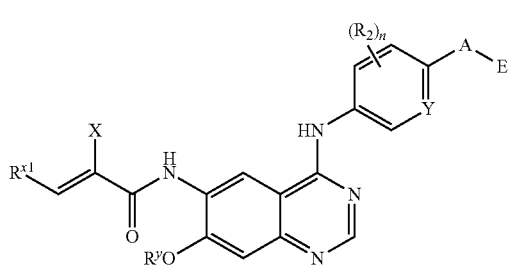

26

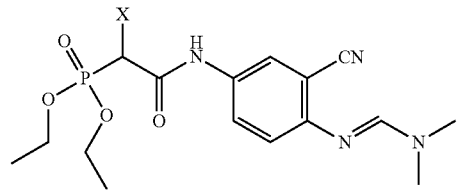

27

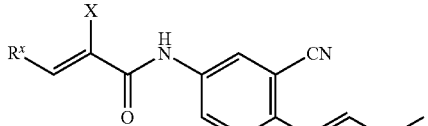

38

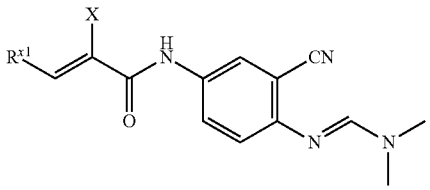

28

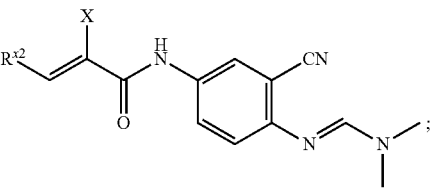

wherein,

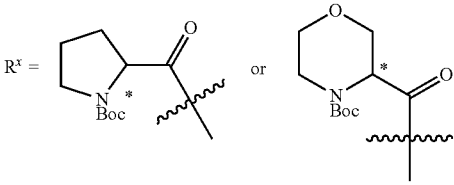

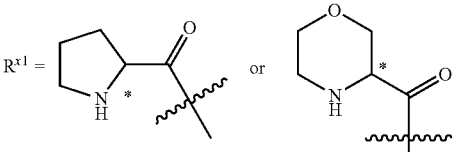

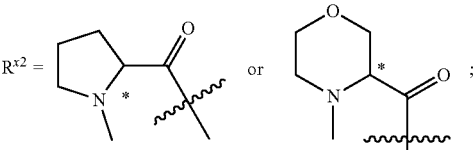

A, E, n, $R^2$, n, X and $R^y$ are as defined above.

The present disclosure also provides a use of the nitrogenous heterocyclic compound, the pharmaceutically acceptable salt thereof, the enantiomer thereof, the diastereomer thereof, the tautomer thereof, the solvate thereof, the metabolite thereof or the prodrug thereof in manufacturing a medicament, the medicament is used for treating a disease by inhibiting EGFR and/or ErbB2 receptor tyrosine kinase.

The "disease treated by selective inhibition of ErbB2 receptor tyrosine kinase" can be breast cancer, gastric cancer and the like (for example, Neratinib for treating breast cancer is an oral irreversible EGFR/ErbB2 inhibitor, referring to ExteNet and NEfERTT clinical trials).

The present disclosure also provides a use of the nitrogenous heterocyclic compound, the pharmaceutically acceptable salt thereof, the enantiomer thereof, the diastereomer thereof, the tautomer thereof, the solvate thereof, the metabolite thereof or the prodrug thereof in manufacturing an inhibitor for EGFR and/or ErbB2 receptor tyrosine kinase. The inhibitor for EGFR and/or ErbB2 receptor tyrosine kinase may be a selective inhibitor for ErbB2 receptor tyrosine kinase.

The present disclosure also provides a pharmaceutical composition comprising the nitrogenous heterocyclic compound, the pharmaceutically acceptable salt thereof, the enantiomer thereof, the diastereomer thereof, the tautomer thereof, the solvate thereof, the metabolite thereof or the prodrug thereof, and at least one pharmaceutical excipient.

The dosage of the nitrogenous heterocyclic compound, the pharmaceutically acceptable salt thereof, the enantiomer thereof, the diastereomer thereof, the tautomer thereof, the solvate thereof, the metabolite thereof or the prodrug thereof can be a therapeutically effective amount.

The selection of the pharmaceutic adjuvant varies depending on the routes of administration and the characteristic of action, and can generally be fillers, diluents, adhesives, wetting agents, disintegrants, lubricants, emulsifiers, suspending agents and the like conventional in the art.

The pharmaceutical composition can be administered by oral administration, injection (intravenous, intramuscular, subcutaneous and intracoronary), sublingual administration, buccal administration, transrectal administration, transurethral administration, transvaginal administration, nasal administration, inhalation or topical administration, preferably oral administration.

In the present disclosure, unless otherwise specified, the following terms in the description and claims of the present disclosure have the following meanings:

The term "alkyl" refers to a saturated linear or branched monovalent hydrocarbon group containing one to twelve carbon atoms (e.g., $C_1$-$C_6$ alkyl, also for example, $C_1$-$C_4$ alkyl). Examples of alkyl include, but are not limited to, methyl, ethyl, 1-propyl, 2-propyl, 1-butyl, 2-methyl-1-butyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl.

The term "alkenyl" refers to a linear or branched monovalent hydrocarbon group containing two to twelve carbon atoms having at least one unsaturated position, i.e., a carbon-carbon $sp^2$ double bond (e.g., $C_2$-$C_6$ alkenyl, also e.g., $C_2$-$C_4$ alkenyl), and includes the groups having "cis" and "trans" orientations or "E" and "Z" orientations. Examples thereof include, but are not limited to, vinyl, allyl, 1-cyclopenta-1-enyl, 1-cyclopenta-2-enyl, 1-cyclopenta-3-enyl, 5-hexenyl, 1-cyclohex-1-enyl, 1-cyclohex-2-enyl, and 1-cyclohex-3-enyl.

The term "alkynyl" refers to a linear or branched monovalent hydrocarbon group containing two to twelve carbon atoms having at least one unsaturated position, i.e., carbon-carbon sp triple bond (e.g., $C_2$-$C_6$ alkynyl, also e.g., $C_2$-$C_4$ alkynyl). Examples thereof include, but are not limited to, ethynyl and propynyl.

The terms "cycloalkyl", "carbocyclyl", and "carbocycle" are interchangeable and refer to a non-aromatic saturated or partially unsaturated monovalent cyclic hydrocarbon radical having three to ten carbon atoms (e.g., $C_3$-$C_6$ cycloalkyl). Examples of monocyclic carbocyclic group include, but are not limited to, cyclopropyl, cyclobutyl, cyclopentyl, 1-cyclopenta-1-enyl, 1-cyclopenta-2-enyl, 1-cyclopenta-3-enyl, cyclohexyl, 1-cyclohex-1-enyl, 1-cyclohex-2-enyl, 1-cyclohex-3-enyl, cyclohexdienyl, cycloheptyl, cyclooctyl, cyclononyl, cyclodecyl, cycloundecyl, and cyclododecyl. The term "cycloalkyl" also includes polycyclic (e.g., bicyclic and tricyclic) cycloalkyl structures, wherein the polycyclic structure optionally includes saturated or partially unsaturated cycloalkyl fused with saturated or partially unsaturated cycloalkyl or heterocyclyl or aryl or heteroaryl. The bicyclic carbocycle having 7 to 12 atoms may be arranged, for example, as a bicyclic [4,5], [5,5], [5,6] or [6,6] system, or as a bridged ring system, for example, biscyclo[2.2.1]heptane, bicyclo[2.2.2]octane, and bicyclo[3.2.2]nonane.

The term "heteroalkyl" refers to a saturated linear or branched monovalent hydrocarbon group containing one to twelve carbon atoms (e.g., $C_1$-$C_6$ heteroalkyl, also e.g., $C_1$-$C_4$ heteroalkyl), wherein at least one carbon atom is replaced by a heteroatom selected from the group consisting of N, O and S, and wherein the group may be a carbon group or a heteroatom group (i.e., the heteroatom may be located in the middle or at the end of the group). The term "heteroalkyl" includes alkoxy and heteroalkoxy.

The term "heteroalkenyl" refers to a linear or branched monovalent hydrocarbon group containing two to twelve carbon atoms having at least one double bond, e.g., vinyl, propenyl, etc., wherein at least one carbon atom is replaced by a heteroatom selected from the group consisting of N, O and S, and wherein the group may be a carbon group or a heteroatom group (i.e., heteroatoms may be located in the middle or at the end of the group). Heteroalkenyl includes a group having "cis" and "trans" orientations or "E" and "Z" orientations.

The term "heteroalkynyl" refers to a linear or branched monovalent hydrocarbon group containing two to twelve carbon atoms having at least one triple bond. Examples thereof include, but are not limited to, ethynyl, propynyl, and the like, wherein at least one carbon atom is replaced by a heteroatom selected from the group consisting of N, O and S, wherein the atomic group may be a carbon group or a heteroatom group (i.e., a heteroatom may be located in the middle or at the end of the group).

The terms "heterocycle" and "heterocyclyl" are used interchangeably and refer to saturated and partially unsaturated carbocyclic groups containing 3 to 8 ring atoms, wherein at least one ring atom is independently a heteroatom selected from the group consisting of N, O, S, SO and $SO_2$, and the remaining ring atoms are C. The group may be a carbon group or a heteroatom group. The term "heterocyclyl" includes heterocycloalkoxy. "Heterocyclyl" also includes a group in which a heterocyclyl is fused to a saturated, partially unsaturated, or completely unsaturated (i.e., aromatic) carbocyclic or heterocyclic ring. Examples of heterocyclyl include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, 4-thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, dihydroindolyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolinyl, 3-azabicyclo[3.1.0]hexanyl, 3-azabicyclo[4.1.0]heptanyl, azabicyclo[2.2.2]hexanyl, 3H-indolyl, quinolizinyl and N-pyridinyl urea. A spiro moiety is also included within the scope of this definition. The heterocyclyl may be C-attached or N-attached as long as it is possible. For example, a group derived from pyrrole may be pyrrol-1-yl (N-attached) or pyrrol-3-yl (C-attached). In addition, the group derived from imidazole may be imidazol-1-yl (N-attached) or imidazol-3-yl (C-attached). Examples of heterocyclyl in which two carbon atoms on the ring are partially substituted with an oxo (=O) are dihydroisoindol-1,3-dionyl and 1,1-dioxo-thiomorpholinyl.

For example and without limitation, a carbon-bonded heterocycle is bonded at position 2, 3, 4, 5 or 6 of a pyridine; bonded at position 3, 4, 5 or 6 of a pyridazine; bonded at position 2, 4, 5 or 6 of a pyrimidine; bonded at position 2, 3, 5 or 6 of a pyrazine; bonded at position 2, 3, 4 or 5 of a furan, tetrahydrofuran, thiophene, pyrrole or tetrahydropyrrole; bonded at position 2, 4 or 5 of an oxazole, imidazole or thiazole; bonded at position 3, 4 or 5 of isoxazole, pyrazole or isothiazole; bonded at position 2 or 3 of an aziridine; bonded at position 2, 3 or 4 of an azetidine; bonded at position 2, 3, 4, 5, 6, 7 or 8 of a quinoline; or bonded at positions 1, 3, 4, 5, 6, 7 or 8 of an isoquinoline. Further examples of carbon-bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

For example and without limitation, a nitrogen-bonded heterocycle is bonded at position 1 of an aziridine, azetidine, pyrrole, pyrrolidine, 2-pyrroline, 3-pyrroline, imidazole, imidazolene, 2-imidazoline, 3-imidazoline, pyrazole, pyrazoline, 2-pyrazoline, 3-pyrazoline, piperidine, piperazine, indole, indoline, 1H-indazole, at position 2 of an isoindole or dihydroisoindole, at position 4 of a morpholine, and at position 9 of a carbazole or β-carbazoline. More typically, the nitrogen-bonded heterocycle includes 1-aziridinyl, 1-azetidinyl, 1-pyrrolyl, 1-imidazolyl, 1-pyrazolyl, and 1-piperidinyl.

The term "aryl" (including when used alone and contained in other groups) refers to any stable monocyclic or bicyclic carbocyclic ring of up to 7 atoms in each ring, wherein at least one ring is an aromatic ring. Examples of the above aryl include phenyl, naphthyl, tetrahydronaphthyl, 2,3-dihydroindenyl, biphenyl, phenanthryl, anthryl or acenaphthyl. It is understood that in the case where the aryl substituent is a bicyclic substituent and one of the rings is a non-aromatic ring, the connection is made through the aromatic ring.

The term "aromatic hetero group" or "heteroaryl" (including when used alone and contained in other groups) refers to a stable monocyclic or bicyclic ring of up to 7 atoms in each ring, wherein at least one ring is an aromatic ring and contains 1-4 heteroatoms selected from the group consisting of O, N, and S. The heteroaryl within the scope of this definition includes, but is not limited to, acridinyl, carbazolyl, cinnolinyl, quinoxalinyl, pyrazolyl, indolyl, benzotriazole, furanyl, thienyl, benzothienyl, benzofuranyl, quinolinyl, isoquinolyl, oxazolyl, isoxazolyl, indolyl, pyrazinyl, pyridazinyl, pyridinyl, pyrimidyl, pyrryl, tetrahydroquinoline. As defined above for "heterocycloalkyl, "heteroaryl" should also be understood to include the N-oxide derivative of any nitrogenous heteroaryl. In the case where the heteroaryl substituent is a bicyclic substituent and one of the rings is a non-aromatic ring or does not contain heteroatom, it is understood that the connection is made through the aromatic ring or through the heteroatom on the ring, respectively.

The term "arylalkyl" refers to an alkyl moiety (as defined above) substituted by one or more than one aryl moiety (as defined above). Examples of arylalkyl include aryl-$C_{1-3}$-alkyl such as, but not limited to, benzyl, phenylethyl, and the like.

The term "heteroarylalkyl" refers to an alkyl moiety (as defined above) substituted with a heteroaryl moiety (as defined above). Examples of heteroarylalkyl include 5 or 6-membered aryl-$C_{1-3}$-alkyl, such as, but not limited to, oxazolylmethyl, pyridinylethyl and the like.

The term "heterocycloalkyl" refers to an alkyl moiety (as defined above) substituted with a heterocycloalkyl moiety (as defined above). Examples of heterocycloalkyl include 5 or 6-membered heterocyclyl-$C_{1-3}$-alkyl, such as but not limited to tetrahydropyranyl methyl.

The term "cycloalkylalkyl" refers to an alkyl moiety (as defined above) substituted with a cycloalkyl moiety (as defined above). Examples of cycloalkylalkyl include 5 or 6-membered cycloalkyl-$C_{1-3}$-alkyl, such as but not limited to cyclopropylmethyl.

The term "halogen" includes F, Cl, Br, I.

The term "oxo" refers to replacing —CH$_2$— with

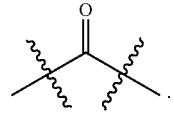 [SMILES: *C(*)=O]

The term "pharmaceutically acceptable salt" refers to the salt formed by a suitable non-toxic organic acid, inorganic acid, organic base or inorganic base with compound I, which retains the biological activity of compound I. The organic acid may be various organic acids which are conventional in the art and capable of salt formation, preferably selected from the group consisting of methanesulfonic acid, p-toluenesulfonic acid, maleic acid, fumaric acid, citric acid, tartaric acid, malic acid, lactic acid, formic acid, acetic acid, propionic acid, trifluoroacetic acid, oxalic acid, succinic acid, benzoic acid, isethionic acid, naphthalenesulfonic acid and salicylic acid. The inorganic acid can be various inorganic acids which are conventional in the art and capable of salt formation, preferably selected from the group consisting of hydrochloric acid, sulfuric acid and phosphoric acid. The organic base can be various organic bases which are conventional in the art and capable of salt formation, preferably selected from the group consisting of pyridine, imidazole, pyrazine, indole, purine, tertiary amine and aniline. The tertiary amine organic base is preferably triethylamine and/or N,N-diisopropylethylamine. The aniline organic base is preferably N,N-dimethylaniline. The pyridine organic base is preferably selected from the group consisting of pyridine, methylpyridine, 4-dimethylaminopyridine and 2-methyl-5-ethylpyridine. The inorganic base may be various inorganic bases which are conventional in the art and capable of salt formation, preferably selected from the group consisting of alkali metal hydride, alkali metal hydroxide, alkali metal alkoxide, potassium carbonate, sodium carbonate, lithium carbonate, cesium carbonate, potassium bicarbonate and sodium bicarbonate. The alkali metal hydride is preferably sodium hydride and/or potassium hydride. The alkali metal hydroxide is preferably selected from the group consisting of sodium hydroxide, potassium hydroxide and lithium hydroxide. The alkali metal alkoxide is preferably selected from the group consisting of sodium methoxide, sodium ethoxide, potassium tert-butoxide and sodium tert-butoxide.

The term "solvate" refers to a substance formed by compound I with a suitable solvent. The solvent is preferably water or an organic solvent.

On the basis of not violating common knowledge in the field, the preferred conditions can be combined arbitrarily to give various preferred embodiments of the present application.

The reagents and raw materials used in the present disclosure are commercially available.

The positive progressive effect of the present disclosure is that the compound has a high inhibitory activity on ErbB2 tyrosine kinase, a relatively good inhibitory activity on human breast cancer cell BT-474 and human gastric cancer cell NCI-N87 and the like with high ErbB2 expression, and a relatively weak inhibitory activity on EGFR kinase, namely the compound is a highly selective small molecule inhibitor targeting ErbB2. Therefore, it is possible to reduce EGFR-related toxic and side effects of drugs in clinical applications and effectively enlarge the safety window during drug administration.

DETAILED DESCRIPTION OF THE INVENTION

The present application will be further described below by way of examples, but the present application is not therefore limited to the scope of the described examples. The specific conditions of the experimental methods that is not specified was selected according to conventional methods and conditions, or according to commercial instructions.

Embodiment 1

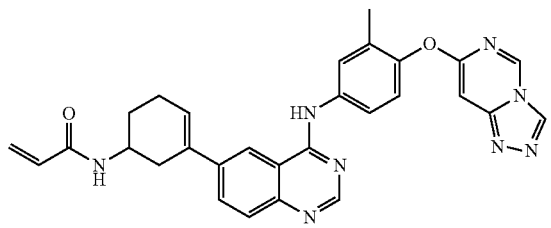 [SMILES: C=CC(=O)NC1CCC=C(c2ccc3ncnc(Nc4ccc(Oc5cc6nncn6cn5)c(C)c4)c3c2)C1]

Synthesis of N-(3-(4-((4-([1,2,4]triazolo[4,3-c]pyrimidin-7-yloxy)-3-methylphenyl)amino)quinazolin-6-yl)cyclohex-3-en-1-yl)acrylamide Step A: Preparation of 2-chloro-6-hydrazinopyrimidine 2,6-Dichloropyrimidine (25 g, 167.81 mmol) was dissolved in 350 mL of isopropanol, and hydrazine hydrate (29.5 g, 503.44 mmol, 85%) was slowly added dropwise under stirring at room temperature. Heat was released and white solid was precipitated out in the dropping process, and stirring at room temperature was performed for 1 hour after the addition. The solvent was removed under reduced pressure. The residue was stirred with water (50 mL) for 30 minutes, filtered, and the filter cake was washed with water, and dried to give 22.4 g of white solid with a yield of 92.3%.

Step B: Preparation of 7-chloro-[1,2,4]triazolo[4,3-c]pyrimidine

2-Chloro-6-hydrazinopyrimidine (21 g, 145.27 mmol) was dispersed in 210 mL of trimethyl orthoformate and stirred overnight at 60° C. to make the reaction solution clear. P-toluenesulfonic acid (0.6 g, 3.48 mmol) was added and the reaction was continued at 60° C. for 1 hour. The solvent was evaporated to dryness under reduced pressure, followed by addition of water (20 mL). The mixture was stirred for 30 minutes, filtered, and the filter cake was washed with water, and dried to give 9.2 g of pale brown solid with a yield of 41%.

Step C: Preparation of 7-(2-methyl-4-nitrophenoxy)-[1,2,4]triazolo[4,3-c]pyrimidine 7-Chloro-[1,2,4]triazolo[4,3-c]pyrimidine (450 mg, 2.91 mmol) was dissolved in 10 mL of N,N-dimethylformamide, followed by addition of 2-methyl-4-nitrophenol (550 mg, 3.59 mmol) and sodium carbonate solid (500 mg, 4.72 mmol). The mixture was heated to 80° C. and stirred overnight. After completion of the reaction, 20 mL of ethyl acetate was added, stirred, filtered, and the filtrate was evaporated to dryness under reduced pressure. The residue was isolated by column chromatography to give 510 mg of pale yellow solid with a yield of 64.46%.

Step D: Preparation of 7-(2-methyl-4-aminophenoxy)-[1,2,4]triazolo[4,3-c]pyrimidine 7-(2-Methyl-4-nitrophenoxy)-[1,2,4]triazolo[4,3-c]pyrimidine (510 mg, 1.88 mmol) was dissolved in 60 mL of a mixed solvent of methanol and ethyl acetate (2:1), followed by addition of a small amount of raney Ni. The reaction was performed under hydrogen atmosphere (balloon), stirred at room temperature for 2 hours. After completion of the reaction, filtration was directly carried out, and the solvent was evaporated to dryness under reduced pressure to give 410 mg of crude product, which was directly used in the next reaction.

Step E: Preparation of (E)-N'-(2-cyano-4-iodophenyl)-N,N-dimethylformamidine

2-Cyano-4-iodoaniline (1 g, 4.1 mmol) was suspended in 2 mL of 1,1-dimethoxy-N,N-dimethylmethylamine. After the reactants were stirred at 90° C. for 1 hour, the reaction solution was evaporated to dryness under reduced pressure to give 1.2 g of brown oil, which was directly used in the next reaction.

Step F: Preparation of N-(4-([1,2,4]triazolo[4,3-c]pyrimidin-7-oxy)-3-methylphenyl)-6-iodoquinazolin-4-amine (E)-N'-(2-cyano-4-iodophenyl)-N,N-dimethylformamidine (306 mg, 1.02 mmol), 3-methyl-4-([1,2,4]triazolo[4,3-c]pyrimidin-7-oxy)aniline (247 mg, 1.02 mmol) and glacial acetic acid (0.5 mL) were mixed in 3 mL of isopropyl acetate, and the mixture was stirred at room temperature overnight. Solid was precipitated out and filtered under reduced pressure to give 320 mg of yellow solid, which was directly used in the next reaction.

Step G: Preparation of Tert-Butyl (3-(4-((4-([1,2,4]triazolo[4,3-c]pyrimidin-7-yloxy)-3-methylphenyl)amino)quinazolin-6-yl)cyclohex-3-en-1-yl) carbamate Tert-butyl (3-(4,4,5,5-tetramethyl-1,3,2-dioxaborolan-2-yl)cyclohex-3-en-1-yl) carbamate (230 mg, 0.71 mmol), N-(4-([1,2,4]triazolo[4,3-c]pyrimidin-7-yloxy)-3-methylphenyl)-6-iodoquinazolin-4-amine (410 mg, 0.83 mmol), sodium bicarbonate (200 mg, 2.38 mmol) and [1,1'-bis(diphenylphosphine)ferrocene]palladium dichloride (150 mg) were added to N,N-dimethylformamide (10 mL). The mixture was heated to 90° C. and stirred for 18 hours under argon atmosphere. After completion of the reaction, the solvent was directly removed under reduced pressure, ethyl acetate was added to dissolve and washed with sodium bicarbonate. The organic phase was dried over anhydrous sodium sulfate, filtered, and the concentrated residue was isolated by column chromatography to give the product, which was 100 mg of pale yellow solid with a yield of 24.9%.

Step H: Preparation of N-(4-([1,2,4]triazolo[4,3-c]pyrimidin-7-yloxy)-3-methylphenyl)-6-(5-aminocyclohex-1-en-1-yl)quinazolin-4-amine Tert-butyl (3-(4-((4-([1,2,4]triazolo[4,3-c]pyrimidin-7-yloxy)-3-methylphenyl)amino)quinazolin-6-yl)cyclohex-3-en-1-yl) carboxylate (190 mg, 0.34 mmol) was dissolved in dichloromethane (2 mL), followed by addition of trifluoroacetic acid (0.4 mL), and the reaction solution was stirred at 6° C. for 4.5 hours. The reaction solution was evaporated to dryness under reduced pressure to give 156 mg of crude yellow oil, which was directly used in the next reaction.

Step I: Preparation of N-(3-(4-((4-([1,2,4]triazolo[4,3-c]pyrimidin-7-yloxy)-3-methylphenyl)amino)quinazolin-6-yl)cyclohex-3-en-1-yl) acrylamide N-(4-([1,2,4]triazolo[4,3-c]pyrimidin-7-yloxy)-3-methylphenyl)-6-(5-aminocyclohex-1-en-1-yl)quinazolin-4-amine (156 mg, 0.34 mmol), HATU (128 mg, 0.34 mmol), DIEA (887 μL, 5.09 mmol) and acrylic acid (24 mg, 0.33 mmol) were mixed in N,N-dimethylformamide (1 mL) and the reactants were stirred at 6° C. for 16 hours. The reaction solution was evaporated to dryness under reduced pressure to give a crude product. The crude product was isolation by silica gel column and purified by preparative liquid phase to give 21.02 mg of yellow solid with a yield of 12.3%. LC-MS: 519.3[M+H] detection value; 1H NMR (400 MHz, DMSO) δ 9.91 (s, 1H), 9.68 (s, 1H), 8.59 (s, 1H), 8.56 (s, 1H), 8.45 (s, 1H), 8.25 (d, J=7.6 Hz, 1H), 8.01 (d, J=8.8 Hz, 1H), 7.77-7.73 (m, 3H), 7.21 (d, J=9.2 Hz, 1H), 7.13 (s, 1H), 6.45 (s, 1H), 6.31 (dd, J=16.8, 10.0 Hz, 1H), 6.14 (dd, J=16.8, 2.0 Hz, 1H), 5.62 (dd, J=10.0, 2.0 Hz, 1H), 4.14 (m, 1H), 2.93 (d, J=16.0 Hz, 1H), 2.47 (m, 1H), 2.42 (m, 2H), 2.21 (s, 3H), 1.90 (m, 1H), 1.69-1.60 (m, 1H).

Embodiment 2

Synthesis of N-(4-([1,2,4]triazolo[4,3-c]pyrimidin-7-yloxy)-3-methylphenyl)-6-(3-amino-1H-pyrazol-5-yl)quinazolin-4-amine Step A: Preparation of tert-butyl 5-bromo-3-((tert-butoxycarbonyl) amino)-1H-pyrazol-1-carboxylate 5-Bromo-1H-pyrazol-3-amine (250 mg, 1.54 mmol), triethylamine (627 mg, 6.19 mmol) and di-tert-butyl dicarbonate (846 mg, 3.87 mmol) were added to dichloromethane (10 mL), followed by addition of 4-dimethylaminopyridine (38 mg, 0.31 mmol), and the resulting reaction solution was stirred at room temperature for 16 hours. After completion of the reaction, the residue obtained by concentration of the reaction solution under reduced pressure was isolated by column chromatography to give 135 mg of white solid with a yield of 24%.

Step B: Preparation of tert-butyl (E)-(5-(3-cyano-4-((dimethylamino) methylene)amino)phenyl)-1H-pyrazol-3-yl) carbamate Tert-butyl 5-bromo-3-((tert-butoxycarbonyl)amino)-1H-pyrazol-1-carboxylate (152 mg, 0.42 mmol), (E)-N'-(2-cyano-4-(4,4,5,5-tetramethyl-1,3,2-dioxaborolan-2-yl)phenyl)-N,N-dimethylformamidine (126 mg, 0.42 mmol), potassium carbonate (116 mg, 0.84 mmol) and [1,1'-bis(diphenylphosphine)ferrocene] palladium dichloride dichloromethane complex (344 mg, 0.42 mmol) were dissolved in a mixed solvent of 1,4-dioxane (10 mL) and water (1 mL). The resulting mixture was reacted at 85° C. for 16 hours under argon atmosphere, and the reaction solution was filtered. The obtained filtrate was isolated by column chromatography to give 110 mg of white solid with a yield of 74%.

Step C: Preparation of tert-butyl (5-(4-((4-([1,2,4]triazolo[4,3-c]pyrimidin-7-yloxy)-3-methylphenyl)amino)quinazolin-6-yl)-1H-pyrazol-3-yl)carbamate Tert-Butyl (E)-(5-(3-cyano-4-((dimethylamino)methylene)amino)phenyl)-1H-pyrazol-3-yl) carbamate (110 mg, 0.31 mmol) and 4-([1,2,4]triazolo[4,3-c]pyrimidin-7-yloxy)-3-methylaniline (75 mg, 0.31 mmol) were dissolved in isopropyl acetate (4 mL) and acetic acid (1 mL). After the mixture was stirred at room temperature for 24 hours, the mixture was concentrated under reduced pressure. The obtained residue was isolated by column chromatography to give 97 mg of yellow solid with a yield of 57%.

Step D: Preparation of N-(4-([1,2,4]triazolo[4,3-c]pyrimidin-7-yloxy)-3-methylphenyl)-6-(3-amino-1H-pyrazol-5-yl)quinazolin-4-amine Tert-butyl (5-(4-((4-([1,2,4]triazolo[4,3-c]pyrimidin-7-yloxy)-3-methylphenyl)amino)quinazolin-6-yl)-1H-pyrazol-3-yl) carbamate (87 mg, 0.16 mmol) was dissolved in trifluoroacetic acid (0.5 mL) and dichloromethane (5 mL). After the reaction solution was stirred at room temperature for 4 hours, the residue obtained by concentration under reduced pressure was isolated by column chromatography to give 61 mg of yellow solid with a yield of 86%. LC-MS: 451.2[M+H] detection value; $^1$H NMR (400 MHz, DMSO) δ10.92 (s, 1H), 9.69 (d, J=1.2 Hz, 1H), 8.90 (s, 1H), 8.81 (s, 1H), 8.61 (s, 1H), 8.39 (d, J=8.8 Hz, 1H), 7.86 (d, J=8.8 Hz, 1H), 7.75 (d, J=2.0 Hz, 1H), 7.72-7.66 (dd, J=2.4 Hz, 4.8 Hz,

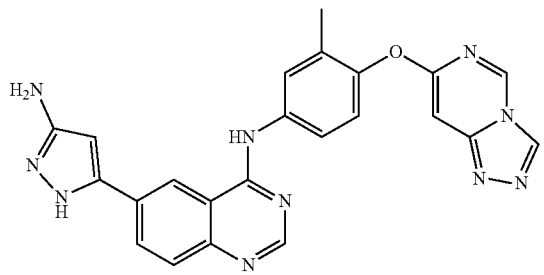 [SMILES: Cc1cc(Nc2ncnc3ccc(-c4cc(N)n[nH]4)cc23)ccc1Oc1cc2nncn2cn1]

1H), 7.30-7.25 (m, 2H), 7.21 (d, J=1.2 Hz, 1H), 7.14 (s, 1H), 7.01 (s, 1H), 6.07 (s, 1H), 2.23 (s, 3H).

Embodiment 3

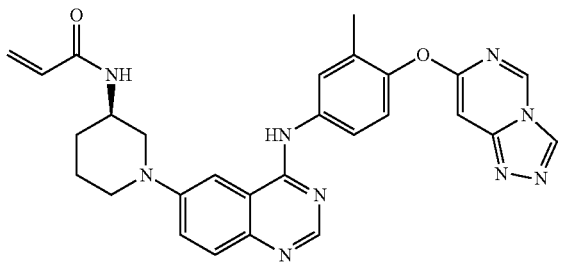 [SMILES: C=CC(=O)N[C@@H]1CCCN(c2ccc3ncnc(Nc4ccc(Oc5cc6nncn6cn5)c(C)c4)c3c2)C1]

Synthesis of (R)—N-(1-(4-((4-([1,2,4]triazolo[4,3-c]pyrimidin-7-yloxy)-3-methylphenyl)amino)quinazolin-6-yl)piperidin-3-yl) acrylamide Step A: Preparation of 2-amino-5-(4,4,5,5-tetramethyl-1,3,2-dioxaborolan-2-yl) benzonitrile 2-Amino-5-bromo-benzonitrile (1000 mg, 5.08 mmol), bis(pinacolato)diboron (1930 mg, 7.60 mmol), potassium acetate (1490 mg, 15.18 mmol) and [1,1'-bis(diphenylphosphine)ferrocene]palladium dichloride dichloromethane complex (21 mg, 0.05 eq.) were mixed in 1,4-dioxane (15 mL), and the mixture was stirred at 80° C. for 16 hours under argon atmosphere. The mixture was filtered with diatomite, and the filtrate was concentrated under reduced pressure. The residue obtained was dissolved in ethyl acetate (10 mL) and washed with saturated brine (10 mL). The organic phase separated was dried over anhydrous sodium sulfate, filtered, and the residue obtained was concentrated and purified by silica gel column to give 1400 mg of white solid with a yield of 100%.

Step B: Preparation of (E)-N'-(2-cyano-4-(4,4,5,5-tetramethyl-1,3,2-dioxaborolan-2-yl)phenyl)-N,N-dimethylformamidine 2-Amino-5-(4,4,5,5-tetramethyl-1,3,2-dioxaborolan-2-yl) benzonitrile (1200 mg, 4.92 mmol) was suspended in 1,1-dimethoxy-N,N-dimethyl-methylamine (1.4 mL), and the mixture was heated to 80° C. and stirred for 2 hours. The reaction solution was concentrated under reduced pressure, and the obtained residue was isolated and purified by silica gel column to give 1630 mg of pale yellow oil with a yield of 100%.

Step C: Preparation of (E)-(3-cyano-4-((dimethylamino)methylene)amino) phenyl) boric acid (E)-N'-(2-cyano-4-(4,4,5,5-tetramethyl-1,3,2-dioxaborolan-2-yl)phenyl)-N,N-dimethylformamidine (1200 mg, 4.01 mmol) was dissolved in a mixed solvent of tetrahydrofuran (10 mL) and water (2.5 mL), followed by addition of sodium periodate (2570 mg, 12.02 mmol), and the mixture was stirred at 8° C. for 16 hours. 2 N dilute hydrochloric acid (30 mL) was added to the reaction mixture, and the mixture became clear and was stirred at 8° C. for 1 hour. The mixture was neutralize with saturated sodium bicarbonate solution to pH=7-8. The mixture was extracted with ethyl acetate (30 mL×3). The organic phases were combined, dried over anhydrous sodium sulfate, filtered, and evaporated to dryness under reduced pressure to give 700 mg of crude orange solid, which was directly used in the next reaction.

Step D: Preparation of tert-butyl (R,E)-(1-(3-cyano-4-((dimethylamino) methylene)amino)phenyl)piperidin-3-yl) carboxylate (E)-(3-cyano-4-((dimethyl amino)methylene)amino)phenyl) boric acid (270 mg, 1.24 mmol), tert-butyl (R)-piperidin-3-yl carboxylate (100 mg, 0.50 mmol), copper acetate (150 mg, 0.83 mmol), pyridine (80 µL, 0.99 mmol) and anhydrous sodium sulfate (200 mg) were mixed in dichloromethane (2 mL), and the reaction solution was stirred at 25° C. for 16 hours under an oxygen atmosphere of 15 psi. The mixture was filtered through diatomite, and the filtrate was evaporated to dryness under reduced pressure to give a crude product. The crude product was isolated by silica gel column to give 92 mg of brown oil with a yield of 49.6%.

Step E: Preparation of Tert-Butyl (R)-(1-(4-((4-([1,2,4]triazolo[4,3-c]pyrimidin-7-yloxy)-3-methylphenyl)amino)quinazolin-6-yl)piperidin-3-yl) carboxylate Tert-butyl (R,E)-(1-(3-cyano-4-((dimethylamino)methylene)amino)phenyl) piperidin-3-yl)carboxylate (128 mg, 0.34 mmol), 4-([1,2,4]triazolo[4,3-c]pyrimidin-7-yloxy)-3-methylaniline (83 mg, 0.34 mmol) and glacial acetic acid (0.5 mL) were mixed in isopropyl acetate (2 mL), and the mixture was stirred at 25° C. for 16 hours. The reaction solution was concentrated under reduced pressure to give crude product. The crude product was isolated and purified by silica gel column to give 73 mg of orange solid with a yield of 37.3%.

Step F: Preparation of (R)—N-(4-([1,2,4]triazolo[4,3-c]pyrimidin-7-yloxy)-3-methylphenyl)-6-(3-aminopiperidin-1-yl)quinazolin-4-amine Tert-butyl (R)-(1-(4-((4-([1,2,4]triazolo[4,3-c]pyrimidin-7-yloxy)-3-methyl phenyl)amino)quinazolin-6-yl)piperidin-3-yl)carboxylate (73 mg, 0.13 mmol) was dissolved in dichloromethane (1.8 mL), followed by addition of trifluoroacetic acid (0.2 mL), and the reaction solution was stirred at 8° C. for 2.5 hours. The reaction solution was evaporated to dryness under reduced pressure to give 60 mg of crude brown oil, which was directly used in the next reaction.

Step G: Preparation of (R)—N-(1-(4-((4-([1,2,4]triazolo[4,3-c]pyrimidin-7-yloxy)-3-methylphenyl)amino)quinazolin-6-yl)piperidin-3-yl) acrylamide (R)—N-(4-([1,2,4]triazolo[4,3-c]pyrimidin-7-yloxy)-3-methylphenyl)-6-(3-aminopiperidin-1-yl)quinazolin-4-amine (60 mg, 0.13 mmol), acrylic acid (14 mg, 0.19 mmol), HATU (73 mg, 0.19 mmol) and DIEA (0.25 mL) were mixed in N,N-dimethylformamide (1 mL) and the mixture was stirred at 8° C. for 16 hours. The reaction solution was concentrated under reduced pressure to give a crude product, which was dissolved in dichloromethane (3 mL), followed by addition of glacial acetic acid (0.3 mL), and the reaction solution was stirred at 17° C. for 40 hours. The reaction solution was evaporated to dryness under reduced pressure to give a crude product, and the crude product was isolated and purified by preparative liquid phase to give 5.84 mg of yellow solid with a yield of 8.72%. LC-MS: 522.3[M+H] detection value; 1H NMR (400 MHz, MeOD) δ 9.45 (s, 1H), 8.43 (s, 1H), 8.41 (s, 1H), 7.79 (d, J=2.0 Hz, 1H), 7.77-7.74 (m, 2H), 7.70 (s, 1H), 7.20 (d, J=8.4 Hz, 1H), 6.95 (s, 1H), 6.33 (d, J=3.6 Hz, 1H), 6.31 (s, 1H), 5.70 (dd, J=7.6, 4.4 Hz, 1H), 4.18-4.11 (m, 1H), 4.00-3.97 (m, 1H), 3.83-3.79 (m, 1H), 3.14-3.06 (m, 1H), 2.97-2.91 (m, 1H), 2.27 (s, 3H), 2.06-2.00 (m, 1H), 1.98-1.92 (m, 1H), 1.86-1.74 (m, 1H), 1.70-1.61 (m, 1H).

Embodiment 4

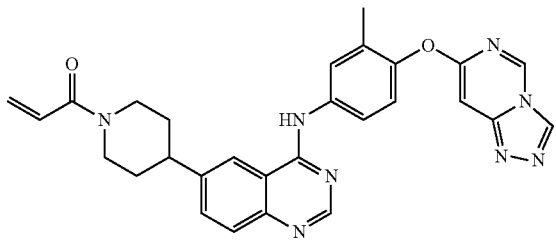 [SMILES: C=CC(=O)N1CCC(c2ccc3ncnc(Nc4ccc(Oc5cc6nncn6cn5)c(C)c4)c3c2)CC1]

Synthesis of 1-(4-(4-((4-([1,2,4]triazolo[4,3-c]pyrimidin-7-yloxy)-3-methyl phenyl)amino)quinazolin-6-yl)piperidin-1-yl)propan-2-en-1-one Step A: Preparation of tert-butyl (E)-4-(3-cyano-4-((dimethylamino) methylene)amino)phenyl)piperidin-1-carboxylate Tert-butyl (E)-4-(3-cyano-4-((dimethylamino)methylene) amino)phenyl)-3,6-dihydropyridin-1(2H)-carboxylate (200 mg, 0.56 mmol) and palladium carbon (23 mg, 0.23 mmol), 10 wt %) were added to methanol (15 mL). After the mixture was reacted for 16 hours at room temperature under the hydrogen atmosphere, the reaction solution was filtered through diatomite and concentrated under reduced pressure to give 185 mg of yellow oil with a yield of 92%.

Step B: Preparation of (E)-N'-(2-cyano-4-(piperidin-4-yl)phenyl)-N,N-dimethylformamidine Tert-butyl (E)-4-(3-cyano-4-((dimethylamino)methylene) amino)phenyl) piperidin-1-carboxylate (180 mg, 0.50 mmol) was dissolved in trifluoroacetic acid (1.5 mL) and dichloromethane (10 mL), and the reaction solution was stirred at room temperature for 2 hours. The residue obtained by concentration under reduced pressure was dissolved in dichloromethane, and washed with aqueous sodium bicarbonate solution. The organic phase was separated, and the aqueous phase was extracted twice with dichloromethane. The organic phases were combined, dried over anhydrous sodium sulfate, and concentrated under reduced pressure to give 125 mg of yellow oil. The yield was 96%.

Step C: Preparation of (E)-N'-(4-(1-acryloylpiperidin-4-yl)-2-cyanophenyl)-N,N-dimethylformamidine (E)-N'-(2-cyano-4-(piperidin-4-yl)phenyl)-N,N-dimethylformamidine (125 mg, 0.48 mmol) and triethylamine (148 mg, 1.46 mmol) were dissolved in dichloromethane (5 mL), and acryloyl chloride (66 mg, 0.73 mmol) was added at 0° C. The temperature of the reaction solution was warmed to room temperature and stirred for 2 hours. After the reaction was completed, the residue obtained by concentration under reduced pressure was isolated by column chromatography to give 80 mg of colorless oil. The yield was 53%.

Step D: Preparation of 1-(4-(4-((4-([1,2,4]triazolo [4,3-c]pyrimidin-7-yloxy)-3-methylphenyl)amino) quinazolin-6-yl)piperidin-1-yl)propan-2-en-1-one (E)-N'-(4-(1-acryloylpiperidin-4-yl)-2-cyanophenyl)-N, N-dimethylamidine (80 mg, 0.26 mmol) and 4-([1,2,4]triazolo[4,3-c]pyrimidin-7-yloxy)-3-methylaniline (62 mg, 0.26 mmol) were dissolved in isopropyl acetate (4 mL) and acetic acid (1 mL). After the mixture was stirred at room temperature for 24 hours, the residue obtained by concentration under reduced pressure was isolated by column chromatography to give 60 mg of yellow solid with a yield of 46%. LC-MS: 507.3[M+H] detection value; $^1$H-NMR (400 MHz, DMSO-$d_6$) δ9.78 (s, 1H), 9.67 (s, 1H), 8.57 (d, J=6.4 Hz, 2H), 8.39 (s, 1H), 7.81-7.72 (m, 4H), 7.25-7.15 (m, 1H), 7.12 (s, 1H), 6.89 (dd, J=16.8, 10.4 Hz, 1H), 6.16 (dd, J=16.8, 2.4 Hz, 1H), 5.71 (dd, J=10.4, 2.4 Hz, 1H), 4.69 (d, J=12.4 Hz, 1H), 4.26 (d, J=12.8 Hz, 1H), 3.23 (t, J=12.4 Hz, 1H), 3.02 (t, J=12.0 Hz, 1H), 2.78 (t, J=12.0 Hz, 1H), 2.20 (s, 3H), 1.97-1.92 (m, 2H), 1.79-1.65 (m, 2H).

Embodiment 5

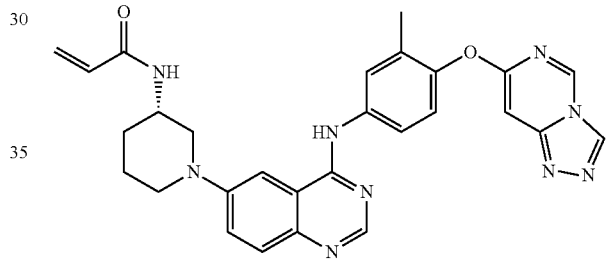

Synthesis of (S)—N-(1-(4-((4-([1,2,4]triazolo[4,3-c] pyrimidin-7-yloxy)-3-methylphenyl)amino)quinazolin-6-yl)piperidin-3-yl)acrylamide Step A: Preparation of tert-butyl (S,E)-(1-(3-cyano-4-((dimethylamino) methylene)amino)phenyl)piperidin-3-yl) carbamate (E)-(3-cyano-4-((dimethylamino)methylene)amino)phenyl) boric acid (430 mg, 1.98 mmol), tert-butyl (S)-piperidin-3-yl carbamate (330 mg, 1.65 mmol), copper acetate (450 mg, 2.47 mmol) and pyridine (261 mg, 3.3 mmol) were mixed in dichloromethane (18 mL), and the mixture was stirred at room temperature under the oxygen atmosphere for 48 hours. The reaction solution was filtered through diatomite, the filtrate was concentrated under reduced pressure to give a residue, and the residue was isolated by column chromatography to give 220 mg of brown oil with a yield of 30%.

Step B: Preparation of (S,E)-N'-(4-(3-aminopiperidin-1-yl)-2-cyanophenyl)-N,N-dimethylformamidine Tert-butyl (S,E)-(1-(3-cyano-4-((dimethylamino)methylene)amino)phenyl) piperidin-3-yl)carbamate (100 mg, 0.27 mmol) was dissolved in trifluoroacetic acid (2 mL) and dichloromethane (5 mL). The reaction solution was stirred at room temperature for 3 hours, then concentrated under reduced pressure to give a residue, followed by addition of aqueous sodium bicarbonate solution and extraction three times with dichloromethane. The organic phases were combined, dried over anhydrous sodium sulfate, and concentrated under reduced pressure to give 76 mg of brown oil with a yield of 100%.

Step C: Preparation of (S,E)-N-(1-(3-cyano-4-((dimethylamino)methylene) amino)phenyl)piperidin-3-yl)acrylamide Acrylic acid (30 mg, 0.42 mmol), HATU (159 mg, 0.42 mmol) and N,N-diisopropylethylamine (108 mg, 0.84 mmol) were added to N,N-dimethylformamide (3.5 mL). After stirring the mixture for 10 minutes, (S,E)-N'-(4-(3-aminopiperidin-1-yl)-2-cyanophenyl)-N,N-dimethylformamidine (76 mg, 0.28 mmol) was added. After stirring the reaction solution at room temperature for 16 hours, the residue obtained by concentration under reduced pressure was isolated by column chromatography to give 63 mg of brown oil with a yield of 69%.

Step D: Preparation of (S)—N-(1-(4-((4-([1,2,4] triazolo[4,3-c]pyrimidin-7-yloxy)-3-methylphenyl) amino)quinazolin-6-yl)piperidin-3-yl)acrylamide (S,E)-N-(1-(3-cyano-4-((dimethylamino)methylene) amino)phenyl)piperidin-3-yl)acrylamide (63 mg, 0.19 mmol) and 4-([1,2,4]triazolo[4,3-c]pyrimidin-7-yloxy)-3-methylaniline (47 mg, 0.19 mmol) were added to isopropyl acetate (4 mL) and acetic acid (1 mL). After the mixture was reacted at room temperature for 24 hours, the residue was obtained by concentration under reduced pressure and isolated by preparative TLC to give 30 mg of yellow solid with a yield of 30%. LC-MS: 522.3[M+H] detection value; $^1$H-NMR (400 MHz, DMSO-d$_6$) δ9.68 (d, J=1.2 Hz, 1H), 9.54 (s, 1H), 8.59 (s, 1H), 8.44 (s, 1H), 8.27 (d, J=7.2 Hz, 1H), 7.87-7.72 (m, 3H), 7.67 (s, 2H), 7.20 (d, J=8.4 Hz, 1H), 7.11 (s, 1H), 6.32 (dd, J=17.2, 10.0 Hz, 1H), 6.17 (dd, J=17.2, 2.4 Hz, 1H), 5.64 (dd, J=10.0, 2.4 Hz, 1H), 4.05-3.95 (m, 1H), 3.83-3.75 (m, 2H), 3.04-2.99 (m, 1H), 2.87-2.82 (m, 1H), 2.21 (s, 3H), 1.91-1.86 (m, 2H), 1.71-1.69 (m, 1H), 1.58-1.53 (m, 1H).

Embodiment 6

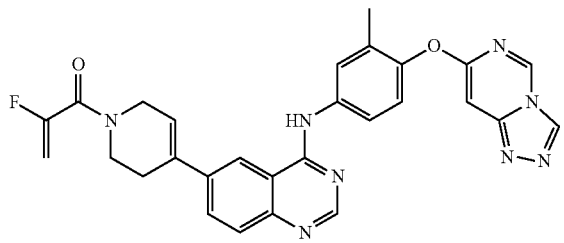 [SMILES: C=C(F)C(=O)N1CC=C(c2ccc3ncnc(Nc4ccc(Oc5cc6nncn6cn5)c(C)c4)c3c2)CC1]

Synthesis of 1-(4-(4-((4-([1,2,4]triazolo[4,3-c]pyrimidin-7-yloxy)-3-methylphenyl)amino)quinazolin-6-yl)-5,6-dihydropyridin-1(2H)-yl)-2-fluoropropyl-2-en-1-one Step A: Preparation of tert-butyl (E)-4-(3-cyano-4-((dimethylamino) methylene)amino)phenyl)-5,6-dihydropyridin-1 (2H)-carbamate (E)-N'-(2-cyano-4-(4,4,5,5-tetramethyl-1,3,2-dioxaborolan-2-yl)phenyl)-N,N-dimethylformamidine (1.0 g, 3.34 mmol), tert-butyl 4-bromine-5,6-dihydropyridin-1(2H)-carbamate (1.4 g, 5.34 mmol), sodium carbonate (200 mg, 6.12 mmol) and [1,1'-bis(diphenylphosphine)ferrocene]palladium dichloride (300 mg) were mixed in a mixed solvent of dioxane (20 mL) and water (5 mL). Under argon atmosphere, the mixture was heated to 100° C. and stirred for 6 hours. After completion of the reaction, the solvent was directly evaporated to dryness under reduced pressure, and the residue was isolated by column chromatography to give 1.0 g of gray solid with a yield of 84.4%.

Step B: Preparation of tert-butyl 4-(4-((4-([1,2,4] triazolo[4,3-c]pyrimidin-7-yloxy)-3-methylphenyl) amino)quinazolin-6-yl)-5,6-dihydropyridin-1(21H)-carbamate Tert-butyl (E)-4-(3-cyano-4-((dimethylamino)methylene) amino)phenyl)-5,6-dihydropyridin-1(2H)-carbamate (1.0 g, 2.82 mmol), 4-([1,2,4]triazolo[4,3-c]pyrimidin-7-yloxy)-3-methylaniline (1.0 g, 4.15 mmol) and glacial acetic acid (6 mL) were mixed in isopropyl acetate (30 mL), and the mixture was stirred at room temperature for 16 hours. A precipitate was generated, and the reaction solution was concentrated under reduced pressure to give a crude product. The crude product was isolated and purified by silica gel column to give 600 mg of yellow solid with a yield of 38.6%.

Step C: Preparation of N-(4-([1,2,4]triazolo[4,3-c] pyrimidin-7-yloxy)-3-methylphenyl)-6-(1,2,3,6-tetrahydropyridin-4-yl)quinazolin-4-amine Tert-butyl 4-(4-((4-([1,2,4]triazolo[4,3-c]pyrimidin-7-yloxy)-3-methyl phenyl)amino)quinazolin-6-yl)-5,6-dihydropyridin-1(2H)-carbamate (400 mg, 0.73 mmol) was added into a sealed tube, followed by addition of 5 mL of dichloromethane solution containing 10% trifluoroacetic acid. The reaction was carried out at room temperature for 4 hours. After completion of the reaction, 700 mg of crude product (trifluoroacetate) was directly obtained by concentration under reduced pressure, which was directly used in the next reaction.

Step D: Preparation of 1-(4-(4-((4-([1,2,4]triazolo [4,3-c]pyrimidin-7-yloxy)-3-methylphenyl)amino) quinazolin-6-yl)-5,6-dihydropyridin-1(2H)-yl)-2-fluoroprop-2-en-1-one The above crude product (700 mg), 2-fluoroacrylic acid (250 mg, 2.78 mmol) and EDCI (500 mg, 2.61 mmol) were dissolved in pyridine (5 mL). The mixture was stirred at 50° C. for 18 hours under argon atmosphere. After completion of the reaction, the solvent was directly evaporated to dryness under reduced pressure, and the residue was washed with sodium bicarbonate and extracted with ethyl acetate. The organic phase was dried over anhydrous sodium sulfate, and filtered. The filtrate was concentrated and isolated by TLC to give 33 mg of pale yellow solid with a yield of 8.7%. LC-MS: 523.2[M+H] detection value; $^1$H-NMR (400 MHz, DMSO-d$_6$) δ 9.89 (s, 1H), 9.69 (s, 1H), 8.60-8.59 (d, J=8 Hz, 2H), 8.52 (s, 1H), 8.06-8.03 (d, J=12 Hz, 1H), 7.79-7.77 (d, J=8 Hz, 2H), 7.24-7.22 (d, J=8 Hz, 1H), 7.15 (s, 1H), 6.46 (s, 1H), 5.40-5.24 (m, 2H), 4.30 (s, 2H), 3.86-3.84 (d, J=8 Hz, 2H), 2.79 (s, 2H), 2.22 (s, 3H).

Embodiment 7

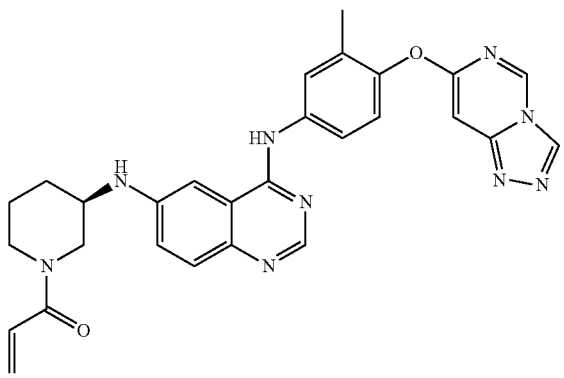 [SMILES: C=CC(=O)N1CCC[C@@H](Nc2ccc3ncnc(Nc4ccc(Oc5cc6nncn6cn5)c(C)c4)c3c2)C1]

Synthesis of (R)-1-(3-((4-((4-([1,2,4]triazolo[4,3-c]pyrimidin-7-yloxy)-3-methylphenyl)amino)quinazolin-6-yl)amino)piperidin-1-yl)propan-2-en-1-one Step A: Preparation of tert-butyl (R,E)-3-((3-cyano-4-((dimethylamino) methylene)amino)phenyl) amino)piperidin-1-carboxylate (E)-(3-cyano-4-((dimethylamino)methylene)amino)phenyl)boric acid (390 mg, 1.78 mmol), tert-butyl (R)-3-aminopiperidin-1-carboxylate (300 mg, 1.49 mmol), copper acetate (546 mg, 3.0 mmol) and pyridine (237 mg, 3.0 mmol) were mixed in dichloromethane (10 mL), and the mixture was stirred at room temperature under oxygen atmosphere for 24 hours. The reaction solution was filtered through diatomite, and the filtrate was concentrated under reduced pressure to give a residue. The residue was isolated by column chromatography to give 330 mg of brown oil with a yield of 49%.

Step B: Preparation of (R,E)-N'-(2-cyano-4-(piperidin-3-ylamino)phenyl)-N,N-dimethylamidine Tert-butyl (R,E)-3-((3-cyano-4-((dimethylamino)methylene)amino)phenyl) piperidin-1-carboxylate (100 mg, 0.27 mmol) was dissolved in a mixed solvent of trifluoroacetic acid (0.5 mL) and dichloromethane (5 mL). After stirring the reaction solution at room temperature for 4 hours, the mixture was concentrated under reduced pressure to give a residue, followed by addition of aqueous sodium bicarbonate solution and extraction with dichloromethane for three times. The organic phases were combined, dried over anhydrous sodium sulfate, and concentrated under reduced pressure to give 70 mg of brown oil, which was directly used in the next reaction.

Step C: Preparation of (R,E)-N'-(4-((1-acryloylpiperidin-3-yl)amino)-2-cyanophenyl)-N,N-dimethylformamidine Acrylic acid (28 mg, 0.39 mmol), HATU (147 mg, 0.39 mmol) and N,N-diisopropylethylamine (100 mg, 0.90 mmol) were added into DMF (2 mL). After stirring the mixture for 10 minutes, (R,E)-N'-(2-cyano-4-(piperidin-3-ylamino) phenyl)-N,N-dimethylformamidine (70 mg, 0.26 mmol) was added. After stirring the reaction solution at room temperature for 16 hours, the residue obtained by concentration under reduced pressure was isolated by column chromatography to give 40 mg of brown oil with a yield of 48%.

Step D: Preparation of (R)-1-(3-((4-((4-([1,2,4]triazolo[4,3-c]pyrimidin-7-yloxy)-3-methylphenyl)amino)quinazolin-6-yl) amino)piperidin-1-yl)propan-2-en-1-one (R,E)-N'-(4-((1-acryloylpiperidin-3-yl)amino)-2-cyanophenyl)-N,N-dimethylformamidine (40 mg, 0.12 mmol) and 4-([1,2,4]triazolo[4,3-c]pyrimidin-7-yloxy)-3-methylaniline (30 mg, 0.12 mmol) were added to isopropyl acetate (4 mL) and acetic acid (1 mL). After the mixture was reacted at room temperature for 48 hours, the residue was obtained by concentration under reduced pressure, and then isolated by preparative TLC to give 10 mg of yellow solid with a yield of 15%. LC-MS: 522.3[M+H] detection value; $^1$H-NMR (400 MHz, DMSO-d$_6$) δ9.68 (s, 1H), 9.32-9.21 (m, 1H), 8.59 (s, 1H), 8.37 (d, J=6.0 Hz, 1H), 7.93-7.82 (m, 1H), 7.77-7.74 (m, 1H), 7.56 (dd, J=8.8, 4.4 Hz, 1H), 7.42-7.28 (m, 2H), 7.20 (d, J=8.8 Hz, 1H), 7.11 (s, 1H), 6.94-6.61 (m, 0.5H, 0.5H), 6.23-6.03 (m, 1.5H, 0.5H), 5.76-5.50 (m, 0.5H, 0.5H), 4.56-3.94 (m, 0.5H, 1.5H), 3.75-3.72 (m, 1H), 3.27-3.20 (m, 2H), 2.20 (s, 3H), 2.12-2.10 (m, 1H), 1.88-1.85 (m, 1H), 1.58-1.55 (m, 2H).

Embodiment 8

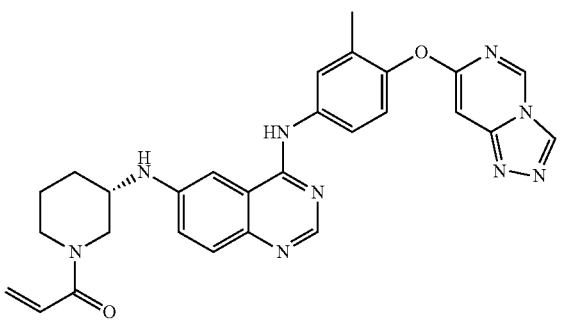 [SMILES: C=CC(=O)N1CCC[C@H](Nc2ccc3ncnc(Nc4ccc(Oc5cc6nncn6cn5)c(C)c4)c3c2)C1]

Synthesis of (R)-1-(3-((4-((4-([1,2,4]triazolo[4,3-c]pyrimidin-7-yloxy)-3-methylphenyl)amino)quinazolin-6-yl)amino)piperidin-1-yl)propan-2-en-1-one The preparation was performed according to the method of Embodiment 7, wherein tert-butyl (S)-3-aminopiperidin-1-carboxylate was used to replace tert-butyl (R)-3-aminopiperidin-1-carboxylate. LC-MS: 262 [M/2+H] detection value; $^1$H-NMR (400 MHz, CD$_3$OD) δ 9.46 (s, 1H), 8.44 (s, 1H), 8.37-8.36 (m, 1H), 7.84 (s, 1H), 7.82-7.66 (m, 1H), 7.61-7.58 (m, 1H), 7.45-7.44 (m, 0.6H), 7.39-7.31 (m, 1H), 7.30 (m, 0.4H), 7.24-7.16 (m, 1H), 6.96-6.95 (m, 1H), 6.91-6.84 (m, 0.6H), 6.66-6.59 (m, 0.4H), 6.36-6.31 (m, 0.6H), 6.17-6.12 (m, 0.4H), 5.83-5.80 (m, 0.6H), 5.58-5.55 (m, 0.4H), 4.81-4.78 (m, 0.51H), 4.11-4.08 (m, 0.5H), 3.99-3.91 (m, 1H), 3.82 (m, 0.5H), 3.60 (m, 0.5H), 3.54-3.42 (m, 1H), 2.78-2.72 (m, 1H), 2.27 (s, 3H), 2.24-2.16 (m, 1H), 1.97 (m, 1H), 1.82-1.64 (m, 2H).

Embodiment 9

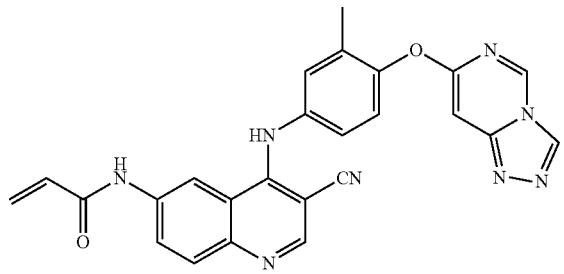 [SMILES: C=CC(=O)Nc1ccc2ncc(C#N)c(Nc3ccc(Oc4cc5nncn5cn4)c(C)c3)c2c1]

Synthesis of N-(4-((4-([1,2,4]triazolo[4,3-c]pyrimidin-7-yloxy)-3-methyl phenyl)amino)-3-cyanoquinolin-6-yl)acrylamide Step A: Preparation of (E)-ethyl 2-cyano-3-((4-nitrophenyl)amino)acrylate 4-Nitroaniline (2 g, 14.48 mmol) and (E)-ethyl 2-cyano-3-ethoxyacrylate (2.9 g, 17 mmol) were added to toluene (12 mL). After the mixture was heated to 120° C. and reacted for 16 hours, the mixture was filtered and washed with petroleum ether to give 3.5 g of light green solid, which was directly used in the next reaction.

Step B: Preparation of 4-hydroxy-6-nitroquinolin-3-carbonitrile (E)-ethyl 2-cyano-3-((4-nitrophenyl) amino) acrylate (8 g, 30.6 mmol) was added into Dowtherm A heat transfer oil. The mixture was heated to 256° C. and maintained for 7 hours under argon atmosphere, then cooled to room temperature, diluted with petroleum ether, filtered to give 5 g of brown solid, and directly used in the next reaction.

Step C: Preparation of 4-chloro-6-nitroquinolin-3-carbonitrile

4-Hydroxy-6-nitroquinolin-3-carbonitrile (1.0 g, 4.6 mmol) was added to phosphorus oxychloride (10 mL). The mixture was reacted at 120° C. for 3 hours, and then cooled to room temperature. The residue obtained by concentration under reduced pressure was dispersed in dichloromethane and aqueous sodium carbonate solution. The organic phases were separated, and the aqueous phase was extracted with dichloromethane three times. The organic phases were combined, dried over anhydrous sodium sulfate, and concentrated under reduced pressure to give 490 mg of yellow solid, which was directly used in the next reaction.

Step D: Preparation of 4-((4-([1,2,4]triazolo[4,3-c]pyrimidin-7-yloxy)-3-methylphenyl)amino)-6-nitroquinolin-3-carbonitrile 4-Chloro-6-nitroquinolin-3-carbonitrile (435 mg, 1.86 mmol) and 4-([1,2,4]triazolo[4,3-c]pyrimidin-7-yloxy)-3-methylaniline (450 mg, 1.86 mmol) were added to isopropanol (15 mL). After the reaction solution was reacted at 90° C. for 16 hours, the reaction solution was cooled and filtered to give 720 mg of yellow solid, which was directly used in the next reaction.

Step E: Preparation of 4-((4-([1,2,4]triazolo[4,3-c]pyrimidin-7-yloxy)-3-methylphenyl)amino)-6-aminoquinolin-3-carbonitrile 4-((4-([1,2,4]Triazolo[4,3-c]pyrimidin-7-yloxy)-3-methylphenyl)amino)-6-nitroquinolin-3-carbonitrile (700 mg, 1.59 mmol), iron powder (626 mg, 11.18 mmol) and ammonium chloride (777 mg, 14.38 mmol) were added to methanol (28 mL) and water (4 mL). The mixture was heated to 85° C. and reacted for 4 hours, followed by hot filtration. The filter cake was washed with hot methanol. The filtrates were combined and concentrated under reduced pressure to give a residue. The residue was dispersed in hot ethyl acetate and aqueous sodium bicarbonate solution. The organic phases were separated, dried over anhydrous sodium sulfate and concentrated under reduced pressure to give a residue. The residue was isolated by column chromatography to give 193 mg of yellow solid with a yield of 30%.

Step F: Preparation of N-(4-((4-([1,2,4]triazolo[4,3-c]pyrimidin-7-yloxy)-3-methylphenyl)amino)-3-cyanoquinolin-6-yl)acrylamide 4-((4-([1,2,4]Triazolo[4,3-c]pyrimidin-7-yloxy)-3-methylphenyl)amino)-6-aminoquinolin-3-carbonitrile (60 mg, 0.15 mmol) and triethylamine (46 mg, 0.45 mmol) were added to tetrahydrofuran (6 mL), and acryloyl chloride (20 mg, 0.22 mmol) was added dropwise at 0° C. The reaction solution was warmed to room temperature and stirred for 4 hours, then concentrated under reduced pressure to give a residue. The residue was isolated and purified by preparative HPLC to give 30 mg of yellow solid with a yield of 44%. LC-MS: 463.2 [M+H] detection value; $^1$H-NMR (400 MHz, DMSO-$d_6$) δ10.58 (s, 1H), 9.89 (s, 1H), 9.72 (d, J=1.2 Hz, 1H), 8.90 (s, 1H), 8.57-8.56 (m, 2H), 7.95 (s, 2H), 7.34 (s, 1H), 7.24 (s, 2H), 6.95 (d, J=1.2 Hz, 1H), 6.55 (dd, J=16.8, 10.0 Hz, 1H), 6.37 (dd, J=16.8, 1.6 Hz, 1H), 5.86 (dd, J=10.0, 1.6 Hz, 1H), 2.19 (s, 3H).

Embodiment 10

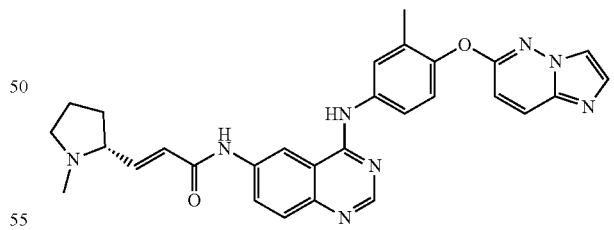

Synthesis of (R,E)-N-(4-((4-(imidazo[1,2-b]pyridazin-6-yloxy)-3-methyl phenyl)amino)quinazolin-6-yl)-3-(1-methylpyrrol-2-yl)acrylamide Step A: Preparation of diethyl (E)-(2-((3-cyano-4-((dimethylamino) methylene)amino)phenyl)amino)-2-oxoethyl)phosphate (E)-N'-(4-amino-2-cyanophenyl)-N,N-dimethylformamidine (2 g, 10.625 mmol), 2-(diethoxyphosphoryl) acetic acid (2.3 g, 12 mmol), EDCI (8.152 g, 42.52 mmol) and N,N-diisopropylethylamine (8.244 g, 63.79 mmol) were mixed in N,N-dimethylformamide (20 mL), and the reaction solution was stirred at 30° C. for 16 hours. Water (30 mL) was added to the reaction solution, then the mixture was extracted twice with ethyl acetate (50 mL), and then extracted twice with a mixed solvent of dichloromethane and methanol (10:1, 40 mL). The organic phases were combined, washed with saturated brine (60 mL), dried and filtered. The filtrate was evaporated under reduced pressure to remove most of the solvent, with solid precipitation, followed by filtration. The filter cake was washed with ethyl acetate to give 2.57 g of crude white solid, which was directly used in the next reaction.

Step B: Preparation of tert-butyl (R)-2-((E)-3-((3-cyano-4-(((E)-(dimethyl amino)methylene)amino)phenyl)amino)-3-oxoprop-1-en-1-yl)pyrrol-1-carboxylate Diethyl (E)-(2-((3-cyano-4-((dimethylamino)methyleneamino)phenyl) amino)-2-oxoethyl)phosphate (A, 1000 mg, 2.729 mmol) was suspended in dry tetrahydrofuran (10 mL), followed by cooling to 0° C. and addition of sodium hydride (218 mg, 5.459 mmol) under argon atmosphere. After the reaction solution was stirred at 0° C. for 30 minutes, a solution of tert-butyl (R)-2-formylpyrrol-1-carboxylate (653 mg, 3.275 mmol) in tetrahydrofuran (1 mL) was added dropwise while maintaining this temperature. The final reaction mixture was slowly heated to 20° C. and stirred for 1.5 hours. The reaction solution was quenched with saturated ammonium chloride (50 mL) and extracted twice with ethyl acetate (20 mL). The organic phases were combined, dried over anhydrous sodium sulfate, filtered, and the filtrate was concentrated under reduced pressure. The obtained residue was isolated and purified by silica gel column to give 820 mg of white solid with a yield of 73%.

Step C: Preparation of (E)-N-(3-cyano-4-(((E)-(dimethylamino)methylene) amino)phenyl)-3-((R)-pyrrol-2-yl)acrylamide Tert-butyl (R)-2-((E)-3-((3-cyano-4-(((E)-(dimethylamino)methylene) amino)phenyl)amino)-3-oxopropyl-1-en-1-yl)pyrrol-1-carboxylate (967 mg, 2.350 mmol) was dissolved in dichloromethane (10.2 mL), and trifluoroacetic acid (1.8 mL) was slowly added dropwise. The reaction solution was stirred at 20° C. for 2 hours, and concentrated under pressure to give 732 mg of trifluoroacetate as the crude product in form of oil, which was directly used in the next reaction.

Step D: Preparation of (E)-N-(3-cyano-4-(((E)-(dimethylamino)methylene) amino)phenyl)-3-((R)-1-methylpyrrol-2-yl)acrylamide The crude product (E)-N-(3-cyano-4-(((E)-(dimethylamino) methylene) amino)phenyl)-3-((R)-pyrrol-2-yl)acrylamide (732 mg, 2.351 mmol) obtained from the above reaction was dissolved in methanol (8 mL), followed by addition of aqueous formaldehyde solution (2.3 mL, 37 mass %). The reaction solution was stirred at 20° C. for 1 hour, followed by addition of sodium borohydride acetate (3.52 g, 16.45 mmol), and the final reaction solution was stirred at 20° C. for 16 hours. The reaction solution was concentrated under reduced pressure, and the residue obtained was isolated and purified by silica gel column to give 390 mg of pale yellow solid with a yield of 51%.

Step E: Preparation of 4-(imidazo[1,2-b]pyridazin-6-yloxy)-3-methylaniline

4-Amino-2-methylphenol (212 mg, 1.72 mmol), 6-chloroimidazo[1,2-b]pyridazine (176 mg, 1.15 mmol) and cesium carbonate (747 mg, 2.29 mmol) were mixed in dimethyl sulfoxide (1 mL), and the reaction solution was stirred for 16 hours at 120° C. under nitrogen atmosphere. Ethyl acetate (10 mL) was added to the reaction solution, washed with water (10 mL), and the organic phase was separated. The aqueous phase was extracted with ethyl acetate (10 mL×2). The organic phases were combined, washed with saturated aqueous sodium chloride solution, dried over anhydrous sodium sulfate, filtered, and the filtrate was evaporated to dryness under reduced pressure to give a crude product. The crude product was isolated and purified by silica gel column to give 309 mg of brown solid with a yield of 100%.

Step F: Preparation of (R,E)-N-(4-((4-(imidazo[1,2-b]pyridazin-6-yloxy)-3-methylphenyl)amino)quinazolin-6-yl)-3-(1-methylpyrrol-2-yl)acrylamide (E)-N-(3-cyano-4-(((E)-(dimethylamino)methylene) amino)phenyl)-3-((R)-1-methylpyrrol-2-yl)acrylamide (50 mg, 0.15 mmol), 4-(imidazo[1,2-b]pyridazin-6-yloxy)-3-methylaniline (36 mg, 0.15 mmol) and glacial acetic acid (0.3 mL) were mixed in isopropyl acetate (1 mL), and the mixture was stirred at 20° C. for 16 hours. The reaction solution was concentrated under reduced pressure to give a crude product. The crude product was isolated and purified by silica gel column to give 24.27 mg of pale brown solid with a yield of 30.3%. LC-MS: 521.2[M+H] detection value; $^1$H-NMR (400 MHz, DMSO) δ 10.46 (s, 1H), 9.87 (s, 1H), 8.84 (s, 1H), 8.55 (s, 1H), 8.20 (d, J=9.8 Hz, 1H), 8.11 (s, 1H), 7.89 (dd, J=8.8, 2.0 Hz, 1H), 7.81-7.79 (m, 2H), 7.74 (dd, J=8.8, 2.4 Hz, 1H), 7.66 (d, J=0.8 Hz, 1H), 7.26 (d, J=8.4 Hz, 1H), 7.18 (d, J=9.6 Hz, 1H), 6.76 (dd, J=15.2, 7.6 Hz, 1H), 6.39 (d, J=15.2 Hz, 1H), 3.11-3.06 (m, 1H), 2.88-2.82 (m, 1H), 2.26 (m, 4H), 2.21 (s, 3H), 2.10-2.01 (m, 1H), 1.82-1.74 (m, 2H), 1.66-1.56 (m, 1H).

Embodiment 11

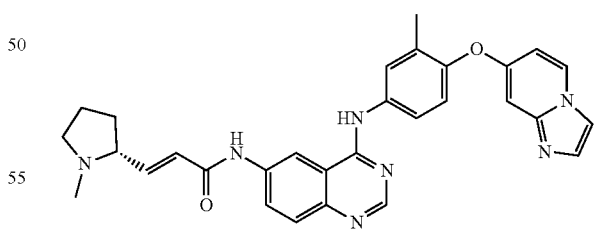

Synthesis of (R,E)-N-(4-((4-(imidazo[1,2-a]pyridin-7-yloxy)-3-methylphenyl) amino)quinazolin-6-yl)-3-(1-methylpyrrolidin-2-yl)acrylamide Step A: Preparation of imidazo[1,2-a]pyridin-7-ol 2-Aminopyridin-4-ol (1.0 g, 9.08 mmol) and 2-chloroacetaldehyde (3.75 mL, 19.0 mmol, 40% aqueous solution)

were dissolved in ethanol (45 mL). After the mixture was reacted at 90° C. for 16 hours, a residue was obtained by concentration under reduced pressure. The residue was isolated by column chromatography to give 1.2 g of colorless oil with a yield of 99%.

Step B: Preparation of 7-(2-methyl-4-nitrophenoxy) imidazo[1,2-a]pyridine

1-Fluoro-2-methyl-4-nitrobenzene (1.38 g, 8.9 mmol), imidazo[1,2-a]pyridin-7-ol (1.2 g, 8.9 mmol) and potassium carbonate (1.48 g, 10.7 mmol) were added to DMF (15 mL). After the reaction solution was reacted at 80° C. for 16 hours, the mixture was filtered and concentrated under reduced pressure to give a residue. The residue was isolated by column chromatography to give 340 mg of yellow solid, with a yield of 14%.

Step C: Preparation of 4-(imidazo[1,2-a]pyridin-7-yloxy)-3-methylaniline 7-(2-Methyl-4-nitrophenoxy)imidazo[1,2-a]pyridine (340 mg, 1.26 mmol) and palladium-carbon (60 mg) were added to methanol (20 mL), and the reaction solution was reacted at room temperature for 4 hours under the hydrogen atmosphere, followed by filtration with diatomite. The filtrate was concentrated to give 300 mg of colorless oil, which was directly used in the next reaction.

Step D: Preparation of (R,E)-N-(4-((4-(imidazo[1,2-a]pyridin-7-yloxy)-3-methylphenyl)amino)quinazolin-6-yl)-3-(1-methylpyrrolidin-2-yl)acrylamide Preparation was performed according to the method of Embodiment 10. LC-MS: 520.1 [M+H] detection value; $^1$H-NMR (400 MHz, CD$_3$OD) δ 8.79 (d, J=2.0 Hz, 1H), 8.50 (s, 1H), 8.43 (d, J=7.2 Hz, 1H), 7.86-7.65 (m, 5H), 7.46 (d, J=1.6 Hz, 1H), 7.14 (d, J=8.4 Hz, 1H), 6.90-6.75 (m, 2H), 6.67 (d, J=2.4 Hz, 1H), 6.40 (d, J=14.8 Hz, 1H), 3.29-3.20 (m, 1H), 3.08 (dd, J=16.8, 8.4 Hz, 1H), 2.53-2.45 (m, 1H), 2.43 (s, 3H), 2.27 (s, 3H), 2.23-2.14 (m, 1H), 2.00-1.89 (m, 2H), 1.87-1.74 (m, 1H).

Embodiment 12

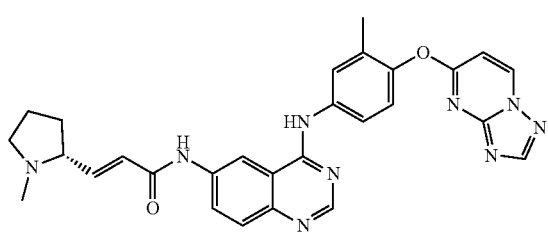 [SMILES: Cc1cc(Nc2ncnc3ccc(NC(=O)/C=C/[C@H]4CCCN4C)cc23)ccc1Oc1ccn2ncnc2n1]

Synthesis of (R,E)-N-(4-((4-([1,2,4]triazolo[1,5-a]pyrimidin-5-yloxy)-3-methylphenyl)amino)quinazolin-6-yl)-3-(1-methylpyrrolidin-2-yl)-acrylamide Preparation was performed according to the method of Embodiment 10. LC-MS: 522.3 [M+H] detection value; $^1$H-NMR (400 MHz, DMSO) δ 10.42 (s, 1H), 9.86 (s, 1H), 9.69 (s, 1H), 8.60 (s, 1H), 8.55 (s, 1H), 7.88-7.75 (m, 3H), 7.20 (d, J=8 Hz, 1H), 6.78-7.72 (m, 1H), 6.37 (d, J=16 Hz, 1H), 5.90 (s, 1H), 3.09-3.03 (m, 1H), 2.85-2.75 (m, 1H), 2.22-2.17 (m, 7H), 2.05-1.95 (m, 1H), 1.80-1.70 (m, 2H), 1.66-1.56 (m, 1H).

Embodiment 14

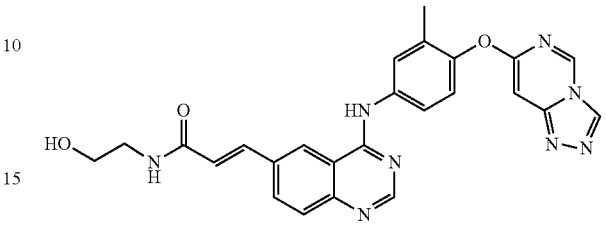

Synthesis of (E)-3-(4-((4-([1,2,4]triazolo[4,3-c]pyrimidin-7-yloxy)-3-methyl phenyl)amino)quinazolin-6-yl)-N-(2-hydroxyethyl)acrylamide Step A: Preparation of (E)-preparation of 3-(4-((4-([1,2,4] triazolo [4,3-c]pyrimidin-7-yloxy)-3-methylphenyl) amino) quinazolin-6-yl)acrylic acid The raw material N-(4-([1,2,4]triazolo[4,3-c]pyrimidin-7-yloxy)-3-methyl phenyl)-6-iodoquinazolin-4-amine (500 mg, 1.01 mmol), acrylic acid (110 mg, 1.53 mmol), tris (dibenzylideneacetone)palladium (20 mg, 0.19 mmol), and triethylamine (510 mg, 5.04 mmol) were mixed in N,N-dimethylformamide (5 mL), then heated to 80° C. and stirred for 16 hours. The mixture was filtered through diatomite and concentrated under reduced pressure to dryness. The residue was dissolved in N,N-dimethylformamide (5 mL), and the water (10 mL) was slowly added dropwise under stirring to precipitate a large amount of solid, followed by filtration. The filter cake was washed with a small amount of water, dried in vacuum to give 440 mg of off-white solid, which was directly used in the next reaction.

Step B: Preparation of (E)-3-(4-((4-([1,2,4]triazolo [4,3-c]pyrimidin-7-yloxy)-3-methylphenyl)amino) quinazolin-6-yl)-N-(2-hydroxyethyl)acrylamide (E)-3-(4-((4-([1,2,4]triazolo[4,3-c]pyrimidin-7-yloxy)-3-methylphenyl)amino) quinazolin-6-yl)acrylic acid (100 mg, 0.23 mmol), 2-aminoethanol (25 mg, 0.41 mmol), 1-ethyl-3-(3-dimethylaminopropyl)carbodiimide hydrochloride (90 mg, 0.58 mmol), 1-hydroxybenzotriazole (62 mg, 0.46 mmol), and N,N-diisopropylethylamine (150 mg, 1.48 mmol) were dissolved in N,N-dimethylformamide (5 mL) and stirred at room temperature for 16 hours. Water (50 mL) and dichloromethane (50 mL) were added into the reaction solution, shaked well and allowed to stand for layering. The organic layer was collected, washed with saturated aqueous sodium chloride solution (50 mL), and dried over anhydrous sodium sulfate for 2 hours, followed by filtration and concentration under reduced pressure, and the residue was isolated and purified by preparative HPLC to give 30 mg of pale yellow solid with a yield of 27.32%. LC-MS: 483.2 [M+H] detection value; $^1$H-NMR (400 MHz, CD$_3$OD) δ 9.44 (d, J=1.2 Hz, 1H), 8.55 (s, 1H), 8.53 (d, J=1.6 Hz, 1H), 8.42 (s, 1H), 8.14 (dd, J=8.8, 1.6 Hz, 1H), 7.86-7.66 (m, 4H), 7.20 (d, J=8.8 Hz, 1H), 6.95 (d, J=1.2 Hz, 1H), 6.82 (d, J=15.6 Hz, 1H), 3.70 (t, J=5.6 Hz, 2H), 3.47 (t, J=5.6 Hz, 2H), 2.26 (s, 3H).

Embodiment 15

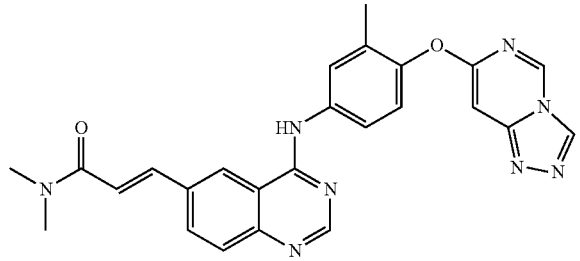 [SMILES: Cc1cc(Nc2ncnc3ccc(/C=C/C(=O)N(C)C)cc23)ccc1Oc1cc2nncn2cn1]

Synthesis of (E)-3-(4-((4-([1,2,4]triazolo[4,3-c]pyrimidin-7-yloxy)-3-methyl phenyl)amino)quinazolin-6-yl)-N,N-dimethylacrylamide Preparation was performed according to the method of Embodiment 14. LC-MS: 467.2 [M+H] detection value; $^1$H-NMR (400 MHz, CD$_3$OD) δ 9.43 (d, J=1.2 Hz, 1H), 8.61 (d, J=1.6 Hz, 1H), 8.55 (s, 1H), 8.42 (s, 1H), 8.19 (dd, J=8.8, 1.6 Hz, 1H), 7.92-7.62 (m, 4H), 7.35 (d, J=15.6 Hz, 1H), 7.20 (d, J=8.8 Hz, 1H), 6.95 (d, J=1.2 Hz, 1H), 3.09 (s, 3H), 2.26 (s, 3H).

Embodiment 16

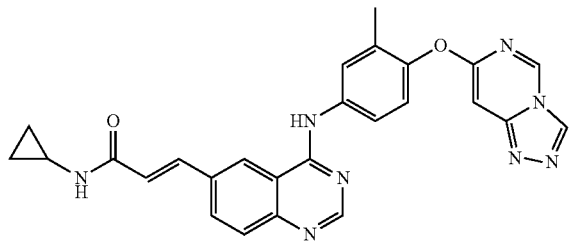 [SMILES: Cc1cc(Nc2ncnc3ccc(/C=C/C(=O)NC4CC4)cc23)ccc1Oc1cc2nncn2cn1]

Synthesis of (E)-3-(4-((4-([1,2,4]triazolo[4,3-c]pyrimidin-7-yloxy)-3-methyl phenyl)amino)quinazolin-6-yl)-N-cyclopropylacrylamide Preparation was performed according to the method of Embodiment 14. LC-MS: 479.2 [M+H] detection value; $^1$H-NMR (400 MHz, CD$_3$OD) δ 9.36 (s, 1H), 8.56 (s, 1H), 8.49 (s, 1H), 8.36 (s, 1H), 8.07 (d, J=8.8 Hz, 1H), 7.85-7.59 (m, 4H), 7.17 (d, J=8.8 Hz, 1H), 6.91 (s, 1H), 6.66 (d, J=15.6 Hz, 1H), 2.92-2.76 (m, 1H), 2.26 (s, 3H), 0.86-0.73 (m, 2H), 0.65-0.52 (m, 2H).

Embodiment 17

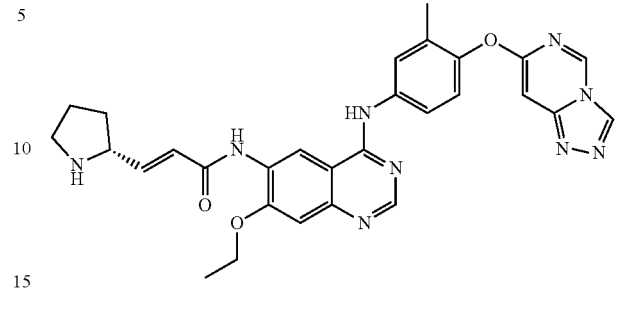

Synthesis of (R,E)-N-(4-((4-([1,2,4]triazolo[4,3-c]pyrimidin-7-yloxy)-3-methylphenyl)amino)-7-ethoxyquinazolin-6-yl)-3-(pyrrolidin-2-yl)acrylamide Step A: Preparation of 7-ethoxy-6-nitroquinazolin-4-ol 7-Fluoro-6-nitroquinazolin-4-ol (4000 mg, 19.13 mmol) was dissolved in tetrahydrofuran (20 mL), cooled to 0° C. in an ice-water bath, and a solution of sodium ethoxide (4000 mg, 58.78 mmol) in anhydrous ethanol (20 mL) was slowly added dropwise into the reaction solution. The mixture was gradually warmed to room temperature, and stirred for 16 hours. Under an ice-water bath, the pH of the reaction solution was adjusted to 5-6 with acetic acid, filtered, and dried in vacuum to give 4000 mg of pale yellow solid, which was directly used in the next reaction.

Step B: Preparation of 4-chloro-7-ethoxy-6-nitroquinazoline

7-Ethoxy-6-nitroquinazolin-4-ol (4000 mg, 17.01 mmol) was dissolved in phosphorus oxychloride (50 mL), and heated and refluxed for 4 hours under stirring. The reaction solution was concentrated under reduced pressure to dryness. The residue was dissolved in dichloromethane (500 mL), washed with water (500 mL) and saturated brine (500 mL) successively, dried over anhydrous sodium sulfate, and concentrated under reduced pressure to give 4000 mg of pale yellow solid with a yield of 92.7%, which was directly used in the next reaction.

Step C: Preparation of N-(4-([1,2,4]triazolo[4,3-c]pyrimidin-7-yloxy)-3-methylphenyl)-7-ethoxy-6-nitroquinazolin-4-amine 4-([1,2,4]Triazolo[4,3-c] pyrimidin-7-yloxy)-3-methylaniline (2853 mg, 11.83 mmol), 4-chloro-7-ethoxy-6-nitroquinazoline (2000 mg, 7.88 mmol), and potassium carbonate (2180 mg, 15.77 mmol) were suspended in N,N-dimethylformamide (40 mL), and stirred at room temperature for 5 hours, followed by filtration. To the filtrate were added dichloromethane (100 mL) and water (100 mL). The organic layer was separated and washed with water (100 ml) and saturated saline (100 ml) successively, dried over anhydrous sodium sulfate, filtered, and concentrated under reduced pressure. The residue was isolated and purified by column chromatography to give 2800 mg of pale yellow solid with a yield of 77.8%.

Step D: Preparation of N⁴-(4-([1,2,4]triazolo[4,3-c]pyrimidin-7-yloxy)-3-methylphenyl)-7-ethoxyquinazolin-4,6-diamine N-(4-([1,2,4]triazolo[4,3-c]pyrimidin-7-yloxy)-3-methylphenyl)-7-ethoxy-6-nitroquinazolin-4-amine (1000 mg, 2.182 mmol) was dissolved in methanol (40 mL), followed by addition of raney nickel. The reaction mixture was stirred at room temperature for 2 hours under hydrogen atmosphere (balloon). The mixture was filtered through diatomite and concentrated under reduced pressure to give 700 mg of earthy yellow solid, which was directly used in the next reaction.

Step E: Preparation of diethyl 2-((4-((4-([1,2,4] triazolo [4,3-c]pyrimidin-7-yloxy)-3-methylphenyl)amino)-7-ethoxyquinazolin-6-yl)amino)-2-oxoethyl) phosphate N⁴-(4-([1,2,4]triazolo[4,3-c]pyrimidin-7-yloxy)-3-methylphenyl)-7-ethoxyquinazolin-4,6-diamine (700 mg, 1.63 mmol), 2-(diethoxyphosphoryl)acetic acid (650 mg, 3.31 mmol), 1-ethyl-(3-dimethylaminopropyl)carbodiimide hydrochloride (1100 mg, 7.09 mmol), and N,N-diisopropylethylamine (1268 mg, 9.81 mmol) were dissolved in N,N-dimethylformamide (15 mL), the mixture was heated to 50° C. and stirred for 16 hours. The reaction mixture was cooled to room temperature, concentrated under reduced pressure, and the residue was isolated and purified by column chromatography to give 500 mg of viscous solid with a yield of 50.45%.

Step F: Preparation of tert-butyl (R,E)-2-(3-((4-((4-([1,2,4]triazolo[4,3-c]pyrimidin-7-yloxy)-3-methylphenyl)amino)-7-ethoxyquinazolin-6-yl)amino)-3-oxopropan-1-enyl)pyrrolidin-1-carboxylate Diethyl (2-((4-((4-([1,2,4]triazolo[4,3-c]pyrimidin-7-yloxy)-3-methylphenyl) amino)-7-ethoxyquinazolin-6-yl)amino)-2-oxoethyl)phosphate (240 mg, 0.40 mmol) was dissolved in tetrahydrofuran (5 mL), cooled to 0° C. in an ice-water bath. Sodium hydride (32 mg, 1.33 mmol) was added to the reaction solution in batches under stirring, and stirred for 30 minutes. A solution of tert-butyl (R)-2-formylpyrrolidin-1-carboxylate (102 mg, 0.51 mmol) in tetrahydrofuran (5 mL) was added dropwise. After the addition was completed, the reaction solution was naturally warmed to room temperature and stirred for 1 hour. 5% aqueous ammonium chloride solution (20 mL) and dichloromethane (40 mL) were added into the reaction solution, shaked well and allowed to stand for layering. The aqueous phase was extracted with dichloromethane (50 mL) again. The organic layers were combined, washed with water (50 mL) and saturated aqueous sodium chloride solution (50 mL) successively, dried over anhydrous sodium sulfate, filtered and concentrated, and the residue was isolated and purified by column chromatography to give 100 mg of pale yellow solid with a yield of 38.8%.

Step G: Preparation of (R,E)-N-(4-((4-([1,2,4]triazolo[4,3-c]pyrimidin-7-yloxy)-3-methylphenyl)amino)-7-ethoxyquinazolin-6-yl)-3-(pyrrolidin-2-yl)acrylamide Tert-butyl (R,E)-2-(3-((4-((4-([1,2,4]triazolo[4,3-c]pyrimidin-7-yloxy)-3-methylphenyl)amino)-7-ethoxyquinazolin-6-yl)amino)-3-oxopropyl-1-alkenyl)pyrrolidin-1-carboxylate (40 mg, 0.06 mmol) was dissolved in a solution of dichloromethane (5 mL) comprising 8% trifluoroacetic acid. The mixture was stirred at room temperature for 2 hours, and concentrated under reduced pressure. The residue was isolated and purified by preparative HPLC chromatography to give 20 mg of pale yellow solid with a yield of 59.07%. LC-MS: 552.3 [M+H] detection value; ¹H-NMR (400 MHz, CD₃OD) δ 9.46 (s, 1H), 8.96 (s, 1H), 8.48 (s, 1H), 8.44 (s, 1H), 7.73 (s, 1H), 7.68 (d, J=8.8 Hz, 1H), 7.26 (s, 1H), 7.20 (d, J=8.8 Hz, 1H), 7.06 (dd, J=15.2, 7.6 Hz, 1H), 6.95 (s, 1H), 6.78 (d, J=15.2 Hz, 1H), 4.45-4.20 (m, 3H), 3.50-3.36 (m, 2H), 2.48-1.86 (m, 5H), 2.27 (s, 3H), 1.58 (t, J=6.8 Hz, 3H).

Embodiment 18

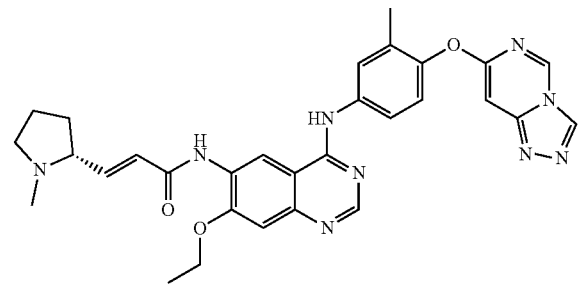 [SMILES: CCOc1cc2ncnc(Nc3ccc(Oc4cc5nncn5cn4)c(C)c3)c2cc1NC(=O)/C=C/[C@H]1CCCN1C]

Synthesis of (R,E)-N-(4-((4-([1,2,4]triazolo[4,3-c]pyrimidin-7-yloxy)-3-methylphenyl)amino)-7-ethoxyquinazolin-6-yl)-3-(1-methylpyrrolidin-2-yl)acrylamide

Step A: Preparation of (R,E)-N-(4-((4-([1,2,4]triazolo[4,3-c]pyrimidin-7-yloxy)-3-methylphenyl)amino)-7-ethoxyquinazolin-6-yl)-3-(1-methylpyrrolidin-2-yl)acrylamide (R,E)-N-(4-((4-([1,2,4]triazolo[4,3-c]pyrimidin-7-yloxy)-3-methylphenyl) amino)-7-ethoxyquinazolin-6-yl)-3-(pyrrolidin-2-yl)acrylamide (60 mg, 0.11 mmol) and 37% aqueous formaldehyde solution (105 mg) were dissolved in methanol (5 mL) and stirred at room temperature for 1 hour. Sodium borohydride acetate (164 mg, 0.77 mmol) was added to the reaction solution in batches and stirred at room temperature for 16 hours. The reaction solution was concentrated under reduced pressure, and the residue was isolated and purified by preparative HPLC to give 30 mg of pale yellow solid with a yield of 48.76%. LC-MS: 566.3 [M+H] detection value; ¹H-NMR (400 MHz, CD₃OD) δ 9.44 (s, 1H), 8.95 (s, 1H), 8.46 (s, 1H), 8.42 (s, 1H), 7.72 (s, 1H), 7.67 (d, J=8.8 Hz, 1H), 7.23 (s, 1H), 7.18 (d, J=8.8 Hz, 1H), 7.02-6.88 (m, 2H), 6.77 (d, J=15.2 Hz, 1H), 4.35 (q, J=6.8 Hz, 2H), 3.93-3.76 (m, 1H), 3.70-3.54 (m, 1H), 3.15-2.95 (m, 1H), 2.79 (s, 3H), 2.25 (s, 3H), 2.50-1.85 (m, 4H), 1.57 (t, J=6.8 Hz, 3H).

Embodiment 19

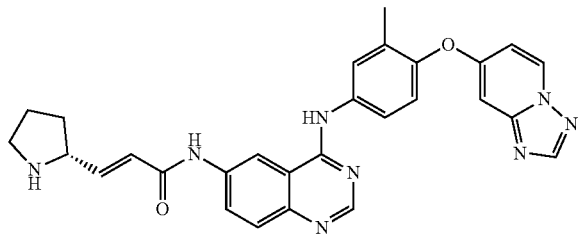 [SMILES: Cc1cc(Nc2ncnc3ccc(NC(=O)/C=C/[C@H]4CCCN4)cc23)ccc1Oc1ccn2ncnc2c1]

Synthesis of (R,E)-N-(4-((4-([1,2,4]triazolo[1,5-a]pyridin-7-yloxy)-3-methylphenyl)amino)quinazolin-6-yl)-3-(pyrrolidin-2-yl)acrylamide

Step A: Preparation of 4-(2-methyl-4-nitrophenoxy)pyridin-2-amine

2-Methyl-4-nitro-phenol (3000 mg, 23.34 mmol), 4-chloropyridin-2-amine (5400 mg, 35.26 mmol) and N,N-diisopropylethylamine (12000 mg, 92.85 mmol) were dissolved in dried N-methylpyrrolidone (20 mL), and stirred at 160° C. under reflux for 48 hours. The mixture was cooled to room temperature, followed by addition of ethyl acetate (600 mL) and water (300 mL). The organic phase was separated, washed with water (2×200 mL) and saturated brine (200 mL) successively, dried over anhydrous sodium sulfate, filtered and evaporated to dryness under reduced pressure. The residue was isolated and purified by column chromatography to give 3000 mg of brown oil (standing for curing) with a yield of 52.4%.

Step B: Preparation of (Z)—N,N-dimethyl-N'-(4-(2-methyl-4-nitrophenoxy) pyridin-2-yl)formamidine 1,1-Dimethoxy-N,N-dimethylmethylamine (3900 mg, 32.73 mmol) was added into 4-(2-methyl-4-nitrophenoxy)pyridin-2-amine (2000 mg, 8.16 mmol) in N,N-dimethylformamide (20 mL) and stirred at 110° C. under reflux for 4 hours. The mixture was naturally cooled to room temperature, and concentrated under reduced pressure to give 2000 mg of crude product as brown oil, which was directly used in the next reaction.

Step C: Preparation of 7-(2-methyl-4-nitrophenoxy)-[1,2,4]triazolo[1,5-a]pyridine (Z)—N,N-dimethyl-N'-(4-(2-methyl-4-nitrophenoxy)pyridin-2-yl)formamidine (1200 mg, 4.00 mmol) was dissolved in anhydrous methanol (25 mL), then cooled to 0° C. in an ice water bath, and pyridine (1100 mg, 3.91 mmol) and hydroxylamine-O-sulfonic acid (800 mg, 7.07 mmol) were successively added into the reaction solution. The mixture was naturally warmed to room temperature, then heated to 60° C. and stirred for 4 hours. The mixture was then naturally cooled to room temperature, and ethyl acetate (250 mL) and saturated aqueous sodium bicarbonate solution (250 mL) were added to the reaction solution. The organic phase was washed with water (250 mL) and saturated brine (250 mL) successively, dried over anhydrous sodium sulfate, filtered, and evaporated to dryness under reduced pressure. The residue was isolated and purified by column chromatography to give 500 mg of white solid with a yield of 46%.

Step D: Preparation of 4-([1,2,4]triazolo[1,5-a]pyridin-7-yloxy)-3-methylaniline 7-(2-Methyl-4-nitrophenoxy)-[1,2,4]triazolo[1,5-a]pyridine (190 mg, 0.70 mmol) was dissolved in methanol (15 mL), followed by addition of raney nickel, and the reactants were stirred for 2 hours under the hydrogen atmosphere. The mixture was filtered through diatomite and concentrated under reduced pressure to give 160 mg of white solid, which was directly used in the next reaction.

Step E: Preparation of N-(4-([1,2,4]triazolo[1,5-a]pyridin-7-yloxy)-3-methylphenyl)-6-nitroquinazolin-4-amine 4-([1,2,4]Triazolo[1,5-a]pyridin-7-yloxy)-3-methylaniline (160 mg, 0.67 mmol) and (E)-N'-(2-cyano-4-nitrophenyl)-N,N-dimethylformamidine (167 mg, 0.76 mmol) were added to the reaction flask, followed by successive addition of acetic acid (0.8 mL) and isopropyl acetate (2.4 mL). After stirring at room temperature for 16 hours, a large amount of solid was precipitated out, and 190 mg of pale yellow solid was obtained by filtration, which was directly used in the next reaction.

Step F: Preparation of $N^4$-(4-([1,2,4]triazolo[1,5-a]pyridin-7-yloxy)-3-methylphenyl)quinazolin-4,6-diamine The raw material N-(4-([1,2,4] triazolo[1,5-a]pyridin-7-yloxy)-3-methyl phenyl)-6-nitroquinazolin-4-amine (190 mg, 0.46 mmol) was dissolved in methanol (5 mL), followed by addition of raney nickel, and the reactants were stirred for 2 hours under the hydrogen atmosphere. The mixture was filtered through diatomite and concentrated under reduced pressure to give 170 mg of yellow solid, which was directly used in the next reaction.

Step G: Preparation of diethyl 2-((4-((4-([1,2,4]triazolo[1,5-a]pyridin-7-yloxy)-3-methylphenyl)amino) quinazolin-6-yl)amino)-2-oxoethyl) phosphate $N^4$-(4-([1,2,4]triazolo[1,5-a]pyridin-7-yloxy)-3-methylphenyl)quinazolin-4,6-diamine (170 mg, 0.44 mmol), 2-(diethoxyphosphoryl)acetic acid (180 mg, 0.92 mmol), 1-ethyl-(3-dimethylaminopropyl)carbodiimide hydrochloride (310 mg, 2.00 mmol), and N,N-diisopropylethylamine (360 mg, 2.79 mmol) were dissolved in N,N-dimethylformamide (5 mL), then heated to 50° C. and stirred for 16 hours. The mixture was cooled to room temperature, and concentrated under reduced pressure to give 200 mg of viscous solid, which was directly used in the next reaction.

Step H: Preparation of tert-butyl (R,E)-2-(3-((4-((4-([1,2,4] triazolo [1,5-a]pyridin-7-yloxy)-3-methylphenyl)amino)quinazolin-6-yl)amino)-3-oxopropyl-1-olefin-1-yl)pyrrolidin-1-carboxylate Diethyl (2-((4-((4-([1,2,4]triazolo[1,5-a]pyridin-7-yloxy)-3-methylphenyl) amino)quinazolin-6-yl)amino)-2-oxoethyl)phosphate (200 mg, 0.36 mmol) was dissolved in tetrahydrofuran (5 mL), and cooled to 0° C. in an ice-water bath. Sodium hydride (32 mg, 1.33 mmol) was added to the reaction solution in batches under stirring, and then stirred for 30 minutes. A solution of tert-butyl (R)-2-formylpyrrolidin-1-carboxylate (130 mg, 0.65 mmol) in tetrahydrofuran (5 mL) was added dropwise to the reaction solution. After the addition was completed, the reaction solution was naturally warmed to room temperature and stirred for 1 hour. Saturated aqueous ammonium chloride solution (40 mL) and dichloromethane (40 mL) were added to the reaction solution, and the organic phase was separated. The aqueous phase was extracted once with dichloromethane (50 mL). The organic phases were combined, washed with water (50 mL) and saturated aqueous sodium chloride solution (50 mL), dried over anhydrous sodium sulfate, filtered, and concentrated. The residue was isolated and purified by column chromatography to give 90 mg of pale yellow solid with a yield of 41.6%.

Step I: Preparation of (R,E)-N-(4-((4-([1,2,4]triazolo[1,5-a]pyridin-7-yloxy)-3-methylphenyl)amino)quinazolin-6-yl)-3-(pyrrolidin-2-yl)acrylamide Tert-butyl (R,E)-2-(3-((4-((4-([1,2,4]triazolo[1,5-a]pyridin-7-yloxy)-3-methylphenyl)amino)quinazolin-6-yl)amino)-3-oxopropyl-1-olefin-1-yl)pyrrolidin-1-carboxylate (50 mg, 0.08 mmol) was dissolved in a solution of 8% trifluoroacetic acid in dichloromethane (5 mL) comprising 8% trifluoroacetic acid, then stirred at room temperature for 2 hours, and concentrated under reduced pressure. The residue was isolated and purified by preparative HPLC to give 20 mg of pale yellow solid with a yield of 47.9%. LC-MS: 507.3 [M+H] detection value; $^1$H-NMR (400 MHz, CD$_3$OD) δ 8.78 (s, 1H), 8.73 (d, J=7.6 Hz, 1H), 8.51 (s, 1H), 8.28 (s, 1H), 7.93-7.67 (m, 4H), 7.18 (d, J=8.8 Hz, 1H), 7.13-6.94 (m, 2H), 6.83 (s, 1H), 6.56 (d, J=15.2 Hz, 1H), 4.46-4.24 (m, 1H), 3.50-3.30 (m, 2H), 2.24 (s, 3H), 2.49-1.84 (m, 4H).

Embodiment 20

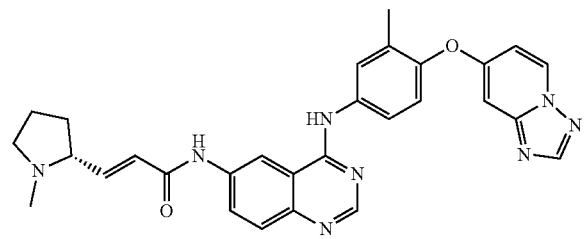 [SMILES: Cc1cc(Nc2ncnc3ccc(NC(=O)/C=C/[C@H]4CCCN4C)cc23)ccc1Oc1ccn2ncnc2c1]

Synthesis of (R,E)-N-(4-((4-([1,2,4]triazolo[1,5-a]pyridin-7-yloxy)-3-methyl phenyl)amino)quinazolin-6-yl)-3-(1-methylpyrrolidin-2-yl)acrylamide Preparation was performed according to the method of Embodiment 18. LC-MS: 521.3 [M+H] detection value; $^1$H-NMR (400 MHz, CD$_3$OD) δ 8.83 (s, 1H), 8.74 (d, J=7.2 Hz, 1H), 8.56 (s, 1H), 8.30 (s, 1H), 7.97-7.70 (m, 4H), 7.21 (d, J=8.8 Hz, 1H), 7.10 (d, J=6.0 Hz, 1H), 6.97 (dd, J=15.2, 8.8 Hz, 1H), 6.89 (s, 1H), 6.57 (d, J=15.2 Hz, 1H), 3.85-3.65 (m, 1H), 3.65-3.50 (m, 1H), 3.15-2.95 (m, 1H), 2.30 (s, 3H), 2.51-1.86 (m, 4H).

Embodiment 21

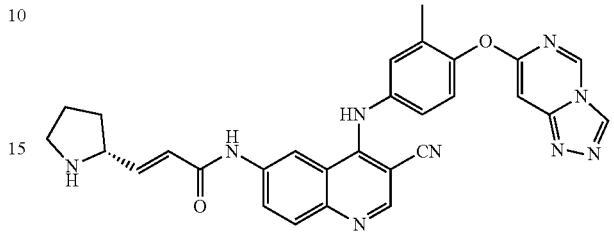

Synthesis of (R,E)-N-(4-((4-([1,2,4]triazolo[4,3-c]pyrimidin-7-yloxy)-3-methylphenyl)amino)-3-cyanoquinolin-6-yl)-3-(pyrrolidin-2-yl)acrylamide Preparation was performed according to the method of Embodiment 19. LC-MS: 532.3 [M+H] detection value; $^1$H-NMR (400 MHz, CD$_3$OD) δ9.45 (s, 1H), 8.79 (s, 1H), 8.45 (s, 1H), 8.39 (s, 1H), 7.98-7.73 (m, 2H), 7.34 (s, 1H), 7.31-7.17 (m, 2H), 6.99 (dd, J=15.2, 7.6 Hz, 1H), 6.93 (s, 1H), 6.52 (d, J=15.2 Hz, 1H), 4.38-4.22 (m, 1H), 3.44-3.30 (m, 2H), 2.22 (s, 3H), 2.42-1.81 (m, 4H).

Embodiment 22

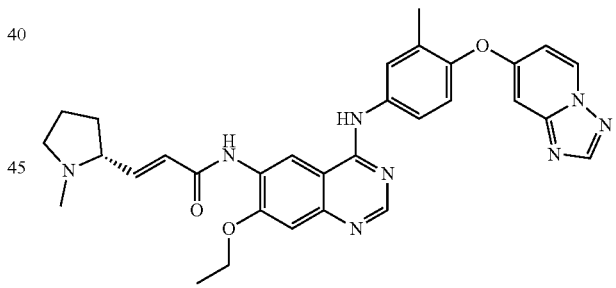

Synthesis of (R,E)-N-(4-((4-([1,2,4]triazolo[1,5-a]pyridin-7-yloxy)-3-methyl phenyl)amino)-7-ethoxyquinazolin-6-yl)-3-(1-methylpyrrolidin-2-yl)acrylamide Preparation was performed according to the methods of Embodiments 17 and 18. LC-MS: 283.3 [M/2+H] detection value; $^1$H-NMR (400 MHz, CD$_3$OD) δ8.96 (s, 1H), 8.74 (d, J=7.6 Hz, 1H), 8.47 (s, 1H), 8.29 (s, 1H), 7.75 (s, 1H), 7.70 (d, J=8.8 Hz, 1H), 7.23 (s, 1H), 7.18 (d, J=8.8 Hz, 1H), 7.08 (dd, J=7.6, 2.0 Hz, 1H), 6.96 (dd, J=15.2, 8.8 Hz, 1H), 6.84 (d, J=2.0 Hz, 1H), 6.79 (d, J=15.2 Hz, 1H), 4.36 (q, J=6.8 Hz, 2H), 3.96-3.78 (m, 1H), 3.74-3.54 (m, 2H), 3.2-3.0 (m, 1H), 2.25 (s, 3H), 2.57-1.90 (m, 4H), 1.57 (t, J=6.8 Hz, 3H).

Embodiment 23

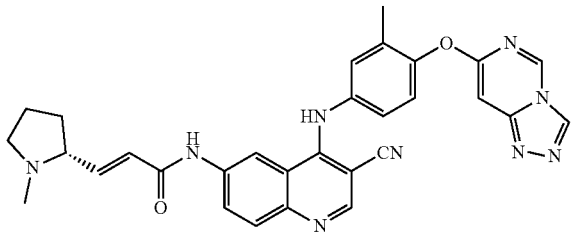 [SMILES: Cc1cc(Nc2c(C#N)cnc3ccc(NC(=O)/C=C/[C@H]4CCCN4C)cc23)ccc1Oc1cc2nncn2cn1]

Synthesis of (R,E)-N-(4-((4-([1,2,4]triazolo[4,3-c]pyrimidin-7-yloxy)-3-methylphenyl)amino)-3-cyanoquinolin-6-yl)-3-(1-methylpyrrolidin-2-yl)acrylamide Preparation was performed according to the method of Embodiment 18. LC-MS: 546.3 [M+H] detection value; $^1$H-NMR (400 MH, CD$_3$OD) δ 9.45 (s, 1H), 8.81 (s, 1H), 8.48 (s, 1H), 8.39 (s, 1H), 7.95-7.72 (m, 2H), 7.40-7.14 (m, 3H), 7.03-6.81 (m, 2H), 6.55 (d, J=15.2 Hz, 1H), 4.05-3.50 (m, 2H), 3.20-2.95 (m, 1H), 2.88-2.65 (m, 3H), 2.23 (s, 3H), 2.45-1.85 (m, 4H).

Embodiment 24

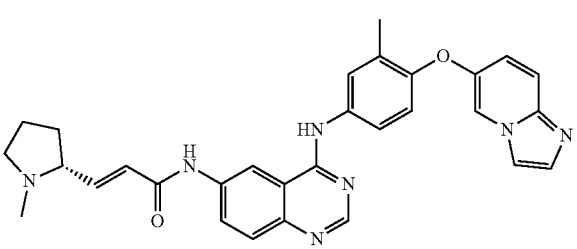 [SMILES: Cc1cc(Nc2ncnc3ccc(NC(=O)/C=C/[C@H]4CCCN4C)cc23)ccc1Oc1ccc2nccn2c1]

Synthesis of (R,E)-N-(4-((4-(imidazo[1,2-a]pyridin-6-yloxy)-3-methylphenyl) amino)quinazolin-6-yl)-3-(1-methylpyrrol-2-yl)acrylamide

Step A: Preparation of 2-chloro-5-(2-methyl-4-nitrophenoxy)pyridine

1-Fluoro-2-methyl-4-nitrobenzene (1.32 g, 8.49 mmol) was added to a suspension of 6-chloropyridin-3-ol (1 g, 7.72 mmol) and potassium carbonate (2.13 g, 15.44 mmol) in N,N-dimethylformamide (20 mL). The reactants were reacted at 70° C. for 16 hours, then cooled to room temperature, poured into water (100 mL), and extracted with ethyl acetate (50 mL×3). The organic phases were combined, washed with saturated brine (100 mL), dried over anhydrous sodium sulfate, filtered, and concentrated. The residue obtained was isolated and purified by silica gel column to give 1.86 g of yellow oil in 91% yield.

Step B: Preparation of 5-(2-methyl-4-nitrophenoxy)pyridin-2-amine

LiHMDS (12 mL, 12.0 mmol) was added dropwise to a solution of 2-chloro-5-(2-methyl-4-nitrophenoxy) pyridine (1.591 g, 6.01 mmol), X-phos (344 mg, 0.72 mmol) and Pd$_2$(dba)$_3$ (275 mg, 0.30 mmol) in tetrahydrofuran (30 mL). The reaction mixture was stirred at 65° C. for 1 hour, then cooled to room temperature and stirred for another 16 hours. The reaction mixture was diluted with saturated aqueous ammonium chloride solution (30 mL) and extracted with dichloromethane (30 mL×3). The organic phases were combined, washed with saturated brine (10 mL), dried over anhydrous sodium sulfate, filtered, and concentrated. The residue obtained was isolated and purified by silica gel column to give 626 mg of yellow oil product with a yield of 42%.

Step C: Preparation of 6-(2-methyl-4-nitrophenoxy)imidazo[1,2-a]pyridine

A solution of 2-acetaldehyde (4.47 g, 22.75 mmol, 4.5 mL) and 5-(2-methyl-4-nitrophenoxy)pyridin-2-amine (0.62 g, 2.53 mmol) in ethanol (15 mL) was heated to 100° C. and stirred for 16 hours, and then the reaction mixture was cooled to room temperature, and concentrated. The obtained residue was isolated and purified by silica gel column to give 0.66 g of yellow oily product with a yield of 97%.

Step D: Preparation of 4-(imidazo[1,2-a]pyridin-6-yloxy)-3-methylaniline

Pd/C (0.261 g, 0.245 mmol) was added to a solution of 6-(2-methyl-4-nitrophenoxy)imidazo[1,2-a]pyridine (0.66 g, 2.45 mmol) in ethanol. The reactants were vacuumized and then filled with hydrogen, after repeating the operation for three times, the reactants were stirred for 1.5 hours at room temperature. The mixture was filtered through diatomite and the filtrate was concentrated under reduced pressure to give 514 mg of green oil, which was directly used in the next reaction.

Step E: Preparation of (R,E)-N-(4-((4-(imidazo[1,2-a]pyridin-6-yloxy)-3-methylphenyl)amino)quinazolin-6-yl)-3-(1-methylpyrrol-2-yl)acrylamide The preparation method was performed according to the method of Embodiment 10. LC-MS: 260.6 [M+H]/2 detection value; $^1$H-NMR (400 MHz, CD$_3$OD) δ 8.79 (d, J=1.9 Hz, 1H), 8.46 (s, 1H), 8.11 (dd, J=2.3, 0.8 Hz, 1H), 7.82-7.76 (m, 3H), 7.68 (d, J=2.6 Hz, 1H), 7.61-7.55 (m, 3H), 7.25 (dd, J=9.8, 2.3 Hz, 1H), 7.03 (d, J=8.7 Hz, 1H), 6.90 (dd, J=15.3, 8.5 Hz, 1H), 6.41 (d, J=15.2 Hz, 1H), 3.18 (q, J=8.4 Hz, 1H), 2.55 (q, J=9.1 Hz, 1H), 2.47 (s, 3H), 2.33 (s, 3H), 2.20 (dt, J=13.4, 7.4 Hz, 1H), 2.02-1.92 (m, 3H), 1.88-1.76 (m, 1H).

Embodiment 25

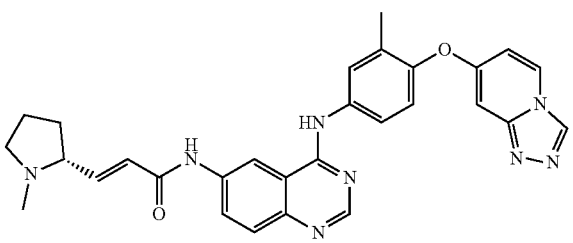 [SMILES: Cc1cc(Nc2ncnc3ccc(NC(=O)/C=C/[C@H]4CCCN4C)cc23)ccc1Oc1ccn2cnnc2c1]

Synthesis of (R,E)-N-(4-((4-([1,2,4]triazolo[4,3-a]pyridin-7-yloxy)-3-methyl phenyl)amino)quinazolin-6-yl)-3-(1-methylpyrrol-2-yl)acrylamide Step A: Preparation of 4-(benzyloxy)-2-chloropyridine Sodium hydride (189 mg, 4.73 mmol, 60%) was suspended in tetrahydrofuran (5 mL), and cooled to 0° C., followed by dropwise addition of a solution of benzyl alcohol (375 mg, 3.47 mmol) in tetrahydrofuran (1 mL) under nitrogen atmosphere. After completion of the addition, the reaction solution was stirred at 0° C. for 30 minutes, and maintained at 0° C., followed by dropwise addition of a solution of 2-chloro-4-nitropyridine (500 mg, 3.15 mmol) in tetrahydrofuran (1 mL). The final reaction solution was heated and refluxed for 16 hours. The reaction solution was quenched with saturated aqueous ammonium chloride solution (50 mL) and extracted with ethyl acetate (20 mL×2). The organic phases were combined and dried over anhydrous sodium sulfate, and filtered. The filtrate was evaporated to dryness under reduced pressure to give a crude product. The crude product was isolated and purified by silica gel column to give 554 mg of yellow solid with a yield of 80.0%.

Step B: Preparation of (Z)-4-(benzyloxy)-2-hydrazino-1,2-dihydropyridine 4-(Benzyloxy)-2-chloropyridine (454 mg, 2.07 mmol) was dissolved in pyridine (10 mL), followed by addition of hydrazine hydrate (7 mL), and the reaction solution was stirred at 120° C. for 38 hours. The reaction solution was evaporated to dryness under reduced pressure to give 450 mg of crude off-white solid, which was directly used in the next reaction.

Step C: Preparation of 7-(benzyloxy)-[1,2,4]triazolo[4,3-a]pyridine (Z)-4-(benzyloxy)-2-hydrazino-1,2-dihydropyridine (450 mg, 2.11 mmol) was suspended in trimethyl orthoformate (5 mL). The reaction solution was heated and refluxed for 1 hour, and cooled to 60° C., followed by addition of p-toluenesulfonic acid (16 mg, 0.08 mmol). The reaction solution was stirred at 60° C. for 1 hour. The crude product was obtained by evaporation under reduced pressure. The crude product was isolated and purified by silica gel column to give 210 mg of orange solid with a yield of 44.2%.

Step D: Preparation of [1,2,4]triazolo[4,3-a]pyridin-7-ol 7-(Benzyloxy)-[1,2,4]triazolo[4,3-a]pyridine (210 mg, 0.93 mmol) was dissolved in methanol (8 mL), followed by addition of Pd/C (40 mg). The reaction solution was stirred at 26° C. for 22 hours in a hydrogen atmosphere of 15 psi. The mixture was filtered through diatomite, and the filtrate was evaporated to dryness under reduced pressure to give 119 mg of crude pale brown solid, which was directly used in the next reaction.

Step E: Preparation of 7-(2-methyl-4-nitrophenoxy)-[1,2,4]triazolo[4,3-a]pyridine

[1,2,4]Triazolo[4,3-a]pyridin-7-ol (119 mg, 0.88 mmol), 1-fluoro-2-methyl-4-nitrobenzene (137 mg, 0.88 mmol), and potassium carbonate (183 mg, 1.32 mmol) were dissolved in N,N-dimethylformamide (1.5 mL), and the reaction solution was heated to 80° C. and stirred for 16 hours. Water (10 mL) was added to the reaction solution and extracted with ethyl acetate (15 mL×3). The organic phases were combined and dried over anhydrous sodium sulfate, and filtered. The filtrate was evaporated to dryness under reduced pressure to give a crude product. The crude product was isolated and purified by silica gel column to give 115 mg of yellow solid with a yield of 48.3%.

Step F: Preparation of 4-([1,2,4]triazolo[4,3-a]pyridin-7-yloxy)-3-methylaniline 7-(2-Methyl-4-nitrophenoxy)-[1,2,4]triazolo[4,3-a]pyridine (115 mg, 0.43 mmol) was suspended in methanol (10 mL), followed by addition of Pd/C (30 mg). The reaction solution was stirred at 26° C. for 2.5 hours under hydrogen atmosphere. The mixture was filtered through diatomite, and the filtrate was evaporated to dryness under reduced pressure to give 30 mg of crude brown oil, which was directly used in the next reaction.

Step g: Preparation of (R,E)-N-(4-((4-([1,2,4]triazolo[4,3-a]pyridin-7-yloxy)-3-methylphenyl)amino)quinazolin-6-yl)-3-(1-methylpyrrol-2-yl)acrylamide.

The preparation was performed according to the method of Embodiment 10. LC-MS: 521.3[M+H] detection value. $^1$H-NMR (400 MHz, DMSO) δ10.46 (s, 1H), 9.87 (s, 1H), 8.84 (s, 1H), 8.55 (s, 1H), 8.20 (d, J=9.8 Hz, 1H), 8.11 (s, 1H), 7.89 (dd, J=8.8, 2.0 Hz, 1H), 7.81-7.79 (m, 2H), 7.74 (dd, J=8.8, 2.4 Hz, 1H), 7.66 (d, J=0.8 Hz, 1H), 7.26 (d, J=8.4 Hz, 1H), 7.18 (d, J=9.6 Hz, 1H), 6.76 (dd, J=15.2, 7.6 Hz, 1H), 6.39 (d, J=15.2 Hz, 1H), 3.11-3.06 (m, 1H), 2.88-2.82 (m, 1H), 2.26 (m, 4H), 2.21 (s, 3H), 2.10-2.01 (m, 1H), 1.82-1.74 (m, 2H), 1.66-1.56 (m, 1H).

Embodiment 26

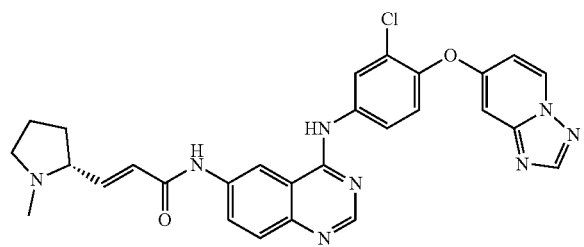 [SMILES: CN1CCC[C@@H]1/C=C/C(=O)Nc1ccc2ncnc(Nc3ccc(Oc4ccn5ncnc5c4)c(Cl)c3)c2c1]

Synthesis of (R,E)-N-(4-((4-([1,2,4]triazolo[1,5-a]pyridin-7-yloxy)-3-chloro phenyl)amino)quinazolin-6-yl)-3-(1-methylpyrrolidin-2-yl)acrylamide 4-([1,2,4]Triazolo[1,5-a]pyridin-7-yloxy)-3-chloroaniline was prepared according to the method of Embodiment 19, wherein 2-methyl-4-nitrophenol was replaced with 2-chloro-4-nitrophenol.

(R,E)-N-(4-((4-([1,2,4]triazolo[1,5-a]pyridin-7-yloxy)-3-chlorophenyl)amino)quinazolin-6-yl)-3-(1-methylpyrrolidin-2-yl)acrylamide was prepared according to the method of Embodiment 10. LC-MS: 541.2[M+H] detection value. $^1$H-NMR (400 MHz, DMSO) δ10.66 (s, 1H), 10.09 (s, 1H), 8.99 (d, J=8.0 Hz, 1H), 8.88 (s, 1H), 8.64 (s, 1H), 8.44 (s, 1H), 8.37-8.29 (m, 1H), 8.06-7.89 (m, 2H), 7.90-7.79 (m, 1H), 7.49 (d, J=8.0 Hz, 1H), 7.10 (dd, J=7.5, 2.6 Hz, 1H), 6.96 (d, J=2.5 Hz, 1H), 6.84 (dd, J=15.1, 8.0 Hz, 1H), 6.52 (d, J=16.0 Hz, 1H), 3.05-3.01 (m, 1H), 2.89-2.83 (m, 1H), 2.25-2.20 (m, 7H), 2.05-1.95 (m, 1H), 1.80-1.70 (m, 2H), 1.66-1.56 (m, 1H).

Embodiment 27

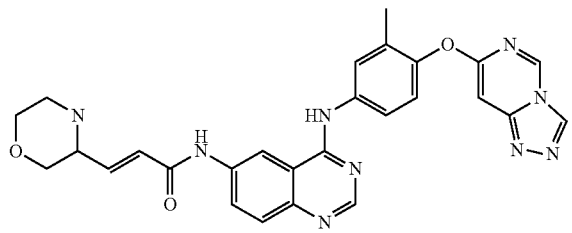 [SMILES: Cc1cc(Nc2ncnc3ccc(NC(=O)/C=C/C4COCCN4)cc23)ccc1Oc1cc2nncn2cn1]

Synthesis of (E)-N-(4-((4-([1,2,4]triazolo[4,3-c]pyrimidin-7-yloxy)-3-methyl phenyl)amino)quinazolin-6-yl)-3-(morpholin-3-yl)acrylamide

Step A: Preparation of tert-butyl 3-formylmorpholin-4-carboxylate

CDI (0.69 g, 4.28 mmol) was added to a suspension of 4-(tert-butoxycarbonyl)morpholin-3-carboxylic acid (0.9 g, 3.89 mmol) in dichloromethane (18 mL) under argon atmosphere at 0° C. After stirring for 5 minutes, the suspension became clear. After 1 hour, the solution was cooled to −80° C. and DIBAL-H (8.2 mL, 8.2 mmol) was added dropwise in 2 minutes. The resulting mixture was stirred at 80° C. for 2 hours, followed by successive addition of water (18 μL), 15% aqueous sodium hydroxide solution (18 μL) and water (45 μL). The mixture was stirred at 0° C. for 1 hour, dried over anhydrous sodium sulfate and filtered. The filter cake was washed with dichloromethane (5 mL). The filtrates were combined, washed with water (10 mL×2) and brine (10 mL), dried over anhydrous sodium sulfate, filtered, and concentrated to give 641 mg of crude yellow oil, which was directly used in the next reaction.

Step B: Preparation of tert-butyl 3-((E)-3-((3-cyano-4-((E)-(dimethylamino) methylene)amino)phenyl)amino)-3-oxoprop-1-en-1-yl)morpholin-4-carboxylate Under argon atmosphere, a solution of diethyl (E)-(2-((3-cyano-4-((dimethyl amino)methylene)amino)phenyl)amino)-2-oxoethyl)phosphate (0.61 g, 1.67 mmol) in anhydrous tetrahydrofuran (21 mL) was cooled to −80° C., and LiHMDS (2.50 mL, 2.50 mmol) was added dropwise in 10 minutes. After stirring the yellow mixture for 1.5 hours, a solution of tert-butyl 3-formylmorpholin-4-carboxylate (0.72 g, 3.33 mmol) in anhydrous tetrahydrofuran (5 mL) was added dropwise in 10 minutes. The resulting mixture was stirred at −80° C. for 1 hour, and then slowly warmed to room temperature and stirred for 16 hours. Saturated aqueous ammonium chloride solution (20 mL) was added to quench the reaction, and the resulting mixture was extracted with dichloromethane (50 mL×3). The organic layers were combined, washed with saturated brine (30 mL), dried over anhydrous sodium sulfate, filtered, and concentrated. The residue was isolated and purified by silica gel column to give 0.51 g of the target compound in a yield of 72%.

Step C: Preparation of tert-butyl (E)-3-(3-((4-((4-([1,2,4]triazolo[4, 3-c]pyrimidin-7-yloxy)-3-methylphenyl)amino)quinazolin-6-yl)amino)-3-oxopropyl-1-en-1-yl)morpholin-4-carboxylate A solution of tert-butyl 3-((E)-3-((3-cyano-4-((E)-(dimethylamino) methylene)amino)phenyl)amino)-3-oxoprop-1-en-1-yl)morpholin-4-carboxylate (0.05 g, 0.12 mmol), 4-([1,2,4]triazolo[4,3-c]pyrimidin-7-yloxy)-3-methylaniline (0.03 g, 0.12 mmol) and acetic acid (0.6 mL) in isopropyl acetate (2 mL) was stirred at room temperature for 16 hours, followed by concentration. The residue was dissolved in dichloromethane (5 mL). Solid sodium bicarbonate and water (1 mL) were added to the solution to adjust the pH to 7. The mixture was dried over anhydrous sodium sulfate, filtered, and concentrated. The obtained residue was isolated and purified by silica gel column to give 0.054 g of yellow solid with a yield of 74%.

Step D: Preparation of (E)-N-(4-((4-([1,2,4]triazolo[4,3-c]pyrimidin-7-yloxy)-3-methylphenyl)amino)quinazolin-6-yl)-3-(morpholin-3-yl)acrylamide To a solution of tert-butyl (E)-3-(3-((4-((4-([1,2,4]triazolo[4,3-c] pyrimidin-7-yloxy)-3-methylphenyl)amino)quinazolin-6-yl)amino)-3-oxoprop-1-en-1-yl)morpholin-4-carboxylate (20 mg, 0.032 mmol) in dichloromethane (0.6 mL) was added trifluoroacetic acid (548 mg, 0.48 mmol), and the mixture was stirred at room temperature for 2 hours. The reaction mixture was poured into water (5 mL), neutralized with saturated aqueous sodium bicarbonate solution, and extracted with dichloromethane (10 mL×3). The organic layers were combined, washed with saturated brine (10 mL), dried over anhydrous sodium sulfate, filtered, and concentrated. The residue obtained was isolated and purified by preparative TLC to give 9 mg of yellow solid with a yield of 54%. LC-MS: 524.2[M+H] detection value. $^1$H-NMR (400 MHz, CD$_3$OD) δ 9.43 (d, J=1.2 Hz, 1H), 8.75 (d, J=2.1 Hz, 1H), 8.48 (s, 1H), 8.42 (s, 1H), 7.82-7.73 (m, 3H), 7.70 (dd, J=8.6, 2.7 Hz, 1H), 7.18 (d, J=8.7 Hz, 1H), 6.94 (d, J=1.2 Hz, 1H), 6.89 (dd, J=15.5, 6.2 Hz, 1H), 6.43 (dd, J=15.5, 1.5 Hz, 1H), 3.95 (dd, J=11.4, 3.4 Hz, 1H), 3.87 (dt, J=11.8, 2.9 Hz, 1H), 3.80-3.72 (m, 1H), 3.62 (m, 1H), 3.43 (dd, J=11.5, 9.6 Hz, 1H), 3.10-3.02 (m, 2H), 2.24 (s, 3H).

Embodiment 28

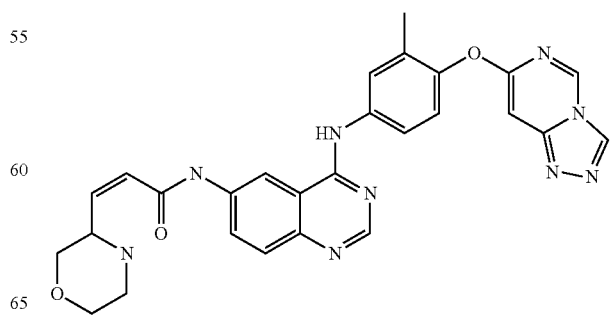

Synthesis of (E)-N-(4-((4-([1,2,4]triazolo[4,3-c]pyrimidin-7-yloxy)-3-methyl phenyl)amino)quinazolin-6-yl)-3-(morpholin-3-yl)acrylamide Preparation was performed according to the method of Embodiment 29. LC-MS: 524.2[M+H] detection value. ¹H-NMR (400 MHz, CDCl₃) δ 9.16 (s, 1H), 8.68 (s, 1H), 8.51 (s, 1H), 8.24 (s, 1H), 7.75-7.64 (m, 3H), 7.52 (dd, J=9.0, 2.6 Hz, 1H), 7.06 (d, J=8.6 Hz, 1H), 6.82 (s, 1H), 6.14 (d, J=11.7 Hz, 1H), 5.96 (dd, J=11.6, 7.7 Hz, 1H), 4.39 (t, J=8.7 Hz, 1H), 3.89 (dd, J=11.3, 3.4 Hz, 1H), 3.79 (d, J=11.5, 3.2 Hz, 1H), 3.39 (t, J=10.4 Hz, 1H), 3.29 (dd, J=15.7, 2.5 Hz, 1H), 3.04-2.90 (m, 2H), 2.18 (s, 3H).

Embodiment 29

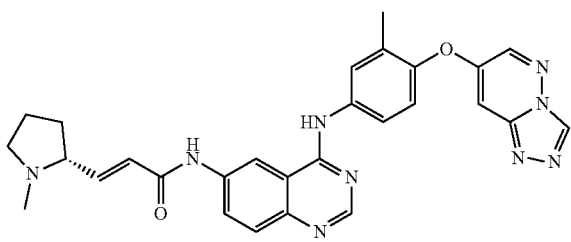 [SMILES: Cc1cc(Nc2ncnc3ccc(NC(=O)/C=C/[C@H]4CCCN4C)cc23)ccc1Oc1cnn2cnnc2c1]

Synthesis of (R,E)-N-(4-((4-([1,2,4]triazolo[4,3-b]pyridazin-7-yloxy)-3-methylphenyl)amino)quinazolin-6-yl)-3-(1-methylpyrrolidin-2-yl) acrylamide Step A: Preparation of 6-chloro-4-hydroxypyridazine 3,5-Dichloropyridazine (800 mg, 5.37 mmol), 1 N sodium hydroxide solution (5 mL) and dioxane (5 mL) were added into a 100 mL single-necked flask, and the reactants were heated to 100° C. and stirred for 2 hours, followed by concentration. The residue obtained was isolated by column chromatography to give 580 mg of pale yellow solid with a yield of 83.09%.

Step B: Preparation of 6-hydrazinopyridazine-4-ol

6-Chloro-4-hydroxypyridazine (420 mg, 3.21 mmol), hydrazine hydrate (10 mL) and dioxane (5 mL) were added into a 100 mL single-necked flask. The reactants were heated to 130° C., stirred for 8 hours, and concentrated to give a crude product, which was directly used for the next reaction.

Step C: Preparation of 7-hydroxy-[1,2,4]triazolo[4,3-b]pyridazine

The crude product obtained in step B was dissolved in formic acid (30 mL, 85%), heated to 130° C. and stirred overnight. The mixture was concentrated, and the residue obtained was isolated and purified by column chromatography and preparative TLC to give 190 mg of the target compound with a yield of 39.75%.

Step D: Preparation of 7-(2-methyl-4-nitrophenoxy)-[1,2,4]triazolo[4,3-b]pyridazine 7-Hydroxy-[1,2,4]triazolo[4,3-b]pyridazine (170 mg, 1.25 mmol) was dissolved in N,N-dimethylformamide (10 mL), and 1-fluoro-2-methyl-4-nitrobenzene (250 mg, 1.61 mmol) and potassium carbonate (200 mg, 1.45 mmol) were added, heated to 80° C. and stirred for 18 hours under nitrogen atmosphere. The mixture was concentrated, and the residue obtained was isolated by column chromatography to give 60 mg of the target compound with a yield of 17.75%.

Step E: Preparation of 7-(2-methyl-4-aminophenoxy)-[1,2,4]triazolo[4,3-b]pyridazine 7-(2-Methyl-4-nitrophenoxy)-[1,2,4]triazolo[4,3-b]pyridazine (60 mg, 0.22 mmol) was dissolved in methanol (20 mL), followed by addition of catalytic amount of raney nickel, and stirred at room temperature for 2 hours under hydrogen atmosphere (balloon). The mixture was filtered through diatomite and the filtrate was concentrated under reduced pressure to give 50 mg of crude product, which was directly used in the next reaction.

Step F: Preparation of (R,E)-N-(4-((4-([1,2,4]triazolo[4,3-b]pyridazin-7-yloxy)-3-methylphenyl)amino)quinazolin-6-yl)-3-(1-methylpyrrolidin-2-yl) acrylamide Preparation was performed according to the method of Embodiment 10. LC-MS: 522.2[M+H] detection value. ¹H-NMR (400 MHz, CD₃OD) δ 9.37 (s, 1H), 8.81 (d, J=2.0 Hz, 1H), 8.69 (d, J=2.6 Hz, 1H), 8.53 (s, 1H), 7.90 (dd, J=9.0, 2.2 Hz, 1H), 7.86-7.72 (m, 3H), 7.27 (d, J=8.7 Hz, 1H), 7.13 (d, J=2.4 Hz, 1H), 6.95 (dd, J=15.2, 8.6 Hz, 1H), 6.55 (d, J=15.2 Hz, 1H), 3.58 (dd, J=16.9, 8.7 Hz, 1H), 3.53-3.45 (m, 1H), 2.84 (dt, J=23.6, 11.8 Hz, 1H), 2.38-2.25 (m, 4H), 2.09 (dt, J=8.5, 6.4 Hz, 2H), 1.93 (dt, J=13.0, 6.9 Hz, 1H).

Embodiment 30

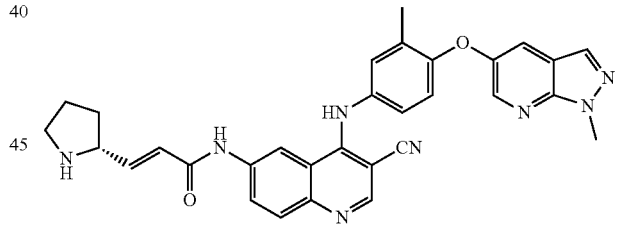

Synthesis of (R,E)-N-(4-((3-methyl-4-((1-methyl-1H-pyrazolo[3,4-b]pyridin-5-yl)oxy)phenyl)amino)quinazolin-6-yl)-3-(1-methylpyrrolidin-2-yl)-acrylamide Step A: Preparation of 1-methyl-5-(4,4,5,5-tetramethyl-1,3,2-dioxolan boron-2-yl)-1H-pyrazolo[3,4-b]pyridine 5-Bromine-1-methyl-1H-pyrazolo[3,4-b]pyridine (2.0 g, 9.43 mmol) was dissolved in N,N-dimethylformamide (60 mL) in a 100 mL single-necked flask. Bis(pinacolato)diboron (4.8 g, 18.90 mmol) and potassium acetate (2.8 g, 28.57 mmol) were added thereto, followed by addition of PdCl₂(PPh₃)₂ (250 mg) under nitrogen atmosphere. The reaction was heated to 100° C. and stirred overnight. After filtration and concentration, the obtained residue was isolated by column chromatography to give 1.4 g of pale yellow crude product with a yield of 57.14%.

Step B: Preparation of 1-methyl-1H-pyrazolo[3,4-b]pyridin-5-ol

1-Methyl-5-(4,4,5,5-tetramethyl-1,3,2-dioxolaneboron-2-yl)-1H-pyrazolo[3,4-b]pyridine (1.13 g, 4.36 mmol) was dissolved in tetrahydrofuran (26 mL) in a 100 mL single-necked flask, followed by addition of glacial acetic acid (1.3 g, 21.67 mmol) and 30% hydrogen peroxide (2.45 g), and stirred at room temperature for 3 hours. The reaction mixture was extracted with ethyl acetate, dried over anhydrous sodium sulfate, filtered and concentrated. The residue obtained was isolated by column chromatography to give 410 mg of the target compound with a yield of 63.08%.

Step C: Preparation of 1-methyl-5-(2-methyl-4-nitrophenoxy)-1H-pyrazolo [3,4-b]pyridine 1-Methyl-1H-pyrazolo[3,4-b]pyridin-5-ol (380 mg, 2.55 mmol) was dissolved in N,N-dimethylformamide (20 mL), followed by addition of 1-fluoro-2-methyl-4-nitrobenzene (500 mg, 3.23 mmol) and potassium carbonate (1.1 g, 7.97 mmol). The mixture was heated to 80° C. and stirred for 18 hours under nitrogen atmosphere. The mixture was filtered and concentrated, and the residue obtained was isolated by column chromatography to give 610 mg of the target compound with a yield of 84.22%.

Step D: Preparation of 3-methyl-4-((1-methyl-1H-pyrazolo[3,4-b]pyridine-5-yl)oxy)aniline 1-Methyl-5-(2-methyl-4-nitrophenoxy)-1H-pyrazolo[3,4-b]pyridine (610 mg, 1.29 mmol) was dissolved in methanol (150 mL), followed by addition of catalytic amount of raney nickel, and stirred for 2 hours at room temperature under hydrogen atmosphere (balloon). The mixture was filtered through diatomite and concentrated under reduced pressure to give 510 mg of crude product, which was directly used in the next reaction.

Step E: Preparation of (R,E)-N-(4-((3-methyl-4-((1-methyl-1H-pyrazolo[3,4-b]pyridin-5-yl)oxy)phenyl) amino)quinazolin-6-yl)-3-(1-methylpyrrolidin-2-yl)-acrylamide Preparation was performed according to the methods of Embodiments 9 and 19. LC-MS: 273.1 [M/2+H] detection value; $^1$H-NMR (400 MHz, CD$_3$OD) δ 8.79 (s, 1H), 8.48 (d, J=2.4 Hz, 1H), 8.44 (s, 1H), 7.94 (s, 1H), 7.92-7.79 (m, 2H), 7.67 (d, J=2.4 Hz, 1H), 7.34 (d, J=2.0 Hz, 1H), 7.22 (dd, J=8.4, 2.4 Hz, 1H), 7.11-6.90 (m, 2H), 6.56 (d, J=15.2 Hz, 1H), 4.40-4.24 (m, 1H), 4.11 (s, 3H), 3.52-3.34 (m, 2H), 2.30 (s, 3H), 2.46-1.79 (m, 4H).

Embodiment 31

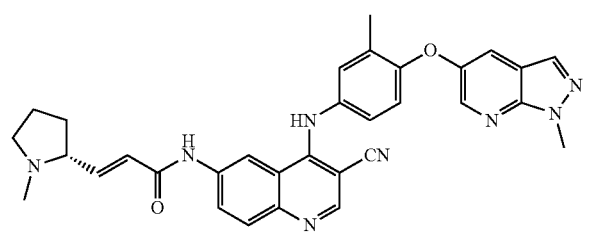 [SMILES: Cc1cc(Nc2c(C#N)cnc3ccc(NC(=O)/C=C/[C@H]4CCCN4C)cc23)ccc1Oc1cnc2c(cnn2C)c1]

Synthesis of (R,E)-N-(3-cyano-4-((3-methyl-4-((1-methyl-1H-pyrazolo[3,4-b]pyridin-5-yl)oxy)phenyl) amino)quinazolin-6-yl)-3-(1-methylpyrrolidin-2-yl) acrylamide Preparation was performed according to the method of Embodiment 18. LC-MS: 559.3[M+H] detection value. $^1$H-NMR (400 MHz, CD$_3$OD) δ8.79 (s, 1H), 8.50 (d, J=2.4 Hz, 1H), 8.45 (s, 1H), 7.96 (s, 1H), 7.89 (s, 2H), 7.69 (d, J=2.4 Hz, 1H), 7.35 (d, J=2.0 Hz, 1H), 7.23 (dd, J=8.4, 2.4 Hz, 1H), 6.98 (d, J=8.4 Hz, 1H), 6.96-6.86 (m, 1H), 6.59 (d, J=15.2 Hz, 1H), 4.12 (s, 3H), 3.90-3.76 (m, 1H), 3.71-3.55 (m, 1H), 3.10-3.00 (m, 1H), 2.79 (s, 3H), 2.31 (s, 3H), 2.46-1.87 (m, 4H).

Embodiment 1-4

I-4

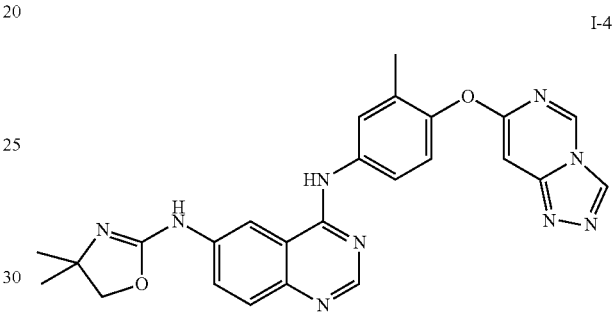

Synthesis of N$^4$-(4-([1,2,4]-triazolo[4,3-c]pyrimidin-7-yloxy)-3-methyl phenyl)-N$^6$-(4,4-dimethyl-4,5-dihydrooxazol-2-yl)-4,6-diaminoquinazoline Step A: Preparation of 2-chloro-6-hydrazinopyrimidine 2,6-Dichloropyrimidine (25 g, 167.81 mmol) was dissolved in 350 mL of isopropanol. Hydrazine hydrate (29.5 g, 503.44 mmol, 85%) was slowly added dropwise under stirring at room temperature, and the heat was released with precipitation of white solid during the dropping process. After completion of the addition, the mixture was stirred at room temperature for 1 hour. The solvent was removed under reduced pressure, and the residue was stirred with water (50 mL) for 30 minutes, and filtered. The filter cake was washed with water, and dried to give 22.4 g of white solid with a yield of 92.3%.

Step B: Preparation of 7-chloro-[1,2,4]triazolo[4,3-c]pyrimidine

2-Chloro-6-hydrazinopyrimidine (21 g, 145.27 mmol) was dispersed in 210 mL of trimethyl orthoformate and stirred overnight at 60° C. to make the reaction solution clear. P-toluenesulfonic acid (0.6 g, 3.48 mmol) was added and the reaction was continued at 60° C. for 1 hour. The mixture was evaporated to dryness under reduced pressure to remove the solvent. Water (20 mL) was added thereto, stirred for 30 minutes, and filtered. The filter cake was washed with water, and dried to give 9.2 g of pale brown solid with a yield of 41%.

Step C: Preparation of 7-(2-methyl-4-nitrophenoxy)-[1,2,4]triazolo[4,3-c]pyrimidine 7-Chloro-[1,2,4]triazolo[4,3-c]pyrimidine (450 mg, 2.91 mmol) was dissolved in 10 mL of N,N-dimethylformamide, followed by addition of 2-methyl-4-nitrophenol (550 mg, 3.59 mmol) and sodium carbonate solid (500 mg, 4.72 mmol), and heated to 80° C. and stirred overnight. After completion of the reaction, 20 mL of ethyl acetate was added, stirred, filtered, and the filtrate was evaporated to dryness under reduced pressure to remove the solvent. The residue was isolated by column chromatography to give 510 mg of pale yellow solid with a yield of 64.46%.

Step D: Preparation of 7-(2-methyl-4-aminophenoxy)-[1,2,4]triazolo[4,3-c]pyrimidine 7-(2-Methyl-4-nitrophenoxy)-[1,2,4]triazolo[4,3-c]pyrimidine (510 mg, 1.88 mmol) was dissolved in 60 mL of the mixed solvent of methanol and ethyl acetate (2:1), followed by addition of a small amount of raney nickel. The reaction was carried out under hydrogen atmosphere (balloon) with stirring at room temperature for 2 hours. After completion of the reaction, the mixture was directly filtrated, and evaporated to dryness under reduced pressure to remove the solvent to give 410 mg of crude product, which was directly used in the next reaction.

Step E: Preparation of 1-(4-((4-([1,2,4]triazolo[4,3-c]pyrimidin-7-yloxy)-3-methylphenyl)amino)quinazolin-6-amino)-3-(1-hydroxy-2-methyl-n-propyl-2-amino) thiourea 3 mL of acetic acid and 30 mL of isopropyl acetate were added to the mixture of 7-(2-methyl-4-aminophenoxy)-[1,2,4]triazolo[4,3-c]pyrimidine (170 mg, 0.71 mmol) and 2-cyano-4-(3-1-hydroxy-2-methylisoprop-2-yl)thioureylphenyl-N,N-dimethylformamidine (240 mg, 0.75 mmol), and stirred at room temperature for 18 hours. After completion of the reaction, a large amount of solid product was precipitated out and directly subjected to filtration. The filter cake was washed with a small amount of isopropyl acetate to give 245 mg of relatively pure product with a yield of 67.42%.

Step F: Preparation of $N^4$-(4-([1,2,4]triazolo[4,3-c]pyrimidin-7-yloxy)-3-methylphenyl)-$N^6$-(4,4-dimethyl-4,5-dihydrooxazol-2-yl)-4,6-diaminoquinazoline 1-(4-((4-([1,2,4]Triazolo[4,3-c]pyrimidin-7-yloxy)-3-methylphenyl)amino)quinazolin-6-amino)-3-(1-hydroxy-2-methyl-n-propyl-2-amino)thiourea (245 mg, 0.48 mmol) was dissolved in 50 mL of tetrahydrofuran, followed by addition of sodium hydroxide (120 mg, 3.0 mmol) and p-toluenesulfonyl chloride (190 mg, 1.0 mmol). The mixture was stirred at room temperature for 18 hours. After completion of the reaction, water was added and extracted with ethyl acetate for three times, and the extracted organic phase was washed with brine, dried over anhydrous sodium sulfate, and then directly filtered. The concentrated crude product was purified by column chromatography to give 40 mg of relatively pure product with a yield of 17.48%. LC-MS: 481.9[M+H] detection value; $^1$H-NMR (400 MHz, CD$_3$OD) δ 9.46 (m, 1H), 8.48 (s, 1H), 8.44 (s, 1H), 8.19 (s, 1H), 7.76-7.72 (m, 3H), 7.63 (d, 1H, J=12 Hz), 7.22 (d, 1H, J=8 Hz), 6.96 (s, 1H), 4.18 (s, 2H), 2.28 (s, 3H), 1.43 (s, 6H).

Embodiment 1-7

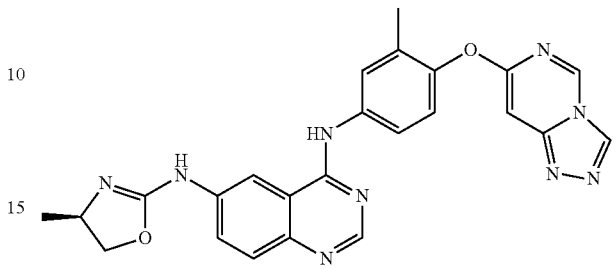

Synthesis of (R)—$N^4$-(4-([1,2,4]triazolo[4,3-c]pyrimidin-7-yloxy)-3-methyl phenyl)-$N^6$-(4-methyl-4,5-dihydrooxazol-2-yl)quinazolin-4,6-diamine

Step A: Preparation of (R,E)-N'-(2-cyano-4-(3-(1-hydroxypropyl-2-)thiourea) phenyl)-N,N-dimethylformamidine N'-(4-amino-2-cyanophenyl)-N,N-dimethylformamidine (500 mg, 2.656 mmol) was suspended in 5 mL of tetrahydrofuran, followed by addition of thiocarbonyldiimidazole (713 mg, 4.001 mmol) at −8° C. After the reaction mixture was stirred at −5 to −8° C. for 30 minutes, a solution of (R)-2-amino-1-propanol (260 mg, 3.462 mmol) in tetrahydrofuran (1 mL) was added dropwise, and the final reaction mixture was stirred overnight at room temperature. The solvent was evaporated to dryness under reduced pressure to give a crude product. The crude product was purified by column chromatography to give 800 mg of orange solid with a yield of 98.6%.

Step B: Preparation of (R,E)-N'-(2-cyano-4-((4-methyl-4,5-dihydrooxazol-2-yl)amino)phenyl)-N,N-dimethylformamidine (R,E)-N'-(2-cyano-4-(3-(1-hydroxyprop-2-yl)thiourea) phenyl)-N,N-dimethylformamidine (150 mg, 0.491 mmol) was dissolved in 3 mL of tetrahydrofuran, followed by addition of sodium hydroxide (118 mg, 2.950 mmol) and p-toluenesulfonyl chloride (187 mg, 0.981 mmol), and the mixture was stirred at room temperature for 1 hour. Water (3 mL) was added and extracted twice with ethyl acetate (5 mL). The organic phases were combined and dried over anhydrous sodium sulfate, filtered, and the solvent was evaporated to dryness under reduced pressure to give crude product. The crude product was purified by column chromatography to give 150 mg of brown oil with a yield of 100%.

Step C: Preparation of (R)—$N^4$-(4-([1,2,4]triazolo[4,3-c]pyrimidin-7-yloxy)-3-methylphenyl)-$N^6$-(4-methyl-4,5-dihydrooxazol-2-yl)quinazolin-4,6-diamine (R,E)-N'-(2-cyano-4-((4-methyl-4,5-dihydrooxazol-2-yl)amino)phenyl)-N,N-dimethylformamidine (80 mg, 0.295 mmol) and glacial acetic acid (0.5 mL) were mixed in 3 mL of isopropyl acetate, followed by addition of 3-methyl-4-([1, 2,4]triazolo[1,4,c]pyrimidin-7-oxy)aniline (71 mg, 0.294 mmol), and the mixture was stirred overnight at room temperature. The reaction mixture was evaporated to dryness under reduced pressure to give a crude product. The crude product was purified by column chromatography to give 2.15 mg of pale yellow solid with a yield of 1.56%. LC-MS: 467.9[M+H] detection value; $^1$H-NMR (400 MHz, CDCl$_3$) δ 8.92 (s, 1H), 8.70 (s, 1H), 8.35 (s, 1H), 8.13 (s, 1H), 7.82 (d, 1H, J=8 Hz), 7.77 (m, 1H), 7.70 (d, 1H, J=8 Hz), 7.51 (d, 1H, J=8 Hz), 7.13 (d, 1H, J=8 Hz), 6.90 (s, 1H), 4.57 (t, 1H, J=8 Hz), 4.29 (m, 1H), 4.01 (t, 1H, J=6 Hz), 2.25 (s, 3H), 1.40 (d, 3H, J=4 Hz).

Embodiment 1-8

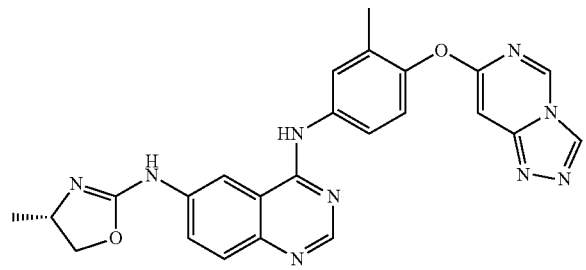 [SMILES: Cc1cc(Nc2ncnc3ccc(NC4=N[C@@H](C)CO4)cc23)ccc1Oc1cc2nncn2cn1]

The preparation was performed according to the method of Embodiment 1-7, wherein (R)-2-amino-1-propanol was replaced with (S)-2-amino-1-propanol. LC-MS: 467.9[M+H] detection value; $^1$H NMR (400 MHz, CD$_3$OD) δ 9.45 (d, 1H, J=1.0 Hz), 8.44 (m, 2H), 8.20 (s, 1H), 7.78-7.72 (m, 3H), 7.61 (dd, 1H, J=9.0, 2.3 Hz), 7.20 (d, 1H, J=8.0 Hz), 6.94 (m, 1H), 4.56 (t, 1H, J=8.2 Hz), 4.27 (dd, 1H, J=14.4, 6.7 Hz), 4.08-3.95 (m, 1H), 2.26 (s, 3H), 1.35 (d, 3H, J=6.4 Hz).

Embodiment 1-9

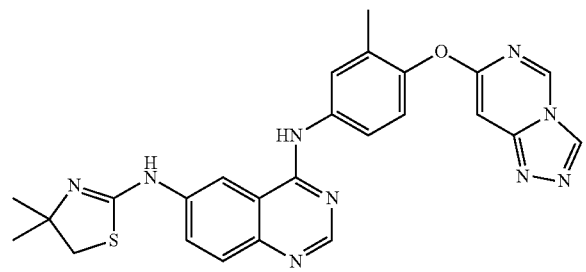 [SMILES: Cc1cc(Nc2ncnc3ccc(NC4=NC(C)(C)CS4)cc23)ccc1Oc1cc2nncn2cn1]

Synthesis of N$^4$-(4-([1,2,4]triazolo[4,3-c]pyrimidin-7-yloxy)-3-methylphenyl)-N$^6$-(4,4-dimethyl-4,5-dihydrothiazole-2-yl)quinazolin-4,6-diamine Step A: The corresponding thiourea was prepared according to the method of Embodiment 1-7, wherein (R)-2-amino-1-propanol was replaced with 2-amino-2-methyl-1-propanol.

Step B: The thiourea (48 mg, 0.09 mmol) prepared in step A and triphenylphosphine (36 mg, 0.14 mmol) were dissolved in 4 mL of N,N-dimethylformamide under ice-water bath cooling, followed by addition of diisopropyl azodicarboxylate (28 mg, 0.14 mmol), and the reaction mixture was stirred at room temperature for 16 hours. 40 mL of ethyl acetate was added, washed once with 20 mL of water and 20 mL of saturated aqueous sodium chloride solution, respectively, dried over anhydrous magnesium sulfate, filtered, and the solvent was evaporated to dryness under reduced pressure to give a crude product. The crude product was isolated by thin layer chromatography to give 22 mg of earthy yellow solid with a yield of 47.5%. LC-MS: 497.80[M+H] detection value; $^1$H NMR (400 MHz, CDCl$_3$) δ 9.20 (m, 1H), 8.70 (s, 1H), 8.32 (s, 1H), 7.85 (d, 1H, J=8.9 Hz), 7.75-7.70 (m, 2H), 7.69 (dd, 1H, J=8.6, 2.5 Hz), 7.54 (dd, 1H, J=8.8, 2.1 Hz), 7.12 (d, 1H, J=8.6 Hz), 6.90 (m, 1H), 3.20 (s, 2H), 2.25 (s, 3H), 1.31 (s, 6H).

Embodiment 1-14

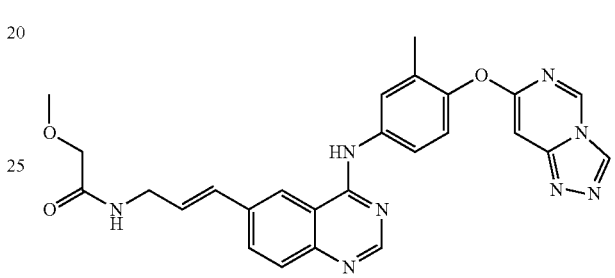

Synthesis of 2-methoxy-N-[(E)-3-[4-[3-methyl-4-([1,2,4]triazolo[4,3-c]pyrimidin-7-yloxy)aniline]-6-quinazolinyl]allyl]acetamide Step A: Preparation of N,N'-di-tert-butoxycarbonylallylamine Allylamine (1.9 g, 33.28 mmol) was dissolved in acetonitrile (13 mL), dimethylaminopyridine (40.6 mg, 0.33 mmol) and di-tert-butoxycarbonyl (8 g, 36.70 mmol) were successively added, and the mixture was stirred at room temperature for 5 h, then the reaction solution was evaporated to dryness under reduced pressure. Acetonitrile (13 mL) was added to dissolve the residue, then dimethylaminopyridine (40.6 mg, 0.33 mmol) and a solution of di-tert-butoxycarbonyl (8 g, 36.70 mmol) in acetonitrile (5 mL) were successively added, the mixture was heated to 60° C. and stirred for 48 hours. After the reaction mixture cooled to room temperature, dichloromethane (50 mL) was added, then washed with a saturated aqueous solution of sodium bicarbonate (20 mL). The aqueous phase was extracted with dichloromethane (20 mL×3). The organic phases were combined, washed once with saturated sodium chloride (20 mL), dried over anhydrous magnesium sulfate for 1 hour, filtered, evaporated to dryness under reduced pressure to give a crude product, which was purified by column chromatography (petroleum ether:ethyl acetate=90:10) to give 2 g of colorless oil with a yield of 23%.

Step B: Preparation of tert-butyl-N-tert-butoxycarbonyl-N-((E)-3-(4-(3-methyl-4-([1,2,4]triazolo[4,3-c]pyrimidin-7-yloxy)anilino)quinazolin-6-yl)allyl)carbamate 6-Iodo-N-(3-methyl-4-([1,2,4]triazolo[4,3-c]pyrimidin-7-yloxy)phenyl)quinazolin-4-amine (250 mg, 0.50 mmol), N,N'-di-tert-butoxycarbonylallyl amide (170 mg, 0.66 mmol), tris(dibenzylideneacetone)dipalladium (5 mg, 0.005 mmol) and triethylamine (255 mg, 2.52 mmol) were mixed in a mixed solvent of isopropanol (2.5 mL) and N,N'-dimethylformamide (1.5 mL), the mixture was heated to 80° C. and stirred for 24 hours, then filtered through celite and evaporated to dryness under reduced pressure to give a crude product, which was purified by thin layer chromatography (dichloromethane:methanol=10:1) to give 140 mg of colorless solid with a yield of 44.4%.

Step C: Preparation of 6-((E)-3-amino-1-propenyl)-N-(3-methyl-4-([1,2,4]triazolo[4,3-c]pyrimidin-7-yloxo)phenyl)quinazolin-4-amine Tert-butyl-N-tert-butoxycarbonyl-N-((E)-3-(4-(3-methyl-4-([1,2,4]triazolo[4,3-c]pyrimidin-7-yloxy)anilino)quinazolin-6-yl)allyl)carbamate (140 mg, 0.22 mmol) was dissolved in 25 mL of 5% trifluoroacetic acid in dichloromethane. The mixture was stirred at room temperature for 16 hours, then concentrated under reduced pressure to give 93 mg of crude product with a yield of 100%, which was used directly in the next step.

Step D: Preparation of 2-methoxy-N-((E)-3-(4-(3-methyl-4-([1,2,4]triazolo [4,3-c] pyrimidin-7-yloxy) anilino)-6-quinazolinyl)allyl)acetamide 6-((E)-3-amino-1-propenyl)-N-(3-methyl-4-([1,2,4]triazolo[4,3-c]pyrimidin-7-yloxo)phenyl)quinazolin-4-amine (93 mg, 0.22 mmol), 1-hydroxybenzotriazole (36 mmg, 0.27 mmol), 1-ethyl-(3-dimethylaminopropyl)carbodiimide hydrochloride (52 mg, 0.33 mmol) and N,N-diisopropylethylamine (145 mg, 1.12 mmol) were successively added to a solution of methoxyacetic acid (24 mg, 0.27 mmol) in dimethylformamide (5 mL) under an ice bath, the reaction solution was gradually warmed to room temperature and stirred for 16 hours. Ethyl acetate (50 mL) was added to the reaction solution, the resulting mixture was washed successively with water (30 mL) and saturated sodium chloride (30 mL), dried over anhydrous magnesium sulfate for 1 hour, filtered, and evaporated to dryness under reduced pressure to give a crude product which was slurried with 10 mL of a mixed solvent (petroleum ether:ethyl acetate=10:1) to give 43 mg of pale yellow solid with a yield of 38.7%. LC-MS: 496.9 [M+H] detection value; $^1$H-NMR (400 MHz, DMSO-$d_6$) δ 9.82 (s, 1H), 9.67 (s, 1H), 8.58-8.54 (m, 3H), 8.16 (m, 1H), 7.96 (d, 1H, J=8.0 Hz), 7.80-7.72 (m, 3H), 7.20 (d, 1H, J=8.0 Hz), 7.13 (s, 1H), 6.64 (d, 1H, J=16.0 Hz), 6.55-6.48 (m, 1H), 3.99 (t, 2H, J=5.4 Hz), 3.88 (s, 2H), 3.36 (s, 3H), 2.20 (s, 3H).

Embodiment 1-16

Synthesis of N-(4-((4-([1,2,4]triazolo[4,3-c]pyrimidin-7-yloxy)-3-methyl phenyl)amino)quinazolin-6-yl)-2-fluoroacrylamide Step A: Preparation of N-(4-([1,2,4]triazolo[4,3-c]pyrimidin-7-yloxy)-3-methylphenyl)-6-nitroquinazoline-4-amine 4-([1,2,4]Triazolo[4,3-c]pyrimidin-7-yloxy)-3-methylaniline (0.5 g, 2 mmol), 4-chloro-6-nitroquinazoline (0.522 g, 2.4 mmol) were suspended in isopropanol (40 mL), the mixture was stirred at room temperature overnight, then evaporated under reduced pressure to give a crude product, which was slurried in a saturated aqueous solution of sodium carbonate and stirred for 30 minutes, then filtered. The filter cake was washed with petroleum ether and dried to give 700 mg of brown solid, which was used directly in the next step.

Step B: Preparation of $N^4$-(4-([1,2,4]triazolo[4,3-c]pyrimidin-7-yloxy)-3-methylphenyl)quinazoline-4,6-diamine N-(4-([1,2,4]triazolo[4,3-c]pyrimidin-7-yloxy)-3-methylphenyl)-6-nitroquinazoline-4-amine (700 mg, 1.69 mmol) was suspended in methanol (50 mL), raney nickel (70 mg) was added and the mixture was stirred under hydrogen atmosphere at room temperature overnight. The mixture was filtered. The filter cake was washed with methanol and the filtrate was evaporated to dryness to give a crude product, which was purified by column chromatography to give 400 mg of yellow solid with a yield of 62%.

Step C: Preparation of N-(4-((4-([1,2,4]triazolo[4,3-c]pyrimidin-7-yloxy)-3-methylphenyl)amino)quinazolin-6-yl)-2-fluoroacrylamide $N^4$-(4-([1,2,4]triazolo[4,3-c]pyrimidin-7-yloxy)-3-methylphenyl)quinazoline-4,6-diamine (100 mg, 0.26 mmol), 2-fluoroacrylic acid (28 mg, 0.39 mmol) and 1-ethyl-(3-dimethylaminopropyl)carbodiimide hydrochloride (150 mg, 0.78 mmol) was dissolved in pyridine (10 mL) and the mixture was stirred at 50° C. for 2 hours. The reaction solution was evaporated to dryness under reduced pressure, then water was added, and the resulting mixture was extracted three times with dichloromethane. The organic phases were combined, washed with saturated brine, dried and concentrated under reduced pressure to give a crude product, which was purified by column chromatography to give 40 mg of pale yellow solid with a yield of 35%. LC-MS: 457.9 [M+H] detection value; $^1$H-NMR (400 MHz, CDCl$_3$) δ 9.22 (s, 1H), 8.79 (s, 1H), 8.70 (s, 1H), 8.33 (s, 1H), 7.88 (d, 1H, J=8.0 Hz), 7.81-7.76 (m, 2H), 7.58 (d, 1H, J=8.0 Hz), 7.15 (d, 1H, J=8.0 Hz), 6.91 (s, 1H), 5.97-5.85 (m, 1H), 5.37 (d, 1H, J=12.0 Hz), 2.27 (s, 3H).

Embodiment 1-19

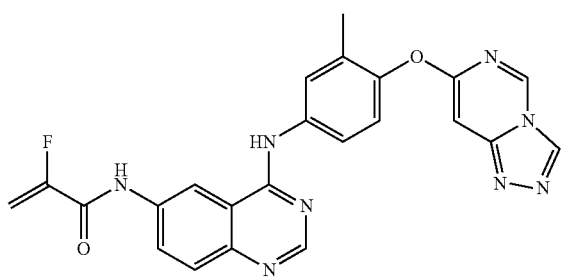 [SMILES: C=C(F)C(=O)Nc1ccc2ncnc(Nc3ccc(Oc4cc5nncn5cn4)c(C)c3)c2c1]

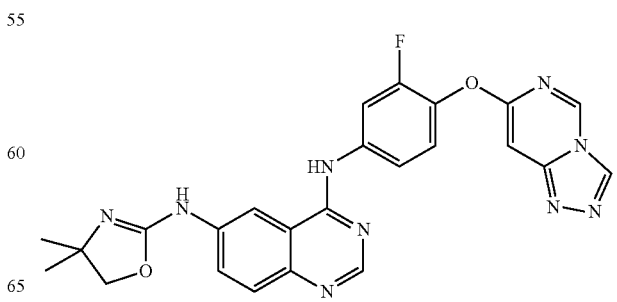

Synthesis of N⁴-(4-([1,2,4]triazolo[4,3-c]pyrimidin-7-yloxy)-3-fluorophenyl)-N⁶-(4,4-dimethyl-4,5-dihydrooxazol-2-yl)-quinazoline-4,6-diamine Step A: Preparation of 7-(2-fluoro-4-nitro-phenoxy)-[1,2,4]triazolo[4,3-c]pyrimidine 2-Fluoro-4-nitro-phenol (1000 mg, 6.36 mmol), 7-chloro-[1,2,4]triazolo[4,3-c]pyrimidine (984 mg, 6.36 mmol) and sodium bicarbonate (700 mg, 8.33 mmol) were suspended in N,N-dimethylformamide (6 mL) and the mixture was stirred at 95° C. for 16 hours. After the reaction solution cooled to room temperature, ethyl acetate (100 mL) and water (100 mL) were added. The organic phase was separated, successively washed with saturated sodium bicarbonate solution (50 mL×3) and saturated aqueous sodium chloride solution (50 mL), dried over anhydrous magnesium sulfate for 2 hours, filtered, and evaporated to dryness under reduced pressure to give a crude product, which was purified by silica gel column to give 300 mg of pale yellow solid with a yield of 17.1%.

Step B: Preparation of 3-fluoro-4-([1,2,4]triazolo[4,3-c]pyrimidin-7-yloxy) aniline 7-(2-Fluoro-4-nitro-phenoxy)-[1,2,4]triazolo[4,3-c]pyrimidine (250 mg, 0.91 mmol) was dissolved in a mixed solvent of methanol (50 mL) and ethyl acetate (50 mL), raney nickel (50 mg) was added, the mixture was purged for three times with argon, then stirred under hydrogen atmosphere (balloon) at room temperature for 3 hours. The mixture was filtered through diatomite and concentrated under reduced pressure to give 240 mg of viscous solid with a yield of 100%, which was used directly in the next step.

Step C: Preparation of N⁴-(4-([1,2,4]triazolo[4,3-c]pyrimidin-7-yloxy)-3-fluorophenyl)-N⁶-(4,4-dimethyl-4,5-dihydrooxazol-2-yl)-quinazoline-4,6-diamine 3-Fluoro-4-([1,2,4]triazolo[4,3-c]pyrimidin-7-yloxy)aniline (260 mg, 1.06 mmol) and N'-(2-cyano-4-((4,4-dimethyl-4,5-dihydrooxazol-2-yl)amino)phenyl)-N,N-dimethylformamidine (302 mg, 1.06 mmol) was added to a reaction flask, then acetic acid (0.9 mL) and isopropyl acetate (2.7 mL) were successively added. The mixture was stirred at room temperature for 48 hours, then evaporated to dryness under reduced pressure to give a crude product, which was purified by thin layer chromatography to give 900 mg of oil, which was purified by acidic preparative HPLC to give 120 mg of pale yellow solid with a yield of 23.2%. LC-MS: 485.9 [M+H] detection value; 1H-NMR (400 MH, DMSO-d₆) δ 9.70 (m, 2H), 8.61 (s, 1H), 8.54 (s, 1H), 8.18-8.15 (m, 2H), 8.02 (s, 1H), 7.80-7.64 (m, 3H), 7.45-7.37 (m, 2H), 4.08 (s, 2H), 1.28 (s, 6H).

Embodiment 1-21

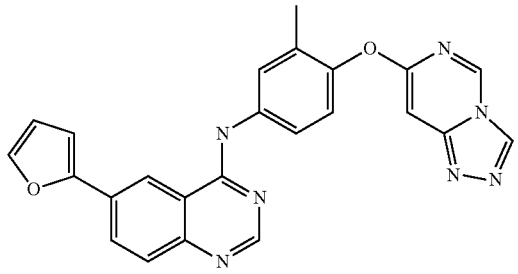 [SMILES: Cc1cc(Nc2ncnc3ccc(-c4ccco4)cc23)ccc1Oc1cc2nncn2cn1]

Synthesis of N-(4-([1,2,4]triazolo[4,3-c]pyrimidin-7-yloxy)-3-methylphenyl)-6-(furan-2-yl)-quinazolin-4-amine Step A: Preparation of N-(4-([1,2,4]triazolo[4,3-c]pyrimidin-7-yloxy)-3-methylphenyl)-6-(furan-2-yl)-quinazolin-4-amine N-(4-([1,2,4]triazolo[4,3-c]pyrimidin-7-yloxy)-3-methylphenyl)-6-iodoquinazolin-4-amine (100 mg, 0.20 mmol), furan-2-boronic acid (39 mg, 0.35 mmol), diisopropylethylamine (150 mg, 1.16 mmol) and [1,1'-bis(diphenylphosphino)ferrocene] dichloropalladium dichloride dichloromethane complex (50 mg) were mixed in tetrahydrofuran (3 mL) and the mixture was heated to 80° C. and stirred for 18 hours, then filtered. The filtrate was washed with saturated sodium bicarbonate solution and extracted with ethyl acetate. The organic phase was washed with saturated brine, dried over anhydrous sodium sulfate, filtered, evaporated under reduced pressure and the residue was purified by column chromatography to give 25.80 mg of product with a yield of 29.4%. LC-MS: 435.9 [M+H] detection value; ¹H-NMR (400 MHz, CD₃OD) δ 9.45 (s, 1H), 8.75 (d, 1H, J=4.0 Hz), 8.52 (s, 1H), 8.44 (s, 1H), 8.21 (d, 1H, J=8.0 Hz), 7.83-7.69 (m, 4H), 7.21 (d, 1H, J=8.0 Hz), 7.05 (s, 1H), 6.96 (s, 1H), 6.63 (dd, 1H, J=8.0, 4.0 Hz), 2.28 (s, 3H).

Embodiment 1-24

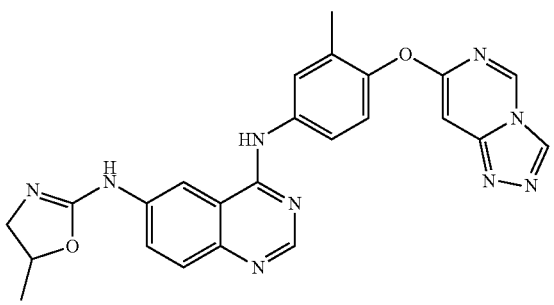 [SMILES: Cc1cc(Nc2ncnc3ccc(NC4=NCC(C)O4)cc23)ccc1Oc1cc2nncn2cn1]

Synthesis of N⁴-(4-([1,2,4]triazolo[4,3-c]pyrimidin-7-yloxy)-3-methylphenyl)-N⁶-(5-methyl-4,5-dihydrooxazol-2-yl)quinazoline-4,6-diamine Preparation was performed according to the method of Embodiment 1-7, wherein (R)-2-amino-1-propanol was replaced with 1-aminopropyl-2-ol. LC-MS: 468.2[M+H]+ detection value. ¹H NMR (400 MHz, DMSO) δ 9.67 (d, J=1.2 Hz, 1H), 9.57 (s, 1H), 8.58 (s, 1H), 8.48 (s, 1H), 8.15 (s, 1H), 7.83 (s, 1H), 7.79 (d, J=8.4 Hz, 1H), 7.67 (d, J=8.0 Hz, 1H), 7.17 (d, J=8.8 Hz, 1H), 7.11 (d, J=1.2 Hz, 1H), 4.80-4.78 (m, 1H), 3.77-3.75 (m, 1H), 3.23-3.21 (m, 1H), 2.19 (s, 3H), 1.37 (d, J=6.4 Hz, 3H).

Embodiment 1-45

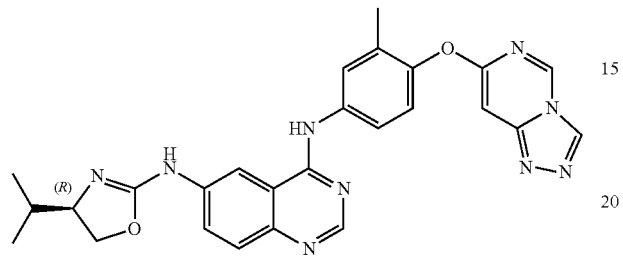

Synthesis of (R)—N⁴-(4-([1,2,4]triazolo[4,3-c]pyrimidin-7-yloxy)-3-methyl phenyl)-N⁶-(4-isopropyl-4,5-dihydrooxazol-2-yl)quinazoline-4,6-diamine Preparation was performed according to the method of Embodiment 1-7, wherein (R)-2-amino-1-propanol was replaced with (2R)-2-amino-3-methylbutyl-1-ol. LC-MS: 496.2[M+H] detection value. ¹H-NMR (400 MHz, DMSO) δ 9.67 (s, 1H), 9.57 (s, 1H), 8.59 (s, 1H), 8.48 (s, 1H), 8.05 (br, s, 1H), 7.84 (s, 1H), 7.80 (d, 1H, J=8.0 Hz), 7.67 (d, 1H, J=8.0 Hz), 7.18 (d, 1H, J=12.0 Hz), 7.12 (d, 1H, J=8.0 Hz), 4.43 (t, 1H, J=8.0 Hz), 4.13 (t, 1H, J=8.0 Hz), 2.19 (s, 3H), 1.75-1.67 (m, 1H), 0.95 (d, 3H, J=4.0 Hz), 0.89 (d, 3H, J=4.0 Hz).

Embodiment 1-57

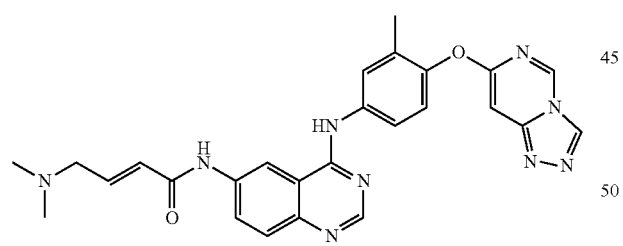

Synthesis of (E)-N-(4-((4-([1,2,4]triazolo[4,3-c]pyrimidin-7-yloxy)-3-methyl phenyl)amino)quinazolin-6-yl)-4-(dimethylamino)-2-butenamide Preparation was performed according to the method of Embodiment 1-16, wherein 2-fluoroacrylic acid was replaced with N,N-dimethyl-2-butenoic acid, stirred under argon atmosphere at room temperature for 38 hours. LC-MS: 495.9[M+H] detection value. ¹H-NMR (400 MHz, CD₃OD) δ 9.42 (s, 1H), 8.79 (s, 1H), 8.53 (s, 1H), 8.40 (s, 1H), 7.81-7.71 (m, 4H), 7.19 (d, 1H, J=8.0 Hz), 6.99-6.94 (m, 2H), 6.53 (d, 1H, J=16.0 Hz), 3.70 (d, 2H, J=8.0 Hz), 2.70 (s, 6H), 2.28 (s, 3H).

Embodiment 1-60

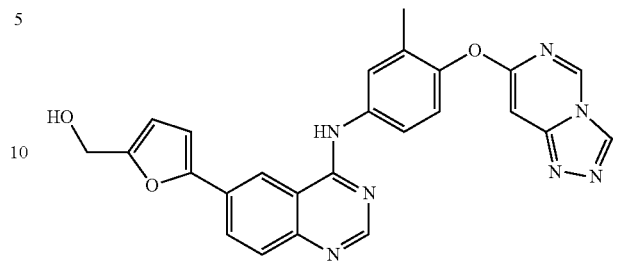

Synthesis of (5-(4-((4-([1,2,4]triazolo[4,3-c]pyrimidin-7-yloxy)-3-methyl phenyl)amino)quinazolin-6-yl)furan-2-yl)methanol Step A: Preparation of (5-(4-((4-([1,2,4]triazolo[4,3-c]pyrimidin-7-yloxy)-3-methylphenyl)amino)quinazolin-6-yl)furan-2-yl)methanol 5-(4-((4-([1,2,4]Triazolo[4,3-c]pyrimidin-7-yloxy)-3-methylphenyl)amino)quinazolin-6-yl)furan-2-carbaldehyde (80 mg, 0.17 mmol) and sodium cyanoborohydride (100 mg, 1.59 mmol) were added into 3 mL of dichloromethane in a 50 mL single-necked flask. The reaction solution was stirred at room temperature for 18 hours, then concentrated directly, washed with saturated sodium bicarbonate and extracted with ethyl acetate. The organic phase was washed with saturated brine, dried over anhydrous sodium sulfate, filtered, and concentrated under reduced pressure. The residue was purified by column chromatography to give 18.5 mg of product with a yield of 23.1%. LC-MS: 466.9[M+H] detection value. ¹H-NMR (400 MHz, DMSO-d₆) δ10.01 (s, 1H), 9.69 (s, 1H), 8.81 (s, 1H), 8.59-8.58 (m, 2H), 8.19 (d, 1H, J=8.0 Hz), 7.81 (m, 3H), 7.23-7.08 (m, 3H), 6.53 (d, 1H, J=4.0 Hz), 5.34 (s, 1H), 4.55 (s, 2H), 2.22 (s, 3H).

Embodiment 1-78

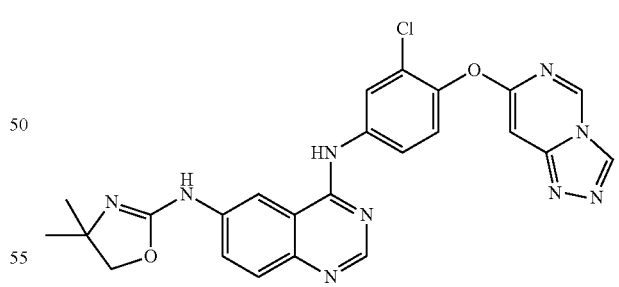

Synthesis of N⁴-[3-chloro-4-([1,2,4]triazolo[4,3-c]pyrimidin-7-yloxy) phenyl)-N⁶-(4,4-dimethyl-4,5-dihydrooxazol-2-yl)quinazolin-4,6-diamine Step A: Preparation of 7-(2-chloro-4-nitrophenoxy)-[1,2,4]triazolo[4,3-c]pyrimidine 2-Chloro-4-nitro-phenol (1000 mg, 5.76 mmol), 7-chloro-[1,2,4]triazolo[4,3-c]pyrimidine (900 mg, 5.82 mmol) and sodium bicarbonate (630 mg, 8.33 mmol) were suspended in N,N-dimethylformamide (6 mL), the mixture was stirred at 95° C. for 16 hours. The reaction solution was cooled to room temperature, then ethyl acetate (100 mL) and water (100 mL) were added. The organic phase was separated, washed with saturated sodium bicarbonate solution (50 mL×3) and saturated aqueous sodium chloride solution (50 mL) successively, dried over anhydrous magnesium sulfate for 2 hours. The mixture was filtered, evaporated to dryness under reduced pressure to give a crude product, which was purified by silica gel column chromatography to give 300 mg of pale yellow solid with a yield of 18.9%.

Step B: Preparation of 3-chloro-4-([1,2,4]triazolo[4,3-c]pyrimidin-7-yloxy) aniline 7-(2-Chloro-4-nitro-phenoxy)-[1,2,4]triazolo[4,3-c]pyrimidine (100 mg, 0.34 mmol) was dissolved in methanol (8 mL), saturated aqueous ammonium chloride solution (2 mL) was added, then the mixture was cooled to 0° C., zinc powder (448 mg, 6.85 mmol) was added, the reaction solution was purged with argon, then warmed to room temperature and stirred for 16 hours. The mixture was filtered through celite and evaporated to dryness under reduced pressure to give 68 mg of yellow solid with a yield of 75.8%, which was used directly in the next step.

Step C: Preparation of $N^4$-[3-chloro-4-([1,2,4]triazolo[4,3-c]pyrimidin-7-yloxy)phenyl)-$N^6$-(4,4-dimethyl-4,5-dihydrooxazol-2-yl)quinazolin-4,6-diamine Preparation was performed according to the method of Embodiment 1-19, wherein 3-fluoro-4-([1,2,4]triazolo[4,3-c]pyrimidin-7-yloxy)aniline was replaced with 3-chloro-4-([1,2,4]triazolo[4,3-c]pyrimidin-7-yloxy)aniline. $^1$HNMR (400 MHz, DMSO) δ 9.72 (s, 1H), 9.69 (s, 1H), 8.61 (s, 1H), 8.54 (s, 1H), 8.29 (s, 1H), 8.16 (s, 1H), 8.03 (s, 1H), 7.95 (d, J=8.8 Hz, 1H), 7.70-7.68 (m, 2H), 7.41 (d, J=8.8 Hz, 1H), 7.36 (s, 1H), 4.08 (s, 2H), 1.28 (s, 6H).

Embodiment 1-80

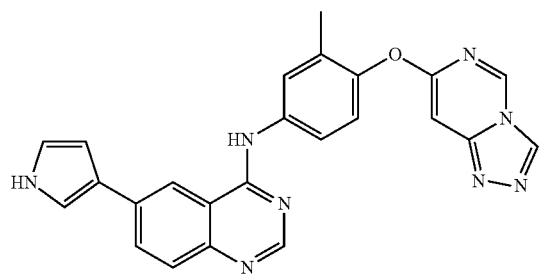 [SMILES: Cc1cc(Nc2ncnc3ccc(-c4cc[nH]c4)cc23)ccc1Oc1cc2nncn2cn1]

Synthesis of N-(4-([1,2,4]triazolo[4,3-c]pyrimidin-7-yloxy)-3-methylphenyl)-6-(1H-pyrrol-3-yl)quinazolin-4-amine Step A: Preparation of N-(4-([1,2,4]triazolo[4,3-c]pyrimidin-7-yloxy)-3-methylphenyl)-6-(1H-pyrrol-3-yl)quinazolin-4-amine N-(4-([1,2,4]triazolo[4,3-c]pyrimidin-7-yloxy)-3-methylphenyl)-6-iodo quinazolin-4-amine (150 mg, 0.30 mmol), (1-(triisopropylsilyl)-1H-pyrrol-3-yl) boronic acid (81 mg, 0.30 mmol), triethylamine (60 mg, 0.59 mmol) and [1,1'-bis(diphenylphosphino)ferrocene]dichloropalladium dichloromethane complex (10 mg) were suspended in tetrahydrofuran (10 mL) and the reaction solution was heated to 80° C. for 48 hours. The mixture was filtered, evaporated to dryness under reduced pressure to give a crude product, which was purified by acidic preparative HPLC to give 15 mg of solid with a yield of 11.4%. LC-MS: 435.9[M+H] detection value. $^1$H NMR (400 MHz, MeOD) δ 9.46 (s, 1H), 8.58 (s, 1H), 8.50 (s, 1H), 8.44 (s, 1H), 8.30-8.09 (m, 1H), 7.85-7.68 (m, 3H), 7.40 (s, 1H), 7.23 (d, J=8.4 Hz, 1H), 6.97 (s, 1H), 6.88 (s, 1H), 6.75 (s, 1H), 2.29 (s, 3H).

Embodiment 1-83

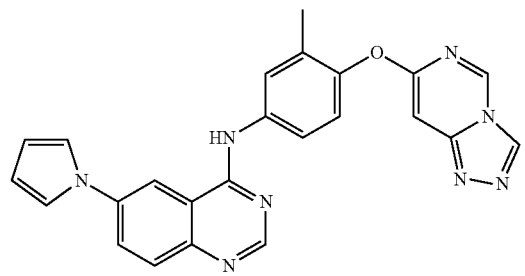 [SMILES: Cc1cc(Nc2ncnc3ccc(-n4cccc4)cc23)ccc1Oc1cc2nncn2cn1]

Synthesis of N-(4-([1,2,4]triazolo[4,3-c]pyrimidin-7-yloxy)-3-methyl phenyl)-6-(1H-pyrrol-1-yl)-quinazolin-4-amine Step A: Preparation of (E)-N-(2-cyano-4-(1H-pyrrol-1-yl)phenyl)-N,N-dimethylformamidine (E)-N'-(2-cyano-4-iodophenyl)-N,N-dimethylformamidine (300 mg, 1.00 mmol), 1H-pyrrole (140 mg, 2.08 mmol), potassium phosphate (530 mg, 2.50 mmol), copper iodide (230 mg, 1.21 mmol) and N,N-dimethylethane-1,2-diamine (110 mg, 1.25 mmol) were suspended in toluene (10 mL) and the reaction solution was heated to 80° C. for 16 hours, then filtered, and purified by silica gel column to give 220 mg of solid with a yield of 92.05%.

Step B: Preparation of N-(4-([1,2,4]triazolo[4,3-c]pyrimidin-7-yloxy)-3-methylphenyl)-6-(1H-pyrrol-1-yl)-quinazolin-4-amine The preparation was performed according to the method of Embodiment 1-7, wherein (R,E)-N'-(2-cyano-4-((4-methyl-4,5-dihydrooxazol-2-yl)amino)phenyl)-N,N-dimethylformamidine was replaced with (E)-N-(2-cyano-4-(1H-pyrrol-1-yl)phenyl)-N,N-dimethylformamidine, and the reaction was conducted at room temperature under stirring for 48 hours. LC-MS: 435.9[M+H] detection value. $^1$H NMR (400 MHz, DMSO) δ 9.83 (s, 1H), 9.68 (d, J=1.2 Hz, 1H), 8.66 (d, J=2.4 Hz, 1H), 8.59 (d, J=2.8 Hz, 2H), 8.20-8.14 (m, 1H), 7.88 (d, J=9.2 Hz, 1H), 7.84-7.76 (m, 2H), 7.63-7.57 (m, 2H), 7.25-7.19 (m, 1H), 7.14 (d, J=1.2 Hz, 1H), 6.47-6.30 (m, 2H), 2.21 (s, 3H).

Embodiment 1-93

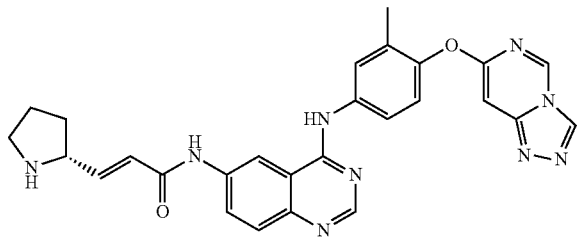 [SMILES: Cc1cc(Nc2ncnc3ccc(NC(=O)/C=C/[C@H]4CCCN4)cc23)ccc1Oc1cc2nncn2cn1]

Synthesis of (R,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide Step A: Preparation of diethyl (2-((4-((4-([1,2,4]triazolo[4,3-c]pyrimidin-7-yloxy)-3-methylphenyl)amino)quinazoline-6-yl)amino)-2-oxoethyl) phosphate N-(4-([1,2,4]triazolo[4,3-c]pyrimidin-7-yloxy)-3-methylphenyl)quinazolin-4,6-diamine (270 mg, 0.70 mmol), 2-(diethoxyphosphoryl)acetic acid (276 mg, 1.41 mmol), 1-ethyl-(3-dimethylaminopropyl)carbodiimide hydrochloride (472 mg, 3.04 mmol), N,N-diisopropylethylamine (545 mg, 4.22 mmol) were dissolved in N,N-dimethylacetamide (5 mL). The mixture was heated to 50° C. and stirred for 16 hours, then cooled to room temperature, water (100 mL) and ethyl acetate (100 mL) were added. The mixture was shaken and allowed to stand to portion. The organic phase was taken, washed with saturated aqueous sodium chloride, dried over anhydrous sodium sulfate for 2 hours, filtered, and concentrated under reduced pressure. The residue was purified by column chromatography to give 350 mg of viscous solid with a yield of 88.6%.

Step B: Preparation of tert-butyl (R,E)-2-(3-((4-((4-([1,2,4]triazolo[4,3-c]pyrimidin-7-yloxy)-3-methylphenyl)amino)quinazolin-6-yl)amino)-3-oxoprop-1-en-1-yl)pyrrolidin-1-carboxylate Diethyl (2-((4-((4-([1,2,4]triazolo[4,3-c]pyrimidin-7-yloxy)-3-methylphenyl) amino)quinazoline-6-yl)amino)-2-oxoethyl) phosphate (123 mg, 0.69 mmol) was dissolved in tetrahydrofuran (5 mL), the solution was cooled to 0° C. under an ice bath, and sodium hydride (30 mg, 1.25 mmol) was added in portions under stirring. The reaction solution was stirred for 30 minutes. A solution of tert-butyl (R)-2-formylpyrrolidin-1-carboxylate (132 mg, 0.66 mmol) in tetrahydrofuran (5 mL) was added dropwise. After completion of the addition, the reaction solution was slowly warmed to room temperature and stirred for another 2 hours. Then 5% aqueous ammonium chloride solution (50 mL) and ethyl acetate (100 mL) were added to the reaction solution, the mixture was shaken and allowed to stand to portion. The organic phase was taken, successively washed with water (50 mL) and saturated aqueous sodium chloride solution (50 mL), dried over anhydrous sodium sulfate, filtered and concentrated. The residue was purified by column chromatography to give 225 mg of pale yellow solid with a yield of 69.4%.

Step C: Preparation of (R,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide Tert-butyl (R,E)-2-(3-((4-((4-([1,2,4]triazolo[4,3-c]pyrimidin-7-yloxy)-3-methylphenyl)amino)quinazolin-6-yl)amino)-3-oxoprop-1-en-1-yl)pyrrolidin-1-carboxylate (100 mg, 0.16 mmol) was dissolved in a solution of dichloromethane (10 mL) comprising 8% trifluoroacetic acid. The reaction solution was stirred at room temperature for 4 hours, and concentrated under reduced pressure to give a crude product, which was purified by preparative HPLC to give 60 mg of pale yellow solid with a yield of 71.8%. LC-MS: 508.3 [M+H] detection value. $^1$H NMR (400 MHz, MeOD) δ 9.43 (s, 1H), 8.75 (s, 1H), 8.49 (s, 1H), 8.41 (s, 1H), 7.96-7.59 (m, 4H), 7.17 (d, J=8.8 Hz, 1H), 7.02 (dd, J=15.2, 7.6 Hz, 1H), 6.93 (s, 1H), 6.56 (d, J=15.2 Hz, 1H), 4.50-4.22 (m, 1H), 3.50-3.34 (m, 2H), 2.43-2.30 (m, 1H), 2.24 (s, 3H), 2.26-2.06 (m, 2H), 2.06-1.88 (m, 1H).

Embodiment 1-94

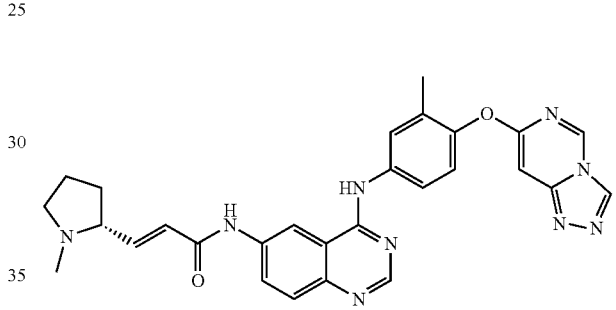

Synthesis of (R,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide Step A: preparation of (R,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide (R,E)-N-(4-((4-([1,2,4]triazolo[4,3-c]pyrimidin-7-yloxy)-3-methylphenyl)amino)quinazolin-6-yl)-3-(pyrrolidin-2-yl)acrylamide (90 mg, 0.18 mmol) and 37% aqueous formaldehyde solution (216 mg) were dissolved in methanol (5 mL), the mixture was stirred at room temperature for 1 hour. Then sodium triacetoborohydride (266 mg, 1.25 mmol) was added to the reaction solution in portions. The resulting mixture was stirred at room temperature for 16 hours, then concentrated under reduced pressure and purified by preparative HPLC to give 80 mg of pale yellow solid with a yield of 86.68%. LC-MS: 522.3 [M+H] detection value. $^1$H NMR (400 MHz, MeOD) δ 9.46 (s, 1H), 8.81 (s, 1H), 8.53 (s, 1H), 8.44 (s, 1H), 8.30 (s, 1H), 7.97-7.62 (m, 4H), 7.21 (d, J=8.8 Hz, 1H), 7.08-6.86 (m, 2H), 6.62 (d, J=14.8 Hz, 1H), 4.05-3.88 (m, 1H), 3.76-3.60 (m, 1H), 3.25-3.05 (m, 1H), 2.86 (d, J=3.6 Hz, 3H), 2.50-2.35 (m, 1H), 2.27 (s, 3H), 2.32-2.12 (m, 2H), 2.12-1.96 (m, 1H).

Embodiment 1-96

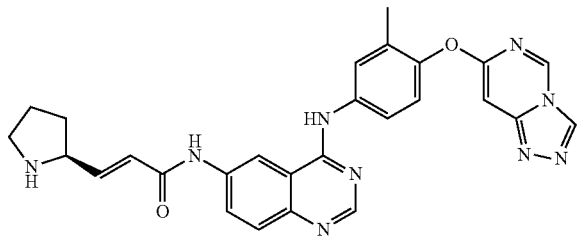 [SMILES: Cc1cc(Nc2ncnc3ccc(NC(=O)/C=C/[C@@H]4CCCN4)cc23)ccc1Oc1cc2nncn2cn1]

Synthesis of (S,E)-N-(4-((4-([1,2,4]triazolo[4,3-c]pyrimidin-7-yloxy)-3-methylphenyl)amino)quinazolin-6-yl)-3-(pyrrolidin-2-yl)acrylamide Preparation was performed according to the method of Embodiment 1-93, wherein tert-butyl (R)-2-formylpyrrolidin-1-carboxylate was replaced with tert-butyl (S)-2-formylpyrrolidin-1-carboxylate. LC-MS: 508.25[M+H] test value. 1H NMR (400 MHz, MeOD) δ 9.47 (s, 1H), 8.81 (s, 1H), 8.54 (s, 1H), 8.45 (s, 1H), 8.42 (s, 1H), 8.06-7.66 (m, 4H), 7.23 (d, J=8.8 Hz, 1H), 7.07 (dd, J=15.2, 7.6 Hz, 1H), 6.97 (s, 1H), 6.59 (d, J=15.2 Hz, 1H), 4.38 (q, J=7.6 Hz, 1H), 3.56-3.38 (m, 2H), 2.49-2.34 (m, 1H), 2.29 (s, 3H), 2.35-2.10 (m, 2H), 2.09-1.90 (m, 1H).

Embodiment 1-97

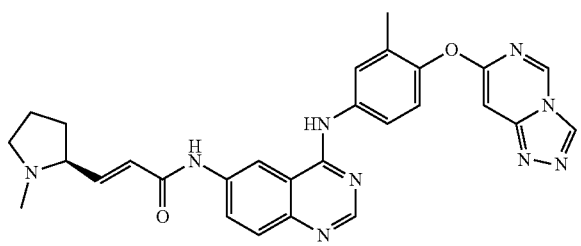 [SMILES: Cc1cc(Nc2ncnc3ccc(NC(=O)/C=C/[C@@H]4CCCN4C)cc23)ccc1Oc1cc2nncn2cn1]

(S,E)-N-(4-((4-([1,2,4]triazolo[4,3-c]pyrimidin-7-yloxy)-3-methylphenyl)amino)quinazolin-6-yl)-3-(1-methylpyrrolidin-2-yl)acrylamide Preparation was performed according to the method of Embodiment 1-94. LC-MS: 522.3 [M+H] detection value. $^1$H NMR (400 MHz, DMSO) δ 10.44 (s, 1H), 9.83 (s, 1H), 9.67 (s, 1H), 8.81 (s, 1H), 8.56 (s, 1H), 8.53 (s, 1H), 7.99-7.64 (m, 4H), 7.18 (d, J=8.8 Hz, 1H), 7.12 (s, 1H), 6.75 (dd, J=15.2, 8.0 Hz, 1H), 6.39 (d, J=15.2 Hz, 1H), 2.60-2.22 (m, 4H), 2.16 (s, 3H), 2.07-2.04 (m, 2H), 1.88-1.71 (m, 2H), 1.72-1.51 (m, 2H).

Embodiment 1-98

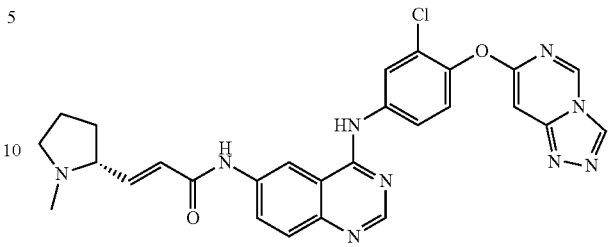

Synthesis of (R,E)-N-(4-((4-([1,2,4]triazolo[4,3-c]pyrimidin-7-yloxy)-3-chlorophenyl)amino)quinazolin-6-yl)-3-(1-methylpyrrolidin-2-yl)acrylamide Step A: Preparation of N-(4-([1,2,4]triazolo[4,3-c]pyrimidin-7-yloxy)-3-chlorophenyl)-6-nitroquinazolin-4-amine 4-([1,2,4]Triazolo[4,3-c]pyrimidin-7-yloxy)-3-chloroaniline (200 mg, 0.76 mmol) and (E)-N'-(2-cyano-4-nitrophenyl)-N,N-dimethylformamidine (220 mg, 1.01 mmol) were dissolved in a mixed solvent of acetic acid (1.2 mL) and isopropyl acetate (3.6 mL). The reaction solution was stirred at room temperature for 48 hours. A large amount of solid precipitated, which were directly filtered. The filter cake was washed with a small amount of isopropyl acetate to give 290 mg of relatively pure product with a yield of 91.6%.

Step B: Preparation of N-(4-([1,2,4]triazolo[4,3-c]pyrimidin-7-yloxy)-3-chlorophenyl)quinazolin-4,6-diamine N-(4-([1,2,4]triazolo[4,3-c]pyrimidin-7-yloxy)-3-chlorophenyl)-6-nitroquinazolin-4-amine (240 mg, 0.55 mmol) was dissolved in methanol (20 mL), a small amount of raney nickel was added, and the reaction system was purged for three times with argon. The reaction solution was stirred under 15 psi hydrogen atmosphere (balloon) for 4 hours, filtered through celite and the filtrate was concentrated under reduced pressure to give 240 mg of pale yellow solid, which was used directly in the next step.

Preparation was performed according to the method of Embodiment 1-93, wherein N-(4-([1,2,4]triazolo[4,3-c]pyrimidin-7-yloxy)-3-methylphenyl)quinazolin-4,6-diamine was replaced with N-(4-([1,2,4]triazolo[4,3-c]pyrimidin-7-yloxy)-3-chlorophenyl)quinazolin-4,6-diamine.

The final product was prepared according to the method of Embodiment 1-94. LC-MS: 543.2 [M+H] detection value. $^1$H NMR (400 MHz, MeOD) δ 9.43 (s, 1H), 8.78 (s, 1H), 8.56 (s, 1H), 8.45 (s, 1H), 8.18 (s, 1H), 7.98-7.70 (m, 3H), 7.36 (d, J=8.8 Hz, 1H), 7.10 (s, 1H), 6.96-6.92 (m, 1H), 6.60 (d, J=15.2 Hz, 1H), 4.00-3.85 (m, 1H), 3.72-3.58 (m, 1H), 3.20-3.00 (m, 1H), 2.83 (s, 3H), 2.50-2.30 (m, 1H), 2.30-2.10 (m, 2H), 2.07-1.96 (m, 1H).

Embodiment 1-124

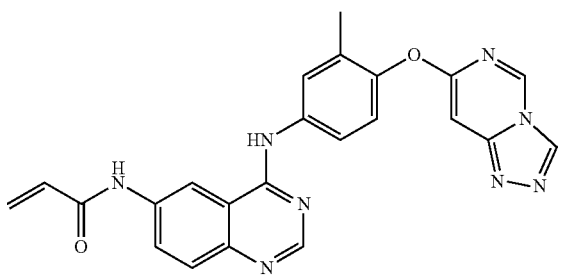 [SMILES: C=CC(=O)Nc1ccc2ncnc(Nc3ccc(Oc4cc5nncn5cn4)c(C)c3)c2c1]

Synthesis of N-(4-((4-([1,2,4]triazolo[4,3-c]pyrimidin-7-yloxy)-3-methyl phenyl)amino)quinazolin-6-yl) acrylamide Preparation was performed according to the method of Embodiment 1-16, wherein 2-fluoroacrylic acid was replaced with acrylic acid. LCMS: 438.9 [M+H] detection value. $^1$H-NMR (DMSO-$d_6$): δ 10.52 (s, 1H), 9.86 (s, 1H), 9.68 (s, 1H), 8.83 (s, 1H), 8.59 (s, 1H), 8.55 (s, 1H), 8.20 (s, 1H), 7.92 (d, 1H, J=9.6 Hz), 7.81 (s, 1H), 7.75 (dd, 1H, J=8.0, 2.2 Hz), 7.19 (d, 1H, J=8.0 Hz), 7.13 (s, 1H), 6.55 (dd, 1H, J=16.0, 8.0 Hz), 6.36 (d, 1H, J=16.0 Hz), 5.85 (dd, 1H, J=8.0, 4.0 Hz), 2.16 (s, 3H).

Embodiment 1-125

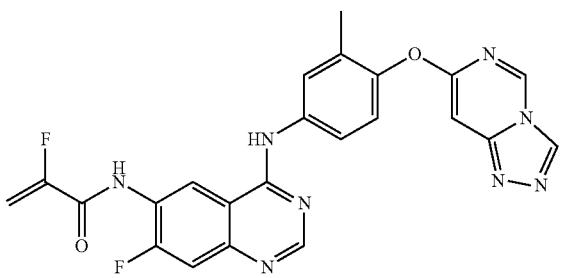 [SMILES: C=C(F)C(=O)Nc1cc2c(Nc3ccc(Oc4cc5nncn5cn4)c(C)c3)ncnc2cc1F]

Synthesis of N-(4-((4-([1,2,4]triazolo[4,3-c]pyrimidin-7-yloxy)-3-methyl phenyl)amino)-7-fluoroquinolin-6-yl)-2-fluoroacrylamide Step A: Preparation of N$^4$-(4-([1,2,4]triazolo[4,3-c]pyrimidin-7-yloxy)-3-methylphenyl)-7-fluoroquinazolin-4,6-diamine N-(4-([1,2,4]triazolo[4,3-c]pyrimidin-7-yloxy)-3-methylphenyl)-7-fluoro-6-nitroquinazolin-4-amine (150 mg, 0.35 mmol) was dissolved in methanol (10 mL), Raney Nickel (50 mg) was added, the reaction system was purged with argon for three times, the reaction solution was stirred under hydrogen atmosphere (balloon) at room temperature for 16 hours, then filtered through celite and concentrated under reduced pressure to give 100 mg brown solid, which was used directly in the next step.

Step B: preparation of N-(4-((4-([1,2,4]triazolo[4,3-c]pyrimidin-7-yloxy)-3-methylphenyl)amino)-7-fluoroquinolin-6-yl)-2-fluoroacrylamide The preparation was performed according to the method of Embodiment 1-16, wherein the mixture was stirred at 50° C. for 16 hours. LCMS: 474.8 [M+H] detection value. $^1$H-NMR (DMSO): δ 10.6 (s, 1H), 9.95 (s, 1H), 9.68 (s, 1H), 8.75 (d, 1H, J=8.0 Hz), 8.62 (s, 1H), 8.60 (s, 1H), 7.79 (s, 1H), 7.76 (dd, 1H, J=12.0, 4.0 Hz), 7.69 (d, 1H, J=12.0 Hz), 7.20 (d, 1H, J=12.0 Hz), 7.16 (s, 1H), 5.81 (dd, 1H, J=48.0, 4.0 Hz), 5.56 (dd, 1H, J=16.0, 4.0 Hz), 2.19 (s, 3H).

Embodiment 1-126

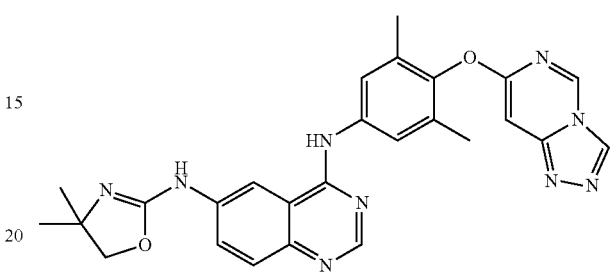

Synthesis of N$^4$-(4-([1,2,4]triazolo[4,3-c]pyrimidin-7-yloxy)-3,5-dimethyl phenyl)-N-(4,4-dimethyl-4,5-dihydrooxazol-2-yl)quinazolin-4,6-diamine Preparation was performed according to the method of Embodiment 1-19, wherein 2-fluoro-4-nitro-phenol was replaced with 2,6-dimethyl-4-nitrophenol, sodium bicarbonate was replaced with sodium carbonate, and the mixture was stirred at 80° C. for 16 hours. LCMS: 495.9 [M+H] detection value. $^1$H-NMR (DMSO): δ 9.65 (s, 1H), 9.52 (s, 1H), 8.58 (s, 1H), 8.48 (s, 1H), 8.16 (s, 1H), 8.03 (s, 1H), 7.67-7.66 (m, 3H), 7.07 (s, 1H), 4.08 (s, 2H), 2.13 (s, 6H), 1.29 (s, 6H).

Embodiment 1-127

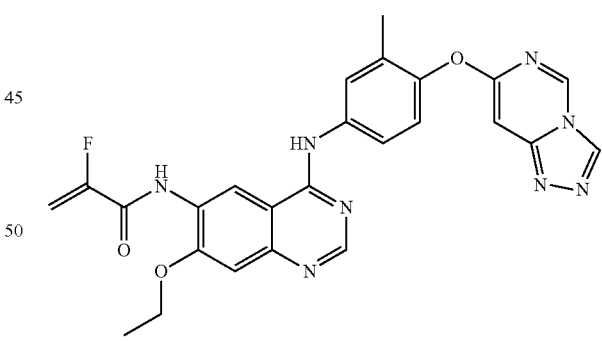

Synthesis of N-(4-((4-([1,2,4]triazolo[4,3-c]pyrimidin-7-yloxy)-3-methyl phenyl)amino)-7-ethoxyquinazolin-6-yl)-2-fluoroacrylamide Step A: Preparation of N-(4-([1,2,4]triazolo[4,3-c]pyrimidin-7-yloxy)-3-methylphenyl)-7-ethoxy-6-nitroquinazolin-4-amine N-(4-([1,2,4]triazolo[4,3-c]pyrimidin-7-yloxy)-3-methylphenyl)-7-fluoro-6-nitroquinazolin-4-amine (200 mg, 0.47 mmol) was suspended in tetrahydrofuran (2 mL), and the solution was cooled to 0° C. Sodium ethoxide (120 mg, 1.76 mmol) was dissolved in ethanol (470 mg, 10.2 mmol) to prepare a solution. The prepared solution of sodium ethoxide was added dropwise to the above reaction mixture maintaining the temperature below 0° C. The final mixture was warmed to room temperature and stirred for 2 hours. A solution of the above crude product (800 mg) in tetrahydrofuran (10 mL) was added dropwise. The reaction solution was allowed to warm to room temperature and stirred for another 18 hours, then concentrated under reduced pressure to give a brown solid, which was used directly in the next step.

Preparation was performed according to the method of Embodiment 1-16, wherein N-(4-([1,2,4]triazolo[4,3-c]pyrimidin-7-yloxy)-3-methylphenyl)-6-nitro quinazolin-4-amine was replaced with N-(4-([1,2,4]triazolo[4,3-c]pyrimidin-7-yloxy)-3-methylphenyl)-7-ethoxy-6-nitroquinazolin-4-amine. LCMS: 500.8 [M+H] detection value.

Embodiment 1-111

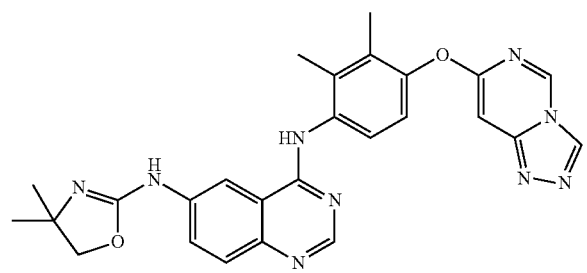 [SMILES: Cc1c(Nc2ncnc3ccc(NC4=NC(C)(C)CO4)cc23)ccc(Oc2cc3nncn3cn2)c1C]

Synthesis of N⁴-(2,3-dimethyl-4-([1,2,4]triazolo[4,3-c]pyrimidin-7-yloxy) phenyl)-N⁶-(4,4-dimethyl-4,5-dihydrooxazol-2-yl)quinazolin-4,6-diamine Preparation was performed according to the method of Embodiment 1-19, wherein 2-fluoro-4-nitro-phenol was replaced with 2,3-dimethyl-4-nitro-phenol, sodium bicarbonate was replaced with sodium carbonate, and the mixture was stirred at 80° C. for 16 hours. LC-MS: 495.9[M+H] detection value. $^1$H NMR (400 MHz, DMSO) δ 9.67 (s, 1H), 9.40 (s, 1H), 8.58 (s, 1H), 8.29 (s, 1H), 8.18 (s, 1H), 7.99 (s, 1H), 7.63 (s, 2H), 7.26 (d, J=8.4 Hz, 1H), 7.14 (s, 1H), 7.06 (d, J=8.4 Hz, 1H), 4.06 (s, 2H), 2.14 (s, 6H), 1.28 (s, 6H).

Embodiment 32

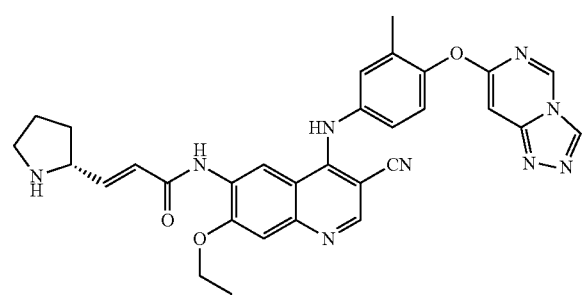 [SMILES: CCOc1cc2ncc(C#N)c(Nc3ccc(Oc4cc5nncn5cn4)c(C)c3)c2cc1NC(=O)/C=C/[C@H]1CCCN1]

Synthesis of (R,E)-N-(4-((4-([1,2,4]triazolo[4,3-c]pyrimidin-7-yloxy)-3-methylphenyl)amino)-3-cyano-7-ethoxyquinolin-6-yl)-3-(pyrrol-2-yl)acrylamide Step A: Preparation of 3-ethoxy-4-nitroaniline 3-Fluoro-4-nitro-aniline (2 g, 12.81 mmol) was added to a solution of sodium ethoxide (3.48 g, 51.1 mmol) in ethanol (40 mL). The reaction mixture was stirred at room temperature for 16 hours, then poured into saturated brine and extracted with ethyl acetate (100 mL×3). The organic phases were combined, dried over anhydrous sodium sulfate, and concentrated under reduced pressure to give 2.12 g of crude yellow solid, which was directly used in the next reaction.

Step B: Preparation of (E)-ethyl 2-cyano-3-((3-ethoxy-4-nitrophenyl)amino) acrylate 3-Ethoxy-4-nitroaniline (2.12 g, 11.6 mmol) and (E)-ethyl 2-cyano-3-ethoxyacrylate (1.97 g, 11.6 mmol) were mixed in toluene (30 mL) and stirred at 130° C. for 16 hours. The reactants were cooled to room temperature, filtered to give 2.5 g of crude yellow solid, which was directly used in the next reaction.

Step C: Preparation of 7-ethoxy-4-hydroxy-6-nitroquinolin-3-carbonitrile (E)-ethyl 2-cyano-3-((3-ethoxy-4-nitrophenyl)amino) acrylate (2.5 g, 8.20 mmol) was suspended in Dowtherm A (50 mL) and stirred for 1.5 hours under argon atmosphere at 256° C. The reactants were cooled to room temperature, diluted with petroleum ether, filtered to give a crude brown solid, which was isolated and purified by silica gel column to give 430 mg of brown solid with a yield of 20%.

Step D: Preparation of 4-chloro-7-ethoxy-6-nitroquinolin-3-carbonitrile

7-Ethoxy-4-hydroxy-6-nitroquinolin-3-carbonitrile (430 mg, 1.66 mmol) was dissolved in phosphorus oxychloride (8 mL) and stirred at 110° C. for 7 hours. The reaction mixture was concentrated to dryness under reduced pressure, and the residue was suspended in aqueous sodium bicarbonate solution and dichloromethane. The organic phase was separated, and the aqueous phase was extracted with dichloromethane (50 mL×3). The organic phases were combined, dried over anhydrous sodium sulfate, filtered, and the concentrated crude product was isolated and purified by silica gel column to give 344 mg of yellow solid with a yield of 74.7%.

Step E: Preparation of 4-((4-([1,2,4]triazolo[4,3-c]pyrimidin-7-yloxy)-3-methylphenyl)amino)-7-ethoxy-6-nitroquinolin-3-carbonitrile 4-Chloro-7-ethoxy-6-nitroquinolin-3-carbonitrile (344 mg, 1.24 mmol) and 3-methyl-4-([1,2,4]triazolo[4,3-c]pyrimidin-7-yloxy)aniline (300 mg) were mixed in isopropanol (8 mL), and then stirred at 90° C. for 16 hours. The reactants were cooled to room temperature and filtered to give 600 mg of crude yellow solid, which was directly used in the next reaction.

Step F: Preparation of 4-((4-([1,2,4]triazolo[4,3-c]pyrimidin-7-yloxy)-3-methylphenyl)amino)-6-amino-7-ethoxyquinolin-3-carbonitrile 4-((4-([1,2,4]Triazolo[4,3-c]pyrimidin-7-yloxy)-3-methylphenyl)amino)-7-ethoxy-6-nitroquinolin-3-carbonitrile (540 mg, 1.12 mmol) and palladium carbon (100 mg) were mixed in methanol (25 mL), followed by addition of triethylamine (2 mL), and the mixture was stirred at room temperature for 5 hours under hydrogen atmosphere (balloon). The mixture was filtered, and the filtrate was concentrated under reduced pressure to give crude product, which was isolated and purified by silica gel column to give 500 mg of brown solid with a yield of 98.71%.

Step G: Preparation of Diethyl (2-((4-([1,2,4]triazolo[4,3-c]pyrimidin-7-yloxy)-3-methylphenyl)amino)-3-cyano-7-ethoxyquinolin-6-yl)amino)-2-oxoethyl)phosphonate N,N'-carbonyldiimidazole (544 mg, 3.36 mmol) was dissolved in tetrahydrofuran (5 mL) and heated to 40° C., followed by addition of a solution of 2-(diethoxyphosphoryl)acetic acid (494 mg, 2.52 mmol) in tetrahydrofuran (2 mL), and the reactants were stirred at 40° C. for 30 minutes to give reaction mixture A. At this temperature, a solution of 4-((4-([1,2,4]triazolo[4,3-c]pyrimidin-7-yloxy)-3-methylphenyl)amino)-6-amino-7-ethoxyquinoline-3-carbonitrile (380 mg, 0.84 mmol) in tetrahydrofuran (5 mL) was added dropwise, and the final reactants were stirred at 40° C. for 16 hours. The mixture was concentrated under reduced pressure to dryness, and the residue was suspended in water and dichloromethane. The organic phase was separated, and the aqueous phase was extracted with dichloromethane. The organic phases were combined, dried over anhydrous sodium sulfate, filtered, and concentrated under reduced pressure to give a crude product, which was isolated and purified by silica gel column to give 326 mg of yellow solid with a yield of 61.6%.

Preparation was performed according to the method of Embodiment 17, wherein diethyl (2-((4-((4-([1,2,4]triazolo[4,3-c]pyrimidin-7-yloxy)-3-methylphenyl) amino)-7-yloxy)-3-methylphenyl)amino)-7-ethoxy quinolin-6-yl)amino)-2-oxoethyl)phosphate was replaced with diethyl (2-((4-((4-([1,2,4]triazolo[4,3-c]pyrimidin-7-yloxy)-3-methylphenyl)amino)-3-cyano-7-ethoxyquinolin-6-yl)amino)-2-oxoethyl)phosphate. LC-MS: 576.3 [M+H] detection value; $^1$H-NMR (400 MHz, CD$_3$OD) δ 9.48 (s, 1H), 9.01 (s, 1H), 8.49 (s, 1H), 8.43 (s, 1H), 7.38 (s, 1H), 7.34 (s, 1H), 7.30-7.20 (m, 2H), 7.04 (dd, J=15.2, 7.6 Hz, 1H), 6.97 (s, 1H), 6.77 (d, J=15.2 Hz, 1H), 4.47-4.25 (m, 3H), 3.47-3.35 (m, 2H), 2.45-2.30 (m, 1H), 2.45-2.30 (s, 3H), 2.24-2.08 (m, 2H), 2.10-1.83 (m, 2H), 1.59 (t, J=6.8 Hz, 3H).

Embodiment 33

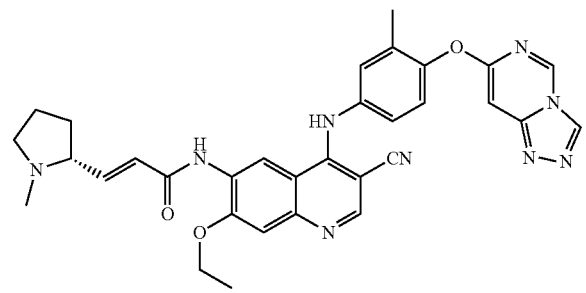 [SMILES: CCOc1cc2ncc(C#N)c(Nc3ccc(Oc4cc5nncn5cn4)c(C)c3)c2cc1NC(=O)/C=C/[C@H]1CCCN1C]

Synthesis of (R,E)-N-(4-((4-([1,2,4]triazolo[4,3-c]pyrimidin-7-yloxy)-3-methylphenyl)amino)-3-cyano-7-ethoxyquinolin-6-yl)-3-(1-methylpyrrol-2-yl)acrylamide Preparation was performed according to the method of Embodiment 18. LC-MS: 590.3 [M+H] detection value; $^1$H-NMR (400 MHz, CD$_3$OD) δ 9.48 (s, 1H), 9.02 (s, 1H), 8.48 (s, 1H), 8.43 (s, 1H), 7.38 (s, 1H), 7.35 (s, 1H), 7.33-7.16 (m, 2H), 6.97 (s, 1H), 6.93 (dd, J=15.2, 8.8 Hz, 1H), 6.76 (d, J=15.2 Hz, 1H), 4.39 (q, J=7.2 Hz, 2H), 3.83-3.65 (m, 1H), 3.65-3.51 (m, 1H), 3.08-2.92 (m, 1H), 2.75 (s, 3H), 2.46-2.29 (m, 1H), 2.26 (s, 3H), 2.30-2.05 (m, 2H), 2.05-1.90 (m, 1H), 1.59 (t, J=6.8 Hz, 3H).

Embodiment 34

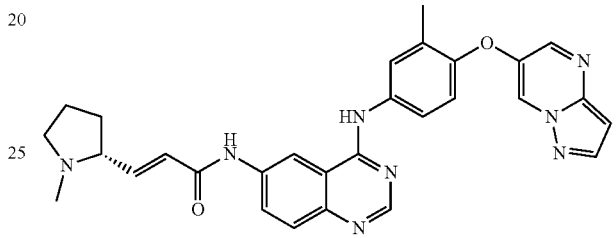

Synthesis of (R,E)-N-(4-((3-methyl-4-(pyrazolo[1,5-a]pyrimidin-6-yloxy) phenyl)amino)quinazolin-6-yl)-3-(1-methylpyrrol-2-yl)acrylamide Step A: Preparation of 6-bromopyrazolo[1,5-a]pyrimidine 1H-pyrazolo-3-amine (738 mg, 8.88 mmol) was dissolved in ethanol (18 mL), followed by addition of 2-bromomalondialdehyde (2.68 g, 17.76 mmol) and acetic acid (0.8 mL). The reaction mixture was refluxed for 4.5 hours and concentrated under reduced pressure, and the obtained crude product was isolated and purified by silica gel column to give 1.05 g of yellow crystalline solid with a yield of 59.7%.

Step B: Preparation of pyrazolo[1,5-a]pyrimidin-6-ol

6-Bromopyrazolo[1,5-a]pyrimidine (1100 mg, 5.56 mmol) was dissolved in methanol (23 mL), followed by addition of potassium hydroxide (732 mg, 12.89 mmol). The reactants were stirred at 56° C. for 32 hours, and concentrated under reduced pressure to give a residue. Ethyl acetate (30 mL) and saturated ammonium chloride solution (30 mL) were added to the residue. The organic layer was separated, washed with saturated ammonium chloride solution (30 mL) and saturated brine (30 mL), and dried over anhydrous sodium sulfate, followed by filtration. The filtrate was concentrated under reduced pressure to give 425 mg of crude orange solid, which was directly used in the next reaction.

3-Methyl-4-(pyrazolo[1,5-a]pyrimidin-6-yloxy)aniline was prepared according to the method of Embodiment 11 and the target compound was prepared according to the method of Embodiment 10. LC-MS: 261.1[M/2+H] detection value. $^1$H-NMR (400 MHz, DMSO) δ 10.44 (s, 1H), 9.83 (s, 1H), 8.92 (d, J=2.0 Hz, 1H), 8.83 (d, J=1.2 Hz, 1H), 8.62 (d, J=2.8 Hz, 1H), 8.52 (s, 1H), 8.22 (d, J=2.4 Hz, 1H), 7.88 (dd, J=8.8, 2.0 Hz, 1H), 7.82 (d, J=2.4 Hz, 1H), 7.78 (d, J=8.8 Hz, 1H), 7.66 (dd, J=8.8, 2.4 Hz, 1H), 7.06 (d, J=8.8 Hz, 1H), 6.81 (dd, J=2.4, 0.8 Hz, 1H), 6.74 (dd, J=15.2, 7.6 Hz, 1H), 6.36 (d, J=15.2 Hz, 1H), 3.10-3.03 (m, 1H), 2.82 (dd, J=15.6, 8.0 Hz, 1H), 2.36 (s, 3H), 2.28-2.15 (m, 4H), 2.09-2.00 (m, 1H), 1.83-1.69 (m, 2H), 1.64-1.55 (m, 1H).

Embodiment 35

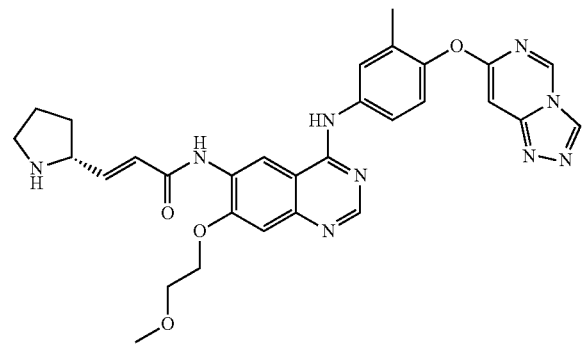 [SMILES: COCCOc1cc2ncnc(Nc3ccc(Oc4cc5nncn5cn4)c(C)c3)c2cc1NC(=O)/C=C/[C@H]1CCCN1]

Synthesis of (R,E)-N-(4-((4-([1,2,4]triazolo[4,3-c]pyrimidin-7-yloxy)-3-methylphenyl)amino)-7-(2-methoxyethoxy)quinazolin-6-yl)-3-(pyrrol-2-yl)acrylamide Step A: Preparation of 7-(2-methoxyethoxy)-6-nitroquinazolin-4-ol After cooling to 0° C. in an ice-water bath, sodium hydride (1500 mg, 24.00 mmol) was slowly added into a solution of 2-methoxyethanol (1500 mg, 19.71 mmol) in anhydrous tetrahydrofuran (20 mL), and stirred for 1 hour. Under an ice-water bath, a solution of 7-fluoro-6-nitroquinazolin-4-ol (2000 mg, 9.56 mmol) in tetrahydrofuran (20 mL) was added dropwise, and then the solution was naturally warmed to room temperature and stirred for 16 hours. The reactants were cooled in an ice-water bath, neutralized to pH 5-6 with acetic acid, filtered and dried in vacuum to give 2400 mg of pale yellow solid with a yield of 88.9%.

Preparation of (R,E)-N-(4-((4-([1,2,4]triazolo[4,3-c]pyrimidin-7-yloxy)-3-methylphenyl)amino)-7-(2-methoxyethoxy)quinazolin-6-yl)-3-(pyrrol-2-yl)acrylamide Preparation was performed according to the method of Embodiment 17. LC-MS: 582.3[M+H] detection value. ¹H NMR (400 MHz, CD₃OD) δ 9.45 (s, 1H), 9.00 (s, 1H), 8.47 (s, 1H), 8.43 (s, 1H), 7.72 (s, 1H), 7.66 (d, J=8.4 Hz, 1H), 7.28 (s, 1H), 7.19 (d, J=8.8 Hz, 1H), 7.05 (dd, J=14.8, 7.6 Hz, 1H), 6.94 (s, 1H), 6.73 (d, J=14.8 Hz, 1H), 4.43 (s, 2H), 3.93 (s, 2H), 3.51 (s, 3H), 3.45-3.35 (m, 2H), 2.45-2.30 (m, 1H), 2.25 (s, 3H), 2.25-2.10 (m, 2H), 2.10-1.90 (m, 2H).

Embodiment 36

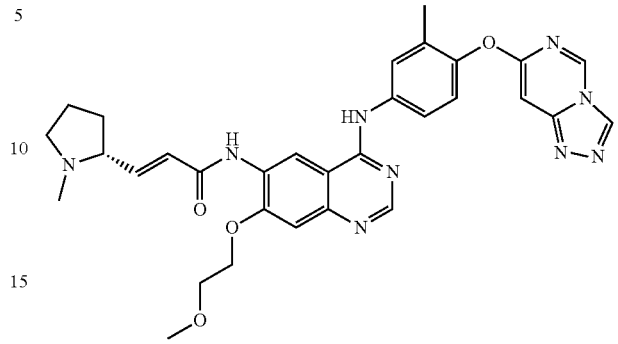

Synthesis of (R,E)-N-(4-((4-([1,2,4]triazolo[4,3-c]pyrimidin-7-yloxy)-3-methylphenyl)amino)-7-(2-methoxyethoxy)quinazolin-6-yl)-3-(1-methylpyrrol-2-yl)acrylamide Preparation was performed according to the method of Embodiment 18. LC-MS: 596.3[M+H] detection value. ¹H NMR (400 MHz, CD₃OD) δ 9.45 (s, 1H), 9.01 (s, 1H), 8.47 (s, 1H), 8.43 (s, 1H), 7.73 (s, 1H), 7.68 (d, J=8.0 Hz, 1H), 7.28 (s, 1H), 7.19 (d, J=8.4 Hz, 1H), 6.99-6.95 (m, 2H), 6.74 (d, J=15.2 Hz, 1H), 4.43 (s, 2H), 3.94 (s, 2H), 3.90-3.73 (m, 1H), 3.71-3.55 (m, 1H), 3.52 (s, 3H), 3.11-2.93 (m, 1H), 2.78 (s, 3H), 2.50-2.30 (m, 1H), 2.26 (s, 3H), 2.20-2.10 (m, 2H), 2.10-1.90 (m, 1H).

Embodiment 37

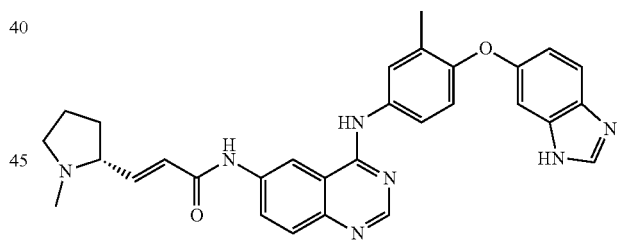

Synthesis of (R,E)-N-(4-((4-((1H-benzo[d]imidazole-6-yl)oxy)-3-methyl phenyl)amino)quinazolin-6-yl)-3-(1-methylpyrrol-2-yl)acrylamide Step A: Preparation of tert-butyl 5-hydroxy-benzimidazole-1-carbonate and tert-butyl 6-hydroxy-benzimidazole-1-carbonate 1H-benzimidazole-5-hydroxy (650 mg, 4.8 mmol), di-tert-butyl carbonate (2.2 g, 10 mmol) and diisopropylethylamine (1.8 g, 14 mmol) were mixed in dioxane (30 mL), and the mixture was stirred at 85° C. for 16 hours. The mixture was concentrated under reduced pressure to give a crude product, which was washed with aqueous sodium bicarbonate solution and extracted with ethyl acetate for three times. The organic phases were combined, dried over anhydrous sodium sulfate, filtered and concentrated to give a cruded product, which was isolated and purified by silica gel column to give 550 mg of mixture with a yield of 48.5%.

Step B: Preparation of tert-butyl 5-(2-methyl-4-nitro-phenoxy)-benzimidazole-1-carbonate and tert-butyl 6-(2-methyl-4-nitro-phenoxy)-benzimidazole-1-carbonate Sodium hydride (180 mg, 7.5 mmol) was added to N,N-dimethylformamide (10 mL), and the reaction mixture was cooled to about 0° C., followed by addition of a mixture of tert-butyl 5-hydroxy-benzimidazole-1-carbonate and tert-butyl 6-hydroxy-benzimidazole-1-carbonate (350 mg, 1.5 mmol). After stirring for 10 minutes, 1-fluoro-2-methyl-4-nitrobenzene (250 mg, 1.6 mmol) was added thereto, and the reactants were stirred at room temperature for 16 hours. The mixture was quenched with ammonium chloride, then extracted with ethyl acetate three times. The organic phases were combined, dried over anhydrous sodium sulfate, filtered and concentrated to give a crude product, which was isolated and purified by silica gel column to give 130 mg of yellow solid with a yield of 23.6%.

Step C: Preparation of Tert-Butyl 5-(4-amino-2-methyl-phenoxy)-benzimidazole-1-carbonate and Tert-Butyl 6-(4-amino-2-methyl-phenoxy)-benzimidazole-1-carbonate Palladium carbon (100 mg) was added to a solution of the mixture of tert-butyl 5-(2-methyl-4-nitro-phenoxy)-benzimidazole-1-carbonate and tert-butyl 6-(2-methyl-4-nitro-phenoxy)-benzimidazole-1-carbonate (230 mg, 0.6 mmol) in methanol (20 mL). The mixture was replaced with hydrogen for 3 times, then stirred at room temperature for 4 hours, filtered, concentrated to give a crude product, which was isolated and purified by silica gel column to give 100 mg of yellow solid with a yield of 47.3%.

Step D: Preparation of tert-butyl (R,E)-5-(2-methyl-4-((6-(3-(1-methylpyrrol-2-yl)acrylamide)quinazolin-4-yl)amino)phenoxy)-1H-benzo[d]imidazole-1-carbonate and tert-butyl (R,E)-6-(2-methyl-4-((6-(3-(1-methylpyrrol-2-yl)acrylamide)quinazolin-4-yl)amino)phenoxy)-1H-benzo[d]imidazole-1-carbonate Preparation was performed according to the method of Embodiment 10, wherein 80 mg of solid mixture was obtained silica gel column.

Step E: Preparation of (R,E)-N-(4-((4-((1H-benzo[d]imidazole-6-yl)oxy)-3-methylphenyl)amino)quinazolin-6-yl)-3-(1-methylpyrrol-2-yl)acrylamide 80 mg of the above solid mixture was dissolved in dichloromethane (5 mL), followed by addition of trifluoroacetic acid (0.5 mL). The reaction mixture was stirred for 5 hours and concentrated, and the crude product was isolated by column chromatography to give 8 mg of pale yellow solid with a yield of 10.5%. LC-MS: 260.7[M/2+H] detection value. $^1$H NMR (400 MHz, CD$_3$OD) δ 8.80 (s, 1H), 8.48 (s, 1H), 8.16 (s, 1H), 7.85-7.79 (m, 2H), 7.67 (s, 1H), 7.62 (d, J=8.0 Hz, 1H), 7.55 (d, J=4.0 Hz, 1H), 7.13 (s, 1H), 7.04 (d, J=8.0 Hz, 1H), 6.97-6.90 (m, 2H), 6.48 (d, J=16.0 Hz, 1H), 3.40-3.34 (m, 1H), 2.73-2.67 (m, 1H), 2.58 (s, 3H), 2.33 (s, 3H), 2.29 (dd, J=16.0 Hz, J=8.0 Hz, 1H), 2.22 (t, J=8.0 Hz, 1H), 2.08-2.00 (m, 2H), 1.94-1.88 (m, 1H).

Embodiment 38

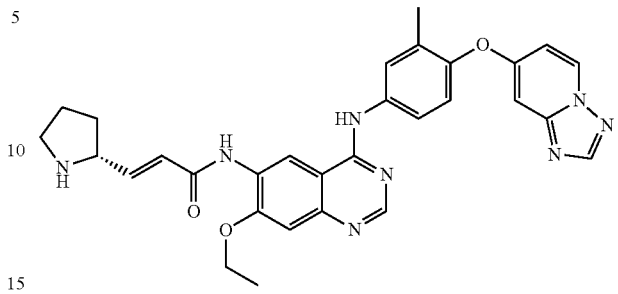

Synthesis of (R,E)-N-(4-((4-([1,2,4]triazolo[1,5-a]pyridin-7-yloxy)-3-methyl phenyl)amino)-7-ethoxy-quinazolin-6-yl)-3-(pyrrolidin-2-yl)acrylamide Preparation was performed according to the method of Embodiment 17, wherein 4-([1,2,4]triazolo[4,3-c]pyrimidin-7-yloxy)-3-methylaniline was replaced with 4-([1,2,4]triazolo[1,5-a]pyridin-7-yloxy)-3-methylaniline. LC-MS: 551.3[M+H] detection value. $^1$H NMR (400 MHz, CD$_3$OD) δ 8.96 (s, 1H), 8.76 (d, J=7.6 Hz, 1H), 8.48 (s, 1H), 8.41 (s, 1H), 8.30 (s, 1H), 7.76 (s, 1H), 7.70 (dd, J=8.8, 2.4 Hz, 1H), 7.26 (s, 1H), 7.19 (d, J=8.8 Hz, 1H), 7.10 (dd, J=7.2, 2.4 Hz, 1H), 7.09-7.03 (m, 1H), 6.85 (d, J=2.4 Hz, 1H), 6.78 (d, J=15.2 Hz, 1H), 4.44-4.29 (m, 2H), 3.51-3.35 (m, 2H), 2.45-2.33 (m, 1H), 2.26 (s, 3H), 2.25-2.10 (m, 2H), 2.10-1.82 (m, 2H), 1.58 (t, J=7.0 Hz, 3H).

Embodiment 39

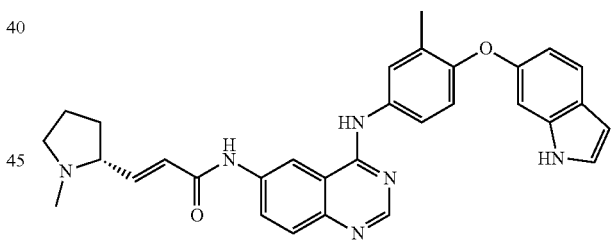

Synthesis of (R,E)-N-(4-((4-((1H-indole-6-yl)oxy)-3-methylphenyl)amino) quinazolin-6-yl)-3-(1-methylpyrrol-2-yl)acrylamide Step A: Preparation of 6-(2-methyl-4-nitrophenoxy)-1H-indole Sodium hydride (240 mg, 6.00 mmol) was suspended in N,N-dimethylformamide (5 mL), cooled to 0° C., and a solution of 1H-indole-6-ol (400 mg, 3.00 mmol) in N,N-dimethylformamide (3 mL) was dropwise added. The reactant was stirred at 0° C. for 5 minutes, followed by addition of 1-fluoro-2-methyl-4-nitrobenzene (513 mg, 3.31 mmol). The reactant was slowly warmed to room temperature, then heated to 60° C. and stirred for 16 minutes. Water (30 mL) was added to the reaction mixture and extracted with ethyl acetate (30 mL×3). The organic phases were combined, dried over anhydrous sodium sulfate, filtered, and the filtrate was evaporated to dryness under reduced pressure to give a crude product, which was isolated and purified by silica gel column to give 250 mg of orange oil with a yield of 31.0%.

Step B: Preparation of tert-butyl 6-(2-methyl-4-nitrophenoxy)-1H-indole-1-carboxylate 6-(2-Methyl-4-nitrophenoxy)-1H-indole (200 mg, 0.75 mmol), di-tert-butyl dicarbonate (195 mg, 0.89 mmol), 4-dimethylaminopyridine (46 mg, 0.38 mmol) and N,N-diisopropylethylamine (156 μL, 0.89 mmol) were mixed in 1,4-dioxane (5 mL). The reactants were stirred at 33° C. for 6 hours, and concentrated under reduced pressure to give a crude product, which was isolated and purified by silica gel column to give 232 mg of yellow oil with a yield of 84.5%.

Step C: Preparation of Tert-Butyl 6-(4-amino-2-methylphenoxy)-1H-indole-1-carboxylate Tert-butyl 6-(2-methyl-4-nitrophenoxy)-1H-indole-1-carboxylate (232 mg, 0.63 mmol) was dissolved in methanol (10 mL), followed by addition of Pd/C (23 mg). The reaction mixture was stirred at 33° C. for 2.5 hours under 15 psi hydrogen atmosphere. The mixture was filtered through diatomite and the filtrate was evaporated to dryness under reduced pressure to give 198 mg of crude off-white solid, which was directly used in the next reaction.

Step D: Preparation of Tert-Butyl (R,E)-6-(2-methyl-4-((6-(3-(1-methylpyrrol-2-yl)acrylamide) quinazolin-4-yl)amino)phenoxy)-1H-indole-1-carboxylate (E)-N-(3-cyano-4-((E)-(dimethylamino)methylene) amino)phenyl)-3-((R)-1-methylpyrrol-2-yl) acrylamide (50 mg, 0.15 mmol) and tert-butyl 6-(4-amino-2-methylphenoxy)-1H-indole-1-carboxylate (53 mg, 0.16 mmol) were mixed in isopropyl acetate (1 mL), followed by addition of glacial acetic acid (0.3 mL), and the mixture was stirred at 33° C. for 16 hours. The reaction mixture was concentrated under reduced pressure to give a crude product, which was isolated and purified by silica gel column and TLC to give 24 mg of orange solid with a yield of 26.3%.

Step E: Preparation of (R,E)-N-(4-((4-((1H-indole-6-yl)oxy)-3-methyl phenyl)amino)quinazolin-6-yl)-3-(1-methylpyrrol-2-yl)acrylamide Tert-butyl (R,E)-6-(2-methyl-4-((6-(3-(1-methylpyrrol-2-yl)acrylamide) quinazolin-4-yl)amino)phenoxy)-1H-indole-1-carboxylate (24 mg, 0.04 mmol) was dissolved in dichloromethane (1 mL), followed by addition of trifluoroacetic acid (0.2 mL), and the mixture was stirred at 30° C. for 3 hours. The reaction mixture was concentrated under reduced pressure to give a crude product, which was isolated and purified by HPLC to give 2.31 mg of pale yellow solid with a yield of 11.5%. $^1$H NMR (400 MHz, DMSO) δ 10.53 (s, 1H), 9.99 (s, 1H), 8.90 (s, 1H), 8.60 (s, 1H), 8.33 (s, br, 1H), 7.96-7.90 (m, 2H), 7.83 (d, J=8.8 Hz, 1H), 7.45 (d, J=8.4 Hz, 1H), 7.35 (d, J=8.4 Hz, 1H), 7.26 (d, J=2.8 Hz, 1H), 6.77 (dd, J=15.2, 7.6 Hz, 1H), 6.64 (dd, J=8.4, 2.0 Hz, 1H), 6.55 (d, J=2.8 Hz, 1H), 6.41 (s, 1H), 3.11-3.06 (m, 1H), 2.84 (m, 1H), 2.23 (m, 4H), 2.04 (m, 4H), 1.79 (m, 2H), 1.62 ms, 1H).

Embodiment 40

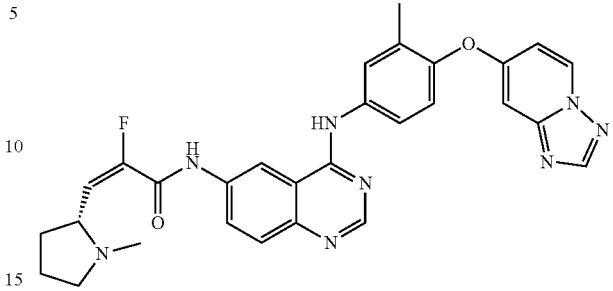

Synthesis of (R,E)-N-(4-((4-([1,2,4]triazolo[1,5-a]pyridin-7-yloxy)-3-methyl phenyl)amino)quinazolin-6-yl)-2-fluoro-3-(1-methylpyrrol-2-yl)acrylamide Step A: Preparation of 2-(diethoxyphosphoryl)-2-fluoroacetic Acid Ethyl 2-diethoxyphosphoryl-2-fluoroacetate (1 g, 4.13 mmol) was dissolved in ethanol (40 mL), cooled to −5° C., and a solution of sodium hydroxide (826 mg, 20.65 mmol) in water (40 mL) was added dropwise. After completion of the addition, the reaction mixture was reacted at −5° C. for 2 hours, and the pH was adjusted to 2-3 with 4N hydrochloric acid. The mixture was concentrated to give a crude product, which was extracted with tetrahydrofuran and filtered. The filtrate was concentrated under reduced pressure to give 880 mg of white waxy solid, which was directly used for the next reaction.

Step B: Preparation of diethyl (E)-(2-((3-cyano-4-((dimethylamino) methylene)amino)phenyl)amino)-1-fluoro-2-oxoethyl)phosphonate 2-(Diethoxyphosphoryl)-2-fluoroacetic acid (880 mg, 4.11 mmol) and (E)-N'-(4-amino-2-cyanophenyl)-N,N-dimethylamidine (773 mg, 4.11 mmol) were mixed in pyridine (15 mL), and cooled to 0° C., followed by dropwise addition of phosphorus oxychloride (1 mL). The reaction mixture was reacted at 0° C. for 1 hour and then quenched with aqueous sodium bicarbonate solution. The mixture was concentrated under reduced pressure to give a crude product, followed by addition of dichloromethane and water. The organic phase was separated, and the aqueous phase was extracted with dichloromethane twice. The organic phases were combined, dried over anhydrous sodium sulfate, filtered and concentrated to give a crude product, which was isolated by column chromatography to give 477 mg of brown oil with a yield of 30%.

Step C: Preparation of tert-butyl (R)-2-(tert-butyl (E)-3-((3-cyano-4-((E)-(dimethylamino)methylene) amino)phenyl)amino)-2-fluoro-3-oxopropanoate-1-en-1-yl)pyrrolidin-1-carboxylate Diethyl (E)-(2-((3-cyano-4-((dimethylamino)methylene) amino)phenyl) amino)-1-fluoro-2-oxoethyl)phosphonate (377 mg, 0.98 mmol) was dissolved in tetrahydrofuran (5 mL), followed by addition of sodium hydride (79 mg, 1.9 mmol, 60%) at 0° C. After stirring for 30 minutes, a solution of tert-butyl (R)-2-formylpyrrolidin-1-carboxylate (235 mg, 1.18 mmol) in tetrahydrofuran (2 mL) was added, and the reaction mixture was reacted at 0° C. for 1 hour. The mixture was quenched with aqueous ammonium chloride solution, extracted with ethyl acetate (50 mL×3). The organic phases were combined, dried over anhydrous sodium sulfate, concentrated under reduced pressure to give a crude product, which was isolated by column chromatography to give 365 mg of colorless oil with a yield of 87%.

Preparation was performed according to the method of Embodiment 10, wherein (E)-N-(3-cyano-4-((E)-(dimethylamino)methylene)amino)phenyl)-3-((R)-1-methylpyrrol-2-yl)acrylamide was replaced with (E)-N-(3-cyano-4-((E)-(dimethylamino)methylene)amino)phenyl)-2-fluoro-3-((R)-1-methylpyrrol-2-yl)acrylamide. LC-MS: 539.3[M+H] Detection value. $^1$H NMR (400 MHz, CD$_3$OD) δ 8.74 (M, 2H), 8.54 (S, 1H), 8.44 (S, 1H), 8.30 (S, 1H), 8.02 (DD, J=9.2, 2.4 Hz, 1H), 7.80 (D, J=9.2 Hz, 1H), 7.78-7.69 (m, 2H), 7.18 (d, J=8.8 Hz, 1H), 7.07 (dd, J=7.2, 2.4 Hz, 1H), 6.84 (s, 1H), 6.12 (dd, J=20.4, 9.6 Hz, 1H), 5.15-5.13 (m, 1H), 3.78-3.65 (m, 1H), 3.23-3.20 (m, 1H), 2.93 (s, 3H), 2.60-2.46 (m, 1H), 2.24 (s, 3H), 2.21-2.18 (m, 2H), 2.07-1.94 (m, 1H).

Embodiment 41

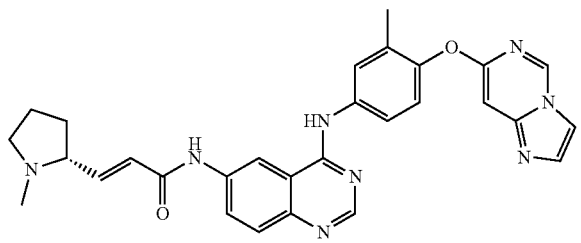 [SMILES: Cc1cc(Nc2ncnc3ccc(NC(=O)/C=C/[C@H]4CCCN4C)cc23)ccc1Oc1cc2nccn2cn1]

Synthesis of (R,E)-N-(4-((4-(imidazo[1,2-c]pyrimidin-7-yloxy)-3-methyl phenyl)amino)quinazolin-6-yl)-3-(1-methylpyrrol-2-yl)acrylamide Step A: Preparation of 4-chloro-6-(2-methyl-4-nitrophenoxy)pyrimidine 2-Methyl-4-nitrophenol (2 g, 13.06 mmol), 4,6-dichloropyrimidine (2.53 g, 17.0 mmol) and potassium carbonate (3.6 g, 26 mmol) were added to N,N-dimethylformamide (60 mL), and the reaction mixture was heated to 80° C. and stirred for 16 hours. The mixture was filtered and concentrated, and then dichloromethane and water were added to the residue. The organic phase was separated, and the aqueous phase was extracted with dichloromethane. The organic phases were combined, dried over anhydrous sodium sulfate, and concentrated under reduced pressure to give 1.9 g of crude product, which was directly used in the next reaction.

Step B: Preparation of 6-(2-methyl-4-nitrophenoxy)pyrimidin-4-amine

4-Chloro-6-(2-methyl-4-nitrophenoxy)pyrimidine (2 g, 7.53 mmol) was added to a mixed solution of ammonia water (25 mL) and isopropanol (25 mL), heated to 90° C. and reacted for 48 hours. The mixture was concentrated under reduced pressure, and the obtained crude product was isolated by column chromatography to give 1 g of yellow solid with a yield of 54%.

Step C: Preparation of 7-(2-methyl-4-nitrophenoxy) imidazo[1,2-c] pyrimidine 6-(2-Methyl-4-nitrophenoxy)pyrimidin-4-amine (200 mg, 0.81 mmol), 2-chloroacetaldehyde (2.4 g, 12 mmol) and magnesium sulfate (2 g, 16.67 mmol) were added to n-butanol (15 mL), sealed, heated to 130° C. and reacted for 2 hours under argon atmosphere. The reaction mixture was cooled to room temperature, filtered, and the filtrate was concentrated under reduced pressure. The residue obtained was isolated by column chromatography to give 123 mg of brown oil with a yield of 56%.

Step D: Preparation of 4-(imidazo[1,2-c]pyrimidin-7-yloxy)-3-methylaniline 7-(2-Methyl-4-nitrophenoxy)imidazo[1,2-c]pyrimidine (123 mg, 0.45 mmol) and palladium carbon (15 mg) were added into methanol (15 mL), and reacted at room temperature for 5 hours under hydrogen atmosphere (balloon). The reaction mixture was filtered through diatomite, and the filtrate was concentrated under reduced pressure to give 108 mg of colorless oil, which was directly used in the next reaction.

Preparation was performed according to the method of Embodiment 10, wherein 4-(imidazo [1,2-b]pyridazin-6-yloxy)-3-methylaniline was replaced with 4-(imidazo[1,2-c]pyrimidin-7-yloxy)-3-methylaniline. LC-MS: 261.1[M/2+H]Detection value. $^1$H NMR (400 MHz, CD$_3$OD) δ9.20 (S, 1H), 8.79 (S, 1H), 8.51 (S, 2H), 7.91 (S, 1H), 7.86 (D, J=8.8 Hz, 1H), 7.82-7.75 (M, 2H), 7.72 (d, J=8.8 Hz, 1H), 7.57 (s, 1H), 7.17 (d, J=8.4 Hz, 1H), 6.95 (dd, J=15.2, 8.4 Hz, 1H), 6.68 (s, 1H), 6.55 (d, J=15.2 Hz, 1H), 3.74-3.63 (m, 1H), 3.61-3.51 (m, 1H), 3.00-2.89 (m, 1H), 2.73 (s, 3H), 2.3-3.33 (m, 1H), 2.28 (s, 3H), 2.17-2.07 (m, 2H), 2.03-1.92 (m, 1H).

Embodiment 42

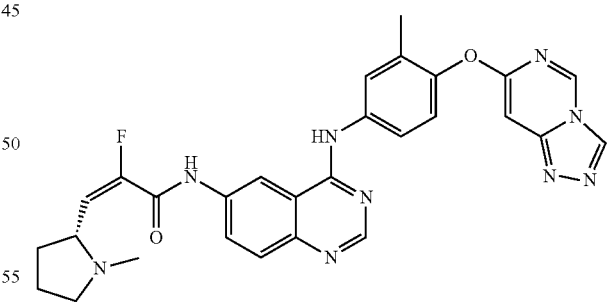

Synthesis of (R,E)-N-(4-((4-([1,2,4]triazolo[4,3-c] pyrimidin-7-yloxy)-3-methylphenyl)amino)quinazolin-6-yl)-2-fluoro-3-(1-methylpyrrol-2-yl)acrylamide Preparation was performed according to the method of Embodiment 10, wherein (E)-N-(3-cyano-4-((E)-(dimethylamino)methylene)amino)phenyl)-3-((R)-1-methylpyrrol-2-yl)acrylamide was replaced with (E)-N-(3-cyano-4-((E)-(dimethylamino) methylene)amino)phenyl)-2-fluoro-3-((R)-1- methylpyrrol-2-yl)acrylamide. LC-MS: 540.3[M+H] Detection value. $^1$H NMR (400 MHz, CD$_3$OD) δ9.47 (D, J=1.2 Hz, 1H), 8.75 (D, J=2.0 Hz, 1H), 8.55 (S, 1H), 8.45 (S, 1H), 8.37 (S, 1H), 8.04 (DD, J=9.2, 2.4 Hz, 1H), 7.84 (d, J=9.2 Hz, 1H), 7.77 (d, J=2.4 Hz, 1H), 7.72 (dd, J=8.8, 2.4 Hz, 1H), 7.23 (d, J=8.8 Hz, 1H), 6.96 (d, J=1.2 Hz, 1H), 6.10-5.99 (m, 1H), 5.04-5.02 (m, 1H), 3.66-3.64 (m, 1H), 3.17-3.15 (m, 1H), 2.89 (s, 3H), 2.57-2.47 (m, 1H), 2.29 (s, 3H), 2.20-2.15 (m, 2H), 2.01-1.92 (m, 1H).

Embodiment 43

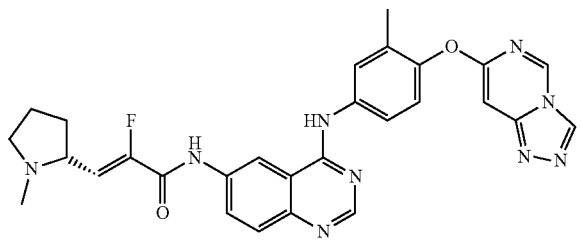

Synthesis of (R,Z)—N-(4-((4-([1,2,4]triazolo[4,3-c] pyrimidin-7-yloxy)-3-methylphenyl)amino)quinazo- lin-6-yl)-2-fluoro-3-(1-methylpyrrol-2-yl) acrylam- ide Preparation of tert-butyl (R)-2-((Z)-3-((3-cyano-4-((E)- (dimethylamino) methylene)amino)phenyl)amino)-2- fluoro-3-oxopropionic acid-1-en-1-yl)pyrrolidin-1-carboxy- late.

Sodium hydroxide (317 mg, 4.76 mmol) was dissolved in a mixed solvent of ethanol (15 mL) and water (1.5 mL), followed by addition of diethyl (E)-(2-((3-cyano-4-((dim- ethylamino)methylene)amino)phenyl)amino)-1-fluoro-2- oxoethyl)phosphonate (380 mg, 0.98 mmol). After the reac- tion mixture became clear, tert-butyl (R)-2- formylpyrrolidin-1-carboxylate (394 mg, 1.98 mmol) was added at 0° C., and the reaction mixture was reacted at room temperature for 16 hours. The pH was adjusted to 6-7 with aqueous citric acid solution. The mixture was concentrated under reduced pressure, and the obtained aqueous solution was extracted with ethyl acetate, dried over anhydrous sodium sulfate, filtered, concentrated under reduced pres- sure to give a crude product, which was isolated by column chromatography to give 98 mg of tert-butyl (R)-2-((Z)-3- ((3-cyano-4-((E)-(dimethylamino)methylene) amino)phe- nyl)amino)-2-fluoro-3-oxopropionic acid-1-en-1-yl)pyrrol- 1-carboxylate with a yield of 23% and 240 mg of tert-butyl (R)-2-((E)-3-((3-cyano-4-((E)-(dimethylamino)methylene) amino)phenyl)amino)-2-fluoro-3-oxopropionicacid-1-en-1- yl)pyrrol-1-carboxylate with a yield of 56%.

Preparation was performed according to the method of Embodiment 10, wherein (E)-N-(3-cyano-4-(((E)-(dimeth- ylamino)methylene)amino)phenyl)-3-((R)-1-methylpyrrol- 2-yl)acrylamide was replaced with (Z)—N-(3-cyano-4- (((E)-dimethyl amino)methylene)amino)phenyl)-2-fluoro- 3-((R)-1-methylpyrrolidin-2-yl)acrylamide. LC-MS: 540.3 [M+H] Detection value. $^1$H NMR (400 MHz, CD$_3$OD) δ9.44 (S, 1H), 8.72 (S, 1H), 8.52 (S, 1H), 8.43 (S, 2H), 7.99 (D, J=8.8 Hz, 1H), 7.79 (D, J=8.8 Hz, 1H), 7.74 (s, 1H), 7.70 (d, J=8.8 Hz, 1H), 7.18 (d, J=8.4 Hz, 1H), 6.94 (s, 1H), 6.37 (dd, J=32.4, 9.2 Hz, 1H), 4.32-4.30 (m, 1H), 3.68-3.65 (m, 1H), 3.18-3.15 (m, 1H), 2.86 (s, 3H), 2.53-2.38 (m, 1H), 2.25 (s, 3H), 2.24-2.20 (m, 2H), 2.06-2.04 (m, 1H).

Embodiment 44

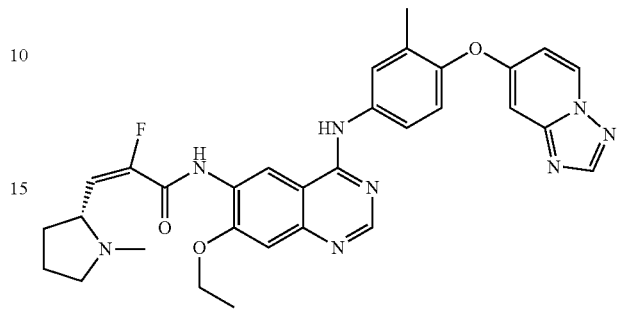

Synthesis of (R,E)-N-(4-((4-([1,2,4]triazolo[1,5-a] pyridin-7-yloxy)-3-methyl phenyl)amino)-7-ethoxy- quinazolin-6-yl)-2-fluoro-3-(1-methylpyrrol-2-yl) acrylamide Preparation of diethyl (2-((4-((4-([1,2,4]triazolo[1, 5-a]pyridin-7-yloxy)-3-methylphenyl)amino)-7- ethoxy quinazolin-6-yl)amino)-1-fluoro-2-oxoethyl) phosphonate N$^4$-(4-([1,2,4]triazolo[1,5-a]pyridin-7-yloxy)-3-meth- ylphenyl)-7-ethoxyquinazolin-4,6-diamine (prepared according to the method of Embodiment 17, wherein 4-([1, 2,4]triazolo[4,3-c]pyrimidin-7-yloxy)-3-methylaniline was replaced with 4-([1,2,4]triazolo[1,5-a]pyridin-7-yloxy)-3- methylaniline) (1.15 g, 2.69 mmol) and 2-diethoxyphospho- ryl-2-fluoro-acetic acid (691 mg), 3.22 mmol) were added to pyridine (20 mL), and phosphorus oxychloride (1.5 mL) was added dropwise at 0° C. The mixture was stirred for 1.5 hours, quenched with aqueous sodium bicarbonate solution, concentrated under reduced pressure to give a residue, followed by addition of dichloromethane and water. The organic phase was separated, and the aqueous phase was extracted with dichloromethane (60 mL×3). The organic phases were combined, dried over anhydrous sodium sul- fate, concentrated under reduced pressure to give a crude product, which was isolated by column chromatography to give 920 mg of yellow solid with a yield of 55%.

Preparation was performed according to the methods of Embodiments 43, 17 and 18. LC-MS: 583.3 [M+H] detec- tion value; $^1$H-NMR (400 MHz, CD$_3$OD) δ 8.97 (s, 1H), 8.76 (d, J=7.6 Hz, 1H), 8.48 (s, 1H), 8.30 (s, 1H), 7.77 (d, J=2.0 Hz, 1H), 7.73 (d, J=8.4, 2.4 Hz, 1H), 7.24 (s, 1H), 7.19 (d, J=8.4 Hz, 1H), 7.09 (dd, J=7.6, 2.4 Hz, 1H), 6.86 (d, J=2.0 Hz, 1H), 5.94 (dd, J=23.6, 9.2 Hz, 1H), 4.36 (q, J=7.2 Hz, 2H), 4.16-4.10 (m, 1H), 3.22-3.12 (m, 1H), 2.41 (s, 3H), 2.38-2.28 (m, 2H), 2.26 (s, 3H), 1.97-1.88 (m, 2H), 1.77- 1.64 (m, 1H), 1.57 (t, J=7.2 Hz, 3H).

Embodiment 45

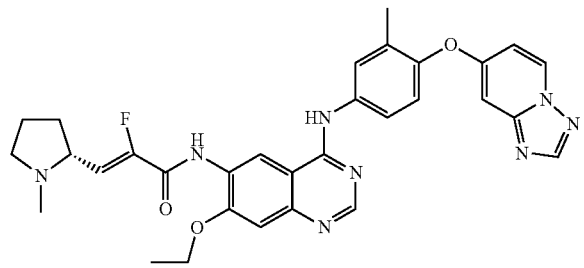 [SMILES: CCOc1cc2ncnc(Nc3ccc(Oc4ccn5ncnc5c4)c(C)c3)c2cc1NC(=O)/C(F)=C/[C@H]1CCCN1C]

Synthesis of (R,Z))—N-(4-((4-([1,2,4]triazolo[1,5-a]pyridin-7-yloxy)-3-methyl phenyl)amino)-7-ethoxy-quinazolin-6-yl)-2-fluoro-3-(1-methylpyrrol-2-yl) acrylamide Preparation was performed according to the method of Embodiment 44. LC-MS: 552.3 [M+H] detection value; $^1$H-NMR (400 MHz, CD$_3$OD) δ 8.97 (s, 1H), 8.76 (d, J=7.6 Hz, 1H), 8.49 (s, 1H), 8.30 (s, 1H), 7.77 (s, 1H), 7.72 (dd, J=8.4, 2.4 Hz, 1H), 7.26 (s, 1H), 7.20 (d, J=8.4 Hz, 1H), 7.10 (dd, J=7.6, 2.4 Hz, 1H), 6.87 (d, J=2.4 Hz, 1H), 6.24 (dd, J=35.6, 9.6 Hz, 1H), 4.37 (q, J=6.8 Hz, 2H), 3.45-3.36 (m, 1H), 3.23-3.13 (m, 1H), 2.50-2.38 (m, 1H), 2.37 (s, 3H), 2.27 (s, 3H), 2.23-2.18 (m, 1H), 2.01-1.89 (m, 2H), 1.81-1.69 (m, 1H), 1.58 (t, J=6.8 Hz, 3H).

Embodiment 46

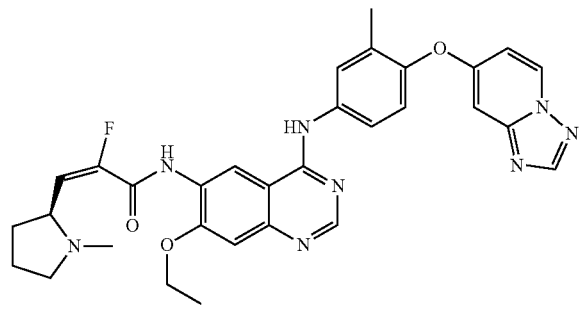 [SMILES: CCOc1cc2ncnc(Nc3ccc(Oc4ccn5ncnc5c4)c(C)c3)c2cc1NC(=O)/C(F)=C\[C@@H]1CCCN1C]

Synthesis of (SE)-N-(4-((4-([1,2,4]triazolo[1,5-a]pyridin-7-yloxy)-3-methyl phenyl)amino)-7-ethoxy-quinazolin-6-yl)-2-fluoro-3-(1-methylpyrrol-2-yl) acrylamide Preparation was performed according to the method of Embodiment 44, wherein tert-butyl (R)-2-formylpyrrol-1-carboxylate was replaced with tert-butyl (S)-2-formylpyrrol-1-carboxylate. LC-MS: 583.3 [M+H] detection value; $^1$H-NMR (400 MHz, CD$_3$OD) δ 8.81 (s, 1H), 8.72 (d, J=7.6 Hz, 1H), 8.40 (s, 1H), 8.28 (s, 1H), 7.77-7.65 (m, 2H), 7.12 (d, J=8.4 Hz, 1H), 7.07 (s, 1H), 7.04 (dd, J=7.6, 2.4 Hz, 1H), 6.83 (d, J=2.4 Hz, 1H), 5.94 (dd, J=23.6, 9.2 Hz, 1H), 4.26 (q, J=7.2 Hz, 2H), 4.16-4.10 (m, 1H), 3.20-3.12 (m, 1H), 2.41 (s, 3H), 2.38-2.32 (m, 1H), 2.29-2.25 (m, 1H), 2.21 (s, 3H), 1.93-1.88 (m, 2H), 1.70-1.62 (m, 1H), 1.53 (t, J=7.2 Hz, 3H).

Embodiment 47

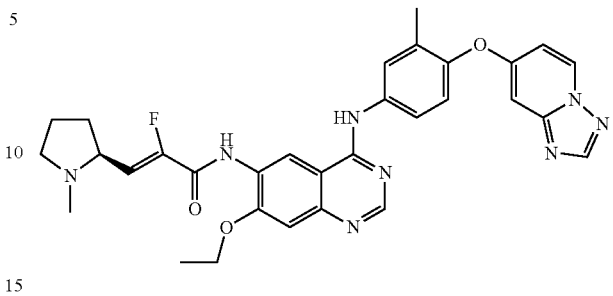

Synthesis of (S,Z)—N-(4-((4-([1,2,4]triazolo[1,5-a]pyridin-7-yloxy)-3-methyl phenyl)amino)-7-ethoxy-quinazolin-6-yl)-2-fluoro-3-(1-methylpyrrol-2-yl) acrylamide Preparation was performed according to the method of Embodiment 44, wherein tert-butyl (R)-2-formylpyrrol-1-carboxylate was replaced with tert-butyl (S)-2-formylpyrrol-1-carboxylate. LC-MS: 583.3 [M+H] detection value; $^1$H-NMR (400 MHz, CD$_3$OD) δ 8.89 (s, 1H), 8.74 (d, J=7.6 Hz, 1H), 8.45 (s, 1H), 8.29 (s, 1H), 7.76 (s, 1H), 7.72 (d, J=8.8 Hz, 1H), 7.18-7.10 (m, 2H), 7.08 (dd, J=7.6, 2.4 Hz, 1H), 6.86 (d, J=2.4 Hz, 1H), 6.24 (dd, J=35.6, 9.2 Hz, 1H), 4.33 (q, J=7.2 Hz, 2H), 3.51-3.36 (m, 1H), 3.25-3.15 (m, 1H), 2.51-2.43 (m, 1H), 2.42 (s, 3H), 2.25 (s, 3H), 2.23-2.16 (m, 1H), 2.03-1.90 (m, 2H), 1.84-1.70 (m, 1H), 1.57 (t, J=7.2 Hz, 3H).

Effect Embodiment

Embodiment A

EGFR/ErbB2 Enzymatic Experiment

Firstly, 1× reaction buffer required for the kinase was prepared, then 5× Enzymatic buffer (HEPES 20 mM pH 7.0, NaN$_3$ 0.1%, BSA 0.05%, sodium orthovanadate 0.5 mM) was diluted in HTRF kinEASE-TK kit by 1 time with deionized water, and 50 nM Supplement Enzymatic buffer (SEB REAGENT), 1 mM MnCl$_2$, 5 mM MfCl$_2$, 1 mM DTT were added. Secondly, 5× compound was prepared, and 10 mM test compound storage solution was diluted in multiple steps with DMSO in a 96-well compound plate to prepare 100× compound as an initial concentration, which was then used as the first concentration to carry out a 3-fold gradient dilution with DMSO to obtain a total of 10 concentrations. Then 1 μL of gradient diluent was added to 19 μL of 1× reaction buffer to prepare 5× compound for later use. Then 2 μL of 5× compound was transferred from the 96-well plate into a 384-well plate. To the compound-free control wells was added 2 μL of the following liquid: 19 μL of 1× reaction buffer with addition of 1 μL of DMSO. To the blank control well was added 2 μL of 250 mM EDTA. In the third step of the enzyme reaction, the kinase, substrate (TK Substrate-biotin) and ATP were formulated into 2.5× enzyme/substrate mixture and 2.5×ATP solution using 1× reaction buffer, respectively. The final concentration of ErbB2 kinase was 0.06 ng/μL and the final concentration of ATP was 4 μM; the final concentration of EGFR kinase was 0.06 units/μL, and the final concentration of ATP was 1.65 μM; 4 μL of 2.5× enzyme/substrate mixture was added to a 384-well plate and incubated for 5 minutes at room temperature; then 4 μL of 2.5×ATP solution was added to each well, and the reaction was carried out at room temperature for 30 minutes. In the fourth step of reaction termination, HTRF Detection buffer was used to prepare a mixture of 2×TK Antibody-EU (K) and Sa-XL665, and the amount of TK Antibody-EU (K) was 5 μL per well. After the enzyme reaction was carried out for 30 minutes, 10 μL of the above liquid was added to a 384-well plate, and the reaction was carried out at room temperature for 1 hour. Data were measured on EnVision™, and the laser of 337 nM wavelength was selected as excitation light. $RFU_{665\ nM}$ and $RFU_{620\ nM}$ were measured, and $RFU_{665\ nM}/RFU_{620\ nM} \times 10000$ was used as final data for analysis.

Embodiment B

In Vitro Proliferation Inhibition Assay of Cell Lines

1. Cell culture and inoculation: on the first day of the experiment, normal cultured cells were taken, and in the exponential growth state, after digestion and dispersion, the cell density was then adjusted to $8.8 \times 10^4$ cells/mL for BT-474, and $6.6 \times 10^4$ cells/mL for N87, and 90 μL of which were inoculated to each well of a 96-well cell culture plate; after the inoculation was completed, the microplate was cultured under the conditions of 37° C. and 5% $CO_2$ overnight. 2. Dosing to the cells: on the second day of the experiment, the microplate was taken out from the incubator, and 10 μL of 10× compound was added to each well of the microplate, setting 2 duplicate wells for each drug concentration and 9 dosing concentrations for each compound. According to different cell lines, the initial concentration of each compound was different. Upon completion of addition, the microplate was placed under the conditions of 37° C. and 5% $CO_2$ for 72 hours. 3. Data acquisition: the microplate was taken out from the incubator and was allowed to equilibrate at room temperature for 30 minutes. 100 μL of CellTiter-Glo® Luminescent Cell Viability Assay reaction solution which had been equilibrated at room temperature was added to each well, and the reaction solution was shaken at 1300 rpm for 2 minutes at room temperature. After that, the microplate was placed in HERAEUS Multifuge X1R centrifuge, centrifuged at 2000 rpm for 1 minute, and allowed to equilibrate at room temperature for 10 minutes. The fluorescence signal value was measured on EnVision™.

Biological Test Data

The data obtained below were all measured according to the methods in the above effect embodiments, and the test data of the compounds in the embodiments were listed. The "--" in the following table indicates that it had not been tested.

| Compound | Kinase $IC_{50}$ (nM) in vitro | | $IC_{50}$ (nM) cell | |
|---|---|---|---|---|
| | ErbB2 | EGFR | N87 | BT-474 |
| Final product of Embodiment 1 | 0.947 | 14.37 | 4.449 | 5.066 |
| Final product of Embodiment 3 | 3.832 | 24.32 | 15.58 | 15.33 |
| Final product of Embodiment 4 | 6.091 | 168 | 5.748 | 4.794 |
| Final product of Embodiment 5 | 2.042 | 62.05 | 20.06 | 14.38 |
| Final product of Embodiment 6 | 2.921 | 232.6 | 24.04 | 16.05 |
| Final product of Embodiment 7 | 0.8509 | 7.086 | 65.47 | 49.54 |
| Final product of Embodiment 8 | 17.52 | 136.2 | 19.45 | 10.26 |
| Final product of Embodiment 9 | 7.978 | 13.83 | 18.76 | 9.624 |
| Final product of Embodiment 10 | 1.34 | 4.62 | 3.52 | 4.56 |
| Final product of Embodiment 11 | 0.73 | 1.02 | 3.18 | 3.27 |
| Final product of Embodiment 12 | 0.99 | 0.42 | 4.19 | 4.01 |
| Final product of Embodiment 15 | 17.49 | 156.5 | 301.3 | 162.1 |
| Final product of Embodiment 16 | 22.0 | 33.7 | 691.7 | 255.6 |
| Final product of Embodiment 17 | 0.488 | 0.2505 | 4.975 | 5.312 |
| Final product of Embodiment 18 | 0.5129 | 0.3577 | 1.576 | 2.104 |
| Final product of Embodiment 19 | 0.7164 | 3.972 | 28.36 | 26.04 |
| Final product of Embodiment 20 | 0.5838 | 3.93 | 2.068 | 3.23 |
| Final product of Embodiment 21 | 8.25 | 3.455 | 94.05 | 54.57 |
| Final product of Embodiment 22 | 0.37 | 0.8 | 0.68 | 1.00 |
| Final product of Embodiment 23 | 7.559 | 1.624 | 5.433 | 4.204 |
| Final product of Embodiment 24 | 6.46 | 4.08 | 2.93 | 4.60 |
| Final product of Embodiment 25 | 8.47 | 23.4 | 68.17 | 50.7 |
| Final product of Embodiment 26 | 0.83 | 2.52 | 3.55 | 5.23 |
| Final product of Embodiment 27 | 1.61 | 2.21 | 77.5 | 25.7 |
| Final product of Embodiment 28 | 3.25 | 5.29 | 33.4 | 11 |
| Final product of Embodiment 29 | 15.25 | 20.48 | 60.4 | 46.6 |
| Final product of Embodiment 30 | 195.1 | 72.04 | 353.6 | 397.1 |
| Final product of Embodiment 31 | 219.8 | 65.17 | 66.47 | 75.97 |
| Final product of Embodiment 1-4 | 2.4 | 44.3 | 23 | 19.7 |
| Final product of Embodiment 1-7 | 8.1 | 164 | 71 | 45 |
| Final product of Embodiment 1-8 | 7.8 | 115 | 68.7 | 43.4 |
| Final product of Embodiment 1-9 | 7.4 | 35.9 | 39.5 | 33.4 |
| Final product of Embodiment 1-14 | 1.7 | 114.6 | 94.1 | 35.2 |
| Final product of Embodiment 1-16 | 3.4 | 32.3 | 5.6 | 7.7 |
| Final product of Embodiment 1-19 | 3.3 | 22.1 | 125 | 98.2 |
| Final product of Embodiment 1-21 | 2.2 | 43.5 | 73.8 | 140 |
| Final product of Embodiment 1-24 | 4.1 | 126.7 | 177.4 | 127.7 |
| Final product of Embodiment 1-45 | 2.8 | 53.4 | 93.4 | 85.4 |
| Final product of Embodiment 1-57 | 1.7 | 2.7 | 12.8 | 5.6 |
| Final product of Embodiment 1-60 | 1.1 | 15.6 | 23.4 | 108 |
| Final product of Embodiment 1-78 | 1.8 | 3.3 | 22.34 | 13.16 |
| Final product of Embodiment 1-80 | 1.0 | 12.6 | 36 | 120 |
| Final product of Embodiment 1-83 | 2.3 | 36.4 | 104 | 72.7 |
| Final product of Embodiment 1-93 | 2.4 | 0.75 | 101.4 | 69.5 |

-continued

| Compound | Kinase IC$_{50}$ (nM) in vitro | | IC$_{50}$ (nM) cell | |
| --- | --- | --- | --- | --- |
| | ErbB2 | EGFR | N87 | BT-474 |
| Final product of Embodiment 1-94 | 2.99 | 3.16 | 4.7 | 4.8 |
| Final product of Embodiment 1-96 | 3.43 | 3.79 | 93.5 | 55.9 |
| Final product of Embodiment 1-97 | 4.84 | 11.41 | 10 | 6.4 |
| Final product of Embodiment 1-98 | 1.78 | 1.6 | 2.5 | 3 |
| Final product of Embodiment 1-124 | 2.8 | 2.3 | 11.4 | 9.5 |
| Final product of Embodiment 1-125 | 3.4 | 14.7 | 6.8 | 13.6 |
| Final product of Embodiment 1-126 | 6.7 | 53 | 82.9 | 143 |
| Final product of Embodiment 1-127 | 5.6 | 6.6 | 30.7 | 8 |
| Final product of Embodiment 32 | 3.128 | 1.064 | 4.2 | 4.0 |
| Final product of Embodiment 33 | 3.563 | 2.144 | 3.2 | 4.2 |
| Final product of Embodiment 34 | 1.086 | 0.757 | 1.598 | 2.65 |
| Final product of Embodiment 35 | 2.672 | 0.514 | 18.89 | 17.71 |
| Final product of Embodiment 36 | 1.098 | 0.53 | 1.642 | 1.894 |
| Final product of Embodiment 37 | 0.689 | 1.497 | 22.61 | 15.42 |
| Final product of Embodiment 38 | 0.5 | 0.6 | 2.4 | 2.8 |
| Final product of Embodiment 41 | 0.6 | 0.6 | 8.5 | 3.9 |
| Final product of Embodiment 43 | 2.6 | 4.7 | 1.3 | 1.8 |
| Final product of Embodiment 44 | 2.4 | 32.6 | 1.2 | 2.0 |
| Final product of Embodiment 45 | 1.8 | 10.5 | 1.3 | 2.1 |
| Final product of Embodiment 46 | 4.6 | 50.9 | 3.1 | 5.9 |
| Final product of Embodiment 47 | 4.2 | 38.5 | 3.8 | 7.1 |
| 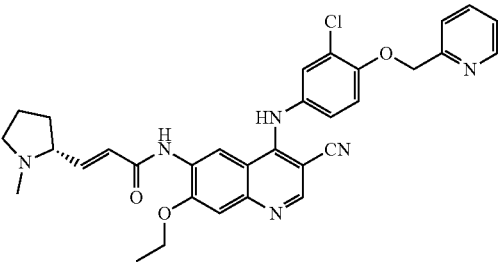 Pyrotinib | 1.67 | 0.26 | 1.20 | 2.56 |
| 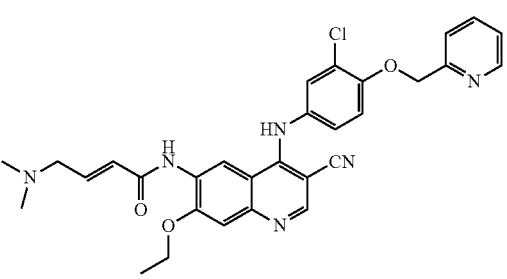 Niratinib | 1.27 | 0.17 | 0.82 | 1.70 |

Study on Direct Inhibition (DI) of CYP3A4, CYP2D6, CYP2C9, CYP2C19, CYP1A2

A system of 100 μL human liver microsomes (final concentration: 0.2 mg/mL) was used for direct inhibition under warm incubation. The system contained NADPH (final concentration: 1 mM), 10 μM compound, a positive inhibitor cocktail (Ketoconazole 10 μM, Quinidine: 10 μM, Sulfaphenazole: 100 μM, Naphthoflavone: 10 μM, Tranylcypromene 1000 μM), a negative control 10 μM DMSO and mixed probe substrates (Midazolam 10 μM, Testosterone 100 μM, Dextromethophan 10 μM, Diclofenac 20 μM, Phenetin 100 μM, Mephenytoin 100 μM). The reaction was terminated after incubation for 20 minutes. The relative activity of the enzymes was calculated by measuring the relative production of metabolites.

Direct Inhibition of the Compounds (DI)* on Five CYP Enzymes

| Compound | 3A4 (Midazolam) | 3A4 (testosterone) | 2D6 (Dextromethorphan) | 2C9 (Diclofenac) | 1A2 (Phenacetin) | 2C19 (Mephenytoin) |
| --- | --- | --- | --- | --- | --- | --- |
| Pyrotinib | 15% | 22% | 55% | 26% | 22% | 43% |
| Final product of Embodiment 1 | 91% | 94% | 25% | 74% | 47% | 37% |
| Final product of Embodiment 3 | 54% | 61% | 4% | 26% | 14% | 9% |
| Final product of Embodiment 4 | 49% | 56% | 7% | 48% | — | 23% |

-continued

| Compound | 3A4 (Midazolam) | 3A4 (testosterone) | 2D6 (Dextromethorphan) | 2C9 (Diclofenac) | 1A2 (Phenacetin) | 2C19 (Mephenytoin) |
|---|---|---|---|---|---|---|
| Final product of Embodiment 5 | 71% | 74% | 14% | 49% | 9% | 18% |
| Final product of Embodiment 6 | 72% | 80% | 30% | 55% | 13% | 41% |
| Final product of Embodiment 17 | 17% | 34% | 4% | 8% | 3% | 9% |
| Final product of Embodiment 18 | 12% | 23% | 4% | 4% | 5% | 8% |
| Final product of Embodiment 8 | 61% | 72% | 11% | 17% | 11% | 28% |
| Final product of Embodiment 20 | 0% | 14% | 61% | — | 6% | 7% |
| Final product of Embodiment 19 | 16% | 38% | 60% | — | 7% | — |
| Final product of Embodiment 23 | — | 18% | 13% | 1% | — | 10% |
| Final product of Embodiment 22 | 12% | 32% | 48% | 10% | 14% | 37% |
| Final product of Embodiment 10 | 12% | 29% | 46% | — | 14% | 9% |
| Final product of Embodiment 11 | 5% | 16% | 87% | 9% | 9% | 26% |
| Final product of Embodiment 12 | — | 4% | 77% | 5% | 2% | 13% |
| Final product of Embodiment 24 | 36% | 48% | 90% | 48% | 18% | 36% |
| Final product of Embodiment 26 | — | 5% | 85% | 19% | 2% | 28% |
| Final product of Embodiment 32 | 8% | 11% | 6% | 66% | — | 75% |
| Final product of Embodiment 33 | 10% | 17% | 3% | 17% | — | 49% |
| Final product of Embodiment 38 | 5% | 16% | 24% | 10% | — | 45% |
| Final product of Embodiment 40 | 3% | 9% | 16% | — | — | 18% |
| Final product of Embodiment 41 | — | 6% | 71% | — | — | 1% |
| Final product of Embodiment 43 | — | — | 69% | — | — | — |
| Final product of Embodiment 44 | — | 13% | 36% | 11% | 12% | 27% |
| Final product of Embodiment 45 | 6% | 24% | 39% | — | 8% | 11% |
| Final product of Embodiment 46 | 14% | 32% | 38% | 21% | 23% | 43% |
| Final product of Embodiment 47 | 33% | 42% | 54% | 34% | 35% | 47% |

\* Evaluation criteria for direct inhibition test of human liver microsomal enzyme: DI < 20% is no direct inhibition, 20% < DI < 50% is weak direct inhibition, 50% < DI < 70% is moderate direct inhibition, DI > 70% is strong direct inhibition.
"—" indicates no inhibitory effect Embodiment C In Vivo Pharmacokinetic Study in Rats and Mice Five male SD rats, weighing 180-220 g (provided by Shanghai Xipuerbikai Experimental Animal Co., Ltd, certificate No. 20130016005408). The rats were fasted for feed but not water for 12-16 hours before the experiment. Two rats were intravenously injected with 3 mg/kg (which was dissolved by the ratio 0.9% physiological saline:PEG 400=7:3, to give a clear solution with a concentration of 1 mg/mL and a dosage volume of 3 mL/kg) of the final product of Embodiment 45. Blood samples were collected before administration and at 2, 5, 15, 30, 60, 90, 120, 240, 360, 480, 600 and 1440 minutes after administration respectively; three rats were intragastricly administrated with 6 mg/kg (0.5% CMC-Na was added and grounded into a uniform suspension with a concentration of 0.75 mg/mL and a dosage volume of 8 mL/kg) of the final product of Embodiment 45. Blood samples were collected before administration and at 5, 15, 30, 60, 90, 120, 240, 360, 480, 600 and 1440 minutes after administration respectively.

24 male ICR mice weighing 18-22 g (provided by Shanghai Xipuerbikai Experimental Animal Co., Ltd, certificate No.: 20130016005759). The mice were fasted for feed but not water for 12-16 hours before the experiment. 24 mice were divided into 2 groups with 12 mice in each group. The first group was intravenously administrated with 3 mg/kg (which was dissolved by the ratio 0.9% physiological saline: PEG 400=8:2, to give a clear solution with a concentration of 0.3 mg/mL and a dosage volume of 10 mL/kg) of the final product of Embodiment 45. Blood samples were collected before administration and 2, 5, 15, 30, 60, 90, 120, 240, 360, 480, 600 and 1440 minutes after administration, respectively. The second group was intragastricly administrated with 10 mg/kg (0.5% CMC-Na was added and grounded into a uniform suspension with a concentration of 0.5 mg/mL and a dosage volume of 20 mL/kg) of the final product of Embodiment 45. Blood samples were collected before administration and at 5, 15, 30, 60, 90, 120, 240, 360, 480, 600 and 1440 minutes after administration respectively. 2-3 time points were taken for each mouse.

0.4 mL of blood was taken from fundus venous plexus of mice and rats into a heparinized centrifuge tube (10 μL heparin sodium solution/tube). The blood samples were centrifuged at 8000 rpm for 5 minutes. To 50 μL of plasma sample was added 200 μL of acetonitrile containing internal standard (propranolol, 25 ng/mL) to precipitate the protein. After vortexing for 10 minutes and centrifuging at 6000 g and 4° C. for 10 minutes, the supernatant was diluted with mobile phase in a 96-well plate, and the drug concentration in plasma was determined by UPLC/MS-MS.

The results of pharmacokinetic studies in rats and mice showed that the bioavailability of the final product of Embodiment 45 was 71.35% in rats and 87.66% in mice.

Embodiment D

In Vivo Pharmacokinetics Study in Beagle Dogs and Cynomolgus Monkeys 6 male beagle dogs (purchased from Beijing Marshall Biotechnology Co., Ltd., certificate No. SCXK (Beijing) 2016-0001) were divided into 2 groups with 3 dogs in each group, and all of the animals were fasted for about 12 hours before administration. One group was orally administrated with 15 mg/kg of the final product of Embodiment 22 (deionized water was added, followed by sonication for 29 minutes and stirring for 4 minutes, and a clear pale yellow dosing solution with a concentration of 3 mg/mL was prepared); the other group was orally administrated with 15 mg/kg of Pyrotinib (deionized water was added, followed by sonication for 28 minutes and stirring for 5 minutes, and a clear yellow dosing solution with a concentration of 3 mg/mL was prepared). Blood samples were collected before administration and at 15, 30, 60, 90, 120, 150, 180, 240, 360, 480, 720 and 1440 minutes respectively after administration.

6 male cynomolgus monkeys (purchased from Guangxi Guidong Primate Development Experiment Co., Ltd., certificate No. SCXK (Guangxi) 2013-0057) were divided into 2 groups with 3 in each group, and all of the animals were fasted for about 12 hours before administration. One group was orally administrated with 15 mg/kg of the final product of Embodiment 22 (deionized water was added, followed by sonication for 30 minutes and stirring for 3 minutes, and a clear pale yellow dosing solution with a concentration of 3 mg/mL was prepared); one group was administrated with 15 mg/kg of Pyrotinib (deionized water was added, followed by sonication for 30 minutes and stirring for 4 minutes, and a clear yellow dosing solution with a concentration of 3 mg/mL was prepared). Blood samples were collected before administration and at 15, 30, 60, 90, 120, 150, 180, 240, 360, 480, 720 and 1440 minutes respectively after administration.

1.0 mL of blood was collected from each animal through jugular vein puncture at each time point and heparin sodium was used for anticoagulation. The blood samples were collected and placed in labeled centrifuge tubes, and plasma was centrifuged (centrifugation conditions: 3500 rpm, 10 minutes, 2-8° C.). To 50 μL of plasma sample was added 300 μL of acetonitrile containing internal standard (Propranolol, 25 ng/mL) to precipitate the protain. After vortexing for 10 minutes and centrifuging at 6000 g for 20 minutes, 100 μL of supernatant was taken and injected into a 96-well plate. The drug concentration in plasma was determined by UPLC/MS-MS.

The results of pharmacokinetic studies of the final product of Embodiment 22 and Pyrotinib in beagle dogs and cynomolgus monkeys showed that the peak oral absorption concentrations of the final product of Embodiment 22 and Pyrotinib in beagle dogs are 432.6 ng/mL and 146.2 ng/mL, respectively, and AUC are 5191(h)*(ng/mL) and 1621(h)*(ng/mL), respectively; in cynomolgus monkeys, the oral absorption peak concentrations are 506.5 ng/mL and 56.42 ng/mL, respectively, and AUC are 5583(h)*(ng/mL) and 325(h)*(ng/mL), respectively. The absorption degree of the final product of Embodiment 22 was higher than that of Pyrotinib at the same dose.

Experiment E

In Vivo Experiment on Humanized Nude Mice Xenograft Model

We have established nude mice xenograft model for HER2 overexpression.

Pharmacodynamic Evaluation of the final product of Embodiment 22 in HER2 overexpressing human gastric cancer NCI-N87 nude mice xenograft model: each male Balb/c nude mice was subcutaneously inoculated with 5*10$^6$ of NCI-N87 cells derived from ATCC. The animals were grouped for administration when the tumor volume reached around 200 mm$^3$; the pharmacodynamic activity of the final product of Embodiment 22 was expressed by tumor volume inhibition rate (GI %), of which calculation formula is: GI (%)=[1−(Ti−T0)/(Vi−V0)]×100 (wherein Ti was tumor volume of the administration group, T0 was tumor volume of administration group on D0 day, Vi was tumor volume of the solvent control group, V0 was tumor volume of the solvent control group on D0 day). After continuous oral administration for 21 days, the animals became tolerant to the final product of Embodiment 22 at doses of 5 mg/kg, 10 mg/kg and 20 mg/kg and a dose-dependent anti-tumor effect in N87 subcutaneous xenograft model was exhibited, with GI values of 51.5%, 130.1% and 146.2% respectively; wherein the doses of 10 mg/kg and 20 mg/kg have significant antitumor effects. The efficacy of the final product of Embodiment 22 at a dose of 10 mg/kg (GI % 130.1%) is equivalent to that of Pyrotinib (GI % 127.0%) at a dose of 10 mg/kg and superior to that of Neratinib at a dose of 10 mg/kg (GI % 112.5%). On the day of the end of the experiment, the weight of animals in each group did not decrease significantly.

What is claimed is:

1. A nitrogenous heterocyclic compound represented by formula I, a pharmaceutically acceptable salt thereof, an enantiomer thereof, a diastereomer thereof, a tautomer thereof, or a solvate thereof;

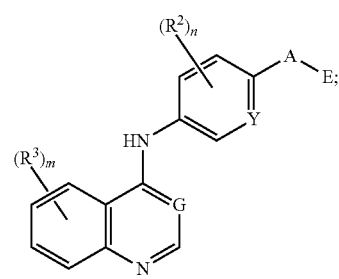

wherein, E is "9-10 membered fused heteroaryl containing 1-4 heteroatoms selected from the group consisting of N, O and S";

A is —O—, —S—, —C(=O)—, —SO— or —SO$_2$—;

n is 0, 1, 2, 3 or 4;

each $R^2$ is independently halogen, or, $C_1$-$C_6$ alkyl;

Y is N or CH;

G is N;

m is 1 or 2;

each $R^3$ is independently halogen, $R^{3-0}$ substituted or unsubstituted $C_1$-$C_6$ alkoxy, $R^{3-1}$ substituted or unsubstituted "3-7 membered heterocycloalkyl containing 1-4 heteroatoms selected from the group consisting of N, O and S", $R^{3-2}$ substituted or unsubstituted 5-7 membered cycloalkenyl, $R^{3-3}$ substituted or unsubstituted "5-7 membered heterocycloalkenyl containing 1-4 heteroatoms selected from the group consisting of N, O and S", $R^{3-5}$ substituted or unsubstituted "5-6 membered heteroaryl containing 1-3 heteroatoms selected from the group consisting of N, O, and S", N($R^{3-6}$)($R^{3-7}$)—, ($R^{3-8}$)($R^{3-9}$)N—(Z)—HC=CH—, ($R^{3-10}$)($R^{3-11}$)C=C($R^{3-12}$)—C(=O)—NH—, or, $R^{3-13}$—O—;

each $R^{3-0}$ is independently $C_1$-$C_6$ alkoxy;

each $R^{3-1}$ is independently H$_2$C=CH—C(=O)—NH— or H$_2$C=C—C(=O)—;

each $R^{3-2}$ is independently H$_2$C=CH—C(=O)—NH—;

each $R^{3-3}$ is independently H$_2$C=CR$^{3-3-1}$—C(=O)—NH— or H$_2$C=CR$^{3-3-1}$—C(=O)—; each $R^{3-3-1}$ is independently H or halogen;

each $R^{3-5}$ is independently amino or hydroxymethyl;

$R^{3-6}$ is $R^{3-6-1}$ substituted or unsubstituted "3-7 membered heterocycloalkyl containing 1-4 heteroatoms selected from the group consisting of N, O and S"; each $R^{3-6-1}$ is independently H$_2$C=CH—C(=O)—NH—;

$R^{3-7}$ is H;

each Z is independently —C(=O)— or —CH$_2$—; each $R^{3-8}$ and $R^{3-9}$ is independently H, hydroxyl substituted or unsubstituted $C_1$-$C_6$ alkyl, $C_3$-$C_6$ cycloalkyl, or, $R^{3-8-1}$—C(=O)—; each $R^{3-8-1}$ is independently oxa-$C_1$-$C_6$ alkyl;

$R^{3-10}$ is $R^{3-10-1}$ substituted or unsubstituted "3-7 membered heterocycloalkyl containing 1-4 heteroatoms selected from the group consisting of N, O and S", or, $C_1$-$C_6$ alkyl; $R^{3-10-1}$ is $C_1$-$C_6$ alkyl;

$R^{3-11}$ is H;

each $R^{3-12}$ is independently H or halogen;

each $R^{3-13}$ is independently "3-7 membered heterocycloalkyl containing 1-4 heteroatoms selected from the group consisting of N, O and S";

when m is 1, then $R^3$ is $R^{3-1}$ substituted "3-7 membered heterocycloalkyl containing 1-4 heteroatoms selected from the group consisting of N, O and S";

or, when m is 1, then $R^3$ is $R^{3-2}$ substituted 5-7 membered cycloalkenyl;

or, when m is 1, then $R^3$ is $R^{3-3}$ substituted "5-7 membered heterocycloalkenyl containing 1-4 heteroatoms selected from the group consisting of N, O and S";

or, when m is 1, then $R^3$ is $N(R^{3-6})(R^{3-7})$—;

or, when m is 1, then $R^3$ is $(R^{3-8})(R^{3-9})N$—(Z)—HC=CH—;

or, when m is 1, then $R^3$ is $(R^{3-10})(R^{3-11})C$=$C(R^{3-12})$—C(=O)—NH—;

when m is 2, then $R^3$ is $R^{3-3}$ substituted "5-7 membered heterocycloalkenyl containing 1-4 heteroatoms selected from the group consisting of N, O and S" and halogen, respectively;

or, when m is 2, then $R^3$ is $(R^{3-8})(R^{3-9})N$—(Z)—HC=CH— and halogen, respectively;

or, when m is 2, then $R^3$ is $(R^{3-10})(R^{3-11})C$=$C(R^{3-12})$—C(=O)—NH— and $R^{3-0}$ substituted or unsubstituted $C_1$-$C_6$ alkoxyl, respectively;

the compound I excludes any one of the compounds as follows:

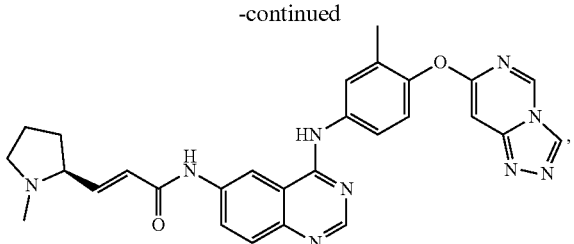

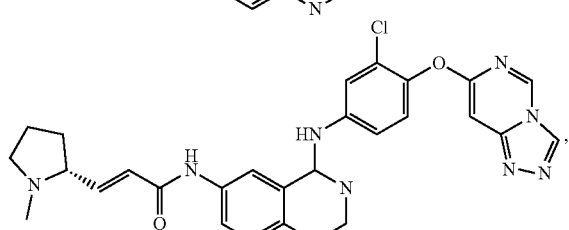

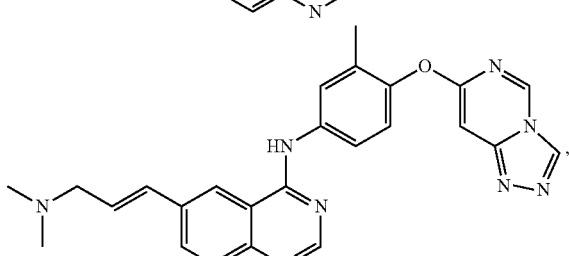

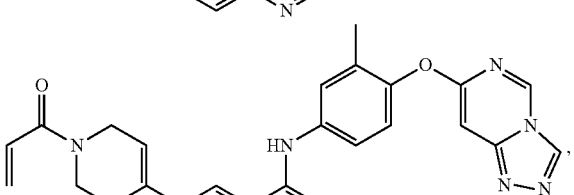

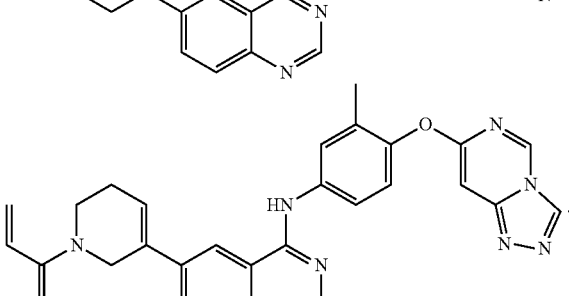

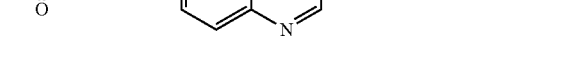

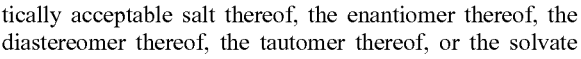

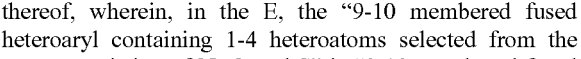

2. The compound I as defined in claim 1, the pharmaceutically acceptable salt thereof, the enantiomer thereof, the diastereomer thereof, the tautomer thereof, or the solvate thereof, wherein, in the E, the "9-10 membered fused heteroaryl containing 1-4 heteroatoms selected from the group consisting of N, O and S" is "9-10 membered fused heteroaryl containing 1-4 N atoms",

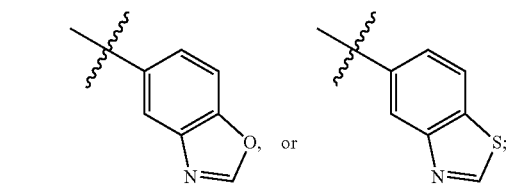 [SMILES: *c1ccc2ocnc2c1 ; *c1ccc2scnc2c1]

or, in the E, the number of the N atom in the ring connected to A in the "9-10 membered fused heteroaryl containing 1-4 heteroatoms selected from the group consisting of N, O and S" is 0, 1 or 2;

or, in the E, the number of the N atom in the ring not connected to A in the "9-10 membered fused heteroaryl containing 1-4 heteroatoms selected from the group consisting of N, O and S" is 1, 2 or 3;

or, in the $R^2$, the $C_1$-$C_6$ alkyl is independently $C_1$-$C_4$ alkyl;

or, in the $R^{3-0}$ substituted or unsubstituted $C_1$-$C_6$ alkoxy, the number of the $R^{3-0}$ is one or more than one, and when a plurality of $R^{3-0}$ exist, any of two $R^{3-0}$ are the same or different;

or, in the $R^{3-0}$ substituted or unsubstituted $C_1$-$C_6$ alkoxy, the "$C_1$-$C_6$ alkoxy" is $C_1$-$C_4$ alkoxy;

or, in the $R^{3-1}$ substituted or unsubstituted "3-7 membered heterocycloalkyl containing 1-4 heteroatoms selected from the group consisting of N, O and S", the number of the $R^{3-1}$ is one or more than one, and when a plurality of $R^{3-1}$ exist, any of two $R^{3-1}$ are the same or different;

or, in the $R^{3-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is "5-6 membered heterocycloalkyl containing 1-2 heteroatoms selected from the group consisting of N, O and S";

or, in the $R^{3-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is connected to

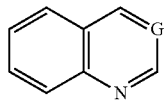

through C atom or N atom;

or, in the $R^{3-1}$ substituted or unsubstituted "3-7 membered heterocycloalkyl containing 1-4 heteroatoms selected from the group consisting of N, O and S", each $R^{3-1}$ is independently located at the ortho, meta or para position relative to the "connection site of heterocycloalkyl and

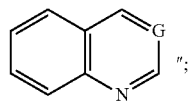

";

or, in the $R^{3-2}$ substituted or unsubstituted 5-7 membered cycloalkenyl, the number of the $R^{3-2}$ is one or more than one, and when a plurality of $R^{3-2}$ exist, any of two $R^{3-2}$ are the same or different;

or, in the $R^{3-2}$ substituted or unsubstituted 5-7 membered cycloalkenyl, the "5-7 membered cycloalkenyl" is cyclohexenyl;

or, in the $R^{3-2}$ substituted or unsubstituted 5-7 membered cycloalkenyl, each $R^{3-2}$ is independently located at the ortho, meta or para position relative to the "connection site of cycloalkenyl and

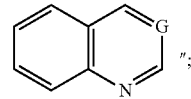

";

or, in the $R^{3-3}$ substituted or unsubstituted "5-7 membered heterocycloalkenyl containing 1-4 heteroatoms selected from the group consisting of N, O and S", the number of the $R^{3-3}$ is one or more than one, and when a plurality of $R^{3-3}$ exist, any of two $R^{3-3}$ are the same or different;

or, in the $R^{3-3}$ substituted or unsubstituted "5-7 membered heterocycloalkenyl containing 1-4 heteroatoms selected from the group consisting of N, O and S", the "5-7 membered heterocycloalkenyl containing 1-4 heteroatoms selected from the group consisting of N, O and S" is a "5-6 membered heterocycloalkenyl containing 1-2 heteroatoms selected from the group consisting of N, O, and S"

or, in the $R^{3-3}$ substituted or unsubstituted "5-7 membered heterocycloalkenyl containing 1-4 heteroatoms selected from the group consisting of N, O and S", the "5-7 membered heterocycloalkenyl containing 1-4 heteroatoms selected from the group consisting of N, O and S" is connected to

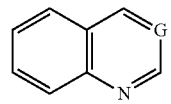

through C atom or N atom;

or, in the $R^{3-3}$ substituted or unsubstituted "5-7 membered heterocycloalkenyl containing 1-4 heteroatoms selected from the group consisting of N, O and S", each $R^{3-3}$ is independently located at the ortho, meta or para position relative to the "connection site of heterocycloalkenyl and

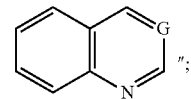

";

or, in the $R^{3-5}$ substituted or unsubstituted "5-6 membered heteroaryl containing 1-3 heteroatoms selected from the group consisting of N, O, and S", the number of the $R^{3-5}$ is one or more than one, when a plurality of $R^{3-5}$ exist, any of two $R^{3-5}$ are the same or different;

or, in the $R^{3-5}$ substituted or unsubstituted "5-6 membered heteroaryl containing 1-3 heteroatoms selected from the group consisting of N, O, and S", the "5-6 membered heteroaryl containing 1-3 heteroatoms selected from the group consisting of N, O, and S" is a "5-6 membered heteroaryl containing 1-2 heteroatoms selected from the group consisting of N, O, and S";

or, in the $R^{3-5}$ substituted or unsubstituted "5-6 membered heteroaryl containing 1-3 heteroatoms selected from the group consisting of N, O, and S", the "5-6 membered heteroaryl containing 1-3 heteroatoms selected from the group consisting of N, O, and S" is connected to

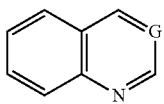

through C atom or N atom;

or, in the $R^{3-5}$ substituted or unsubstituted "5-6 membered heteroaryl containing 1-3 heteroatoms selected from the group consisting of N, O, and S", each $R^{3-5}$ is independently located at the ortho, meta or para position relative to the "connection site of heteroaryl and

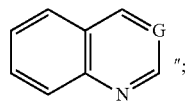

or, in the $(R^{3-8})(R^{3-9})N$—(Z)—HC=CH—, the double bond is Z-configured, E-configured or a mixture thereof;

or, in the $(R^{3-10})(R^{3-11})C=C(R^{3-12})$—C(=O)—NH—, the double bond is Z-configured, E-configured or a mixture thereof;

or, in the $R^{3-0}$, the $C_1$-$C_6$ alkoxy is independently $C_1$-$C_4$ alkoxy;

or, in the $R^{3-1}$, the $H_2C$=C—C(=O)—NH— is connected to the C atom in the "3-7 membered heterocycloalkyl containing 1-4 heteroatoms selected from the group consisting of N, O and S";

or, in the $R^{3-1}$, the $H_2C$=C—C(=O)—NH— is connected to the N atom in the "3-7 membered heterocycloalkyl containing 1-4 heteroatoms selected from the group consisting of N, O and S";

or, in the $R^{3-6-1}$ substituted or unsubstituted "3-7 membered heterocycloalkyl containing 1-4 heteroatoms selected from the group consisting of N, O and S", the number of the $R^{3-6-1}$ is one or more than one, and when a plurality of $R^{3-6-1}$ exist, any of two $R^{3-6-1}$ are the same or different;

or, in the $R^{3-6-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is a "5-6 membered heterocycloalkyl containing 1-2 heteroatoms selected from the group consisting of N, O and S";

or, in the $R^{3-6-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is connected to the N atom through the C atom;

or, in the $R^{3-6-1}$ substituted or unsubstituted "3-7 membered heterocycloalkyl containing 1-4 heteroatoms selected from the group consisting of N, O and S", each $R^{3-6-1}$ is independently located at the ortho, meta or para position relative to the "connection site of heterocycloalkyl and the N atom";

or, in the hydroxyl substituted or unsubstituted $C_1$-$C_6$ alkyl, the number of the hydroxyl is one or more than one;

or, in the hydroxyl substituted or unsubstituted $C_1$-$C_6$ alkyl, the "$C_1$-$C_6$ alkyl" is $C_1$-$C_4$ alkyl;

or, in the $R^{3-8}$ and $R^{3-9}$, the $C_3$-$C_6$ cycloalkyl is independently cyclopropyl or cyclobutyl;

or, in the $R^{3-8-1}$, the number of the oxa is one or more than one;

or, in the $R^{3-8-1}$, the "$C_1$-$C_6$ alkyl" is $C_1$-$C_4$ alkyl;

or, in the $R^{3-10-1}$ substituted or unsubstituted "3-7 membered heterocycloalkyl containing 1-4 heteroatoms selected from the group consisting of N, O and S", the number of the $R^{3-10-1}$ is one or more than one, when a plurality of $R^{3-10-1}$ exist, any of two $R^{3-10-1}$ are the same or different;

or, in the $R^{3-10-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is a "5-6 membered heterocycloalkyl containing 1-2 heteroatoms selected from the group consisting of N, O and S";

or, in the $R^{3-10-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is connected to the double bond through the C atom or N atom;

or, in the $R^{3-10-1}$ substituted or unsubstituted "3-7 membered heterocycloalkyl containing 1-4 heteroatoms selected from the group consisting of N, O and S", each $R^{3-10-1}$ is independently located at the ortho, meta or para position relative to the "connection site of heterocycloalkyl and the double bond";

or, in the $R^{3-10-1}$, the $C_1$-$C_6$ alkyl is $C_1$-$C_4$ alkyl;

or, in the $R^{3-13}$, the "3-7 membered heterocycloalkyl containing 1-4 heteroatoms selected from the group consisting of N, O and S" is a "5-6 membered heterocycloalkyl containing 1-2 heteroatoms selected from the group consisting of N, O and S";

or, in the $R^{3-13}$, the "3-7 membered heterocycloalkyl containing 1-4 heteroatoms selected from the group consisting of N, O and S" is connected to the 0 atom through the C atom.

3. The compound I as defined in claim 2, the pharmaceutically acceptable salt thereof, the enantiomer thereof, the diastereomer thereof, the tautomer thereof, or the solvate thereof, wherein, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

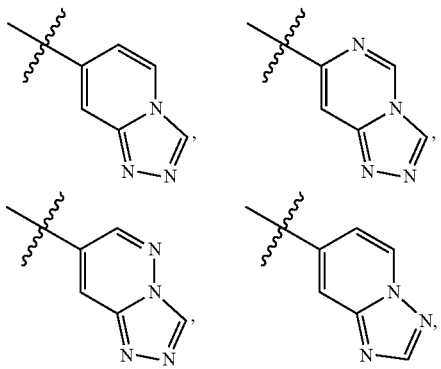

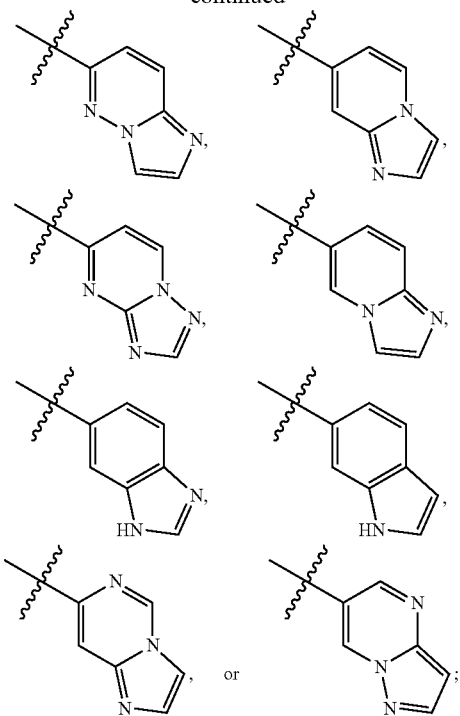

or

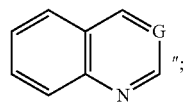

or, in the R³⁻² substituted or unsubstituted 5-7 membered cycloalkenyl, when the number of the R³⁻² is one or more than one, the number being more than one is 2, 3, 4 or 5;

or, in the R³⁻² substituted or unsubstituted 5-7 membered cycloalkenyl, the "5-7 membered cycloalkenyl" is cyclohexene-1-yl;

or, in the R³⁻² substituted or unsubstituted 5-7 membered cycloalkenyl, each R³⁻² is independently located at the meta position relative to the "connection site of cycloalkenyl and

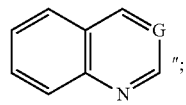

or, in the R³⁻³ substituted or unsubstituted "5-7 membered heterocycloalkenyl containing 1-4 heteroatoms selected from the group consisting of N, O and S", when the number of the R³⁻³ is one or more than one, the number being more than one is 2, 3, 4 or 5;

or, in the R³⁻³ substituted or unsubstituted "5-7 membered heterocycloalkenyl containing 1-4 heteroatoms selected from the group consisting of N, O and S", the "5-7 membered heterocycloalkenyl containing 1-4 heteroatoms selected from the group consisting of N, O and S" is 1,2,5,6-tetrahydropyridyl;

or, in the R³⁻³ substituted or unsubstituted "5-7 membered heterocycloalkenyl containing 1-4 heteroatoms selected from the group consisting of N, O and S", each R³⁻³ is independently located at the para position relative to the "connection site of heterocycloalkenyl and

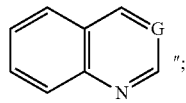

or, in the E, the number of the N atom in the ring connected to A in the "9-10 membered fused heteroaryl containing 1-4 heteroatoms selected from the group consisting of N, O and S" is 1 or 2;

or, in the E, the number of the N atom in the ring not connected to A in the "9-10 membered fused heteroaryl containing 1-4 heteroatoms selected from the group consisting of N, O and S" is 2 or 3;

or, in the R², the halogen is independently chlorine;

or, in the R², when the $C_1$-$C_6$ alkyl is independently $C_1$-$C_4$ alkyl, the $C_1$-$C_4$ alkyl is independently methyl, ethyl, n-propyl, isopropyl, n-butyl, isobutyl, sec-butyl or tert-butyl;

or, in the R³, the halogen is independently fluorine;

or, in the R³⁻⁰ substituted or unsubstituted $C_1$-$C_6$ alkoxy, when the number of the R³⁻⁰ is one or more than one, the number being more than one is 2, 3, 4 or 5;

or, in the R³⁻⁰ substituted or unsubstituted $C_1$-$C_6$ alkoxy, when the "$C_1$-$C_6$ alkoxy" is $C_1$-$C_4$ alkoxy, the "$C_1$-$C_4$ alkoxy" is methoxy, ethoxy, n-propoxy, isopropoxy, n-butoxy, isobutoxy, sec-butoxy or tert-butoxy;

or, in the R³⁻¹ substituted or unsubstituted "3-7 membered heterocycloalkyl containing 1-4 heteroatoms selected from the group consisting of N, O and S", when the number of the R³⁻¹ is one or more than one, the number being more than one is 2, 3, 4 or 5;

or, in the R³⁻¹ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is piperidinyl;

or, in the R³⁻¹ substituted or unsubstituted "3-7 membered heterocycloalkyl containing 1-4 heteroatoms selected from the group consisting of N, O and S", each R³⁻¹ is independently located at the meta or para position relative to the "connection site of heterocycloalkyl and or, in the R³⁻⁵ substituted or unsubstituted "5-6 membered heteroaryl containing 1-3 heteroatoms selected from the group consisting of N, O, and S", when the number of the R³⁻⁵ is one or more than one, the number being more than one is 2, 3, 4 or 5;

or, in the R³⁻⁵ substituted or unsubstituted "5-6 membered heteroaryl containing 1-3 heteroatoms selected from the group consisting of N, O, and S", the "5-6 membered heteroaryl containing 1-3 heteroatoms selected from the group consisting of N, O, and S" is pyrazolyl or furanyl;

or, in the R³⁻⁵ substituted or unsubstituted "5-6 membered heteroaryl containing 1-3 heteroatoms selected from the group consisting of N, O, and S", each R³⁻⁵ is independently located at the meta position relative to the "connection site of heteroaryl and

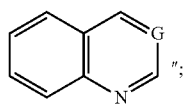;

or, in the (R$^{3-8}$)(R$^{3-9}$)N—(Z)—HC═CH—, the double bond is E-configured;

or, in the (R$^{3-10}$)(R$^{3-11}$)C═C(R$^{3-12}$)—C(═O)—NH—, the double bond is E-configured, or Z-configured;

or, in the R$^{3-0}$, when the C$_1$-C$_6$ alkoxy is independently a C$_1$-C$_4$ alkoxy, the C$_1$-C$_4$ alkoxy is methoxy, ethoxy, n-propoxy, isopropoxy, n-butoxy, isobutoxy, sec-butoxy or tert-butoxy;

or, in the R$^{3-3-1}$, the halogen is fluorine;

or, in the R$^{3-6-1}$ substituted or unsubstituted "3-7 membered heterocycloalkyl containing 1-4 heteroatoms selected from the group consisting of N, O and S", when the number of the R$^{3-6-1}$ is one or more than one, the number being more than one is 2, 3, 4 or 5;

or, in the R$^{3-6-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is piperidyl;

or, in the R$^{3-6-1}$ substituted or unsubstituted "3-7 membered heterocycloalkyl containing 1-4 heteroatoms selected from the group consisting of N, O and S", each R$^{3-6-1}$ is independently located at the meta position relative to the "connection site of heterocycloalkyl and the N atom";

or, in the hydroxyl substituted or unsubstituted C$_1$-C$_6$ alkyl, when the number of the hydroxyl is one or more than one, the number being more than one is 2, 3, 4 or 5;

or, in the hydroxyl substituted or unsubstituted C$_1$-C$_6$ alkyl, when the "C$_1$-C$_6$ alkyl" is a C$_1$-C$_4$ alkyl, the C$_1$-C$_4$ alkyl is methyl, ethyl, n-propyl, isopropyl, n-butyl, isobutyl, sec-butyl or tert-butyl;

or, in the R$^{3-8}$ and R$^{3-9}$, the C$_3$-C$_6$ cycloalkyl is independently cyclopropyl;

or, in the R$^{3-8-1}$, when the number of the oxa is one or more than one, the number being more than one is 2, 3, 4 or 5;

or, in the R$^{3-8-1}$, when the "C$_1$-C$_6$ alkyl" is a C$_1$-C$_4$ alkyl, the C$_1$-C$_4$ alkyl is methyl, ethyl, n-propyl, isopropyl, n-butyl, isobutyl, sec-butyl or tert-butyl;

or, in the R$^{3-10-1}$ substituted or unsubstituted "3-7 membered heterocycloalkyl containing 1-4 heteroatoms selected from the group consisting of N, O and S", when the number of the R$^{3-10-1}$ is one or more than one, the number being more than one is 2, 3, 4 or 5;

or, in the R$^{3-10-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is pyrrolidinyl or morpholinyl;

or, in the R$^{3-10-1}$ substituted or unsubstituted "3-7 membered heterocycloalkyl containing 1-4 heteroatoms selected from the group consisting of N, O and S", each R$^{3-10-1}$ is independently located at the ortho position relative to the "connection site of heterocycloalkyl and the double bond";

or, in the R$^{3-10-1}$, when the C$_1$-C$_6$ alkyl is a C$_1$-C$_4$ alkyl, the C$_1$-C$_4$ alkyl is methyl, ethyl, n-propyl, isopropyl, n-butyl, isobutyl, sec-butyl or tert-butyl;

or, in the R$^{3-12}$, the halogen is independently fluorine;

or, in the R$^{3-13}$, the "3-7 membered heterocycloalkyl containing 1-4 heteroatoms selected from the group consisting of N, O and S" is furanyl.

4. The compound I as defined in claim 2, the pharmaceutically acceptable salt thereof, the enantiomer thereof, the diastereomer thereof, the tautomer thereof, or the solvate thereof, wherein, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

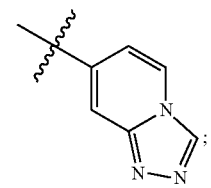 [SMILES: *c1ccn2cnnc2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

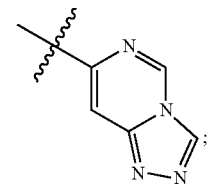 [SMILES: *c1cc2nncn2cn1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

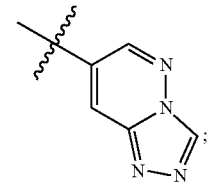 [SMILES: *c1cnn2cnnc2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

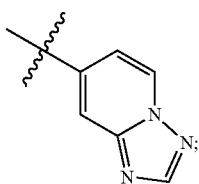 [SMILES: *c1ccn2ncnc2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

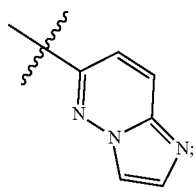 [SMILES: *c1ccc2nccn2n1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

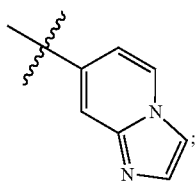 [SMILES: *c1ccn2ccnc2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

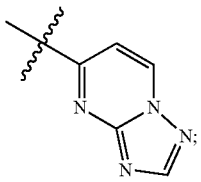 [SMILES: *c1ccn2ncnc2n1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

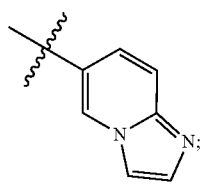 [SMILES: *c1ccc2nccn2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

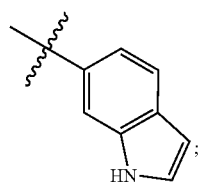 [SMILES: *c1ccc2cc[nH]c2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

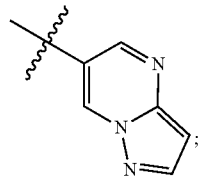 [SMILES: *c1cnc2ccnn2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms"

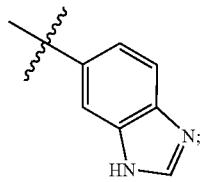 [SMILES: *c1ccc2nc[nH]c2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

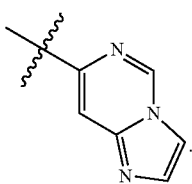

5. The compound I as defined in claim 3, the pharmaceutically acceptable salt thereof, the enantiomer thereof, the diastereomer thereof, the tautomer thereof, or the solvate thereof, wherein, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

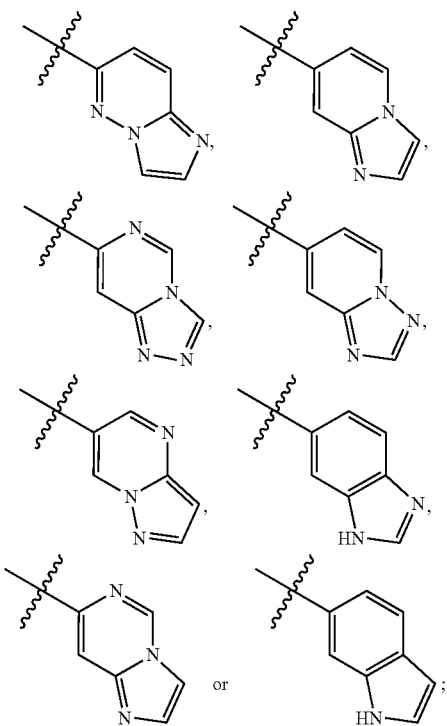

or, in the $R^2$, when the $C_1$-$C_6$ alkyl is independently $C_1$-$C_4$ alkyl, then the $C_1$-$C_4$ alkyl is independently methyl;

or, in the $R^{3-0}$ substituted or unsubstituted $C_1$-$C_6$ alkoxy, when the "$C_1$-$C_6$ alkoxy" is a $C_1$-$C_4$ alkoxy, then the $C_1$-$C_4$ alkoxy is independently ethoxy;

or, in the $R^{3-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is piperidin-1-yl or piperidin-4-yl;

or, in the $R^{3-3}$ substituted or unsubstituted "5-7 membered heterocycloalkenyl containing 1-4 heteroatoms selected from the group consisting of N, O and S", the "5-7 membered heterocycloalkenyl containing 1-4 heteroatoms selected from the group consisting of N, O and S" is 1,2,5,6-tetrahydropyridin-4-yl;

or, in the $R^{3-5}$ substituted or unsubstituted "5-6 membered heteroaryl containing 1-3 heteroatoms selected from the group consisting of N, O, and S", when the "5-6 membered heteroaryl containing 1-3 heteroatoms selected from the group consisting of N, O, and S" is pyrazolyl, then the pyrazolyl is pyrazole-5-yl or pyrazole-1-yl;

or, in the $R^{3-5}$ substituted or unsubstituted "5-6 membered heteroaryl containing 1-3 heteroatoms selected from the group consisting of N, O, and S", when the "5-6 membered heteroaryl containing 1-3 heteroatoms selected from the group consisting of N, O, and S" is furanyl, then the furanyl is furan-2-yl;

or, in the $R^{3-0}$, when the $C_1$-$C_6$ alkoxy is independently $C_1$-$C_4$ alkoxy, then the $C_1$-$C_4$ alkoxy is methoxy;

or, in the $R^{3-6-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is piperidin-3-yl;

or, in the hydroxyl substituted or unsubstituted $C_1$-$C_6$ alkyl, when the "$C_1$-$C_6$ alkyl" is $C_1$-$C_4$ alkyl, then the $C_1$-$C_4$ alkyl is methyl or ethyl;

or, in the $R^{3-8-1}$, when the "$C_1$-$C_6$ alkyl" is $C_1$-$C_4$ alkyl, then the $C_1$-$C_4$ alkyl is methyl or ethyl;

or, in the $R^{3-10-1}$ substituted or unsubstituted "3-7 membered heterocycloalkyl containing 1-4 heteroatoms selected from the group consisting of N, O and S", when the "3-7 membered heterocycloalkyl containing 1-4 heteroatoms selected from the group consisting of N, O and S" is pyrrolidinyl, then the pyrrolidin-2-yl is 2S-pyrrolidin-2-yl, 2R-pyrrolidin-2-yl or a mixture thereof;

or, in the $R^{3-10-1}$ substituted or unsubstituted "3-7 membered heterocycloalkyl containing 1-4 heteroatoms selected from the group consisting of N, O and S", when the "3-7 membered heterocycloalkyl containing 1-4 heteroatoms selected from the group consisting of N, O and S" is morpholinyl, then the morpholinyl is morpholinyl-3-yl;

or, in the $R^{3-10-1}$, when the $C_1$-$C_6$ alkyl is $C_1$-$C_4$ alkyl, then the $C_1$-$C_4$ alkyl is methyl or ethyl;

or, in the $R^{3-13}$, the "3-7 membered heterocycloalkyl containing 1-4 heteroatoms selected from the group consisting of N, O and S" is furan-3-yl.

6. The compound I as defined in claim 1, the pharmaceutically acceptable salt thereof, the enantiomer thereof, the diastereomer thereof, the tautomer thereof, or the solvate thereof, wherein, the $R^{3-0}$ substituted or unsubstituted $C_1$-$C_6$ alkoxy is

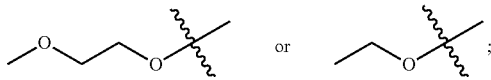

or, the "$R^{3-1}$ substituted or unsubstituted 3-7 membered heterocycloalkyl containing 1-4 heteroatoms selected from the group consisting of N, O and S" is

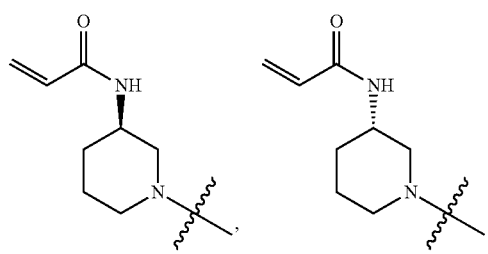

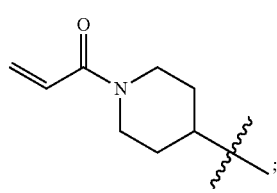

or, the R³⁻² substituted or unsubstituted 5-7 membered cycloalkenyl is

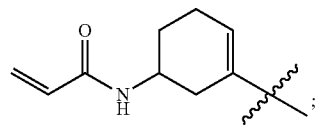 [SMILES: *C1=CCCC(NC(=O)C=C)C1]

or, the "R³⁻³ substituted or unsubstituted 5-7 membered heterocycloalkenyl containing 1-4 heteroatoms selected from the group consisting of N, O and S" is

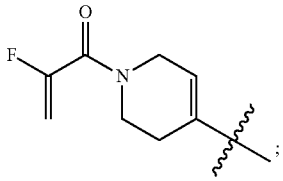 [SMILES: *C1=CCN(C(=O)C(=C)F)CC1]

or, the "R³⁻⁵ substituted or unsubstituted 5-6 membered heteroaryl containing 1-3 heteroatoms selected from the group consisting of N, O and S" is

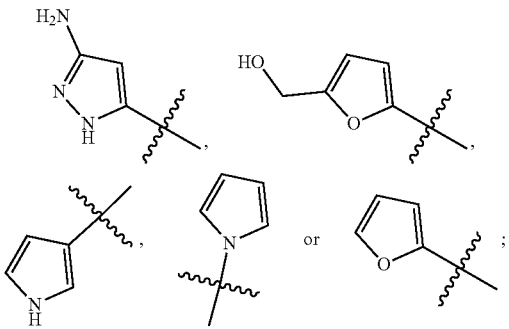

or, the NR³⁻⁶R³⁻⁷— is

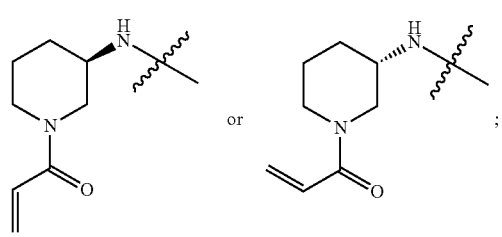 [SMILES: *N[C@@H]1CCCN(C(=O)C=C)C1 ; *N[C@H]1CCCN(C(=O)C=C)C1]

or, the (R³⁻⁸)(R³⁻⁹)N—(Z)—HC=CH— is

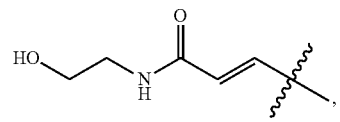

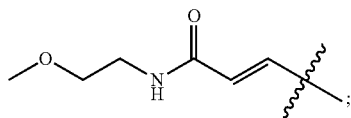

or, the (R³⁻¹⁰)(R³⁻¹¹)C=C(R³⁻¹²)—C(=O)—NH— is

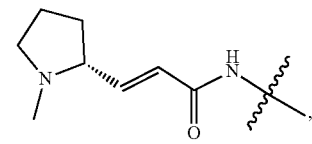

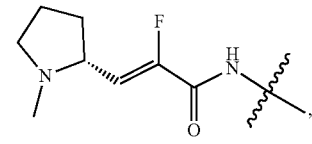

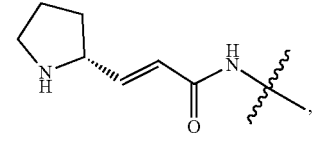

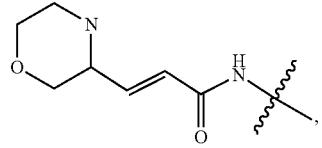

-continued

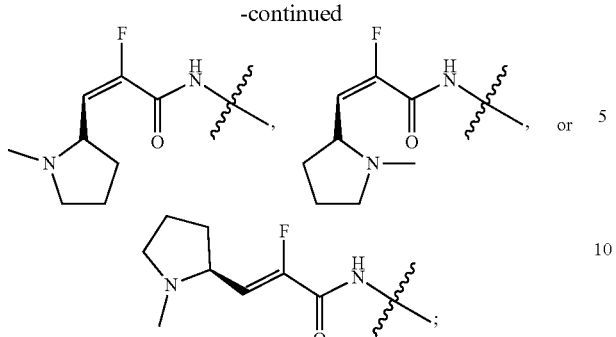

or, the R$^{3-13}$—O— is

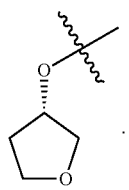

7. The compound I as defined in claim 1, the pharmaceutically acceptable salt thereof, the enantiomer thereof, the diastereomer thereof, the tautomer thereof, or the solvate thereof, wherein, A is —O—;
or, n is 1;
or, Y is CH;
or, G is N;
or, m is 1 or 2.

8. The compound I as defined in claim 1, the pharmaceutically acceptable salt thereof, the enantiomer thereof, the diastereomer thereof, the tautomer thereof, or the solvate thereof, wherein, in R$^3$, R$^{3-3}$ substituted or unsubstituted "5-7 membered heterocycloalkenyl containing 1-4 heteroatoms selected from the group consisting of N, O and S", "5-6 membered heteroaryl containing 1-3 heteroatomes selected from the group consisting of N, O and S", (R$^{3-8}$)(R$^{3-9}$)N—(Z)—HC═CH—, or, (R$^{3-10}$)(R$^{3-11}$)C═C(R$^{3-12}$)—C(═O)—NH—, is located at the para position relative to the N atom in

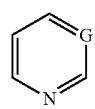

of compound I;
or, in the (R$^{3-10}$)(R$^{3-11}$)C═C(R$^{3-12}$)—C(═O)—NH—, when R$^{3-12}$ is H, then the double bond is E-configured;
or, in the (R$^{3-10}$)(R$^{3-11}$)C═C(R$^{3-12}$)—C(═O)—NH—, when R$^{3-12}$ is halogen, then the double bond is Z-configured.

9. The compound I as defined in claim 1, the pharmaceutically acceptable salt thereof, the enantiomer thereof, the diastereomer thereof, the tautomer thereof, or the solvate thereof, wherein, the A is —O—;

or, when n is 1, then the compound I is

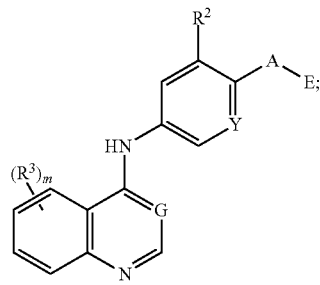

I-1 or, when m is 1, then the compound I is

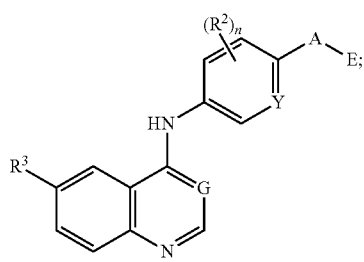

I-2 or, when m is 2, then the compound I is

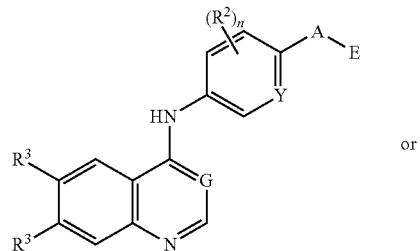

I-3 or

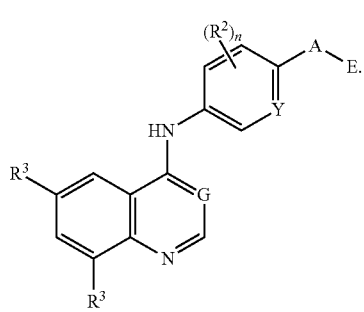

I-4

10. The compound I as defined in claim 1, the pharmaceutically acceptable salt thereof, the enantiomer thereof, the diastereomer thereof, the tautomer thereof, or the solvate thereof, wherein, E is

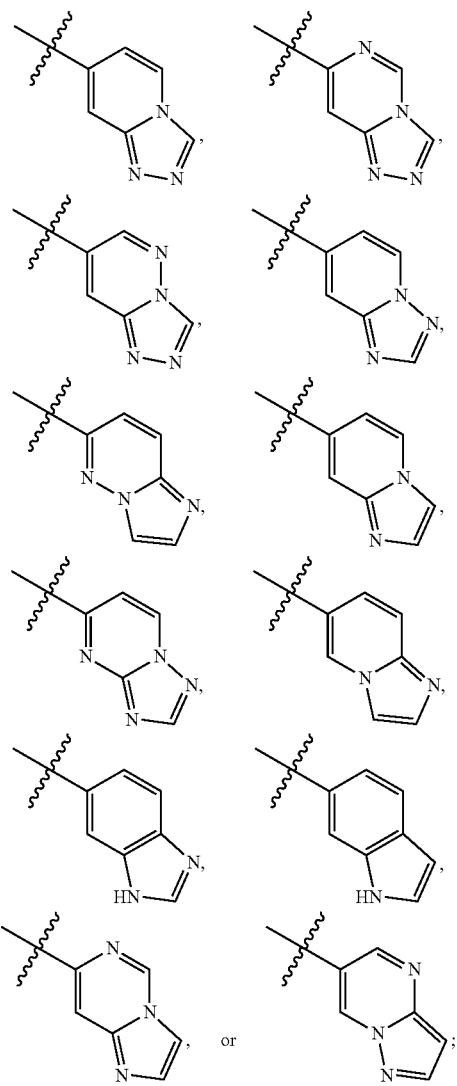

A is —O—;
n is 1;
Y is CH;
G is N;
m is 1 or 2;
each $R^2$ is independently halogen, or, $C_1$-$C_6$ alkyl;
each $R^3$ is independently $R^{3-0}$ substituted or unsubstituted $C_1$-$C_6$ alkoxyl, $R^{3-1}$ substituted or unsubstituted "3-7 membered heterocycloalkyl containing 1-4 heteroatoms selected from the group consisting of N, O and S", $R^{3-2}$ substituted or unsubstituted 5-7 membered cycloalkenyl, $R^{3-3}$ substituted or unsubstituted "5-7 membered heterocycloalkenyl containing 1-4 heteroatoms selected from the group consisting of N, O and S", $R^{3-5}$ substituted or unsubstituted "5-6 membered heteroaryl containing 1-3 heteroatomes selected from the group consisting of N, O and S", $N(R^{3-6})(R^{3-7})$—, $(R^{3-8})(R^{3-9})N$—(Z)—HC=CH—, or, $(R^{3-10})(R^{3-11})C$=C($R^{3-12}$)—C(=O)—NH—;
each $R^{3-3}$ is independently $H_2C$=C$R^{3-3-1}$—C(=O)—;
each $R^{3-5}$ is independently amino;

$R^{3-6}$ is $R^{3-6-1}$ substituted or unsubstituted "3-7 membered heterocycloalkyl containing 1-4 heteroatoms selected from the group consisting of N, O and S";

$R^{3-7}$ is H;

each Z is independently —C(=O)—;

each $R^{3-8}$ and $R^{3-9}$ is independently H, hydroxyl substituted or unsubstituted $C_1$-$C_6$ alkyl, or, $C_3$-$C_6$ cycloalkyl;

$R^{3-10}$ is $R^{3-10-1}$ substituted or unsubstituted "3-7 membered heterocycloalkyl containing 1-4 heteroatoms selected from the group consisting of N, O and S";

$R^{3-11}$ is H.

11. The compound I as defined in claim 1, the pharmaceutically acceptable salt thereof, the enantiomer thereof, the diastereomer thereof, the tautomer thereof, or the solvate thereof, wherein, E is

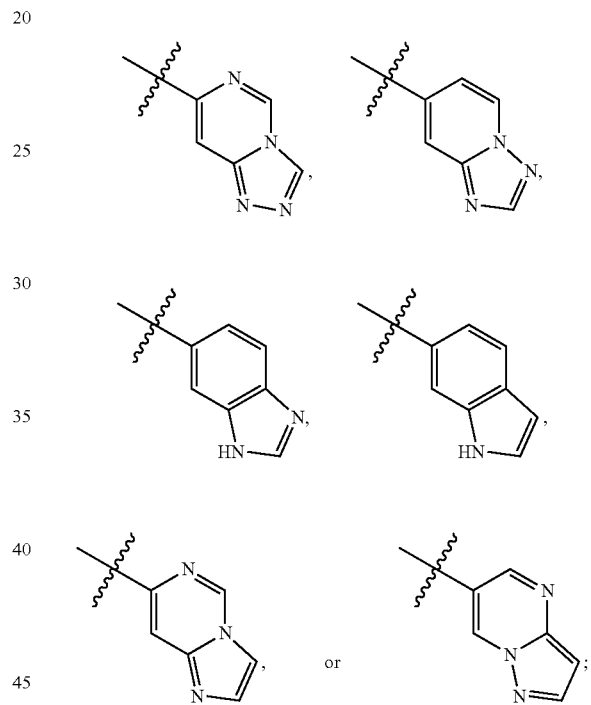

A is —O—;
n is 1;
Y is CH;
G is N;
m is 1 or 2;
each $R^2$ is independently $C_1$-$C_6$ alkyl;
each $R^3$ is independently $R^{3-0}$ substituted or unsubstituted $C_1$-$C_6$ alkoxyl, or, $(R^{3-10})(R^{3-11})C$=C($R^{3-12}$)—C(=O)—NH—;

$R^{3-10}$ is $R^{3-10-1}$ substituted or unsubstituted "3-7 membered heterocycloalkyl containing 1-4 heteroatoms selected from the group consisting of N, O and S";

$R^{3-11}$ is H.

12. The compound I as defined in claim 1, the pharmaceutically acceptable salt thereof, the enantiomer thereof, the diastereomer thereof, the tautomer thereof, or the solvate thereof;

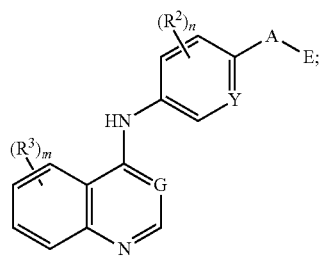

wherein, E is "9-10 membered fused heteroaryl containing 1-4 heteroatoms selected from the group consisting of N, O and S";
A is —O—, —S—, —C(=O)—, —SO— or —$SO_2$—;
n is 0, 1, 2, 3 or 4;
each $R^2$ is independently halogen, or, $C_1$-$C_6$ alkyl;
Y is N or CH;
G is N;
m is 1 or 2;
each $R^3$ is independently halogen, $R^{3-0}$ substituted or unsubstituted $C_1$-$C_6$ alkoxy, $R^{3-1}$ substituted or unsubstituted "3-7 membered heterocycloalkyl containing 1-4 heteroatoms selected from the group consisting of N, O and S", $R^{3-2}$ substituted or unsubstituted 5-7 membered cycloalkenyl, $R^{3-3}$ substituted or unsubstituted "5-7 membered heterocycloalkenyl containing 1-4 heteroatoms selected from the group consisting of N, O and S", $R^{3-5}$ substituted or unsubstituted "5-6 membered heteroaryl containing 1-3 heteroatoms selected from the group consisting of N, O, and S", $N(R^{3-6})(R^{3-7})$—, $(R^{3-8})(R^{3-9})N$—(Z)—HC=CH—, $(R^{3-10})(R^{3-11})C$=C($R^{3-12}$)—C(=O)—NH—, or, $R^{3-13}$—O—;
each $R^{3-0}$ is independently $C_1$-$C_6$ alkoxy;
each $R^{3-1}$ is independently $H_2C$=CH—C(=O)—NH— or $H_2C$=C—C(=O)—;
each $R^{3-2}$ is independently $H_2C$=CH—C(=O)—NH—;
each $R^{3-3}$ is independently $H_2C$=CR$^{3-3-1}$—C(=O)—NH—; each $R^{3-3-1}$ is independently H or halogen;
each $R^{3-5}$ is independently amino or hydroxymethyl;
$R^{3-6}$ is $R^{3-6-1}$ substituted or unsubstituted "3-7 membered heterocycloalkyl containing 1-4 heteroatoms selected from the group consisting of N, O and S"; each $R^{3-6-1}$ is independently $H_2C$=CH—C(=O)—NH—;
$R^{3-7}$ is H;
each Z is independently —C(=O)— or —$CH_2$—; each $R^{3-8}$ and $R^{3-9}$ is independently H, hydroxyl substituted or unsubstituted $C_1$-$C_6$ alkyl, $C_3$-$C_6$ cycloalkyl, or, $R^{3-8-1}$—C(=O)—; each $R^{3-8-1}$ is independently oxa-$C_1$-$C_6$ alkyl;
$R^{3-10}$ is $R^{3-10-1}$ substituted or unsubstituted "3-7 membered heterocycloalkyl containing 1-4 heteroatoms selected from the group consisting of N, O and S", or $C_1$-$C_6$ alkyl; $R^{3-10-1}$ is $C_1$-$C_6$ alkyl;
$R^{3-11}$ is H;
each $R^{3-12}$ is independently H or halogen;
each $R^{3-13}$ is independently "3-7 membered heterocycloalkyl containing 1-4 heteroatoms selected from the group consisting of N, O and S";
when m is 1, then $R^3$ is $R^{3-1}$ substituted "3-7 membered heterocycloalkyl containing 1-4 heteroatoms selected from the group consisting of N, O and S";
or, when m is 1, then $R^3$ is $R^{3-2}$ substituted 5-7 membered cycloalkenyl;

or, when m is 1, then $R^3$ is $R^{3-3}$ substituted "5-7 membered heterocycloalkenyl containing 1-4 heteroatoms selected from the group consisting of N, O and S";
or, when m is 1, then $R^3$ is $N(R^{3-6})(R^{3-7})$—;
or, when m is 1, then $R^3$ is $(R^{3-8})(R^{3-9})N$—(Z)—HC=CH—;
or, when m is 1, then $R^3$ is $(R^{3-10})(R^{3-11})C$=C($R^{3-12}$)—C(=O)—NH—;
when m is 2, then $R^3$ is $R^{3-3}$ substituted "5-7 membered heterocycloalkenyl containing 1-4 heteroatoms selected from the group consisting of N, O and S" and halogen, respectively;
or, when m is 2, then $R^3$ is $(R^{3-8})(R^{3-9})N$—(Z)—HC=CH— and halogen, respectively;
or, when m is 2, then $R^3$ is $(R^{3-10})(R^{3-11})C$=C($R^{3-12}$)—C(=O)—NH— and $R^{3-10}$ substituted or unsubstituted $C_1$-$C_6$ alkoxyl, respectively;
with the proviso that the compound I excludes any one of the compounds as follows:

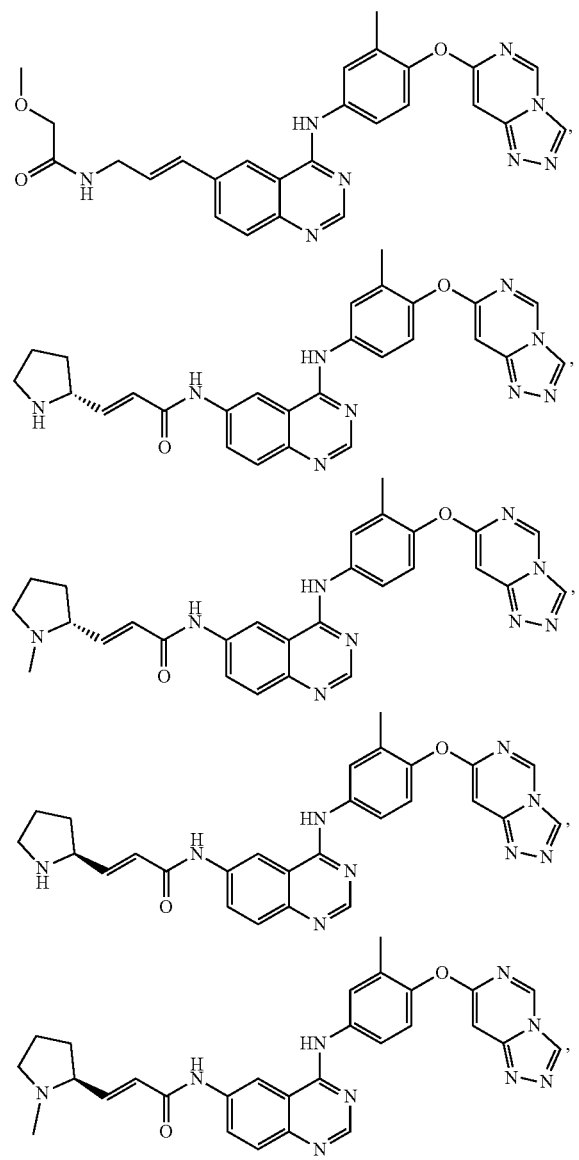

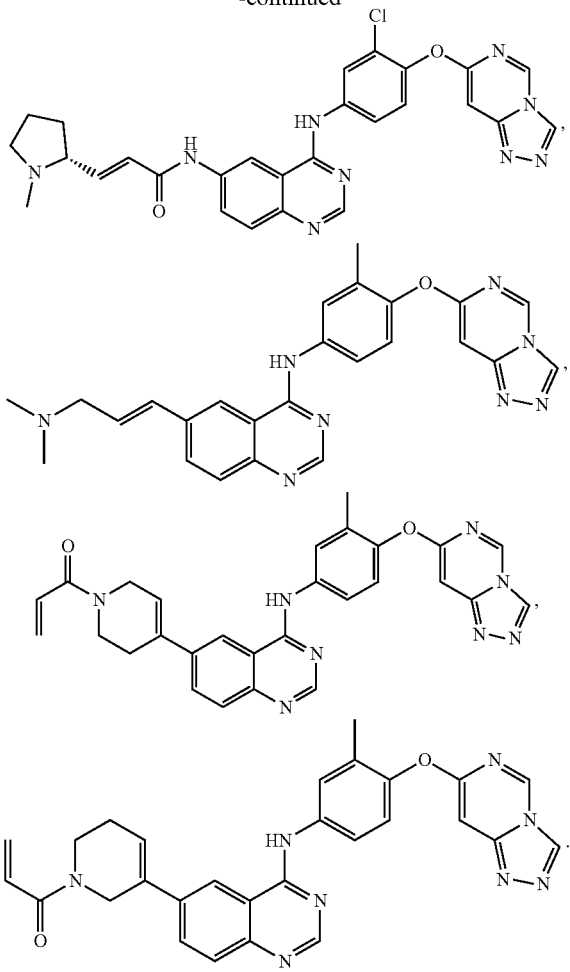

13. The compound I as defined in claim 12, the pharmaceutically acceptable salt thereof, the enantiomer thereof, the diastereomer thereof, the tautomer thereof, or the solvate thereof, wherein, in the E, the "9-10 membered fused heteroaryl containing 1-4 heteroatoms selected from the group consisting of N, O and S" is "9-10 membered fused heteroaryl containing 1-4 N atoms",

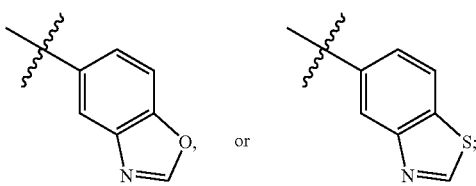 [SMILES: *c1ccc2ocnc2c1 ; "or" ; *c1ccc2scnc2c1]

or, in the E, the number of the N atom in the ring connected to A in the "9-10 membered fused heteroaryl containing 1-4 heteroatoms selected from the group consisting of N, O and S" is 0, 1 or 2;

or, in the E, the number of the N atom in the ring not connected to A in the "9-10 membered fused heteroaryl containing 1-4 heteroatoms selected from the group consisting of N, O and S" is 1, 2 or 3;

or, in the $R^2$, the $C_1$-$C_6$ alkyl is independently $C_1$-$C_4$ alkyl;

or, in the $R^{3-0}$ substituted or unsubstituted $C_1$-$C_6$ alkoxy, the number of the $R^{3-0}$ is one or more than one, and when a plurality of $R^{3-0}$ exist, any of two $R^{3-0}$ are the same or different;

or, in the $R^{3-0}$ substituted or unsubstituted $C_1$-$C_6$ alkoxy, the "$C_1$-$C_6$ alkoxy" is $C_1$-$C_4$ alkoxy;

or, in the $R^{3-1}$ substituted or unsubstituted "3-7 membered heterocycloalkyl containing 1-4 heteroatoms selected from the group consisting of N, O and S", the number of the $R^{3-1}$ is one or more than one, and when a plurality of $R^{3-1}$ exist, any of two $R^{3-1}$ are the same or different;

or, in the $R^{3-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is a "5-6 membered heterocycloalkyl containing 1-2 heteroatoms selected from the group consisting of N, O and S";

or, in the $R^{3-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is connected to

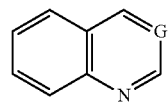

through C atom or N atom;

or, in the $R^{3-1}$ substituted or unsubstituted "3-7 membered heterocycloalkyl containing 1-4 heteroatoms selected from the group consisting of N, O and S", each $R^{3-1}$ is independently located at the ortho, meta or para position relative to the "connection site of heterocycloalkyl and

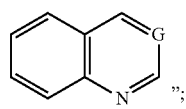

";

or, in the $R^{3-2}$ substituted or unsubstituted 5-7 membered cycloalkenyl, the number of the $R^{3-2}$ is one or more than one, and when a plurality of $R^{3-2}$ exist, any of two $R^{3-2}$ are the same or different;

or, in the $R^{3-2}$ substituted or unsubstituted 5-7 membered cycloalkenyl, the "5-7 membered cycloalkenyl" is cyclohexenyl;

or, in the $R^{3-2}$ substituted or unsubstituted 5-7 membered cycloalkenyl, each $R^{3-2}$ is independently located at the ortho, meta or para position relative to the "connection site of cycloalkenyl and

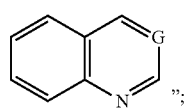

";

or, in the $R^{3-3}$ substituted or unsubstituted "5-7 membered heterocycloalkenyl containing 1-4 heteroatoms selected from the group consisting of N, O and S", the number of the $R^{3-3}$ is one or more than one, and when a plurality of $R^{3-3}$ exist, any of two $R^{3-3}$ are the same or different;

or, in the $R^{3-3}$ substituted or unsubstituted "5-7 membered heterocycloalkenyl containing 1-4 heteroatoms selected from the group consisting of N, O and S", the "5-7 membered heterocycloalkenyl containing 1-4 heteroatoms selected from the group consisting of N, O and S" is a "5-6 membered heterocycloalkenyl containing 1-2 heteroatoms selected from the group consisting of N, O, and S";

or, in the $R^{3-3}$ substituted or unsubstituted "5-7 membered heterocycloalkenyl containing 1-4 heteroatoms selected from the group consisting of N, O and S", the "5-7 membered heterocycloalkenyl containing 1-4 heteroatoms selected from the group consisting of N, O and S" is connected to

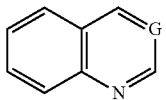

through C atom or N atom;

or, in the $R^{3-3}$ substituted or unsubstituted "5-7 membered heterocycloalkenyl containing 1-4 heteroatoms selected from the group consisting of N, O and S", each $R^{3-3}$ is independently located at the ortho, meta or para position relative to the "connection site of heterocycloalkenyl and

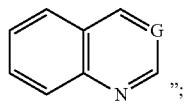

";

or, in the $R^{3-5}$ substituted or unsubstituted "5-6 membered heteroaryl containing 1-3 heteroatoms selected from the group consisting of N, O, and S", the number of the $R^{3-5}$ is one or more than one, when a plurality of $R^{3-5}$ exist, any of two $R^{3-5}$ are the same or different;

or, in the $R^{3-5}$ substituted or unsubstituted "5-6 membered heteroaryl containing 1-3 heteroatoms selected from the group consisting of N, O, and S", the "5-6 membered heteroaryl containing 1-3 heteroatoms selected from the group consisting of N, O, and S" is a "5-6 membered heteroaryl containing 1-2 heteroatoms selected from the group consisting of N, O, and S";

or, in the $R^{3-5}$ substituted or unsubstituted "5-6 membered heteroaryl containing 1-3 heteroatoms selected from the group consisting of N, O, and S", the "5-6 membered heteroaryl containing 1-3 heteroatoms selected from the group consisting of N, O, and S" is connected to

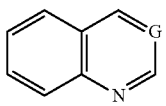

through C atom or N atom;

or, in the $R^{3-5}$ substituted or unsubstituted "5-6 membered heteroaryl containing 1-3 heteroatoms selected from the group consisting of N, O, and S", each $R^{3-5}$ is independently located at the ortho, meta or para position relative to the "connection site of heteroaryl and

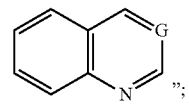

";

or, in the $(R^{3-8})(R^{3-9})N$—$(Z)$—$HC$=$CH$—, the double bond is Z-configured, E-configured or a mixture thereof;

or, in the $(R^{3-10})(R^{3-11})C$=$C(R^{3-12})$—$C(=O)$—$NH$—, the double bond is Z-configured, E-configured or a mixture thereof;

or, in the $R^{3-0}$, the $C_1$-$C_6$ alkoxy is independently $C_1$-$C_4$ alkoxy;

or, in the $R^{3-1}$, the $H_2C$=$C$—$C(=O)$—$NH$— is connected to the C atom in the "3-7 membered heterocycloalkyl containing 1-4 heteroatoms selected from the group consisting of N, O and S";

or, in the $R^{3-1}$, the $H_2C$=$C$—$C(=O)$—$NH$— is connected to the N atom in the "3-7 membered heterocycloalkyl containing 1-4 heteroatoms selected from the group consisting of N, O and S";

or, one of $R^{3-6}$ and $R^{3-7}$ is H;

or, in the $R^{3-6-1}$ substituted or unsubstituted "3-7 membered heterocycloalkyl containing 1-4 heteroatoms selected from the group consisting of N, O and S", the number of the $R^{3-6-1}$ is one or more than one, and when a plurality of $R^{3-6-1}$ exist, any of two $R^{3-6-1}$ are the same or different;

or, in the $R^{3-6-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is a "5-6 membered heterocycloalkyl containing 1-2 heteroatoms selected from the group consisting of N, O and S";

or, in the $R^{3-6-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is connected to the N atom through the C atom;

or, in the $R^{3-6-1}$ substituted or unsubstituted "3-7 membered heterocycloalkyl containing 1-4 heteroatoms selected from the group consisting of N, O and S", each $R^{3-6-1}$ is independently located at the ortho, meta or para position relative to the "connection site of heterocycloalkyl and the N atom";

or, in the hydroxyl substituted or unsubstituted $C_1$-$C_6$ alkyl, the number of the hydroxyl is one or more than one;

or, in the hydroxyl substituted or unsubstituted $C_1$-$C_6$ alkyl, the "$C_1$-$C_6$ alkyl" is $C_1$-$C_4$ alkyl;

or, in the $R^{3-8}$ and $R^{3-9}$, the $C_3$-$C_6$ cycloalkyl is independently cyclopropyl or cyclobutyl;

or, in the $R^{3-8-1}$, the number of the oxa is one or more than one;

or, in the $R^{3-8-1}$, the "$C_1$-$C_6$ alkyl" is $C_1$-$C_4$ alkyl;

or, in the $R^{3-10-1}$ substituted or unsubstituted "3-7 membered heterocycloalkyl containing 1-4 heteroatoms selected from the group consisting of N, O and S", the number of the $R^{3-10-1}$ is one or more than one, when a plurality of $R^{3-10-1}$ exist, any of two $R^{3-10-1}$ are the same or different;

or, in the $R^{3-10-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is a "5-6 membered heterocycloalkyl containing 1-2 heteroatoms selected from the group consisting of N, O and S";

or, in the $R^{3-10-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is connected to the double bond through the C atom or N atom;

or, in the $R^{3-10-1}$ substituted or unsubstituted "3-7 membered heterocycloalkyl containing 1-4 heteroatoms selected from the group consisting of N, O and S", each $R^{3-10-1}$ is independently located at the ortho, meta or para position relative to the "connection site of heterocycloalkyl and the double bond";

or, in the $R^{3-10-1}$, the $C_1$-$C_6$ alkyl is $C_1$-$C_4$ alkyl;

or, in the $R^{3-13}$, the "3-7 membered heterocycloalkyl containing 1-4 heteroatoms selected from the group consisting of N, O and S" is a "5-6 membered heterocycloalkyl containing 1-2 heteroatoms selected from the group consisting of N, O and S";

or, in the $R^{3-13}$, the "3-7 membered heterocycloalkyl containing 1-4 heteroatoms selected from the group consisting of N, O and S" is connected to the O atom through the C atom.

14. The compound I as defined in claim 13, the pharmaceutically acceptable salt thereof, the enantiomer thereof, the diastereomer thereof, the tautomer thereof, or the solvate thereof, wherein, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

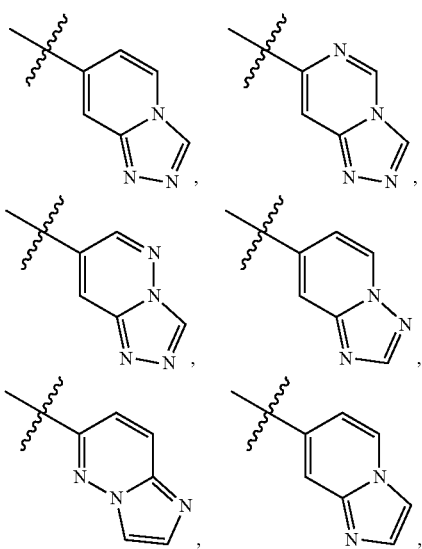

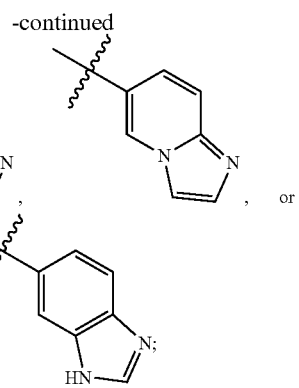

or, in the E, the number of the N atom in the ring connected to A in the "9-10 membered fused heteroaryl containing 1-4 heteroatoms selected from the group consisting of N, O and S" is 1 or 2;

or, in the E, the number of the N atom in the ring not connected to A in the "9-10 membered fused heteroaryl containing 1-4 heteroatoms selected from the group consisting of N, O and S" is 2 or 3;

or, in the $R^2$, the halogen is independently chlorine;

or, in the $R^2$, when the $C_1$-$C_6$ alkyl is independently $C_1$-$C_4$ alkyl the $C_1$-$C_4$ alkyl is independently methyl, ethyl, n-propyl, isopropyl, n-butyl, isobutyl, sec-butyl or tert-butyl;

or, in the $R^3$, the halogen is independently fluorine;

or, in the $R^{3-0}$ substituted or unsubstituted $C_1$-$C_6$ alkoxy, when the number of the $R^{3-0}$ is one or more than one, the number being more than one is 2, 3, 4 or 5;

or, in the $R^{3-0}$ substituted or unsubstituted $C_1$-$C_6$ alkoxy, when the "$C_1$-$C_6$ alkoxy" is $C_1$-$C_4$ alkoxy, the "$C_1$-$C_4$ alkoxy" is methoxy, ethoxy, n-propoxy, isopropoxy, n-butoxy, isobutoxy, sec-butoxy or tert-butoxy;

or, in the $R^{3-1}$ substituted or unsubstituted "3-7 membered heterocycloalkyl containing 1-4 heteroatoms selected from the group consisting of N, O and S", when the number of the $R^{3-1}$ is one or more than one, the number being more than one is 2, 3, 4 or 5;

or, in the $R^{3-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is piperidinyl;

or, in the $R^{3-1}$ substituted or unsubstituted "3-7 membered heterocycloalkyl containing 1-4 heteroatoms selected from the group consisting of N, O and S", each $R^{3-1}$ is independently located at the meta or para position relative to the "connection site of heterocycloalkyl and

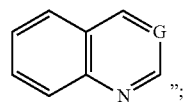

or, in the $R^{3-2}$ substituted or unsubstituted 5-7 membered cycloalkenyl, when the number of the $R^{3-2}$ is one or more than one, the number being more than one is 2, 3, 4 or 5;

or, in the $R^{3-2}$ substituted or unsubstituted 5-7 membered cycloalkenyl, the "5-7 membered cycloalkenyl" is cyclohexene-1-yl;

or, in the $R^{3-2}$ substituted or unsubstituted 5-7 membered cycloalkenyl, each $R^{3-2}$ is independently located at the meta position relative to the "connection site of cycloalkenyl and

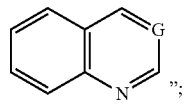
";

or, in the $R^{3-3}$ substituted or unsubstituted "5-7 membered heterocycloalkenyl containing 1-4 heteroatoms selected from the group consisting of N, O and S", when the number of the $R^{3-3}$ is one or more than one, the number being more than one is 2, 3, 4 or 5;

or, in the $R^{3-3}$ substituted or unsubstituted "5-7 membered heterocycloalkenyl containing 1-4 heteroatoms selected from the group consisting of N, O and S", the "5-7 membered heterocycloalkenyl containing 1-4 heteroatoms selected from the group consisting of N, O and S" is 1,2,5,6-tetrahydropyridyl;

or, in the $R^{3-3}$ substituted or unsubstituted "5-7 membered heterocycloalkenyl containing 1-4 heteroatoms selected from the group consisting of N, O and S", each $R^{3-3}$ is independently located at the para position relative to the "connection site of heterocycloalkenyl and

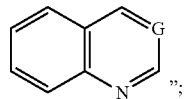
";

or, in the $R^{3-5}$ substituted or unsubstituted "5-6 membered heteroaryl containing 1-3 heteroatoms selected from the group consisting of N, O, and S", when the number of the $R^{3-5}$ is one or more than one, the number being more than one is 2, 3, 4 or 5;

or, in the $R^{3-5}$ substituted or unsubstituted "5-6 membered heteroaryl containing 1-3 heteroatoms selected from the group consisting of N, O, and S", the "5-6 membered heteroaryl containing 1-3 heteroatoms selected from the group consisting of N, O, and S" is pyrazolyl or furanyl;

or, in the $R^{3-5}$ substituted or unsubstituted "5-6 membered heteroaryl containing 1-3 heteroatoms selected from the group consisting of N, O, and S", each $R^{3-5}$ is independently located at the meta position relative to the "connection site of heteroaryl and

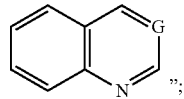
";

or, in the $(R^{3-8})(R^{3-9})N$—(Z)—HC=CH—, the double bond is E-configured;

or, in the $(R^{3-10})(R^{3-11})C=C(R^{3-12})$—C(=O)—NH—, the double bond is E-configured;

or, in the $R^{3-0}$, when the $C_1$-$C_6$ alkoxy is independently $C_1$-$C_4$ alkoxy, then the $C_1$-$C_4$ alkoxy is methoxy, ethoxy, n-propoxy, isopropoxy, n-butoxy, isobutoxy, sec-butoxy or tert-butoxy;

or, in the $R^{3-3-1}$, the halogen is fluorine;

or, in the $R^{3-6-1}$ substituted or unsubstituted "3-7 membered heterocycloalkyl containing 1-4 heteroatoms selected from the group consisting of N, O and S", when the number of the $R^{3-6-1}$ is one or more than one, the number being more than one is 2, 3, 4 or 5;

or, in the $R^{3-6-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is piperidyl;

or, in the $R^{3-6-1}$ substituted or unsubstituted "3-7 membered heterocycloalkyl containing 1-4 heteroatoms selected from the group consisting of N, O and S", each $R^{3-6-1}$ is independently located at the meta position relative to the "connection site of heterocycloalkyl and the N atom";

or, in the hydroxyl substituted or unsubstituted $C_1$-$C_6$ alkyl, when the number of the hydroxyl is one or more than one, the number being more than one is 2, 3, 4 or 5;

or, in the hydroxyl substituted or unsubstituted $C_1$-$C_6$ alkyl, when the "$C_1$-$C_6$ alkyl" is $C_1$-$C_4$ alkyl, then the $C_1$-$C_4$ alkyl is methyl, ethyl, n-propyl, isopropyl, n-butyl, isobutyl, sec-butyl or tert-butyl;

or, in the $R^{3-8}$ and $R^{3-9}$, the $C_3$-$C_6$ cycloalkyl is independently cyclopropyl;

or, in the $R^{3-8-1}$, when the number of the oxa is one or more than one, the number being more than one is 2, 3, 4 or 5;

or, in the $R^{3-8-1}$, when the "$C_1$-$C_6$ alkyl" is $C_1$-$C_4$ alkyl, then the $C_1$-$C_4$ alkyl is methyl, ethyl, n-propyl, isopropyl, n-butyl, isobutyl, sec-butyl or tert-butyl;

or, in the $R^{3-10-1}$ substituted or unsubstituted "3-7 membered heterocycloalkyl containing 1-4 heteroatoms selected from the group consisting of N, O and S", when the number of the $R^{3-10-1}$ is one or more than one, the number being more than one is 2, 3, 4 or 5;

or, in the $R^{3-10-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is pyrrolidinyl or morpholinyl;

or, in the $R^{3-10-1}$ substituted or unsubstituted "3-7 membered heterocycloalkyl containing 1-4 heteroatoms selected from the group consisting of N, O and S", each $R^{3-10-1}$ is independently located at the ortho position relative to the "connection site of heterocycloalkyl and the double bond";

or, in the $R^{3-10-1}$, when the $C_1$-$C_6$ alkyl is $C_1$-$C_4$ alkyl, the $C_1$-$C_4$ alkyl is methyl, ethyl, n-propyl, isopropyl, n-butyl, isobutyl, sec-butyl or tert-butyl;

or, in the $R^{3-12}$, the halogen is independently fluorine;

or, in the $R^{3-13}$, the "3-7 membered heterocycloalkyl containing 1-4 heteroatoms selected from the group consisting of N, O and S" is furanyl.

15. The compound I as defined in claim 13, the pharmaceutically acceptable salt thereof, the enantiomer thereof, the diastereomer thereof, the tautomer thereof, or the solvate thereof, wherein, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

203

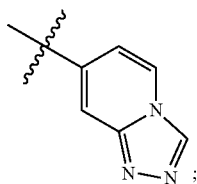

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

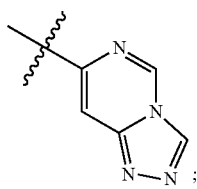 [SMILES: *c1cc2nncn2cn1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

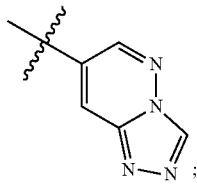 [SMILES: *c1cnn2cnnc2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

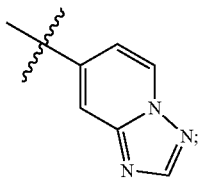

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

204

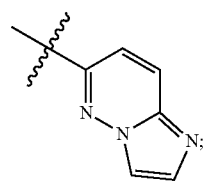 [SMILES: *c1ccc2nccn2n1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

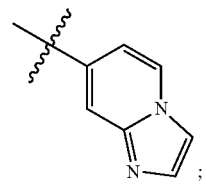

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms"

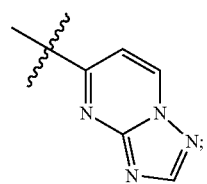 [SMILES: *c1ccn2ncnc2n1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

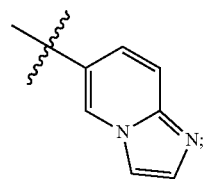 [SMILES: *c1ccc2nccn2c1]

or, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

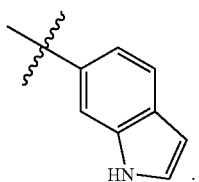 [SMILES: *c1ccc2cc[nH]c2c1]

16. The compound I as defined in claim 14, the pharmaceutically acceptable salt thereof, the enantiomer thereof, the diastereomer thereof, the tautomer thereof, or the solvate thereof, wherein, in the E, when the "9-10 membered fused heteroaryl containing 1-4 heteroatoms selected from the group consisting of N, O and S" is "9-10 membered fused heteroaryl containing 1-4 N atoms", the "9-10 membered fused heteroaryl containing 1-4 N atoms" is

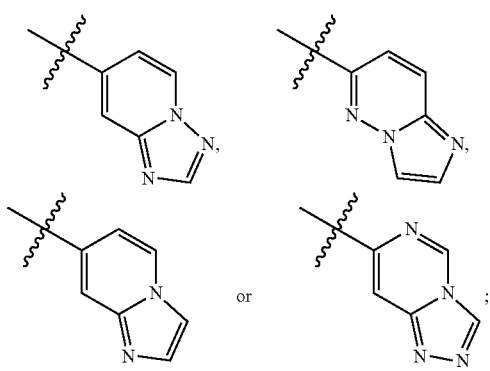

or, in the $R^2$, when the $C_1$-$C_6$ alkyl is independently $C_1$-$C_4$ alkyl, then the $C_1$-$C_4$ alkyl is independently methyl;

or, in the $R^{3-0}$ substituted or unsubstituted $C_1$-$C_6$ alkoxy, when the "$C_1$-$C_6$ alkoxy" is $C_1$-$C_4$ alkoxy, then the $C_1$-$C_4$ alkoxy is independently ethoxy;

or, in the $R^{3-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is piperidin-1-yl or piperidin-4-yl;

or, in the $R^{3-3}$ substituted or unsubstituted "5-7 membered heterocycloalkenyl containing 1-4 heteroatoms selected from the group consisting of N, O and S", the "5-7 membered heterocycloalkenyl containing 1-4 heteroatoms selected from the group consisting of N, O and S" is 1,2,5,6-tetrahydropyridin-4-yl;

or, in the $R^{3-5}$ substituted or unsubstituted "5-6 membered heteroaryl containing 1-3 heteroatoms selected from the group consisting of N, O, and S", when the "5-6 membered heteroaryl containing 1-3 heteroatoms selected from the group consisting of N, O, and S" is pyrazolyl, then the pyrazolyl is pyrazole-5-yl or pyrazole-1-yl;

or, in the $R^{3-5}$ substituted or unsubstituted "5-6 membered heteroaryl containing 1-3 heteroatoms selected from the group consisting of N, O, and S", when the "5-6 membered heteroaryl containing 1-3 heteroatoms selected from the group consisting of N, O, and S" is furanyl, then the furanyl is furan-2-yl;

or, in the $R^{3-0}$, when the $C_1$-$C_6$ alkoxy is independently $C_1$-$C_4$ alkoxy, then the $C_1$-$C_4$ alkoxy is methoxy;

or, in the $R^{3-6-1}$ substituted or unsubstituted "3-7 membered heterocycloalkyl containing 1-4 heteroatoms selected from the group consisting of N, O and S", the "3-7 membered heterocycloalkyl containing 1-4 heteroatoms selected from the group consisting of N, O and S" is piperidin-3-yl;

or, in the hydroxyl substituted or unsubstituted $C_1$-$C_6$ alkyl, when the "$C_1$-$C_6$ alkyl" is $C_1$-$C_4$ alkyl, then the $C_1$-$C_4$ alkyl is methyl or ethyl;

or, in the $R^{3-8-1}$, when the "$C_1$-$C_6$ alkyl" is $C_1$-$C_4$ alkyl, then the $C_1$-$C_4$ alkyl is methyl or ethyl;

or, in the $R^{3-10-1}$ substituted or unsubstituted "3-7 membered heterocycloalkyl containing 1-4 heteroatoms selected from the group consisting of N, O and S", when the "3-7 membered heterocycloalkyl containing 1-4 heteroatoms selected from the group consisting of N, O and S" is pyrrolidinyl, then the pyrrolidin-2-yl is 2S-pyrrolidin-2-yl, 2R-pyrrolidin-2-yl or a mixture thereof;

or, in the $R^{3-10-1}$ substituted or unsubstituted "3-7 membered heterocycloalkyl containing 1-4 heteroatoms selected from the group consisting of N, O and S", when the "3-7 membered heterocycloalkyl containing 1-4 heteroatoms selected from the group consisting of N, O and S" is morpholinyl, then the morpholinyl is morpholinyl-3-yl;

or, in the $R^{3-10-1}$, when the $C_1$-$C_6$ alkyl is $C_1$-$C_4$ alkyl, then the $C_1$-$C_4$ alkyl is methyl or ethyl;

or, in the $R^{3-13}$, the "3-7 membered heterocycloalkyl containing 1-4 heteroatoms selected from the group consisting of N, O and S" is furan-3-yl.

17. The compound I as defined in claim 12, the pharmaceutically acceptable salt thereof, the enantiomer thereof, the diastereomer thereof, the tautomer thereof, or the solvate thereof, wherein, the $R^{3-0}$ substituted or unsubstituted $C_1$-$C_6$ alkoxy is

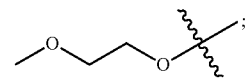 [SMILES: *OCCOC]

or, the "$R^{3-1}$ substituted or unsubstituted 3-7 membered heterocycloalkyl containing 1-4 heteroatoms selected from the group consisting of N, O and S" is

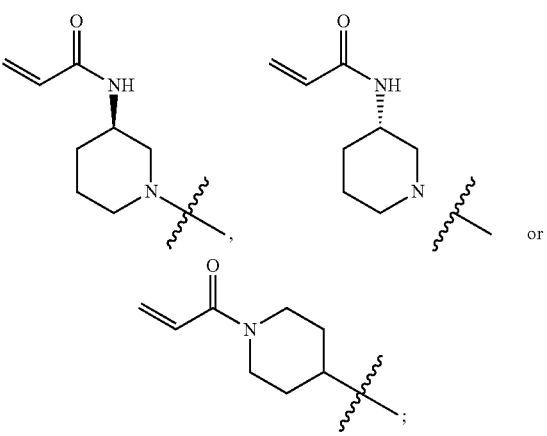

or, the $R^{3-2}$ substituted or unsubstituted 5-7 membered cycloalkenyl is

207

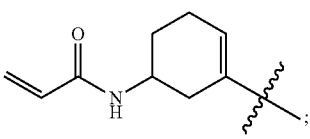 [SMILES: *C1=CCCC(NC(=O)C=C)C1]

or, the "$R^{3-3}$ substituted or unsubstituted 5-7 membered heterocycloalkenyl containing 1-4 heteroatoms selected from the group consisting of N, O and S" is

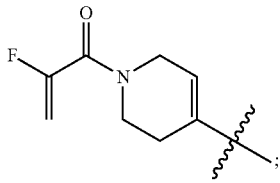 [SMILES: *C1=CCN(C(=O)C(=C)F)CC1]

or, the "$R^{3-5}$ substituted or unsubstituted 5-6 membered heteroaryl containing 1-3 heteroatoms selected from the group consisting of N, O and S" is

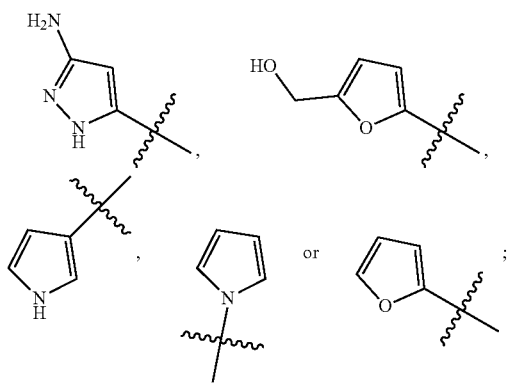

or, the $NR^{3-6}R^{3-7}$— is

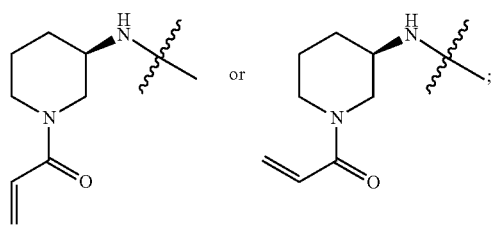 [SMILES: *N[C@@H]1CCCN(C(=O)C=C)C1 ; *N[C@@H]1CCCN(C(=O)C=C)C1]

or, the $(R^{3-8})(R^{3-9})N—(Z)—HC=CH—$ is

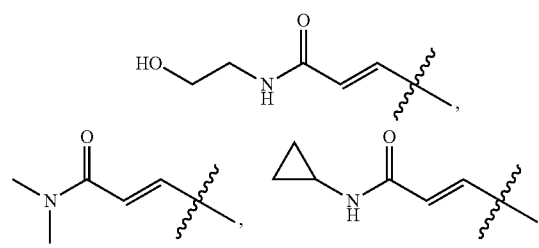

208

-continued

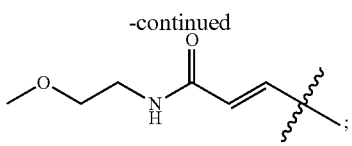

or, the $(R^{3-10})(R^{3-11})C=C(R^{3-12})—C(=O)—NH—$ is

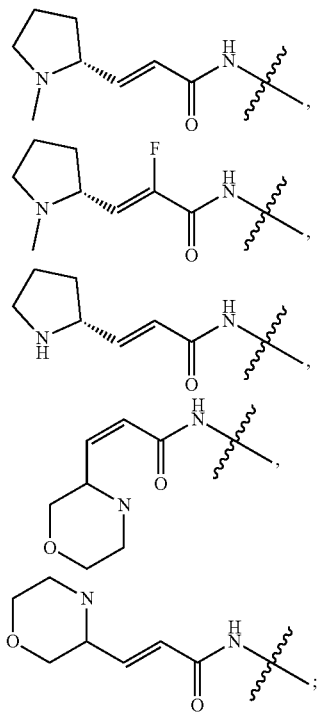

or, the $R^{3-13}—O—$ is

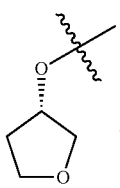

18. The compound I as defined in claim 12, the pharmaceutically acceptable salt thereof, the enantiomer thereof, the diastereomer thereof, the tautomer thereof, or the solvate thereof, wherein, A is —O— or —S—;
or, n is 1;
or, Y is CH;
or, G is N.

19. The compound I as defined in claim 12, the pharmaceutically acceptable salt thereof, the enantiomer thereof, the diastereomer thereof, the tautomer thereof, or the solvate thereof, wherein, when m is 2, then $R^3$ is $(R^{3-10})(R^{3-11})C=C(R^{3-12})—C(=O)—NH—$ and $C_1$-$C_6$ alkoxyl, respectively.

20. The compound I as defined in claim 12, the pharmaceutically acceptable salt thereof, the enantiomer thereof, the diastereomer thereof, the tautomer thereof, or the solvate thereof, wherein, in $R^3$, $R^{3-3}$ substituted or unsubstituted "5-7 membered heterocycloalkenyl containing 1-4 heteroatoms selected from the group consisting of N, O and S", "5-6 membered heteroaryl containing 1-3 heteroatomes selected from the group consisting of N, O and S", $(R^{3-8})(R^{3-9})N$—(Z)—HC=CH—, or, $(R^{3-10})(R^{3-11})C$=C$(R^{3-12})$—C(=O)—NH—, is located at the para position relative to the N atom in

of compound I.

21. The compound I as defined in claim 12, the pharmaceutically acceptable salt thereof, the enantiomer thereof, the diastereomer thereof, the tautomer thereof, or the solvate thereof, wherein, the A is —O—;

or, when n is 1, then the compound I is

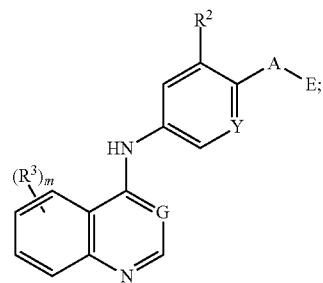

I-1 or, when m is 1, then the compound I is

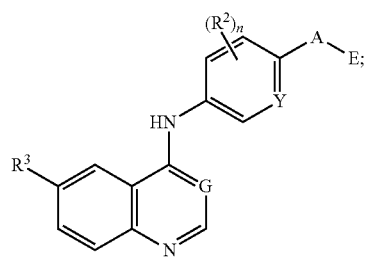

I-2 or, when m is 2, then the compound I is

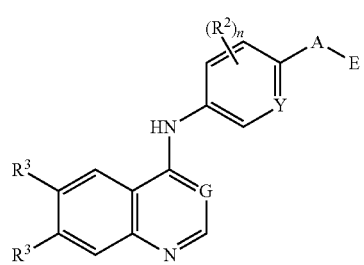

I-3 or

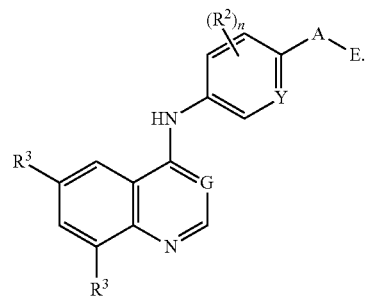

I-4

22. A compound I as defined in claim 1, the pharmaceutically acceptable salt thereof, the enantiomer thereof, the diastereomer thereof, the tautomer thereof, or the solvate thereof, wherein, the compound is any one of the following compounds:

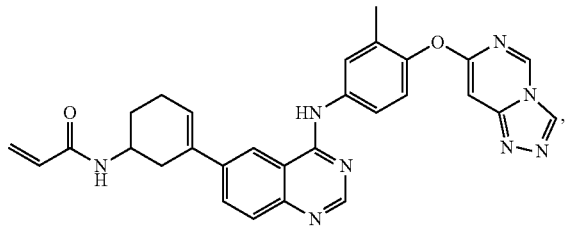

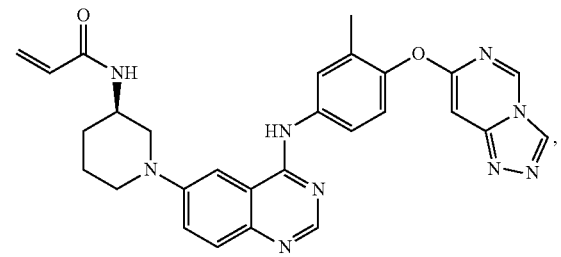

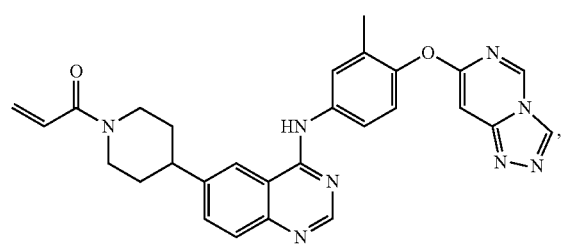

211
-continued
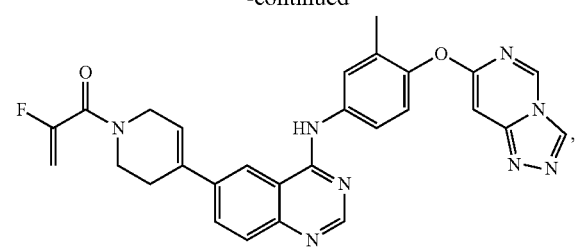
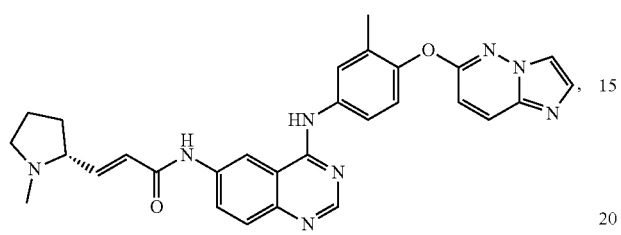
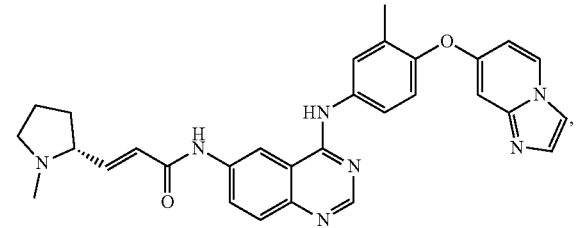
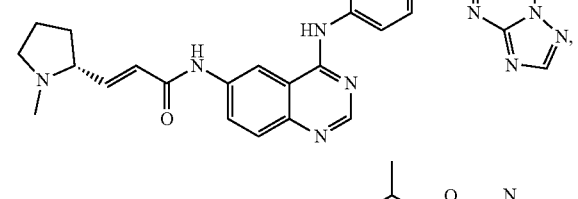
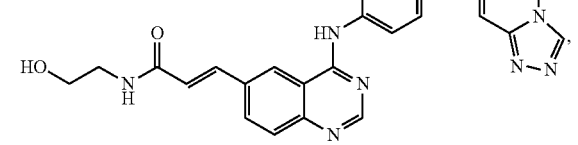
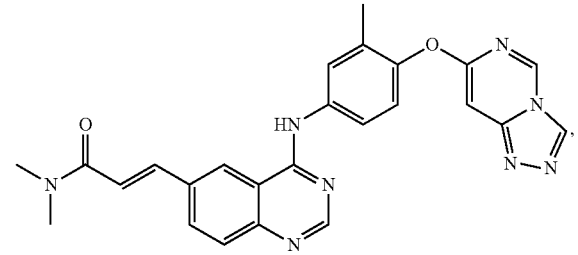
212
-continued
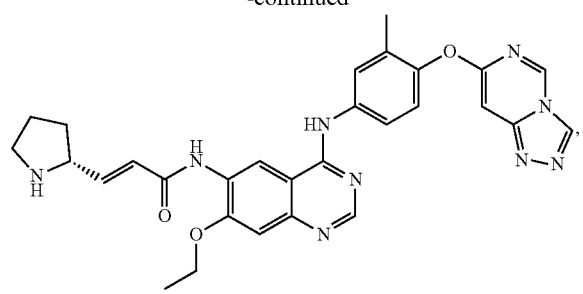
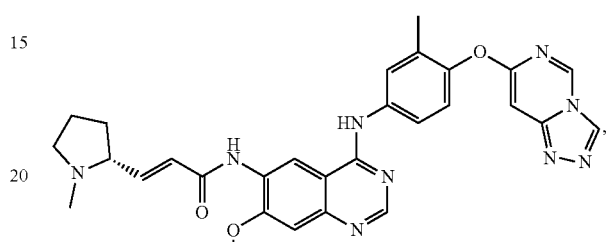
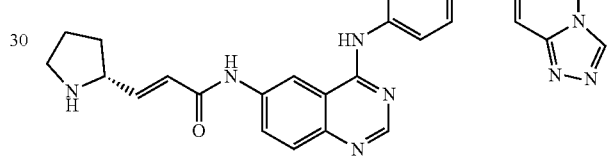
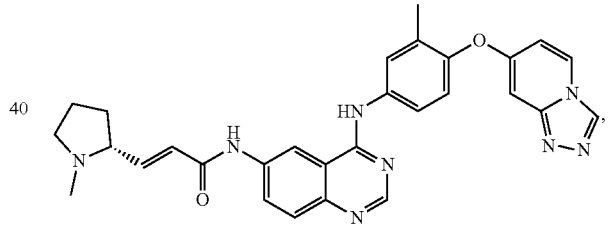
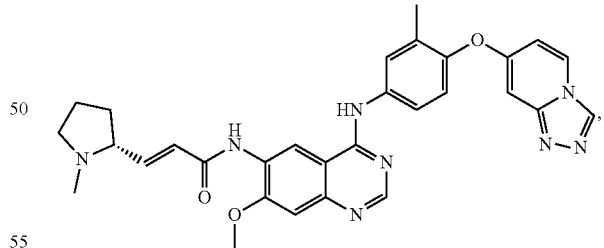
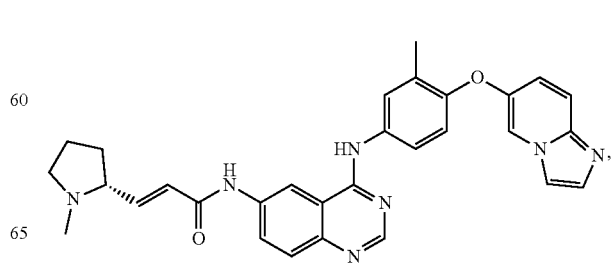

213
-continued
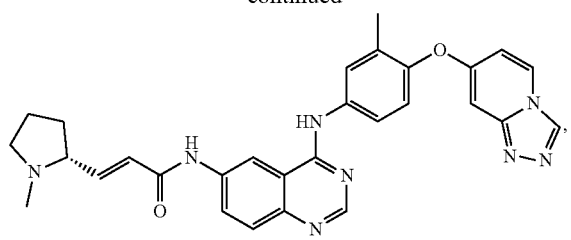
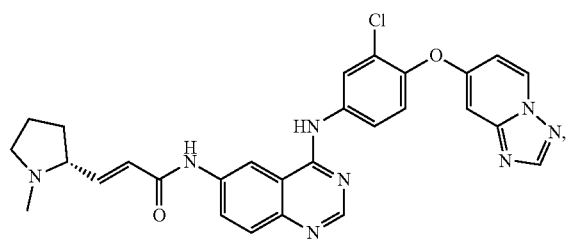
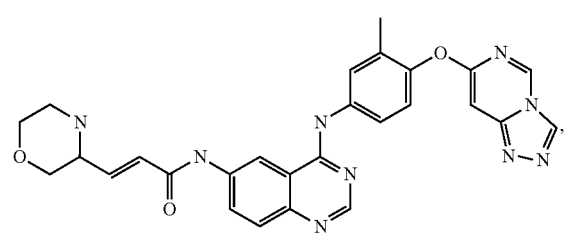
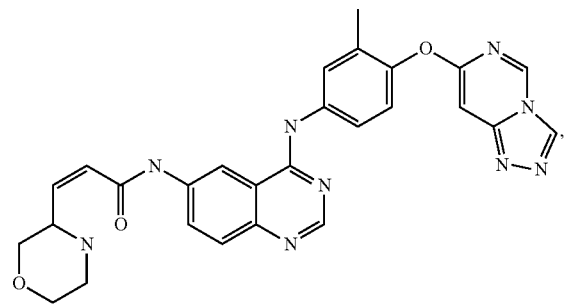
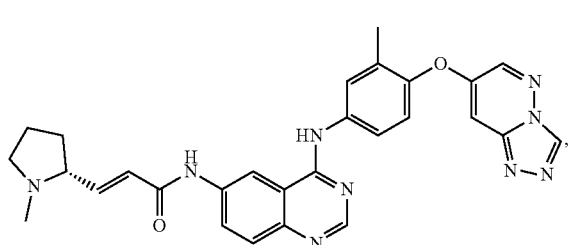
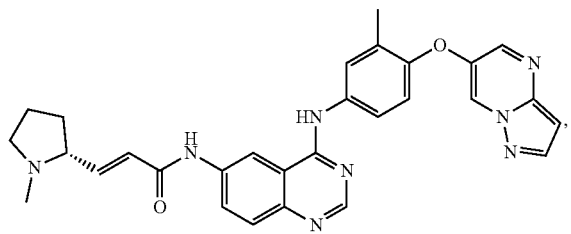
214
-continued
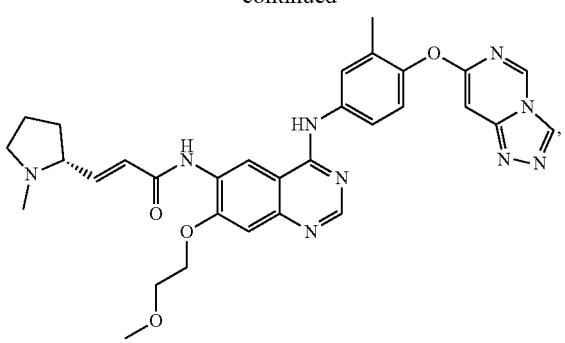
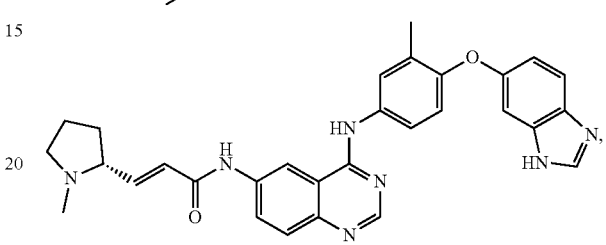
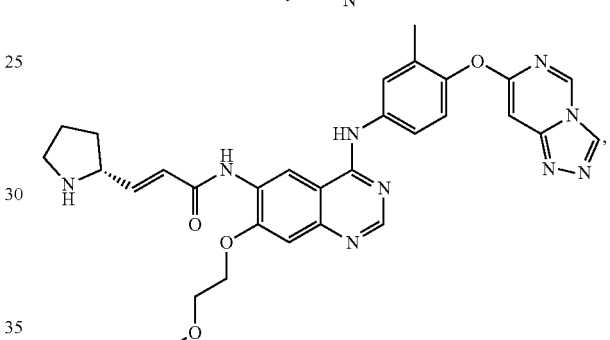
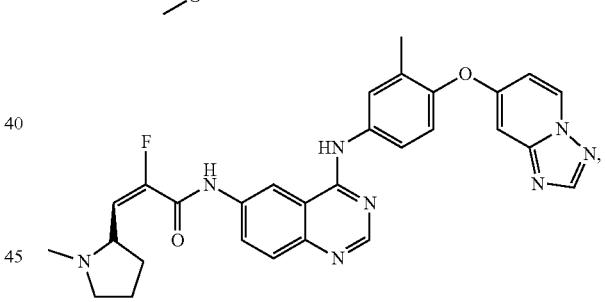
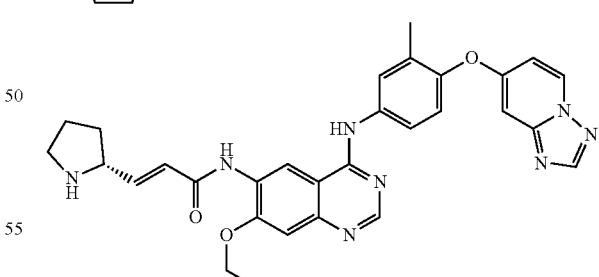
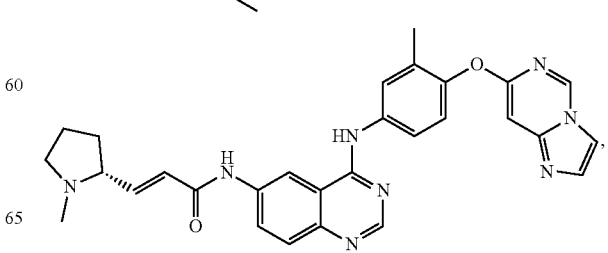

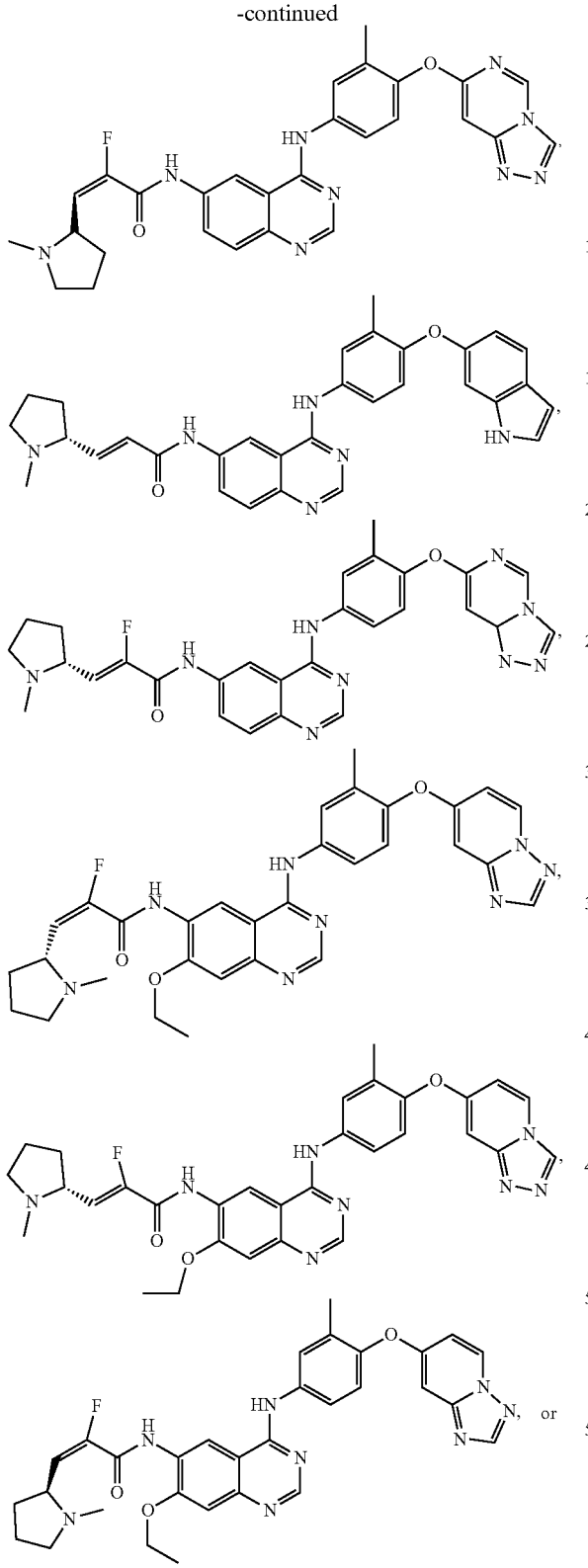

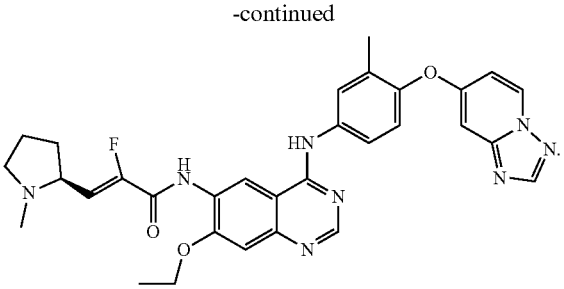

23. A compound 37 as shown below:

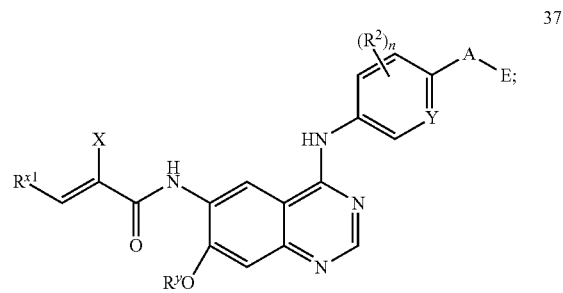

wherein,

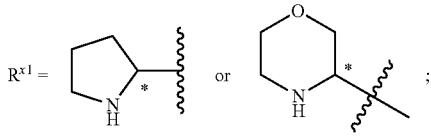 [SMILES: *C1CCCN1 ; *C1COCCN1]

X is H or F; $R^y$ is

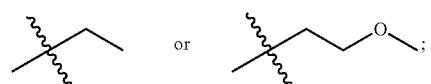

A, E, n, $R^2$ and Y are as defined in claim 1.

24. A pharmaceutical composition, comprising the nitrogenous heterocyclic compound, the pharmaceutically acceptable salt thereof, the enantiomer thereof, the diastereomer thereof, the tautomer thereof, or the solvate thereof as defined in claim 1, and at least one pharmaceutical excipient.

* * * * *